US009896694B2

(12) United States Patent
Roberts et al.

(10) Patent No.: US 9,896,694 B2
(45) Date of Patent: Feb. 20, 2018

(54) ACYLTRANSFERASE POLYNUCLEOTIDES, POLYPEPTIDES AND METHODS OF USE

(71) Applicants: Agresearch Limited, Hamilton (NZ); National Research Council of Canada (NRC), Ottawa (CA)

(72) Inventors: Nicholas John Roberts, Feilding (NZ); Amy Christina Curran, San Diego, CA (US); Somrutai Winichayakul, Palmerston North (NZ); Marissa Roldan, Palmerston North (NZ); Richard William Scott, Palmerston North (NZ); David Charles Taylor, Saskatoon (CA); Elizabeth-France Marillia, Asquith (CA)

(73) Assignees: Agresearch Limited, Hamilton (NZ); National Research Council of Canada, Ottawa (CA)

( * ) Notice: Subject to any disclaimer, the term of this patent is extended or adjusted under 35 U.S.C. 154(b) by 0 days.

(21) Appl. No.: 14/438,768

(22) PCT Filed: Oct. 22, 2013

(86) PCT No.: PCT/IB2013/059526
§ 371 (c)(1),
(2) Date: Apr. 27, 2015

(87) PCT Pub. No.: WO2014/068439
PCT Pub. Date: May 8, 2014

(65) Prior Publication Data
US 2015/0284736 A1 Oct. 8, 2015

Related U.S. Application Data

(60) Provisional application No. 61/720,119, filed on Oct. 30, 2012.

(51) Int. Cl.
*C12N 15/82* (2006.01)
*C12N 9/10* (2006.01)
*C10L 1/02* (2006.01)
*C12P 7/64* (2006.01)
*A23K 20/147* (2016.01)

(52) U.S. Cl.
CPC ........ *C12N 15/8247* (2013.01); *A23K 20/147* (2016.05); *C10L 1/026* (2013.01); *C12N 9/1029* (2013.01); *C12P 7/6409* (2013.01); *C07K 2319/00* (2013.01); *C10L 2200/0476* (2013.01); *C10L 2270/026* (2013.01); *C12Y 203/0102* (2013.01)

(58) Field of Classification Search
None
See application file for complete search history.

(56) References Cited

U.S. PATENT DOCUMENTS

| 4,795,855 A | 1/1989 | Fillatti et al. |
| 4,943,674 A | 7/1990 | Houck et al. |
| 5,004,863 A | 4/1991 | Umbeck |
| 5,086,169 A | 2/1992 | Mascarenhas |
| 5,159,135 A | 10/1992 | Umbeck |
| 5,177,010 A | 1/1993 | Goldman et al. |
| 5,187,073 A | 2/1993 | Goldman et al. |
| 5,188,958 A | 2/1993 | Moloney et al. |
| 5,412,085 A | 5/1995 | Allen et al. |
| 5,416,011 A | 5/1995 | Hinchee et al. |
| 5,463,174 A | 10/1995 | Moloney et al. |
| 5,536,653 A | 7/1996 | Barry et al. |
| 5,545,169 A | 8/1996 | Yarger |
| 5,545,546 A | 8/1996 | Allen et al. |
| 5,563,055 A | 10/1996 | Townsend et al. |
| 5,569,834 A | 10/1996 | Hinchee et al. |
| 5,591,616 A | 1/1997 | Hiei et al. |
| 5,608,150 A | 3/1997 | Conner |
| 5,639,952 A | 6/1997 | Quail et al. |
| 5,656,496 A | 8/1997 | Quail et al. |
| 5,750,385 A | 5/1998 | Shewmaker et al. |

(Continued)

FOREIGN PATENT DOCUMENTS

| WO | WO 1998/055631 A1 | 12/1998 |
| WO | WO 2000/001713 A2 | 1/2000 |

(Continued)

OTHER PUBLICATIONS

Alam et al. (1999) "Transgenic insect-resistant maintainer line (IR68899B) for improvement of hybrid rice," Plant Cell Rep. 18:572-575.
Altpeter et al. (2004) "Comparison of Transgene Expression Stability after Agrobacterium-mediated or Biolistic Gene Transfer into Perennial Ryegrass (*Lolium perenne* L.)," Developments in Plant Breeding. 11(7):255-260.
Altschul et al. (1997) "Gapped BLAST and PSI-BLAST: a new generation of protein database search programs," Nucleic Acids Res. 25:3389-3402.

(Continued)

*Primary Examiner* — Eileen B O Hara
(74) *Attorney, Agent, or Firm* — Lathrop Gage LLP

(57) ABSTRACT

The invention provides chimeric DGAT1 proteins comprising: a) at their N-terminal ends, an N-terminal portion of a first DGAT1 protein, and b) at their C-terminal ends, a C-terminal portion of a second DGAT1 protein. The chimeric DGAT proteins show enhanced activity relative to at least one of the first DGAT1 protein and the second DGAT1 protein. The chimeric DGAT proteins of the invention can be expressed in cells to increase cellular lipid accumulation and/or modify the cellular lipid profile. The invention also provides polynucleotides encoding the chimeric DGAT1 proteins, cells and compositions comprising the polynucleotides or chimeric DGAT1 proteins, and methods using the chimeric DGAT1 proteins to produce oil.

44 Claims, 14 Drawing Sheets

(56) References Cited

U.S. PATENT DOCUMENTS

| | | | |
|---|---|---|---|
| 5,750,871 | A | 5/1998 | Moloney et al. |
| 5,792,935 | A | 8/1998 | Arntzen et al. |
| 5,795,855 | A | 8/1998 | Schneider et al. |
| 5,824,877 | A | 10/1998 | Hinchee et al. |
| 5,837,848 | A | 11/1998 | Ely et al. |
| 5,846,797 | A | 12/1998 | Strickland |
| 5,952,543 | A | 9/1999 | Firoozabady et al. |
| 5,968,830 | A | 10/1999 | Dan et al. |
| 5,981,840 | A | 11/1999 | Zhao et al. |
| 6,020,539 | A | 2/2000 | Goldman et al. |
| 6,037,522 | A | 3/2000 | Dong et al. |
| 6,074,877 | A | 6/2000 | D'Halluin et al. |
| 6,100,077 | A | 8/2000 | Sturley et al. |
| 6,127,179 | A | 10/2000 | DellaPenna et al. |
| 6,184,443 | B1 | 2/2001 | Pedersen et al. |
| 6,228,643 | B1 | 5/2001 | Greenland et al. |
| 6,229,067 | B1 | 5/2001 | Sonnewald et al. |
| 6,342,657 | B1 | 1/2002 | Thomas et al. |
| 6,344,548 | B1 | 2/2002 | Farese, Jr. et al. |
| 7,081,565 | B2 | 7/2006 | Ohlrogge et al. |
| 7,141,424 | B2 | 11/2006 | Shin et al. |
| 7,153,953 | B2 | 12/2006 | Marraccini et al. |
| 7,371,928 | B2 | 5/2008 | Suh et al. |
| 7,405,345 | B2 | 7/2008 | Ohlrogge et al. |
| 7,629,454 | B2 | 12/2009 | Chan et al. |
| 7,642,346 | B2 | 1/2010 | Chaudhary et al. |
| 7,667,097 | B2 | 2/2010 | Scheirlinck et al. |
| 7,745,697 | B2 | 6/2010 | Perez et al. |
| 8,101,819 | B2 * | 1/2012 | Roesler ................ C12N 9/1029 435/410 |
| 8,809,026 | B2 * | 8/2014 | Vanhercke ............ C07K 14/415 435/134 |
| 2001/0047525 | A1 | 11/2001 | Bruce et al. |
| 2003/0115632 | A1 | 6/2003 | Lardizabal et al. |
| 2004/0067506 | A1 | 4/2004 | Scheres et al. |
| 2009/0094717 | A1 | 4/2009 | Troukhan et al. |
| 2009/0293152 | A1 * | 11/2009 | Roesler ................ C12N 9/1029 800/281 |
| 2010/0024079 | A1 | 1/2010 | Andersen et al. |
| 2011/0167514 | A1 | 7/2011 | Brover et al. |
| 2012/0156360 | A1 | 6/2012 | Roesler et al. |
| 2015/0252378 | A1 | 9/2015 | Roberts et al. |
| 2015/0275223 | A1 | 10/2015 | Roberts et al. |

FOREIGN PATENT DOCUMENTS

| | | |
|---|---|---|
| WO | WO 2000/032756 A2 | 6/2000 |
| WO | WO 2002/000894 A2 | 1/2002 |
| WO | WO 2004/011671 A2 | 2/2004 |
| WO | WO 2006/052914 A1 | 5/2006 |
| WO | WO 2009/143397 A2 | 11/2009 |
| WO | WO 2011/048119 | 4/2011 |
| WO | WO 2011/053169 A1 | 5/2011 |

OTHER PUBLICATIONS

Andrianov et al. (2009) "Tobacco as a production platform for biofuel: overexpression of *Arabidopsis* DGAT and LEC2 genes increases accumulation and shifts the composition of lipids in green biomass," Plant Biotechnol. J. 8:277-287.

Bairoch et al. (1994) "PROSITE: recent developments," Nucleic Acids Res. 22:3583-3589.

Baxevanis (2001) "The Molecular Biology Database Collection: an updated compilation of biological database resources," Nucleic Acids Res. 29:1-10.

Beopoulos et al. (Mar. 31, 2011) "An overview of lipid metabolism in yeasts and its impact on biotechnological processes," Appl. Microbiol. Biotechnol. 90:1193-1206.

Birch (1997) "Plant Transformations: Problems and Strategies for Practical Applications," Ann. Rev. Plant Phys. Plant Mol. Biol. 48:297-326.

Birney et al. (2004) "GeneWise and Genomewise," Genome Res. 14:988-995.

Bouvier-Navé et al. (2000) "Expression in yeast and tobacco of plant cDNAs encoding acyl CoA:diacylglycerol acyltransferase," Eur. J. Biochem. 267:85-96.

Bowie et al. (1990) "Deciphering the message in protein sequences: tolerance to amino acid substitutions," Science. 247:1306-1310.

Cahoon et al. (2007) "Engineering oilseeds for sustainable production of industrial and nutritional feedstocks: solving bottlenecks in fatty acid flux," Current Opinion in Plant Biology. 10:236-244.

Cardoza et al. (2006) "Canola (*Brassica napus* L.)," Methods Mol. Biol. 343:257-266.

Christou et al. (1991) "Production of Transgenic Rice (*Oryza sativa* L.) Plants from Agronomically Important Indica and Japonica Varieties via Electric Discharge Particle Acceleration of Exogenous DNA into Immature Zygotic Embryos," Nature Biotech. 9:957-962.

Clough et al. (1998) "Floral dip: a simplified method for Agrobacterium-mediated transformation of *Arabidopsis thaliana*," Plant J. 16(6):735-743.

Dan et al. (2006) "MicroTom—a high-throughput model transformation system for functional genomics," Plant Cell Reports. 25:432-441.

Durrett et al. (2008) "Plant triacylglycerols as feedstocks for the production of biofuels," Plant J. 54:593-607.

Elble (1992) "A simple and efficient procedure for transformation of yeasts," BioTechniques. 13:18-20.

Ellerström et al. (1996) "Functional dissection of a napin gene promoter: identification of promoter elements required for embryo and endosperm-specific transcription," Plant Molecular Biology. 32(6):1019-1027.

Falquet et al. (2002) "The PROSITE database, its status in 2002," Nucleic Acids Res. 30:235-238.

Feng et al. (1987) "Progressive sequence alignment as a prerequisite to correct phylogenetic trees," J. Mol. Evol. 25:351-360.

Folta et al. (2006) "Characterization of LF9, an octoploid strawberry genotype selected for rapid regeneration and transformation," Planta. 224(5):1058-1067.

Fortman et al. (2008) "Biofuel alternatives to ethanol: pumping the microbial well," Trends Biotechnol. 26:375-381.

Frohman (1993) "Rapid amplification of complementary DNA ends for generation of full-length complementary DNAs: thermal RACE," Methods Enzymol. 218:340-356.

Giesen et al. (1998) "A formula for thermal stability (Tm) prediction of PNA/DNA duplexes," Nucleic Acids Res. 26(21):5004-5006.

Gonzalez Padilla et al. (2003) "Early antibiotic selection and efficient rooting and acclimatization improve the production of transgenic plum plants (*Prunus domestica* L.)," Plant Cell Rep. 22(1):38-45.

Graham et al. (1995) "Agrobacterium-mediated transformation of soft fruit Rubus, Ribes, and Fragaria," Methods Mol. Biol. 44:129-133.

Halford et al. (1998) "SNF1-related protein kinases: global regulators of carbon metabolism in plants?" Plant Mol. Biol. 37:735-748.

Hellens et al. (2000) "pGreen: a versatile and flexible binary Ti vector for Agrobacterium-mediated plant transformation," Plant Mol. Biol. 42:819-832.

Hellens et al. (2005) "Transient expression vectors for functional genomics, quantification of promoter activity and RNA silencing in plants," Plant Methods. 1:13 pp. 1-14.

Herrera-Estrella et al. (1993) "Expression of chimaeric genes transferred into plant cells using a Ti-plasmid-derived vector," Nature. 303:209-213.

Hofmann et al. (1999) "The PROSITE database, its status in 1999," Nucleic Acids Res. 27:215-219.

Horsch et al. (1985) "A simple and general method for transferring genes into plants," Science. 227:1229-1231.

Huang (1994) "On Global Sequence Alignment," Computer Applications in the Biosciences. 10:227-235.

James et al. (Sep. 27, 2010) "Disruption of the *Arabidopsis* CGI-58 homologue produces Chanarin-Dorfman-like lipid droplet accumulation in plants," Proc. Natl. Acad. Sci. USA. 107:17833-17838.

Jang et al. (2006) "Functional classification, genomic organization, putatively cis-acting regulatory elements, and relationship to quantitative trait loci, of sorghum genes with rhizome-enriched expression," Plant Physiol. 142:1148-1159.

(56) References Cited

OTHER PUBLICATIONS

Jeanmougin et al. (1998) "Multiple sequence alignment with Clustal X," Trends Biochem. Sci. 23:403-405.
Josefsson et al. (1987) "Structure of a gene encoding the 1.7 S storage protein, napin, from *Brassica napus*," J. Biol. Chem. 262(25):12196-12201.
Kaup et al. (2002) "A role for diacylglycerol acyltransferase during leaf senescence," Plant Physiol. 129(4):1616-1626.
Krens et al. (1997) "Transgenic caraway, *Carum carvi* L.: a model species for metabolic engineering," Plant Cell Rep. 17:39-43.
Kumar et al. (1996) "Potato plants expressing antisense and sense S-adenosylmethionine decarboxylase (SAMDC) transgenes show altered levels of polyamines and ethylene: antisense plants display abnormal phenotypes," Plant J. 9(2):147-158.
Li et al. (2003) "Transgenic rose lines harboring an antimicrobial protein gene, Ace-AMP1, demonstrate enhanced resistance to powdery mildew ( Sphaerotheca pannosa)," Planta, 218:226-232.
Li et al. (Jan. 27, 2010) "DGAT1, DGAT2 and PDAT expression in seeds and other tissues of epoxy and hydroxy fatty acid accumulating plants," Lipids. 45:145-157.
Lung et al. (2006) "Diacylglycerol acyltransferase: a key mediator of plant triacylglycerol synthesis," Lipids. 41(12):1073-1088.
Matsuda et al. (2005) "Development of an Agrobacterium-mediated transformation method for pear (*Pyrus communis* L.) with leaf-section and axillary shoot-meristem explants," Plant Cell Rep. 24(1):45-51.
McFie et al. (Sep. 27, 2010) "Topological orientation of acyl-CoA:diacylglycerol acyltransferase-1 (DGAT1) and identification of a putative active site histidine and the role of the N terminus in dimer/tetramer formation," J. Biol. Chem. 285:37377-37387.
Michelmore et al. (1987) "Transformation of lettuce (*Lactuca sativa*) mediated by Agrobacterium tumefaciens," Plant Cell Rep. 6:439-442.
Moloney et al. (1989) "High efficiency transformation of *Brassica napus* using Agrobacterium vectors," Plant Cell Rep. 8:238-242.
Mu et al. (2008) "Leafy COTYLEDON1 is a key regulator of fatty acid biosynthesis in *Arabidopsis*," Plant Physiol. 148:1042-1054.
Needleman et al. (1970) "A general method applicable to the search for similarities in the amino acid sequence of two proteins," J. Mol. Biol. 48:443-453.
Nielsen et al. (1991) "Sequence-selective recognition of DNA by strand displacement with a thymine-substituted polyamide," Science. 254(5037):1497-1500.
Niu et al. (1998) "Transgenic peppermint (*Mentha x piperita* L.) plants obtained by cocultivation with Agrobacterium tumefaciens," Plant Cell Rep. 17:165-171.
Notredame et al. (2000) "A novel method for fast and accurate multiple sequence alignment," J. Mol. Biol. 302:205-217.
Nykiforuk et al. (2002) "Characterization of cDNAs encoding diacylglycerol acyltransferase from cultures of *Brassica napus* and sucrose-mediated induction of enzyme biosynthesis," Biochimica et Biophysica Acta. 1580:95-109.
Ohlrogge et al. (2009) "Energy. Driving on biomass," Science. 324:1019-1020.
Oosumi et al. (2006) "High-efficiency transformation of the diploid strawberry (*Fragaria vesca*) for functional genomics," Planta. 223(6):1219-1230.
Orlikowska et al. (1995) "Factors influencing Agrobacterium tumefaciens-mediated transformation and regeneration of the safflower cultivar 'centennial,'" Plant Cell Tissue and Organ Culture. 40:85-91.
Ortiz et al. (1996) "Hygromycin resistance as an efficient selectable marker for wheat stable transformation," Plant Cell Rep. 15:877-881.
Pena et al. (1995) "High efficiency Agrobacterium-mediated transformation and regeneration of citrus," Plant Sci.104:183-191.
Potrykus et al.: Eds. (1995) *Gene Transfer to Plants*. Springer-Verlag. Berlin, Germany. pp. i-xxii.

Ramesh et al. (2006) "Improved methods in Agrobacterium-mediated transformation of almond using positive (mannose/pmi) or negative (kanamycin resistance) selection-based protocols," Plant Cell Rep. 25(8):821-828.
Rice et al. (2000) "EMBOSS: The European Molecular Biology Open Software Suite," Trends in Genetics. 16(6):276-277.
Rose et al. (1989) "KAR2, a karyogamy gene, is the yeast homolog of the mammalian BiP/GRP78 gene," Cell. 57:1211-1221.
Salse et al. (2008) "Identification and characterization of shared duplications between rice and wheat provide new insight into grass genome evolution," Plant Cell. 20:11-24.
Sandager et al. (2002) "Storage lipid synthesis is non-essential in yeast," The Journal of Biological Chemistry. 277:6478-6482.
Sanjaya et al. (Oct. 2011) "Increasing the energy density of vegetative tissues by diverting carbon from starch to oil biosynthesis in transgenic *Arabidopsis*," Plant Biotechnol. J. 9:874-883.
Santos-Mendoza et al. (2008) "Deciphering gene regulatory networks that control seed development and maturation in *Arabidopsis*," Plant J. 54:608-620.
Schenk et al. (2001) "Promoters for pregenomic RNA of banana streak badnavirus are active for transgene expression in monocot and dicot plants," Plant Molecular Biology. 47:399-412.
Schrott (1995) "Selectable Marker and Reporter Genes," Ch. 31 In; Potrykus et al.: Eds. *Gene Transfer to Plants*. Springer-Verlag. Berlin, Germany. pp. 325-336.
Scott et al. (Oct. 2010) "Elevation of oil body integrity and emulsion stability by polyoleosins, multiple oleosin units joined in tandem head-to-tail fusions," Plant Biotechnology Journal. 8:912-927.
Shockey et al. (2006) "Tung tree DGAT1 and DGAT2 have nonredundant functions in triacylglycerol biosynthesis and are localized to different subdomains of the endoplasmic reticulum," Plant Cell. 18:2294-2313.
Smeets et al. (1997) "Developmental Regulation of Lectin and Alliinase Synthesis in Garlic Bulbs and Leaves," Plant Physiol. 113:765-771.
Song et al. (2005) "Transformation of Montmorency sour cherry (*Prunus cerasus* L.) and Gisela 6 (*P. cerasus* x *P. canescens*) cherry rootstock mediated by Agrobacterium tumefaciens," Plant Cell Rep. 25(2):117-123.
Tatusova et al. (1999) "Blast 2 sequences—a new tool for comparing protein and nucleotide sequences," FEMS Microbiol. Lett. 174:247-250.
Tatusova et al. (1999) "Erratum: Blast 2 sequences—a new tool for comparing protein and nucleotide sequences [FEMS Microbiol. 174 (1999) 247-250]," FEMS Microbiol. Lett. 177:187-188.
Thompson et al. (1994) "CLUSTAL W: improving the sensitivity of progressive multiple sequence alignment through sequence weighting, position-specific gap penalties and weight matrix choice," Nucleic Acids Res. 22:4673-4680.
Triglia et al. (1988) "A procedure for in vitro amplification of DNA segments that lie outside the boundaries of known sequences," Nucleic Acids Res. 16:8186.
Wang et al. (2006) "Transformation of Actinidia eriantha: a potential species for functional genomics studies in Actinidia," Plant Cell Rep. 25(5):425-431.
Wang et al. (2009) "Maize Transformation," In; *Handbook of Maize*. Bennetzen, J. L.; Hake, S. C.: Eds. Springer-Verlag. New York, New York. pp. 609-639.
Wheeler et al. (2001) "Database resources of the National Center for Biotechnology Information," Nucleic Acids Res. 29:11-16.
Winichayakul et al. (2009) "Head-to-tail fusions of camelid antibodies can be expressed in planta and bind in rumen fluid," Biotechnol. Appl. Biochem. 53:111-122.
Xu et al. (2008) "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content," Plant Biotechnol. J. 6:799-818.
Yang et al. (2009) "Turnover of fatty acids during natural senescence of *Arabidopsis*, Brachypodium, and switchgrass and in *Arabidopsis* beta-oxidation mutants," Plant Physiol. 150:1981-1989.

(56) References Cited

OTHER PUBLICATIONS

Yao et al. (1995) "Regeneration of transgenic plants from the commercial apple cultivar Royal Gala," Plant Cell Reports. 14:407-412.
U.S. Appl. No. 14/438,758, filed Apr. 27, 2015, 2015/0275223, Oct. 1, 2015.
U.S. Appl. No. 14/438,784, filed Apr. 27, 2015, 2015/0252378, Sep. 10, 2015.
Bolton et al. (1962) "A General Method for the Isolation of RNA Complementary to DNA," Proc. Natl. Acad. Sci. USA. 48:1390-1397.
Browse et al. (1986) "Fatty acid composition of leaf lipids determined after combined digestion and fatty acid methyl ester formation from fresh tissue," Anal. Biochem. 152:141-145.
GenBank (Jul. 25, 2006) "diacylglycerol acyltransferase [*Oryza sativa* Japonica Group]," Accession No. AAW47581. Accessible on the Internet at URL: http://www.ncbi.nlm.nih.gov/protein/AAW47581. [Last Accessed Dec. 17, 2015].
GenBank (Feb. 25, 2009) "unknown [*Zea mays*]," Accession No. ACN35495. Accessible on the Internet at URL: http://www.ncbi.nlm.nih.gov/protein/ACN35495. [Last Accessed Dec. 17, 2015].
Guiheneuf et al. (2011) "Cloning and molecular characterization of a novel acyl-CoA:diacylglycerol acyltransferase 1-like gene (PtDGAT1) from the diatom Phaeodactylum tricornutum," The FEBS Journal. 278:3651-3666.
Li et al. (1996) "Genetic transformation of cassava (*Manihot esculenta crantz*)," Nat. Biotechnol. 14:736-740.
European Supplemental Search Report, dated Apr. 19, 2016, corresponding to European Application No. 13851770.1 (filed Oct. 22, 2013), a related application, 7 pp.
Kamisaka et al. (2010) "Activation of Diacylglycerol Acyltransferase Expressed in *Saccharomyces cerevisiae*: Overexpression of Dga1p Lacking the N-terminal Region in the Δsnf2 Disruptant Produces a Significant Increase in its Enzyme Activity," Appl Microbial Biotechnol 88:105-115.
International Search Report for International application No. PCT/IB2013/059526, dated May 23, 2014, 3 pgs.

\* cited by examiner

```
              N   P   F   S   F   L   L   L   L   F   R   E   N   F   A
          E   S   F   F   L   S   S   S   S   S   L   Q   R   K   L   C   F  ·
      *   I   L   F   P   F   F   F   F   F   S   S   E   K   T   L   L  ·
   1  TGAATCCTTT TTCCTTTCTT CTTCTTCTTC TCTTCAGAGA AAACTTTGCT
      S   L   S   I   R   N   Q   T   R   I   P   F   P   P   I   S   *  ·
     ·S   F   Y   K   E   P   D   T   N   P   I   P   T   D   F   L  ·
     ·L   F   L   *   G   T   R   H   E   S   H   S   H   R   F   L   S  ·
  51  TCTCTTTCTA TAAGGAACCA GACACGAATC CCATTCCCAC CGATTTCTTA
     ·L   L   P   S   I   R   S   F   P   L   H   *   I   L   F   P   L  ·
      A   S   S   F   N   P   L   F   P   S   P   L   D   S   V   S   S  ·
     ·F   F   L   Q   S   A   L   S   L   S   I   R   F   C   F   L
 101  GCTTCTTCCT TCAATCCGCT CTTTCCCTCT CCATTAGATT CTGTTTCCTC
     ·S   I   S   S   A   C   F   S   I   L   S   D   A   S   F   L
     ·F   N   F   F   C   M   L   D   S   L   *   R   L   F   S   P  ·
      F   Q   F   L   L   H   A   S   R   F   S   L   T   P   L   F   S  ·
 151  TTTCAATTTC TTCTGCATGC TTCTCGATTC TCTCTGACGC CTCTTTTCTC
      P   T   L   F   R   Q   T   L   F   E   M   A   I   L   D   S   A  ·
     ·D   A   V   S   S   N   A   F   R   N   G   D   F   G   F   C
     ·R   R   C   F   V   K   R   F   S   K   W   R   F   W   I   L   L  ·
 201  CCGACGCTGT TCGTCAAAC GCTTTTCGAA ATGGCGATTT TGGATTCTGC
     ·G   V   T   T   V   T   E   N   G   G   G   E   F   V   D   L   D  ·
      W   R   Y   Y   G   D   G   E   R   W   R   R   V   R   R   S   *  ·
     ·A   L   L   R   *   R   R   T   V   A   E   S   S   S   I   L
 251  TGGCGTTACT ACGGTGACGG AGAACGGTGG CGGAGAGTTC GTCGATCTTG
     ·R   L   R   R   R   K   S   R   S   D   S   S   N   G   L   L
     ·*   A   S   S   T   E   I   E   I   G   F   F   *   R   T   S   S  ·
      I   G   F   V   D   G   N   R   D   R   I   L   L   T   D   F   F  ·
 301  ATAGGCTTCG TCGACGGAAA TCGAGATCGG ATTCTTCTAA CGGACTTCTT
      L   S   G   S   D   N   N   S   P   S   D   D   V   G   A   P   A  ·
     ·L   W   F   R   *   *   F   S   F   G   *   C   W   S   S   R
     ·S   L   V   P   I   I   I   L   L   R   M   M   L   E   L   P   P  ·
 351  CTCTCTGGTT CCGATAATAA TTCTCCTTCG GATGATGTTG GAGCTCCCGC
     ·D   V   R   D   R   I   D   S   V   V   N   D   D   A   Q   G   T  ·
      R   R   *   G   S   D   *   F   R   C   *   R   *   R   S   G   N  ·
     ·T   L   G   I   G   L   I   P   L   L   T   M   T   L   R   E
 401  CGACGTTAGG GATCGGATTG ATTCCGTTGT TAACGATGAC GCTCAGGGAA
     ·A   N   L   A   G   D   N   N   G   G   G   D   N   N   G   G
     ·S   Q   F   G   R   R   *   *   R   W   W   R   *   *   R   W   W  ·
      Q   P   I   W   P   E   I   I   T   V   V   A   I   I   T   V   V  ·
 451  CAGCCAATTT GGCCGGAGAT AATAACGGTG GTGGCCATAA TAACGGTGGT
      G   R   G   G   G   E   G   R   G   N   A   D   A   T   F   T   Y  ·
     ·K   R   R   R   R   R   K   R   K   R   R   C   Y   V   Y   V
     ·E   E   A   A   E   K   E   E   E   T   P   M   L   R   L   R   I  ·
 501  GGAAGAGGCG GCGGAGAAGG AAGAGGAAAC GCCGATGCTA CGTTTACGTA
     ·R   P   S   V   P   A   H   R   R   A   R   E   S   P   L   S   S  ·
      S   T   V   G   S   S   S   S   E   G   E   R   E   S   T   *   L  ·
     ·D   R   R   F   Q   L   I   G   G   R   E   R   V   H   L   A
 551  TCGACGTCG GTTCCAGCTC ATCGGAGGGC GAGAGAGAGT CCACTTAGCT
     ·D   A   I   F   K   Q   V   *   N   L   R   N   L   R   I   W
     ·R   R   N   L   Q   T   G   L   K   S   Q   K   S   S   N   L   V  ·
      P   T   Q   S   S   N   R   F   K   I   S   E   I   F   E   F   G  ·
 601  CCGACGCAAT CTTCAAACAG GTTTAAAATC TCAGAAATCT TCGAATTTGG
      C   L   L   V   V   L   Y   G   I   E   F   G   D   C   F   A   L  ·
     ·F   A   C   C   F   I   W   N   *   V   W   *   L   F   C   I
     ·V   C   L   L   F   Y   M   E   L   S   L   V   I   V   L   H   C  ·
 651  TGTTTGCTTG TTGTTTTATA TGGAATTGAG TTTGGTGATT GTTTGCATT
     ·Q   S   H   A   G   L   F   N   L   C   V   V   V   L   I   A   V  ·
      A   E   P   C   R   I   I   Q   P   L   C   S   S   S   Y   C   C  ·
     ·R   A   M   P   D   Y   S   T   S   V   *   *   F   L   L   L
 701  GCAGAGCCAT GCCGGATTAT TCAACCTCTG TGTAGTAGTT CTTATTGCTG
     ·N   S   R   L   I   I   E   N   L   M   K   V   C   C   Y   L
     ·K   Q   *   T   H   H   R   K   S   Y   E   G   L   L   L   L   V  ·
      *   T   V   D   S   S   S   K   I   L   *   R   F   A   V   T   C  ·
 751  TAAACAGTAG ACTCATCATC GAAAATCTTA TGAAGGTTTG CTGTTACTTG
      F   L   L   G   I   E   L   L   E   N   L   S   E   T   N   N  ·
     ·S   P   F   R   N   *   I   A   *   K   F   I   R   D   E   *
     ·F   S   F   *   E   L   N   C   L   K   I   Y   Q   R   R   I   T  ·
 801  TTTCTCCTTT TAGGAATTGA ATTGCTTGAA AATTTATCAG AGACGAATAA
```

Figure 1

```
              · F   V   V    A   I   I   H    V   V   W    L   V   D    Q   N   G   F ·
              L   C   C   C    Y   H   S    C   S   M    V   G   *    S   E   R   I ·
              · L   L   L    L   S   F    M   *   Y   G    W   L   I    R   T   D
        851   CTTTGTTGTT GCTATCATTC ATGTAGTATG GTTGGTTGAT CAGAACGGAT
              · L   V   *    F   K   I    A   A   R   L    A   A   F    H   V   L
              · S   G   L    V   Q   D    R   C   E   I    G   R   F    S   C   V   G ·
              F   W   F   S    S   R   S    L   R   D    W   P   L   F    M   C   W ·
        901   TTCTGGTTTA GTTCAAGATC GCTGCGAGAT TGGCCGCTTT TCATGTGTTG
              V   K   E   D    V   F   Y    F   Q   Q    C   Y   I   V    I   R   I ·
              · K   R   R    C   F   L    F   P   A   M    L   H   C    Y   T   Y
              · *   K   K    M   F   F   I    S   S   N    V   T   L    L   Y   V  * ·
        951   GTAAAAGAAG ATGTTTTTTA TTTCCAGCAA TGTTACATTG TTATACGTAT
              · M   M   S    L   V   I   K    F   L   F    D   S   S    F   L   L   Q ·
              N   D   E   F    S   D   Q    V   P   L    *   F   F   F    L   V   A ·
              · *   *   V    *   *   S    S   S   S   L    I   L   L    S   C   C
       1001   AATGATGAGT TTAGTGATCA AGTTCCTCTT TGATTCTTCT TTCTTGTTGC
              · Y   I   P    F   D   L    S   F   G   C    L   Y   G    *   E   I
              · V   Y   P    F   R   S   F    L   W   L    P   L   R    L   R   N   W ·
              S   I   S   L    S   I   F    P   L   A   A    F   T   V    E   K   L ·
       1051   AGTATATCCC TTTCGATCTT TCCTTTGGCT GCCTTTACGG TTGAGAAATT
              G   T   S   E    I   H   I    R   T   C    E   *   L   L    F   S   S ·
              · Y   F   R    N   T   Y    Q   N   L    *   V   I   T    I   L   Q
              · V   L   Q    K   Y   I   S    E   P   V    S   N   Y    Y   S   P   A ·
       1101   GGTACTTCAG AAATACATAT CAGAACCTGT GAGTAATTAC TATTCTCCAG
              · H   Y   C    N   F   Y    *   R   Q   V    C   I   M    K   N   L   Q ·
              P   L   L    *   F   L   L    K   T   S    L   Y   H   E    E   L   T ·
              · I   T   V    I   F   I    E   D   K   F    V   S   *    R   T   Y
       1151   CCATTACTGT AATTTTTATT GAAGACAAGT TTGTATCATG AAGAACTTAC
              · V   L   F    *   K   C    S   R   L   S    S   F   F    I   L   L
              · S   S   V    L   K   M   L    K   V   V    I   F   L    H   I   I   I ·
              K   F   C   F    E   N   A    Q   G   C    H   L   S   S    Y   Y   Y ·
       1201   AAGTTCTGTT TTGAAAATGC TCAAGGTTGT CATCTTTCTT CATATTATTA
              S   P   *    Q   R   F   C    I   Q   F    T   S   P    *   G   D   T ·
              · T   M   T    E   V   L    Y   P   V   Y    V   T   L    R   *   Y
              · H   H   D    R   G   F   V    S   S   L    R   H   P    K   V   I   L ·
       1251   TCACCATGAC AGAGGTTTTG TATCCAGTTT ACGTCACCCT AAGGTGATAC
              · V   F   L    V   S   V    C   D   T   V    F   K   F    S   C   L   T ·
              C   F   S   G    L   S   L    *   Y   C    F   *   V    *   L   S   D ·
              · F   F   W    S   Q   F    V   I   L   F    L   S   L    V   V   *
       1301   TGTTTTTCTG GTCTCAGTTT GTGATACTGT TTTTAAGTTT AGTTGCTGA
              · R   *   S    *   K   W    T   G   V   I    L   L   F    Y   Q   V
              · P   V   I    L   K   M   D    R   C   D    S   A   F    L   S   G   V ·
              P   G   D   L    E   N   G    Q   V   *    F   C   F   F    I   R   C ·
       1351   CCCGGTGATC TTGAAAATGG ACAGGTGTGA TTCTGCTTTT TTATCAGGTG
              S   L   *    C   S   S   L    A   L   C    G   *   S   W    F   L   M ·
              · T   L   M    L   L   T    C   I   V   W    L   K   L    V   S   Y
              · H   F   D    A   P   H   L    H   C   V    A   K   V    G   F   L   C ·
       1401   TCACTTTGAT GCTCCTCACT TGCATTGTGT GGCTAAAGTT GGTTTCTTAT
              · L   I   L    A   M   T    *   D   P   *    P   M   Q    L   I   R   * ·
              A   H   T   S    Y   D   I    R   S   L    A   N   A   A    D   K   V ·
              · S   Y   *    L   *   H    K   I   P   S    Q   C   S    *   *   G
       1451   GCTCATACTA GCTATGACAT AAGATCCCTA GCCAATGCAG CTGATAAGGT
              · N   T   K    K   K   R    M   Y   *   S    L   A   L    C   Y   C
              · K   Y   E    K   E   A   Y    V   L   V    T   C   T    V   L   L   F ·
              K   I   R   K    R   S   V    C   I   S    H   L   H   C    V   T   V ·
       1501   AAAATACGAA AAGAAGCGT ATGTATTAGT CACTTGCACT GTGTTACTGT
              F   N   Q   T    L   L   *    T   L   G    Q   S   *    S   L   L   L ·
              · *   P   N    T   V   M    N   F   R   P    I   L   K    S   P   T
              · L   T   K    H   C   Y   E    L   *   A    N   P   E    V   S   Y   Y ·
       1551   TTTAACCAAA CACTGTTATG AACTTTAGGC CAATCCTGAA GTCTCCTACT
              · R   *   L    E   E   L   G    I   F   H    G   R   S    H   I   V   L ·
              T   L   A    *   R   A   W    H   I   S    W   S   L   P    H   C   V ·
              · V   S   L    K   S   L    A   Y   F   M    V   A   P    T   L   C
       1601   ACGTTAGCTT GAAGAGCTTG GCATATTTCA TGGTCGCTCC CACATTGTGT
              · S   G   N    C   K   V    H   Q   P   F    L   Y   L    Q   E   F
              · I   R   *    L   Q   S    A   S   T   I    L   I   L    A   R   V   S ·
              Y   Q   V   T    A   K   C    I   N   H    S   Y   T   C    K   S   F ·
       1651   TATCAGGTAA CTGCAAAGTG CATCAACCAT TCTTATACTT GCAAGAGTTT
              L   V   *    T   S   D   L    C   F   S    P   A   K   L    S   T   F ·
              · C   L   N    L   G   S    L   L   F   P    S   Q   V    I   H   V
              · L   S   K    P   R   I   F    A   F   P    Q   P   S    Y   P   R   S ·
       1701   CTTGTCTAAA CCTCGGATCT TTGCTTTTCC CCAGCCAAGT TATCCACGTT
```

Figure 1 cont.

```
                  · C  M  Y   T  E  G  L   G  G  S   S  I  C   K  T  G  H ·
                 L  H  V  Y   G  R  V   G  W  L   V  N  L  Q   N  W  S ·
                · A  C  I   R  K  G   W  V  A  R   Q  F  A   K  L  V
         1751  CTGCATGTAT ACGGAAGGGT TGGGTGGCTC GTCAATTTGC AAAACTGGTC
                 · I  H  R   I  H  G   I  Y  N  R   T  S  T   F  S  H
                · Y  S  P   D  S  W  D   L  *  *   N  K  Y   V  F  T  S ·
                I  F  T  G   F  M  G   F  I  I   E  Q  V  R   F  H  I ·
         1801  ATATTCACCG GATTCATGGG ATTTATAATA GAACAAGTAC GTTTTCACAT
                L  A  L  L   V  F  L   G  E  N   H  H  P  C   V  V  T ·
                 · C  F  I   S  F  P   W  *  K  S   S  S  L   R  C  H
                · L  L  Y   *  F  S  L   V  K  I   I  I  P   A  L  S  P ·
         1851  CTTGCTTTAT TAGTTTTCCT TGGTGAAAAT CATCATCCCT GCGTTGTCAC
                · T  *  L   H  V  L  L   L  H  F   G  S  I   *  I  L  L ·
                H  L  T  S   C  S  F   V  T  F   W  Q  Y  I   N  P  I ·
                 · L  D  F   M  F  F   C  Y  I  L   A  V  Y   K  S  Y
         1901  CACTTGACTT CATGTTCTTT TGTTACATTT TGGCAGTATA TAAATCCTAT
                 · S  G  T   Q  S  I  L   *  K  A   I  F  Y   M  L  L
                · V  R  N   S  K  H  P   L  K  G   D  L  L   Y  A  I  E ·
                C  Q  E  L   K  A  S   F  E  R  R   S  S  I   C  Y  * ·
         1951  TGTCAGGAAC TCAAAGCATC CTTTGAAAGG CGATCTTCTA TATGCTATTG
                K  E  C  *   S  F  Q   F  Q  I   Y  M  C  G   S  A  C ·
                 · R  V  L   K  L  S   V  P  N  L   Y  V  W   L  C  M
                · K  S  V   E  A  F  S   S  K  F   I  C  V   A  L  H  V ·
         2001  AAAGAGTGTT GAAGCTTTCA GTTCCAAATT TATATGTGTG GCTCTGCATG
                 · S  T  A   S  S  T  F   G  M  L   *  S  H   L  F  Q  N ·
                F  Y  C  F   F  H  L   W  Y  A   V  I  P  S   L  S  K ·
                 · L  L  L   L  P  P   L  V  C  C   D  P  I   S  F  K
         2051  TTCTACTGCT TCTTCCACCT TTGGTATGCT GTGATCCCAT CTCTTTCAAA
                 · N  L  Q   I  R  K   T  E  K  G   *  I  S   Y  E  F
                · *  F  A   N  S  K  N   R  K  R   L  N  L   I  R  I  * ·
                I  I  C  K   F  E  K   P  K  K   A  K  S  H   T  N  L ·
         2101  ATAATTTGCA AATTCGAAAA ACCGAAAAAG GCTAAATCTC ATACGAATTT
                D  I  F  S   F  L  E   S  V  M   *  F  Q  L   L  N  A ·
                 · Y  F  *   F  L  R   V  G  D  V   I  S  V   T  E  R
                · I  F  L   V  S  *  S   R  *  C   N  F  S   Y  *  T  Q ·
         2151  GATATTTTTA GTTCTTAGA GTCGGTGATG TAATTTCAGT TACTGAACGC
                 · N  L  L   S  K  G   *  T  Y  W   Q  S  F   S  A  S  G ·
                K  S  L  V   Q  R  L   N  I  L   A  E  L  L   C  F  G ·
                 · I  S  C   P  K  V   K  H  I  G   R  A  S   L  L  R
         2201  AAATCTCTTG TCCAAAGGTT AAACATATTG GCAGAGCTTC TCTGCTTCGG
                 · I  V  N   S  T  K   I  G  G  M   Q  K  V   W  E  M
                · D  R  E   F  Y  K  D   W  W  N   A  K  S   V  G  D  V ·
                G  S  *  I   L  Q  R   L  V  E   C  K  K  C   G  R  C ·
         2251  GGATCGTGAA TTCTACAAAG ATTGGTGGAA TGCAAAAAGT GTGGGAGATG
                 *  A  I  L   L  K  R   K  L  M   I  F  N  V   V  V  V ·
                · S  Y  F   T  Q  K   K  T  Y  D   F  *  C   C  R  C
                · E  L  F   Y  S  K  E   N  L  *   F  L  M   L  S  L  F ·
         2301  TGAGCTATTT TACTCAAAAG AAAACTTATG ATTTTAATG TTGTCGTTGT
                · F  G  S   S  N  *  P   N  S  C   I  H  C   L  P  L  S ·
                F  W  V  I   *  L  T   K  F  M   Y  S  L  S   S  F  I ·
                 · L  G  H   L  T  N   Q  I  H  V   F  T  V   F  L  Y
         2351  TTTTGGGTCA TCTAACTAAC CAAATTCATG TATTCACTGT CTTCCTTTAT
                 · V  L  E   N  V  E   Y  G  M  V   L  F  L   N  I  T
                · S  T  G   E  C  G  I   W  Y  G   S  L  P   K  H  H  L ·
                Q  Y  W  R   M  W  N   M  V  W   F  S  S  *   T  S  P ·
         2401  CAGTACTGGA GAATGTGGAA TATGGTATGG TTCTCTTCCT AAACATCACC
                F  F  C  T   Q  N  R   R  R  E   L  I  K  I   L  F  S ·
                 · L  L  Y   T  K  *   K  K  R  A   N  *  D   L  V  F
                · S  F  V   H  K  I  E   E  E  S   *  L  R   S  C  F  P ·
         2451  TTCTTTTGTA CACAAAATAG AAGAAGAGAG CTAATTAAGA TCTTGTTTTC
                · L  T  A   C  S  *  M   D  G  S   T  Y  I   L  P  V  L ·
                L  D  S  L   F  I  N   G  W  F   D  I  Y  T   S  R  A ·
                 · *  Q  P   V  H  K   W  M  V  R   H  I  Y   F  P  C
         2501  CTTGACAGCC TGTTCATAAA TGGATGGTTC GACATATATA CTTCCCGTGC
                 · A  Q  Q   D  T  K   G  E  *  D   I  Y  R   Y  A  I
                · C  A  A   R  Y  Q  R   *  V  R   Y  I  P   I  C  N  C ·
                L  R  S  K   I  P  K   V  S  E   I  Y  T  D   M  Q  L ·
         2551  TTGCGCAGCA AGATACCAAA GGTGAGTGAG ATATATACCG ATATGCAATT
                V  E  I  C   F  C  D   I  N  L   T  L  H  T   L  V  F ·
                 · R  D  L   F  L  *   Y  K  F  N   P  P  H   T  C  F
                · S  R  F   V  S  V  I   *  I  *   P  S  T   H  L  F  F ·
         2601  GTCGAGATTT GTTTCTGTGA TATAAATTTA ACCCTCCACA CACTTGTTTT
```

Figure 1 cont.

```
       · Q   T   L   A   I   I   I   A   F   L   V   S   A   V   F   H   E ·
         S   D   T   R   H   Y   H   C   F   P   S   L   C   S   L   S   *  ·
       · R   H   S   P   L   S   L   L   S   *   S   L   Q   S   F   M
2651   TCAGACACTC GCCATTATCA TTGCTTTCCT AGTCTCTGCA GTCTTTCATG
       · V   Y   I   L   S   T   L   P   C   L   *   T   H   E   H   T
       · G   I   H   T   F   Y   I   A   L   S   L   D   A   *   T   H   A ·
         R   Y   T   Y   F   L   H   C   P   V   S   R   R   M   N   T   R ·
2701   AGGTATACAT ACTTTCTACA TTGCCCTGTC TCTAGACGCA TGAACACACG
         L   V   K   E   M   L   I   F   K   A   L   F   L   L   N   D   L ·
       · S   E   R   N   A   N   I   Q   S   I   V   F   T   *   R   S
       · *   *   K   K   C   *   Y   S   K   H   C   F   Y   L   T   I   L ·
2751   CTAGTGAAAG AAATGCTAAT ATTCAAAGCA TTGTTTTTAC TTAACGATCT
       · V   L   Q   I   S   F   *   Q   L   C   I   A   V   P   C   R   L ·
         C   V   T   N   F   L   L   T   A   M   H   R   S   S   L   S   S ·
       · C   Y   K   F   P   F   D   S   Y   A   S   Q   F   L   V   V
2801   TGTGTTACAA ATTTCCTTTT GACAGCTATG CATCGCAGTT CCTTGTCGTC
       · F   K   L   W   A   F   L   G   I   M   F   Q   V   K   K   L
       · L   Q   A   M   G   F   S   W   D   Y   V   S   G   *   K   I   T ·
         S   S   S   Y   G   L   F   L   G   L   C   F   R   L   K   N   Y ·
2851   TCTTCAAGCT ATGGGCTTTT CTTGGGATTA TGTTTCAGGT TAAAAAATTA
         L   N   C   C   S   R   F   L   L   N   S   N   L   I   F   *   P ·
       · K   L   L   Q   S   I   F   T   K   L   *   S   H   I   L   T
       · *   T   A   A   V   D   F   Y   *   T   L   I   S   Y   S   D   Q ·
2901   CTAAACTGCT GCAGTCGATT TTTACTAAAC TCTAATCTCA TATTCTGACC
       · T   N   L   F   E   *   V   P   L   V   F   I   T   N   Y   L   Q ·
         N   Q   F   V   *   V   G   A   F   G   L   H   H   K   L   S   T ·
       · P   I   C   L   S   R   C   L   W   S   S   S   Q   T   I   Y
2951   AACCAATTTG TTTGAGTAGG TGCCTTTGGT CTTCATCACA AACTATCTAC
       · E   R   F   G   S   T   V   C   S   Q   N   P   R   K   *   N
       · G   K   V   W   L   N   G   M   L   S   K   P   E   K   I   E   R ·
         R   K   G   L   A   Q   R   Y   A   L   K   T   R   E   N   R   T ·
3001   AGGAAAGGTT TGGCTCAACG GTATGCTCTC AAAACCCGAG AAAATAGAAC
         E   *   L   F   L   S   *   P   S   H   L   N   R   N   A   E   T ·
       · I   T   L   S   F   I   A   *   P   F   K   S   Q   C   *   N
       · N   N   S   F   F   H   S   L   A   I   *   I   A   M   L   K   L ·
3051   GAATAACTCT TTCTTTCATA GCCTAGCCAT TTAAATCGCA ATGCTGAAAC
       · *   *   *   R   *   S   V   L   E   W   D   H   I   I   R   W   G ·
         L   I   I   K   V   I   C   F   G   M   G   S   Y   Y   *   V   G ·
       · N   N   K   G   D   L   F   W   N   G   I   I   L   L   G   G
3101   TTAATAATAA AGGTGATCTG TTTTGGAATG GGATCATATT ATTAGGTGGG
       · T   *   S   S   G   S   S   S   A   F   S   D   N   R   C   V
       · N   M   I   F   W   F   I   F   C   I   F   G   Q   P   M   C   V ·
         E   H   D   L   L   V   H   L   L   H   F   R   T   T   D   V   C ·
3151   GAACATGATC TTCTGGTTCA TCTTCTGCAT TTTCGGACAA CCGATGTGTG
         C   F   F   I   T   T   T   *   *   T   E   K   D   R   C   H   E ·
       · L   L   Y   Y   H   D   L   M   N   R   K   G   S   M   S   *
       · A   S   L   L   P   R   P   D   E   P   K   R   I   D   V   M   K ·
3201   TGCTTCTTTA TTACCACGAC CTGATGAACC GAAAAGGATC GATGTCATGA
       · T   T   V   Q   K   M   T   F   F   K   H   L   W   P   R   W   I ·
         N   N   C   S   K   N   D   F   L   Q   T   S   M   A   S   L   D ·
       · Q   L   F   K   K   *   L   S   S   N   I   Y   G   L   V   G
3251   AACAACTGTT CAAAAAATGA CTTTCTTCAA ACATCTATGG CCTCGTTGGA
       · S   V   D   V   V   V   V   L   M   L   K   R   Q   I   V   L
       · L   R   *   C   C   G   G   S   D   A   K   T   T   N   S   V   I ·
         S   P   L   M   L   W   W   F   *   C   *   N   D   K   *   C   Y ·
3301   TCTCCGTTGA TGTTGTGGTG GTTCTGATGC TAAAACGACA AATAGTGTTA
       · *   P   L   K   K   K   R   K   L   E   L   L   Y   L   Q   K   F ·
       · T   I   E   E   E   K   K   I   R   V   V   V   S   A   K   I
       · N   H   *   R   R   K   E   N   *   S   C   C   I   C   K   N   F ·
3351   TAACCATTGA AGAAGAAAAG AAAATTAGAG TTGTTGTATC TGCAAAAATT
       · W   *   R   H   A   N   P   F   G   F   C   Y   G   V   K   K   F ·
         L   V   E   T   R   E   P   V   W   I   L   L   W   C   K   E   I ·
       · G   R   D   T   R   T   R   L   D   F   V   M   V   *   R   N
3401   TTGGTAGAGA CACGCGAACC CGTTTGGATT TTGTTATGGT GTAAAGAAAT
       · Q   S   K   N   C   C   N   N   C   Y   Q   K   E   M   L   F
       · S   I   K   K   L   L   *   *   L   L   P   K   R   N   A   F   L ·
         F   N   Q   K   T   V   V   I   I   V   T   K   K   K   C   F   S ·
3451   TTCAATCAAA AAACTGTTGT AATAATTGTT ACCAAAAAGA AATGCTTTTC
         W   K   R   G   E   K   *   *   F   C       (SEQ ID NO: 165)
       · E   T   R   G   K   I   V   V   L           (SEQ ID NO: 166)
       · G   N   E   G   K   N   S   S   F   V       (SEQ ID NO: 167)
3501   TGGAAACGAG GGGAAAAATA GTAGTTTTGT T            (SEQ ID NO: 128)
```

Figure 1 cont.

```
              G   P   A   P   L   H   A   C   R   L   R   S   R   R   P   W
          W   P   R   P   P   P   C   L   P   P   P   I   A   P   A   L   A ·
          M   A   P   P   P   S   M   P   A   A   S   D   R   A   G   P   G ·
    1     ATGGCCCCGC CCCCCTCCAT GCCTGCCGCC TCCGATCGCG CCGGCCCTGG
          P   R   R   G   R   L   V   L   P   S   P   P   P   R   P   L   S ·
        · A   T   R   A   T   R   P   P   F   A   S   A   A   P   P   Q
        · R   D   A   G   D   S   S   S   L   R   L   R   R   A   P   S   A ·
   51     CCGCGACGCG GGCGACTCGT CCTCCCTTCG CCTCCGCCGC GCCCCCTCAG
        · R   R   R   R   P   C   R   R   F   L   G   R   L   A   G   E   R ·
          P   T   P   A   T   L   P   A   I   P   R   *   A   C   G   R   T ·
        · D   A   G   D   L   A   G   D   S   S   V   G   L   R   E   N
  101     CCGACGCCGG CGACCTTGCC GGCGATTCCT CGGTAGGCTT GCGGGAGAAC
        · R   A   A   T   A   D   E   S   A   A   A   G   A   A   A   A
        · A   S   R   N   R   R   R   I   R   R   R   R   S   S   S   S   S ·
          G   E   P   Q   P   P   T   N   P   P   P   Q   E   Q   Q   Q   Q ·
  151     GGCGAGCCGC AACCGCCGAC GAATCCGCCG CCGCAGGAGC AGCAGCAGCA
          A   R   D   A   I   L   P   R   V   G   A   R   P   P   P   R   Q ·
        · T   R   C   Y   T   T   A   R   R   P   P   T   A   A   S
        · H   E   M   L   Y   Y   R   A   S   A   P   A   H   R   R   V   K ·
  201     GCACGAGATG CTATACTACC GCGCGTCGGC GCCCGCCCAC CGCCGCGTCA
        · G   E   P   P   Q   L   *   R   H   L   P   A   G   E   E   T   R ·
          R   R   A   P   S   A   L   T   P   S   S   G   R   *   G   D   A ·
        · E   S   P   L   S   S   D   A   I   F   R   Q   V   R   R   R
  251     AGGAGAGCCC CCTCAGCTCT GACGCCATCT TCCGGCAGGT GAGGACGC
        · I   L   G   S   L   F   V   S   D   C   L   I   P   A   L   V
        · N   F   R   L   A   V   C   K   R   L   F   D   P   R   A   C   A ·
          E   F   *   A   R   C   L   *   A   I   V   *   S   P   R   L   C ·
  301     GAATTTTAGG CTCGCTGTTT GTAAGCGATT GTTTGATCCC CGCGCTTGTG
          L   R   S   T   P   V   A   K   S   C   K   L   F   V   A   S   S ·
        · S   I   H   A   S   C   K   I   L   Q   I   V   C   C   F   Q
        · F   D   P   R   Q   L   Q   N   P   A   N   C   L   L   L   P   V ·
  351     CTTCGATCCA CGCCAGTTGC AAAATCCTGC AAATTGTTTG TTGCTTCCAG
        · Q   L   C   L   C   F   F   L   V   G   V   C   V   C   V   C   V ·
          S   T   L   P   L   F   F   F   G   W   C   V   C   V   C   V   C ·
        · N   S   A   S   V   F   F   W   L   V   C   V   C   V   C   V
  401     TCAACTCTGC CTCTGTTTTT TTTTGGTTGG TGTGTGTGTG TGTGTGTGTG
        · Q   I   T   L   C   A   I   G   S   L   T   L   P   V   A   I
        · S   N   H   T   L   C   Y   R   *   L   N   T   A   G   C   H   L ·
          F   K   S   H   F   V   L   S   V   A   *   H   C   R   L   P   S ·
  451     TTCAAATCAC ACTTTGTGCT ATCGGTAGCT TAACACTGCC GGTTGCCATC
          S   R   A   R   M   F   Y   C   G   P   W   A   S   E   L   W   I ·
        · A   R   T   D   V   L   L   W   A   L   G   F   G   I   V   D
        · R   A   H   G   C   F   I   V   G   L   G   L   R   N   C   G   * ·
  501     TCGCGCGCAC GGATGTTTTA TTGTGGGCCT TGGGCTTCGG AATTGTGGAT
        · D   C   A   R   V   L   E   W   A   Q   F   V   S   W   G   A   Y ·
          R   L   C   A   C   T   R   M   G   T   I   R   F   V   G   G   I ·
        · I   V   R   V   Y   S   N   G   H   N   S   F   R   G   G   H
  551     AGATTGTGCG CGTGTACTCG AATGGGCACA ATTCGTTTCG TGGGGGGCAT
        · A   A   A   I   E   V   G   V   Y   L   F   W   D   Q   G   D
        · C   C   C   D   *   G   R   C   L   L   V   L   G   S   G   G   P ·
          M   L   L   R   L   R   S   V   F   T   C   F   G   I   R   G   T ·
  601     ATGCTGCTGC GATTGAGGTC GGTGTTTACT TGTTTTGGGA TCAGGGGGAC
          Q   C   R   C   A   G   A   R   C   M   P   R   R   I   W   H   R ·
        · V   P   V   R   G   C   Q   M   H   A   T   Q   N   L   A   S
        · S   A   G   A   R   V   P   D   A   C   H   A   E   F   G   I   G ·
  651     CAGTGCCGGT GCGCGGGTGC CAGATGCATG CCACGCAGAA TTTGGCATCG
        · P   A   E   A   A   N   N   E   R   N   R   Y   H   W   R   S   F ·
          A   G   *   S   S   K   Q   R   A   *   P   L   P   L   E   E   L ·
        · R   L   K   Q   Q   T   T   S   V   T   V   T   T   G   G   A
  701     GCCGGCTGAA GCAGCAAACA ACGAGCGTAA CCGTTACCAC TGGAGGAGCT
        · G   L   S   K   R   M   T   G   *   A   N   E   S   L   N   S
        · W   L   V   E   T   D   D   W   M   S   E   *   I   I   E   F   I ·
          L   A   C   R   N   G   *   L   D   E   R   M   N   H   *   I   H ·
  751     TTGGCTTGTC GAAACGGATG ACTGGATGAG CGAATGAATC ATTGAATTCA
          L   L   A   V   L   T   I   V   M   W   T   V   V   G   T   A   P ·
        · V   G   G   T   H   Y   S   D   V   D   S   C   W   D   S   T
        · C   W   R   Y   S   L   *   *   C   G   Q   L   L   G   Q   H   L ·
  801     TTGTTGGCGG TACTCACTAT AGTGATGTGG ACAGTTGTTG GGACAGCACC
        · A   V   P   P   V   L   L   M   L   T   F   L   T   T   M   R   V ·
          C   S   A   P   S   I   I   N   A   D   F   S   N   Y   N   A   C ·
        · Q   C   P   Q   Y   Y   *   C   *   L   F   *   L   Q   C   V
  851     TGCAGTGCCC CCAGTATTAT TAATGCTGAC TTTTCTAACT ACAATGCGTG
```

Figure 2

```
                  · T  L  F     V  H  L     G  F  P     W  G  I     A  S  C
                  · Y  I  V     C  T  P     W  L  S     C  L  G     H  C  F  L  L ·
                    L  H  C  L     Y  T  L     A  F  L     L  G  A  L     L  L  V ·
             901  TTACATTGTT TGTACACCTT GGCTTTCCTG CTTGGGGCAT TGCTTCTTGT
                  *  G  P  Y     N  C  A     P  T  *     N  C  I     G  P  L  V ·
                  · R  T  I  *     L  C  T     Y  I  E     L  Y  W     T  T  C
                  · E  D  H     I  T  V  H     L  H  R     T  V  L     D  H  L  * ·
             951  TGAGGACCAT ATAACTGTGC ACCTACATAG AACTGTATTG GACCACTTGT
                  · S  F  N     W  L  A  L     H  F  L     I  G  I     L  L  D  N ·
                    K  F  *     L  V  S     P  F  F     N  R  Y     I  I  R  Q ·
                  · V  L  T     G  *  P     S  I  F  *     *  V  Y     Y  *  T
            1001  AAGTTTTAAC TGGTTAGCCC TCCATTTTTT AATAGGTATA TTATTAGACA
                  · F  Y  C     H  *  H     Y  F  C  L     L  L  S     E  P  F
                  · F  L  L     S  L  T  L     F  L  F     A  T  L     G  A  L  F ·
                    I  F  I  V     I  D  I     I  F  V     C  Y  S  R     S  P  F ·
            1051  ATTTTTATTG TCATTGACAT TATTTTGTT TGCTACTCTC GGAGCCCTTT
                    S  Q  C  N     L  N  R     A  Q  I     T  A  E  T     R  E  T ·
                  · P  V  *     S  *  *     G  S  N  H     S  R  N     T  *  D
                  · P  S  V     I  L  I  G     L  K  S     Q  Q  K     H  V  R  R ·
            1101  TCCCAGTGTA ATCTTAATAG GGCTCAAATC ACAGCAGAAA CACGTGAGAC
                  · *  F  S     S  D  T  F     I  R  L     C  C  F     C  T  Y  S ·
                    V  I  F  *     *  Y  F     Y  *  T     L  L  F  L     H  I  L ·
                  · N  F  L     V  I  L     L  L  D  F     V  V  S     A  H  T
            1151  GTAATTTTCT AGTGATACTT TTATTAGACT TTGTTGTTTC TGCACATACT
                  · K  S  V     L  K  V     G  V  L  I     W  M  I     N  N  P
                  · *  I  C     F  E  G  R     S  A  Y     L  D  D     K  *  S  S ·
                    L  N  L  F     *  R  *     E  C  L     F  G  *  *     I  I  L ·
            1201  CTAAATCTGT TTTGAAGGTA GGAGTGCTTA TTTGGATGAT AAATAATCCT
                    L  L  V  A     *  I  F     I  H  H     M  P  P  T     W  F  L ·
                  · V  S  C     M  N  I     Y  T  S  H     A  S  Y     M  V  P
                  · C  *  L     H  E  Y  L     Y  I  T     C  L  L     H  G  S  W ·
            1251  CTGTTAGTTG CATGAATATT TATACATCAC ATGCCTCCTA CATGGTTCCT
                  · G  L  H     S  G  Q  R     F  D  N     *  V  H     A  N  L  I ·
                    G  I  T  Q     W  T  T     L  *  *     L  S  P  C     *  L  D ·
                  · D  Y  T     V  D  N     A  L  I  I     E  S  M     L  T  *
            1301  GGGATTACAC AGTGGACAAC GCTTTGATAA TTGAGTCCAT GCTAACTTGA
                  · I  I  Y     Q  Y  S     I  Y  H  F     I  L  Y     F  N  *
                  · Y  N  I     S  V  F  H     I  S  F     Y  L  V     L  Q  L  R ·
                    L  *  Y  I     S  I  P     Y  I  I     L  S  C  T     S  T  E ·
            1351  TTATAATATA TCAGTATTCC ATATATCATT TTATCTTGTA CTTCAACTGA
                    D  H  P  Y     F  L  Q     T  V  F     I  G  C  S     G  E  L ·
                  · S  S  L     F  F  A  N     R  I  Y     W  L  L     W  R  I
                  · I  I  L     I  F  C  K     P  Y  L     L  V  A     L  E  N  * ·
            1401  GATCATCCTT ATTTTTTGCA AACCGTATTT ATTGGTTGCT CTGGAGAATT
                  · K  S  *     N  *  A  L     L  L  I     A  E  P     C  W  S  S ·
                    E  V  L  K     L  S  T     S  P  D     C  R  A  M     L  V  F ·
                  · S  L  E     T  K  H     F  S  *  L     Q  S  H     A  G  L
            1451  GAAGTCTTGA AACTAAGCAC TTCTCCTGAT TGCAGAGCCA TGCTGGTCTT
                  · E  S  M     H  C  C     S  D  R  S     E  Q  Q     T  H  Y
                  · *  I  Y     A  L  L  F     *  S  Q     *  T  A     D  S  L  L ·
                    L  N  L  C     I  V  V     L  I  A     V  N  S  R     L  I  I ·
            1501  CTGAATCTAT GCATTGTTGT TCTGATCGCA GTGAACAGCA GACTCATTAT
                    *  E  F  N     E  G  L     L  L  S     F  F  F  H     F  P  H ·
                  · R  I  *     *  R  F     I  T  F  F     L  F  S     F  S  S
                  · E  N  L     M  K  V  Y     Y  F  L     S  F  F     I  F  L  T ·
            1551  TGAGAATTTA ATGAAGGTTT ATTACTTTCT TTCTTTTTTC ATTTTCCTCA
                  · L  H  L     Q  I  P  Q     S  I  S     F  *  N     T  S  G  L ·
                    P  S  F  T     D  P  S     I  H  L     L  L  K  Y     I  W  S ·
                  · F  I  Y     R  S  L     N  P  S  P     S  E  I     H  L  V
            1601  CCTTCATTTA CAGATCCCTC AATCCATCTC CTTCTGAAAT ACATCTGGTC
                  · L  P  A     H  L  S     S  V  N  L     T  H  S     V  F  Y
                  · S  S  C     A  F  V  *     C  K  S     D  T  F     C  V  L  F ·
                    F  F  L  R     I  C  L     V  *  I     *  H  I  L     C  F  I ·
            1651  TTCTTCCTGC GCATTTGTCT AGTGTAAATC TGACACATTC TGTGTTTTAT
                    L  N  W  L     V  Q  Y     G  L  L     I  R  A  G     F  W  F ·
                  · K  L  A     G  A  V     W  P  V  D     K  S  W     I  L  V
                  · *  I  G     W  C  S  M     A  C  *     *  E  L     D  F  G  L ·
            1701  TTAAATTGGC TGGTGCAGTA TGGCCTGTTG ATAAGAGCTG GATTTTGGTT
                  · S  A  R     S  L  G  D     W  P  L     L  M  C     W  *  K  L ·
                    *  C  K  I     A  G  *     L  A  P     S  N  V  L     V  E  I ·
                  · V  Q  D     R  W  V     T  G  P  F     *  C  A     G  R  N
            1751  TAGTGCAAGA TCGCTGGGTC ACTGGCCCCT TCTAATGTGC TGGTAGAAAT
```

Figure 2 cont.

```
      · L  S  F     L  I  Q     M  G  F  K     *  E     W  S  N
      · V  V  I     F  N  S  D     G  F  Q     · I  R  T     V  E  *  S ·
        C  C  H  F     *  F     R  W  V  S     N  K  N     C  G  V  I ·
1801  TGTTGTCATT TTTAATTCAG ATGGGTTTCA AATAAGAACT GTGGAGTAAT
        Q  S  V  N     F  S  L     T  L  P     V  F  P  L     V  A  L ·
      · I  C  Q     F  Q  P     H  S  T  S     F  P  T     S  C  T
      · N  L  S     I  S  A  S     L  Y  Q     F  S  H     *  L  H  S ·
1851  CAATCTGTCA ATTTCAGCCT CACTCTACCA GTTTTCCCAC TAGTTGCACT
      · M  A  E     K  L  I  T     R  K  L     I  G  E     H  V  S  L ·
        H  G  *  E     A  D  H     K  K  A     H  W  *     T  C  K  F ·
      · W  L  R     S  *  S     Q  E  S  S     L  V  N     M  *  V
1901  CATGGCTGAG AAGCTGATCA CAAGAAAGCT CATTGGTGAA CATGTAAGTT
      · T  H  K     I  A  *     Y  F  V  E     K  F  S     F  V  I
      · D  S  Q     D  C  V  V     F  C  R     E  V  L     F  C  Y  F ·
        *  L  T  R     L  R  S     I  L  *     R  S  S     L  L  F ·
1951  TGACTCACAA GATTGCGTAG TATTTTGTAG AGAAGTTCTC TTTTGTTATT
        S  *  V  *     V  L  R     I  E  L     D  V  K  L     D  S  P ·
      · L  G  I     S  V  E  D     *  I  R     C  K  T     R  Q  S
      · L  R  Y     K  C  *     G  L  N  *     M  *  N     *  T  V  L ·
2001  TCTTAGGTAT AAGTGTTGAG GATTGAATTA GATGTAAAAC TAGACAGTCC
      · L  F  C     I  F  Q  V     P  F  I     V  Y  D     F  Y  T  P ·
        S  I  L  H     L  P  G     A  I  Y     R  L  *     L  L  Y  T ·
      · Y  S  A     S  S  R     C  H  L  S     F  M  T     S  I  H
2051  TCTATTCTGC ATCTTCCAGG TGCCATTTAT CGTTTATGAC TTCTATACAC
      · L  A  G     G  Y  S     T  P  Y  H     Y  Y  N     I  C  H
      · S  C  R     W  L  F  Y     S  I  S     L  L  Q     H  L  P  L ·
        L  L  Q  V     V  I  L     L  H  I     I  I  T  T     S  A  I ·
2101  CTCTTGCAGG TGGTTATTCT ACTCCATATC ATTATTACAA CATCTGCCAT
        C  L  S  S     C  C  D     S  *  V     S  I  S  F     C  F  A ·
      · S  I  Q     L  L  *     L  L  S  K     H  F  F     L  L  C
      · V  Y  P     V  V  V  T     L  K  *     A  F  L     S  A  L  Q ·
2151  TGTCTATCCA GTTGTTGTGA CTCTTAAGTA AGCATTTCTT TCTGCTTTGC
      · V  C  L     D  A  S     Y  F  D  I     R  *  A     L  V  F  H ·
        S  L  F  G     C  I  L     F  *  H     S  L  S  S     S  I  S ·
      · F  V  W     M  H  L     I  L  T  F     V  E  L     *  Y  F
2201  AGTTTGTTTG GATGCATCTT ATTTTGACAT TCGTTGAGCT CTAGTATTTC
      · G  M  E     Y  I  Q     L  I  L  F     V  I  C     C  T  S
      · W  Y  G     I  H  S  I     N  L  V     R  N  L     L  Y  F  M ·
        M  V  W  N     T  F  N     *  S  C     S  *  F     A  V  L  H ·
2251  ATGGTATGGA ATACATTCAA TTAATCTTGT TCGTAATTTG CTGTACTTCA
        W  Y  G  G     Q  L  H     Y  C  A     P  N  I  *     S  F  P ·
      · V  W  W     P  T  T     L  L  C  P     K  H  L     V  F  P
      · G  M  V     A  N  Y  I     I  V  P     Q  T  F     S  L  S  L ·
2301  TGGTATGGTG GCCAACTACA TTATTGTGCC CCAAACATTT AGTCTTTCCC
      · S  R  Y     V  L  Y  Y     A  N  W     V  D  K     K  V  A  T ·
        F  K  I  R     T  I  L     C  K  L     G  G  *     K  G  S  Y ·
      · Q  D  T     Y  Y  T     M  Q  I  G     W  I  K     R  *  L
2351  TTCAAGATAC GTACTATACT ATGCAAATTG GGTGGATAAA AAGGTAGCTA
      · *  H  F     Y  L  I     V  S  G  D     S  T  L     *  Y  K
      · I  T  L     L  F  N  C     I  W  *     L  H  T     I  I  Q  R ·
        H  N  T  F     I  *  L     Y  L  V     T  P  H  Y     N  T  K ·
2401  CATAACACTT TTATTTAATT GTATCTGGTG ACTCCACACT ATAATACAAA
        E  T  Q  L     S  S  I     F  K  K     K  M  Y  L     V  I  K ·
      · N  A  T     L  Q  H     I  Q  E  K     N  V  S     G  D  K
      · K  R  N     S  P  A  Y     S  R  K     K  C  I     W  *  *  K ·
2451  GAAACGCAAC TCTCCAGCAT ATTCAAGAAA AAAATGTATC TGGTGATAAA
      · I  Y  C     K  C  S  F     I  S  S     R  R  N     P  Y  Y  L ·
        N  L  L  Q     M  F  I     Y  L  *     *  K  K  S     L  L  S ·
      · S  I  A     N  V  H     L  S  L  V     E  E  I     L  T  I
2501  AATCTATTGC AAATGTTCAT TTATCTCTAG TAGAAGAAAT CCTTACTATC
      · T  L  S     *  S  V  H     *  L  H     L  I  G     K  I  C
      · Y  S  V     L  I  C  S     L  T  A     S  N  R     E  D  L  L ·
        L  L  C  L     D  L  F     T  D  C     I  *  *     G  R  F  V ·
2551  TTACTCTGTC TTGATCTGTT CACTGACTGC ATCTAATAGG GAAGATTTGT
        *  S  I  N     I  D  T     H  F  I     M  Q  I  F     C  F  F ·
      · V  H  Q     Y  *  Y     T  F  Y  Y     A  D  I     L  F  L
      · S  P  S     I  L  I  H     I  L  L     C  R  Y     F  V  S  F ·
2601  TAGTCCATCA ATATTGATAC ACATTTATT ATGCAGATAT TTTGTTTCTT
      · H  V  A     S  S  L  *     P  L  S     *  H  E     A  D  L  S ·
        S  C  S  F     *  L  V     T  P  F     L  T  *  S     *  S  F ·
      · M  *  L     L  A  C     N  P  F  P     N  M  K     L  I  F
2651  TCATGTAGCT TCTAGCTTGT AACCCCTTTC CTAACATGAA GCTGATCTTT
```

Figure 2 cont.

```
                · I  V  Q  E  K  L  D  I  F  V  H  M  L  G  N  *
                · H  C  T  R  K  I  G  Y  I  C  S  H  A  W  K  L  N ·
                  P  L  Y  K  K  N  W  I  Y  L  F  T  C  L  E  I  E ·
     2701       CCATTGTACA AGAAAAATTG GATATATTTG TTCACATGCT TGGAAATTGA
                  I  N  K  L  *  Y  F  *  C  *  C  A  S  S  R  L  W ·
                · K  Q  T  V  V  F  L  M  L  M  C  K  *  *  T  L
                ·  *  T  N  C  S  I  S  D  V  D  V  Q  V  V  D  F  G ·
     2751       ATAAACAAAC TGTAGTATTT CTGATGTTGA TGTGCAAGTA GTAGACTTTG
                · L  S  Q  L  L  S  L  K  K  S  H  *  E  Q  V  T  F ·
                  V  E  S  I  V  I  S  Q  K  E  P  L  G  A  S  Y  L ·
                ·  *  V  N  C  Y  L  S  K  R  A  I  R  S  K  L  P
     2801       GTTGAGTCAA TTGTTATCTC TCAAAAAGAG CCATTAGGAG CAAGTTACCT
                · S  L  I  I  F  S  V  R  L  Q  E  L  R  M  L  Y
                · F  I  D  Y  I  F  C  E  T  A  R  V  K  N  V  V  W ·
                  F  H  *  L  Y  F  L  *  D  C  K  S  *  E  C  C  M ·
     2851       TTTCATTGAT TATATTTTCT GTGAGACTGC AAGAGTTAAG AATGTTGTAT
                  G  *  C  L  M  L  F  S  L  S  L  L  *  L  P  R  N ·
                · L  M  P  Y  A  V  *  F  K  F  V  I  I  A  K  K
                · V  D  A  L  C  C  L  V  *  V  C  Y  N  C  Q  E  M ·
     2901       GGTTGATGCC TTATGCTGTT TAGTTTAAGT TTGTTATAAT TGCCAAGAAA
                · V  T  *  K  D  I  V  P  C  I  N  Y  G  L  S  V  Q ·
                  C  Y  L  K  R  Y  C  P  M  H  Q  L  W  I  I  S  S ·
                · L  L  E  K  I  L  S  H  A  S  I  M  D  Y  Q  F
     2951       TGTTACTTGA AAAGATATTG TCCCATGCAT CAATTATGGA TTATCAGTTC
                · S  Y  S  E  K  F  Q  V  *  L  S  S  T  I  W  I
                · V  I  F  R  K  I  S  G  V  T  Q  Q  Y  Y  L  D  L ·
                  S  H  I  P  K  N  F  R  C  D  S  A  V  L  S  G  F ·
     3001       AGTCATATTC CGAAAAATTT CAGGTGTGAC TCAGCAGTAC TATCTGGATT
                  C  A  N  V  S  C  E  H  H  V  D  E  A  C  L  L  C ·
                · C  *  C  F  L  R  A  S  C  G  *  S  L  S  L  M
                · V  L  M  F  L  A  S  I  M  W  M  K  L  V  S  Y  A ·
     3051       TGTGCTAATG TTTCTTGCGA GCATCATGTG GATGAAGCTT GTCTCTTATG
                · T  Y  K  L  *  Y  K  G  I  V  Q  K  Y  *  E  G  N ·
                  H  I  Q  I  M  I  *  G  Y  C  P  K  V  L  R  R  * ·
                · H  T  N  Y  D  I  R  V  L  S  K  S  T  E  K  V
     3101       CACATACAAA TTATGATATA AGGGTATTGT CCAAAAGTAC TGAGAAGGTA
                · A  L  T  C  *  S  E  S  V  Q  I  F  C  *  H  V
                · C  I  D  M  L  I  *  I  S  S  N  I  L  L  T  C  C ·
                  M  H  *  H  V  N  L  N  Q  F  K  Y  F  V  N  M  L ·
     3151       ATGCATTGAC ATGTTAATCT GAATCAGTTC AAATATTTTG TTAACATGTT
                  A  H  F  S  K  L  I  C  *  R  S  N  F  S  *  N  S ·
                · P  F  L  K  I  D  L  L  T  F  K  L  F  L  K  L
                · P  I  S  Q  N  *  F  V  D  V  Q  T  F  L  K  T  P ·
     3201       GCCCATTTCT CAAAATTGAT TGTTGACGT TCAAACTTTT CTTAAAACTC
                · F  W  W  P  N  F  S  E  A  R  I  S  P  T  C  L  N ·
                  L  L  V  A  K  F  F  *  S  *  N  I  S  H  L  F  K ·
                · F  G  G  Q  I  F  L  K  L  E  Y  L  P  L  V  *
     3251       CTTTTGGTGG CCAAATTTTT CTGAAGCTAG AATATCTCCC ACTTGTTTAA
                · F  F  S  S  F  I  S  *  M  S  Y  I  *  F  Q  F
                · L  L  F  Q  F  H  F  M  N  V  L  Y  L  V  S  I  F ·
                  T  S  F  P  V  S  F  H  E  C  L  I  S  S  F  N  F ·
     3301       ACTTCTTTTC CAGTTTCATT TCATGAATGT CTTATATCTA GTTTCAATTT
                  L  H  R  M  K  C  G  A  N  Q  Y  T  L  P  S  R  E ·
                · A  *  D  E  M  W  C  Q  S  I  Y  V  T  I  K  R
                · C  I  G  *  N  V  V  P  I  N  I  R  Y  H  Q  E  S ·
     3351       TTGCATAGGA TGAAATGTGG TGCCAATCAA TATACGTTAC CATCAAGAGA
                ·  *  K  N  C  S  *  L  L  I  Q  C  F  C  Y  M  G  * ·
                  V  K  K  L  F  L  T  S  H  T  V  F  L  L  H  G  L ·
                · K  K  I  V  L  N  F  S  Y  S  V  F  V  T  W  A
     3401       GTAAAAAAAT TGTTCTTAAC TTCTCATACA GTGTTTTTGT TACATGGGCT
                · S  Y  I  L  S  C  V  S  L  T  V  S  V  Y  L  Y
                · I  I  Y  T  L  M  C  *  L  N  C  *  C  I  P  L  L ·
                  D  H  I  Y  S  H  V  L  A  *  L  L  V  Y  T  S  I ·
     3451       GATCATATAT ACTCTCATGT GTTAGCTTAA CTGTTAGTGT ATACCTCTAT
                  C  N  G  P  W  S  T  *  P  C  Y  I  N  A  F  P  T ·
                ·  *  W  A  L  V  H  L  T  L  L  Y  Q  C  I  P  N
                · V  M  G  L  G  P  P  N  P  V  I  S  M  H  S  Q  P ·
     3501       TGTAATGGGC CTTGGTCCAC CTAACCCTGT TATATCAATG CATTCCCAAC
                · L  I  R  V  R  V  S  L  I  L  T  S  G  N  G  S  I ·
                  P  N  *  G  *  G  F  P  H  S  N  F  R  Q  R  *  H ·
                ·  *  L  G  L  G  F  P  S  F  *  L  Q  A  T  V  A
     3551       CCTAATTAGG GTTAGGGTTT CCCTCATTCT AACTTCAGGC AACGGTAGCA
```

Figure 2 cont.

```
                  . * L Y  P F I   F I F H   A N N   H Y C
                  . M I I  S L H F  H F S   C K *   P L L L .
                  Y D Y I  P S F   S F F   M Q I T  T I A .
           3601   TATGATTATA TCCCTTCATT TTCATTTTTC ATGCAAATAA CCACTATTGC
                  Y I L I  F R V   L H M   E I M S  I L R .
                  . Y S Y  F * G   A A Y G  N Y V   D P E
                  . I F L  F L G   C I W   K L C R  S * E
           3651   TATATTCTTA TTTTTAGGGT GCTGCATATG GAAATTATGT CGATCCTGAG
                  . I * K  I Q P   L K V * C T S   C W P Q
                  N M K D  P T F   K S L   V Y F M  L A P .
                  . Y E R  S N L   * K S S  V L H   V G P
           3701   AATATGAAAG ATCCAACCTT TAAAAGTCTA GTGTACTTCA TGTTGGCCCC
                  . H F V  T R Y   Y Y W T  N A P   F L F
                  . T L C  Y Q V L  L L D   Q C P   V F V F .
                  N T L L  P G T   I I G   P M P R  F C F .
           3751   AACACTTTGT TACCAGGTAC TATTATTGGA CCAATGCCCC GTTTTTGTTT
                  L M S T  L C F   S S S   R L S S  Y A S .
                  . N V Y  T L L   F F I A  S I *   L C Q
                  . * C L  H S A F  L H R   V Y L   V M P V .
           3801   TTAATGTCTA CACTCTGCTT TTCTTCATCG CGTCTATCTA GTTATGCCAG
                  . D N M  N F L M  S L W   H V M   Q P T Y .
                  * Q H E  F P D   V T L   A C Y A  A N L .
                  . T T *  I S *   C H F G  M L C   S Q L
           3851   TGACAACATG AATTTCCTGA TGTCACTTTG GCATGTTATG CAGCCAACTT
                  . P Q T  T C I   R K G W  V T Q   Q L I
                  . S S N  Y M Y * K G L   G D P   A T H K .
                  I L K L  H V L   E R V   G * P S  N S * .
           3901   ATCCTCAAAC TACATGTATT AGAAAGGGTT GGGTGACCCA GCAACTCATA
                  K C V V  F T G   L M G   F I I E  Q V S .
                  . V R G  F Y R   L D G L  H N *   A S E
                  . S A W  F L Q A  * W A   S * L   S K * A
           3951   AAGTGCGTGG TTTTTACAGG CTTGATGGGC TTCATAATTG AGCAAGTGAG
                  . L L Y  S L S N  L Y L   Y I T   L D * I
                  P P I F  L K *   L V F   I H N F  G L N .
                  . S Y I  P * V   T C I Y  T * L   W I K
           4001   CCTCCTATAT TCCTTAAGTA ACTTGTATTT ATACATAACT TTGGATTAAA
                  . T N F  S S I   L Q Y I  N P I   V K N
                  . Y Q F  F F Y F  A V Y   K P N   C E E F .
                  L P I F  L L F   C S I   * T Q L  * R I
           4051   TTACCAATTT TTCTTCTATT TTGCAGTATA TAAACCCAAT TGTGAACAAT
                  S K H P  L K G   N F L   N A I E  R V L .
                  . Q T S  T E R   E F F E  C Y R   K S L
                  . P N I  H * K G  I F *   M L *   K E S * .
           4101   TCCAAACATC CACTGAAAGG GAATTTTTTG AATGCTATAG AAAGAGTCTT
                  . K L S  V P T L  Y V W   L C M   F Y C F .
                  K T L S  A N I   I C M   A L H V  L L L .
                  . N S Q  C Q H   Y M Y G  F A C   S I A
           4151   AAAACTCTCA GTGCCAACAT TATATGTATG GCTTTGCATG TTCTATTGCT
                  . F H L  W L V   S C F S  S T V   P * I
                  . F S F  M V S   I L L Q  F N S   T L N L .
                  F F I Y  G * Y   L A S   V Q Q Y  L K F .
           4201   TTTTTCATTT ATGGTTAGTA TCTTGCTTCA GTTCAACAGT ACCTAAATT
                  C A A V  I G L   Y N R   L I G F  * P A .
                  . C G S  D W F   I * Q V  N W V   L T C
                  . V R Q  * L V Y  I T G   * L G   F D L H
           4251   TGTGCGGCAG TGATTGGTTT ATATAACAGG TTAATTGGGT TTTGACCTGC
                  . W D F  D F H F  P W H   S C L   L F W L .
                  M G L *  F P F   S M A   F L F A  L L V .
                  . G T L  I S I   F H G I  L V C   S F G
           4301   ATGGGACTTT GATTTCCATT TTCCATGGCA TTCTTGTTTG CTCTTTTGGT
                  . V S G  * T L   * L N S  S V S   V T V
                  . G F R  L N I   V A E L  L C F   G D R E .
                  W F Q A  E H C S  * T P   L F R   * P * .
           4351   TGGTTTCAGG CTGAACATTG TAGCTGAACT CCTCTGTTTC GGTGACCGTG
                  N S I R  T G G   M P K   L L K R  * D A .
                  . F Y K  D W W   N A K T  V E E   V R C
                  . I L *  G L V   E C Q N  C * R   G E M P .
           4401   AATTCTATAA GGACTGGTGG AATGCCAAAA CTGTTGAAGA GGTGAGATGC
                  . C * N  * V R F  * S E N  F K *   D * .
                  L L K L  S S F   L L K   * E L *  I G L .
                  . V K I  E F V   S F E V  R T L   N R T
           4451   CTGTTAAAAT TGAGTTCGTT TCTTTTGAAG TGAGAACTTT AAATAGGACT
```

Figure 2 cont.

```
               · H  Q  L  Y  S  H  V  L  K  C  D  G  I  L  G  L
               · T  S  I  I  F  S  C  T  *  M  *  W  Y  F  G  A  L  ·
                 D  I  N  Y  I  L  M  Y  L  N  V  M  V  F  W  G  F  ·
         4501  GACATCAATT ATATTCTCAT GTACTTAAAT GTGATGGTAT TTTGGGGCTT
                 Y  L  S  T  G  G  C  G  T  W  *  S  F  C  Y  F  Y  ·
               · P  Q  Y  W  R  M  W  N  M  V  I  F  L  L  L  L
               · T  S  V  L  E  D  V  E  H  G  N  L  F  V  T  S  I  ·
         4551  TACCTCAGTA CTGGAGGATG TGGAACATGG TAATCTTTTT GTTACTTCTA
               · I  Q  I  L  Y  P  F  I  *  L  R  L  C  Y  L  T  K  ·
                 Y  S  D  S  I  P  F  Y  L  V  E  T  L  L  L  N  *  ·
               · F  R  F  Y  T  L  L  F  S  *  D  F  V  T  *  L
         4601  TATTCAGATT CTATACCCTT TTATTTAGTT GAGACTTTGT TACTTAACTA
               · D  S  C  D  G  S  G  T  L  L  F  S  *  D  F  L
               · G  Q  L  *  W  *  W  Y  S  S  I  *  L  R  L  P  *  ·
                 R  T  V  V  M  V  V  L  F  Y  L  V  K  T  S  L  ·
         4651  AGGACAGTTG TGATGGTAGT GGTACTCCTT TATTTAGTTA AGACTTCCTT
                 N  F  C  H  *  A  *  D  I  C  L  I  I  S  F  K  *  ·
               · L  L  S  L  S  L  R  Y  L  S  N  N  I  F  Q  I
               · T  S  V  T  E  L  E  I  F  V  *  *  Y  L  S  N  N  ·
         4701  AACTTCTGTC ACTGAGCTTG AGATATTTGT CTAATAATAT CTTTCAAATA
               · L  T  I  S  L  F  F  V  S  L  F  I  S  G  S  S  D  ·
                 T  D  N  *  S  I  F  C  Q  P  V  H  K  W  I  I  R  ·
               · *  Q  L  V  Y  F  L  S  A  C  S  *  V  D  H  Q
         4751  ACTGACAATT AGTCTATTTT TTGTCAGCCT GTTCATAAGT GGATCATCAG
               · T  Y  I  F  H  V  *  G  K  A  F  P  G  *  L  L
               · H  I  Y  F  P  C  I  R  K  G  F  S  R  V  I  A  S  ·
                 T  H  I  F  S  M  Y  K  E  R  L  F  Q  G  N  C  F  ·
         4801  ACACATATAT TTTCCATGTA TAAGGAAAGG CTTTTCCAGG GTAATTGCTT
                 L  Y  V  Y  K  T  L  H  L  F  F  A  F  E  F  S  K  ·
               · I  C  V  Q  N  S  T  F  V  L  C  F  *  I  L  Q
               · Y  M  C  T  K  L  Y  I  C  S  L  L  L  N  S  P  N  ·
         4851  CTATATGTGT ACAAAACTCT ACATTTGTTC TTTGCTTTTG AATTCTCCAA
               · C  S  L  V  W  N  I  D  A  I  *  N  S  Q  Y  T  N  ·
                 M  Q  F  S  L  E  H  R  C  N  I  E  F  T  I  Y  K  ·
               · A  V  *  F  G  T  S  M  Q  Y  R  I  H  N  I  Q
         4901  ATGCAGTTTA GTTTGGAACA TCGATGCAAT ATAGAATTCA CAATATACAA
               · D  V  L  *  K  M  G  K  Q  S  W  T  E  C  *  H
               · *  C  S  L  E  N  G  E  A  E  L  D  R  V  L  A  L  ·
                 M  M  F  F  R  K  W  G  S  R  A  G  Q  S  V  S  T  ·
         4951  ATGATGTTCT TTAGAAAATG GGGAAGCAGA GCTGGACAGA GTGTTAGCAC
                 S  I  V  N  L  S  *  *  *  *  I  Q  L  N  K  W  L  ·
               · N  C  Q  F  V  I  I  I  M  N  T  T  E  Q  V  A
               · Q  L  S  I  C  H  N  N  N  E  Y  N  *  T  S  G  *  ·
         5001  TCAATTGTCA ATTTGTCATA ATAATAATGA ATACAACTGA ACAAGTGGCT
               · K  L  L  *  E  N  Q  N  T  S  G  Q  Y  Y  L  H  S  ·
                 E  T  V  V  R  K  S  E  H  *  W  S  I  L  F  A  *  ·
               · N  C  C  E  K  I  R  T  L  V  V  N  I  I  C  I
         5051  GAAACTGTTG TGAGAAAATC AGAACACTAG TGGTCAATAT TATTTGCATA
               · K  S  I  W  *  C  K  L  R  Y  E  V  L  T  S  Y
               · *  I  N  L  V  M  *  I  K  I  *  S  S  Y  F  L  Y  ·
                 V  N  Q  F  G  N  V  N  *  D  M  K  F  L  L  L  I  ·
         5101  GTAAATCAAT TTGGTAATGT AAATTAAGAT ATGAAGTTCT TACTTCTTAT
                 I  K  I  Y  Y  A  *  I  L  *  W  L  K  L  Y  C  S  ·
               · K  D  L  L  C  L  N  F  I  V  A  E  T  L  L  F
               · *  R  F  T  M  L  E  F  Y  S  G  *  N  F  T  V  L  ·
         5151  ATAAAGATTT ACTATGCTTG AATTTTATAG TGGCTGAAAC TTTACTGTTC
               · W  I  K  I  L  N  K  N  K  G  Y  L  D  L  A  T  K  ·
                 L  D  K  D  F  K  *  K  Q  R  I  S  R  L  G  N  K  ·
               · G  *  R  F  *  I  K  T  K  D  I  *  T  W  Q  Q
         5201  TTGGATAAAG ATTTTAAATA AAAACAAAGG ATATCTAGAC TTGGCAACAA
               · C  C  L  L  L  T  G  K  S  K  L  D  N  V  N  T
               · M  L  P  S  A  D  W  Q  K  *  I  R  Q  C  E  Y  M  ·
                 N  A  A  F  C  *  L  A  K  V  N  *  T  M  *  I  H  ·
         5251  AATGCTGCCT TCTGCTGACT GGCAAAAGTA AATTAGACAA TGTGAATACA
                 W  T  Y  I  K  F  C  W  S  F  H  F  C  R  T  D  M  ·
               · D  I  H  K  I  L  L  V  L  S  F  L  Q  N  *  H
               · G  H  T  *  N  F  V  G  P  F  I  F  A  E  L  T  *  ·
         5301  TGGACATACA TAAAATTTTG TTGGTCCTTT CATTTTTGCA GAACTGACAT
               · I  F  T  A  Y  F  S  N  S  Y  C  I  Y  T  A  G  C  ·
                 D  F  H  C  L  L  L  K  F  V  L  Y  L  H  C  R  V  ·
               · F  S  L  P  T  S  Q  I  R  I  V  S  T  L  Q  G
         5351  GATTTTCACT GCCTACTTCT CAAATTCGTA TTGTATCTAC ACTGCAGGGT
```

Figure 2 cont.

```
             ·  S  Y  S     N  L  V     S  G  F  S     C  I  P     *  G  T
             ·  *  L  F     *  S  R  F     W  F  Q     L  Y  S     M  R  Y  F ·
             V  A  I  L     I  S  F     L  V  S     A  V  F  H     E  V  L  ·
       5401  GTAGCTATTC TAATCTCGTT TCTGGTTTCA GCTGTATTCC ATGAGGTACT
             L  S  S  S     E  A  F     F  M  I     G  S  I  S     V  F  P  ·
             ·  K  F  F     R  S  L     F  H  D  R     F  N  F     C  F  S
             ·  *  V  L     Q  K  P  F     S  *     S  V  Q  F     L  F  F  L ·
       5451  TTAAGTTCTT CAGAAGCCTT TTTCATGATC GGTTCAATTT CTGTTTTCC
             ·  K  T  C     Y  C  S  N     S  T  Q     H  I  T     N  N  T  F ·
             *  D  M  L     L  F  E     F  H  S     A  H  Y     *  Q  Y  V  ·
             ·  R  H  A     I  V  R     I  P  L  S     T  L  L     T  I  R
       5501  TAAGACATGC TATTGTTCGA ATTCCACTCA GCACATTACT AACAATACGT
             ·  D  L  T     Y  Q  Y     I  I  T  T     S  L  F     T  L  *
             ·  *  P  Y     V  P  I  Y     H  H  H     I  S  F     Y  I  V  N ·
             L  T  L  R     T  N  I     S  S  P     H  L  F  L     H  C  E  ·
       5551  TTGACCTTAC GTACCAATAT ATCATCACCA CATCTCTTTT TACATTGTGA
             I  H  R  Y     V  L  R     C  R  A  T     F  S  N     S  G  H  ·
             ·  S  Q  I     C  I  A     V  P  C  H     I  F  K     F  W  A
             ·  F  T  D     M  Y  C     G  A  V  P     H  F  Q     I  L  G  I ·
       5601  ATTCACAGAT ATGTATTGCG GTGCCGTGCC ACATTTCAA ATTCTGGGCA
             ·  F  L  G     S  C  F  R     Y  R  N     N  T  N  I     *  L  L ·
             F  S  G  I     M  F  Q     V  *  K     *  H  *  Y     I  T  T  ·
             ·  F  W  D     H  V  S     G  I  E  I     T  L  I     Y  N  Y
       5651  TTTTCTGGGA TCATGTTTCA GGTATAGAAA TAACACTAAT ATATAACTAC
             ·  P  P  F     R  I  I     S  L  S  G     L  A  F     L  V  T
             ·  T  S  I     P  N  Y  K     S  F  W     L  G  F     S  S  Y  I ·
             Y  L  H  S     E  L  *     V  F  L     A  W  L  F     *  L  H  ·
       5701  TACCTCCATT CCGAATTATA AGTCTTTCTG GCTTGGCTTT TCTAGTTACA
             L  Y  *  V     Y  I  *     I  I  I     V  I  Y  L     D  I  V  ·
             ·  I  L  G     I  Y  L     D  Y  N  S     Y  I  S     R  H  C
             ·  Y  T  R     Y  I  S  R     L  *  *     L  Y  I     *  T  L  C ·
       5751  TTATACTAGG TATATATCTA GATTAATAATA GTTATATATC TAGACATTGT
             ·  Y  I  *     M  H  T  K     C  Y  L     S  R  K     *  D  H  G ·
             V  Y  L  D     A  Y  Q     M  L  P     I  *  K  I     G  S  W  ·
             ·  I  S  R     C  I  P     N  V  T  Y     L  E  N     R  I  M
       5801  GTATATCTAG ATGCATACCA AATGTTACCT ATCTAGAAAA TAGGATCATG
             ·  F  R  Y     R  S  S     N  N  I  I     T  T  T     S  I  S
             ·  F  Q  V     *  K  *  *     *  Y  N     N  Y  Y     L  H  F  E ·
             V  S  G  I     E  V  V     I  I  *     *  L  L  P     P  F  R  ·
       5851  GTTTCAGGTA TAGAAGTAGT AATAATATAA TAACTACTAC CTCCATTTCG
             N  C  K  S     L  *  L     G  F  Y     R  *  C  *     E  L  Y  ·
             ·  L  *  V     I  M  T     W  L  L  *     I  M  L     R  V  I
             ·  T  V  S     H  Y  D  L     A  F  I     D  N  A     K  S  Y  I ·
       5901  AACTGTAAGT CATTATGACT TGGCTTTTAT AGATAATGCT AAGAGTTATA
             ·  I  W  T     L  S  R  C     V  A  T     N  L  G     K  L  E  R ·
             Y  L  D  I     I  *  M     R  S  Y     E  S  R  K     T  R  T  ·
             ·  S  G  H     Y  L  D     A  *  L  R     I  *  E     N  *  N
       5951  TATCTGGACA TTATCTAGAT GCGTAGCTAC GAATCTAGGA AAACTAGAAC
             ·  L  V  I     I  P  A     F  S  F  E     S  I  S     V  Y  S
             ·  T  C  N     Y  P  C  L     F  F  *     V  H  Q     C  L  F  S ·
             D  L  *  L     S  L  P     F  L  L     S  P  S  V     S  I  L  ·
       6001  GACTTGTAAT TATCCCTGCC TTTTCTTTTG AGTCCATCAG TGTCTATTCT
             L  T  F  *     F  H  H     Y  I  H     K  N  N  T     T  S  W  ·
             ·  Y  V  L     I  P  S     L  H  P  *     E  Q  Y     Y  I  L
             ·  L  R  F     D  S  I  I     T  S  I     R  T  I     L  H  L  G ·
       6051  CTTACGTTTT GATTCCATCA TTACATCCAT AAGAACAATA CTACATCTTG
             ·  I  Q  C     T  F  H  C     F  H  I     G  *  H     W  L  M  S ·
             D  T  M  Y     L  P  L     F  S  H     R  L  T  L     V  D  V  ·
             ·  Y  N  V     P  S  T     V  F  T  *     A  D  T     G  *  C
       6101  GATACAATGT ACCTTCCACT GTTTTCACAT AGGCTGACAC TGGTTGATGT
             ·  D  S  Q     I  P  L     V  F  L  T     R  Y  L     H  A  T
             ·  *  L  T     D  T  V  G     I  L  D     K  I  S     P  C  Y  V ·
             L  T  H  R     Y  R  W  Y     S  *     Q  D  I  S     M  L  R  ·
       6151  CTGACTCACA GATACCGTTG GTATTCTTGA CAAGATATCT CCATGCTACG
             F  K  H  V     M  V  R     C  V  N     Y  V  L  F     F  P  L  ·
             ·  Q  A  C     N  G  T     L  C  Q  L     C  P  F     F  P  I
             ·  S  S  M     *  W  Y  A     V  S  I     M  S  F     F  S  H  Y ·
       6201  TTCAAGCATG TAATGGTACG CTGTGTCAAT TATGTCCTTT TTTTCCCATT
             ·  P  L  A     T  T  *     P  S  S  S     Y  L  A     G  G  Q  H ·
             T  S  C  H     Y  L  T     I  I  F     L  F  G  R     W  A  T  ·
             ·  L  L  P     L  P  N     H  H  L  L     I  W  Q     V  G  N
       6251  ACCTCTTGCC ACTACCTAAC CATCATCTTC TTATTTGGCA GGTGGGCAAC
```

Figure 2 cont.

```
               ·  D  I  L     V  L  Q     Y  S  R  T     A  D  V     C  P  S
               ·  *  Y  F     G  S  S  V     *  S  D     S  R  C     V  S  F  Y  ·
                  M  I  F  W     F  F  S     I  V  G     Q  P  M     C  V  L  L  ·
     6301      ATGATATTTT GGTTCTTCAG TATAGTCGGA CAGCCGATGT GTGTCCTTCT
                  I  L  P  *     R  H  E     Q  A  G     P  G  K     *  I       (SEQ ID NO: 168)
               ·  T  T  M     T  S  *     T  G  R     P  R  Q     V  D          (SEQ ID NO: 169)
               ·  Y  Y  H     D  V  M  N     R  Q  A     Q  A  S     R  *       (SEQ ID NO: 170)
     6351      ATACTACCAT GACGTCATGA ACAGGCAGGC CCAGGCAAGT AGATAG(SEQ ID NO: 129)
```

ACYLTRANSFERASE POLYNUCLEOTIDES, POLYPEPTIDES AND METHODS OF USE

CROSS-REFERENCE TO RELATED APPLICATIONS

This application is a U.S. National Stage Application filed under 35 U.S.C. § 371 of International Application No. PCT/IB2013/059526, filed Oct. 22, 2013, which claims the benefit of U.S. Provisional Patent Application No. 61/720,119, filed Oct. 30, 2012. Both of these applications are hereby incorporated by reference in their entireties.

TECHNICAL FIELD

The invention relates to compositions and methods for the manipulation of cellular lipid production and/or cellular lipid profile.

BACKGROUND

Plant oil is an economically important product not only due to its broad utilization in the food industry and as a component of feed ingredients but it also has a wide range of applications as biofuels or in the manufacture of various nutraceutical and industrial products. Within the plant itself, oil is essential to carry out a number of metabolic processes which are vital to growth and development particularly during seed germination and early plant growth stages. Considering its value, there is a growing research interest within the biotechnology field to improve plant oil production and make the supply more sustainable.

The major component of plant oil is triacylglyceride (TAG). It is the main form of storage lipid in oil seeds and the primary source of energy for seed germination and seedling development. TAG biosynthesis via the Kennedy pathway involves sequential acylation steps starting from the precursor sn-glycerol-3-phosphate (G3P). Firstly, G3P is esterified by an acyl-CoA to form lysophosphatidic acid (LPA) in a reaction catalyzed by glycerol-3-phosphate acyltransferase (GPAT, EC 2.3.1.15). This is followed by a second acylation step catalyzed by lysophosphatidic acid acyltransferase (LPAT; EC 2.3.1.51) forming phosphatidic acid (PA), a key intermediate in the biosynthesis of glycerolipids. The PA is then dephosphorylated by the enzyme phosphatidic acid phosphatase (PAP; EC3.1.3.4) to release the immediate precursor for TAG, the sn-1,2-diacylglycerol (DAG). Finally, DAG is acylated in the sn-3 position by the enzyme diacylglycerol acyltransferase (DGAT; EC 2.3.1.20) to form TAG.

Since this last catalytic action is the only unique step in TAG biosynthesis, DGAT is termed as the committed triacylglycerol-forming enzyme. As DAG is located at the branch point between TAG and membrane phospholipid biosyntheses, DGAT potentially plays a decisive role in regulating the formation of TAG in the glycerolipid synthesis pathway (Lung and Weselake, 2006, Lipids. December 2006; 41(12):1073-88). There are two different families of DGAT proteins. The first family of DGAT proteins ("DGAT1") is related to the acyl-coenzyme A:cholesterol acyltransferase ("ACAT") and has been described in the U.S. Pat. Nos. 6,100,077 and 6,344,548. A second family of DGAT proteins ("DGAT2") is unrelated to the DGAT1 family and is described in PCT Patention Publication WO 2004/011671 published Feb. 5, 2004. Other references to DGAT genes and their use in plants include PCT Publication Nos. WO2004/011,671, WO1998/055,631, and WO2000/001,713, and US Patent Publication No. 20030115632.

DGAT1 is typically the major TAG synthesising enzyme in both the seed and senescing leaf (Kaup et al., 2002, Plant Physiol. 129(4):1616-26; for reviews see Lung and Weselake 2006, Lipids. 41(12):1073-88; Cahoon et al., 2007, Current Opinion in Plant Biology. 10:236-244; and Li et al., 2010, Lipids. 45:145-157).

Raising the yield of oilseed crops (canola, sunflower, safflower, soybean, corn, cotton, linseed, flax etc) has been a major target for the agricultural industry for decades. Many approaches (including traditional and mutational breeding as well as genetic engineering) have been tried, typically with modest success (Xu et al., 2008, Plant Biotechnol J., 6:799-818 and references therein).

Although liquid biofuels offer considerable promise the reality of utilising biological material is tempered by competing uses and the quantities available. Consequently, engineering plants and microorganisms to address this is the focus of multiple research groups; in particular the accumulation of triacylglycerol (TAG) in vegetative tissues and oleaginous yeasts and bacteria (Fortman et al., 2008, Trends Biotechnol 26, 375-381; Ohlrogge et al., 2009, Science 324, 1019-1020). TAG is a neutral lipid with twice the energy density of cellulose and can be used to generate biodiesel a high energy density desirable biofuel with one of the simplest and most efficient manufacturing processes. Engineering TAG accumulation in leaves has so far resulted in a 5-20 fold increase over WT utilising a variety of strategies which includes: the over-expression of seed development transcription factors (LEC1, LEC2 and WRI1); silencing of APS (a key gene involved in starch biosynthesis); mutation of CGI-58 (a regulator of neutral lipid accumulation); and upregulation of the TAG synthesising enzyme DGAT (diacylglycerol O acyltransferase, EC 2.3.1.20) in plants and also in yeast (Andrianov et al., 2009, Plant Biotech J 8, 1-11; Mu et al., 2008, Plant Physiol 148, 1042-1054; Sanjaya et al., 2011, Plant Biotech J 9, 874-883; Santos-Mendoza, et al., 2008, Plant J 54, 608-620; James et al., 2010, Proc. Natl. Acad. Sci. USA 107, 17833-17838; Beopoulos et al., 2011, Appl Microbiol Biotechnol 90, 1193-1206; Bouvier-Nave et al., 2000, Eur J Biochem 267, 85-96; Durrett et al., 2008, Plant J 54, 593-607). However, it has been acknowledged that to achieve further increases in TAG, preventing its catabolism may be crucial within non oleaginous tissues and over a range of developmental stages (Yang and Ohlrogge, 2009, Plant Physiol 150, 1981-1989).

Positively manipulating the yield and quality of triacylglycerides (TAG) in eukaryotes is difficult to achieve. The enzyme diacylglycerol-O-acyltransferase (DGAT) has the lowest specific activity of the Kennedy pathway enzymes and is regarded as a 'bottleneck' in TAG synthesis.

Attempts have been made previously to improve DGAT1 by biotechnological methods, with limited success. For example Nykiforuk et al., (2002, Biochimica et Biophysica Acta 1580:95-109) reported N-terminal truncation of the *Brassica napus* DGAT1 but reported approximately 50% lower activity. McFie et al., (2010, JBC., 285:37377-37387) reported that N-terminal truncation of the mouse DGAT1 resulted in increased specific activity of the enzyme, but also reported a large decline in the level of protein that accumulated.

Xu et al., (2008, Plant Biotechnology Journal, 6:799-818) recently identified a consensus sequence (X-Leu-X-Lys-X-X-Ser-X-X-X-Val) (SEQ ID NO: 158) within *Tropaeolum majus* (garden nasturtium) DGAT1 (TmDGAT1) sequences as a targeting motif typical of members of the SNF1-related protein kinase-1 (SnRK1) with Ser being the residue for phosphorylation. The SnRK1 proteins are a class of Ser/Thr protein kinases that have been increasingly implicated in the global regulation of carbon metabolism in plants, e.g. the inactivation of sucrose phosphate synthase by phosphorylation (Halford & Hardie 1998, Plant Mol Biol. 37:735-48. Review). Xu et al., (2008, Plant Biotechnology Journal, 6:799-818) performed site-directed mutagenesis on six putative functional regions/motifs of the TmDGAT1 enzyme. Mutagenesis of a serine residue (S197) in a putative SnRK1 target site resulted in a 38%-80% increase in DGAT1 activity, and over-expression of the mutated TmDGAT1 in *Arabidopsis* resulted in a 20%-50% increase in oil content on a per seed basis.

It would be beneficial to provide improved forms of DGAT1, which overcome one or more of the deficiencies in the prior art, and which can be used to increase cellular oil production.

It is an object of the invention to provide enhanced DGAT1 proteins and methods for their use to alter at least one of cellular lipid production and cellular lipid profile, and/or at least to provide the public with a useful choice.

SUMMARY OF THE INVENTION

The inventors have shown that it is possible to produce chimeric DGAT1 proteins with advantageous properties over either of the parental DGAT1 molecules used to produce the chimeric DGAT1 proteins. The chimeric DGAT1 proteins of the invention can be expressed in cells to alter lipid content and lipid profile of the cells, or organisms containing the cells.

Polynucleotide Encoding a Polypeptide

In the first aspect the invention provides an isolated polynucleotide encoding a chimeric DGAT1 protein that comprises:

a) at its N-terminal end, an N-terminal portion of a first DGAT1 protein, and
b) at its C-terminal end, a C-terminal portion of a second DGAT1 protein.

In one embodiment the chimeric DGAT1 protein has at least one of:
i) increased DGAT1 activity
ii) increased stability
iii) altered oligomerisation properties
iv) substantially normal cellular protein accumulation properties
v) substantially normal cellular targeting properties
relative to the first DGAT1, the second DGAT1, or both the first DGAT1 and the second DGAT1.

In a further embodiment the chimeric DGAT1 protein has at least one of:
i) increased DGAT1 activity
ii) increased stability
iii) altered oligomerisation properties
iv) substantially normal cellular protein accumulation properties
v) substantially normal cellular targeting properties
relative to the first DGAT1.

In a further embodiment the chimeric DGAT1 protein has at least one of:
i) increased DGAT1 activity
ii) increased stability
iii) altered oligomerisation properties
iv) substantially normal cellular protein accumulation properties
v) substantially normal cellular targeting properties
relative to the second DGAT1.

In a further embodiment the chimeric DGAT1 protein has at least one of:
i) increased DGAT1 activity
ii) increased stability
iii) altered oligomerisation properties
iv) substantially normal cellular protein accumulation properties
v) substantially normal cellular targeting properties
relative to both the first DGAT1 and the second DGAT1.

In one embodiment the N-terminal portion of a first DGAT1 protein is the N-terminal cytoplasmic region of the first DGAT1 protein. In one embodiment the N-terminal cytoplasmic region of the first DGAT1 protein extends from the N-terminus of the first DGAT1 protein to the end of the acyl-CoA binding domain of the first DGAT1 protein. In a further embodiment the N-terminal cytoplasmic region of the first DGAT1 protein is the region upstream of the first transmembrane domain.

The position of the acyl-CoA binding domain and the first transmembrane domain, for a number of DGAT1 proteins, is shown in FIG. 3.

In one embodiment the junction between the N-terminal portion of a first DGAT1 protein and the C-terminal portion of a second DGAT1 protein is upstream of the first transmembrane domain.

In a further embodiment the junction between the N-terminal portion of a first DGAT1 protein and the C-terminal portion of a second DGAT1 protein is in the acyl-CoA binding site of first and second DGAT1 protein.

In a further embodiment the junction between the N-terminal portion of a first DGAT1 protein and the C-terminal portion of a second DGAT1 protein is at a corresponding position in the acyl-CoA binding site of the first and second DGAT1 protein.

In one embodiment the junction between the N-terminal portion of a first DGAT1 protein and the C-terminal portion of a second DGAT1 protein is within the conserved LSS (Leu-Ser-Ser) in the acyl-CoA binding site of the first and second DGAT1 protein.

In a preferred embodiment the chimeric DGAT1 has an intact acyl-CoA binding site.

In one embodiment the acyl-CoA binding site in the chimeric DGAT1 is of the same length as the acyl-CoA binding site in the first DGAT1 protein.

In a further embodiment the acyl-CoA binding site in the chimeric DGAT1 is of the same length as the acyl-CoA binding site in the second DGAT1 protein.

In a preferred embodiment the acyl-CoA binding site in the chimeric DGAT1 is of the same length as the acyl-CoA binding site in the first and second DGAT1 protein.

In a further embodiment the polypeptide of the invention, when expressed in the cell, has altered substrate specificity relative to at least one of the first and second DGAT1 proteins.

Construct

In a further embodiment the invention provides a genetic construct comprising a polynucleotide of the invention.

Cells

In a further embodiment the invention provides a cell comprising a polynucleotide of the invention.

In a further embodiment the invention provides a cell comprising a genetic construct of the invention.

In a preferred embodiment the cell expresses the chimeric DGAT1.

In one embodiment the chimeric DGAT1 protein, when expressed in the cell, has at least one of:

i) increased DGAT1 activity,
ii) increased stability,
iii) altered oligomerisation properties,
iv) substantially normal cellular protein accumulation properties, and
v) substantially normal subcellular targeting properties relative to the first DGAT1, the second DGAT1, or both the first DGAT1 and the second DGAT1.

In one embodiment the chimeric DGAT1 protein, when expressed in the cell, has at least one of:
i) increased DGAT1 activity,
ii) increased stability,
iii) altered oligomerisation properties,
iv) substantially normal cellular protein accumulation properties, and
v) substantially normal subcellular targeting properties relative to the first DGAT1 when expressed in a cell.

In one embodiment the chimeric DGAT1 protein, when expressed in the cell, has at least one of:
i) increased DGAT1 activity,
ii) increased stability,
iii) altered oligomerisation properties,
iv) substantially normal cellular protein accumulation properties, and
v) substantially normal subcellular targeting properties relative to the second DGAT1 when expressed in a cell.

In a further embodiment the chimeric DGAT1 protein has at least one of:
i) increased DGAT1 activity
ii) increased stability
iii) altered oligomerisation properties
iv) substantially normal cellular protein accumulation properties
v) substantially normal cellular targeting properties relative to both the first DGAT1 and the second DGAT1.

In a further embodiment the cell produces more lipid than does a control cell.

In one embodiment the cell produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control cell.

In a further embodiment the cell has an altered lipid profile relative to a control cell.

In one embodiment the proportion of 16:0 in the triacylglycerol is altered relative to that in a control cell.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in a control cell.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control cell.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 18:1 in the triacylglycerol in the range 39% to 55%. In this embodiment the proportion of 18:1 in the triacylglycerol is altered within the range 39% to 55%.

The control cell may be any cell of the same type that is not transformed with the polynucleotide, or construct, of the invention to express the chimeric DGAT1.

In one embodiment the control cell is an untransformed cell. In a further embodiment the control cell is transformed cell to express the first DGAT1. In a further embodiment the control cell is transformed cell to express the second DGAT1.

Cells Also Transformed to Express an Oleosin

In one embodiment the cell is also transformed to express at least one of: an oleosin, steroleosin, caloleosin, polyoleosin, and an oleosin including at least one artificially introduced cysteine (WO2011/053169).

Plant

In a further embodiment the invention provides a plant comprising a polynucleotide of the invention.

In a further embodiment the invention provides a plant comprising a genetic construct of the invention.

In a preferred embodiment the plant expresses the chimeric DGAT1.

In one embodiment the chimeric DGAT1 protein when expressed in the plant has at least one of:
i) increased DGAT1 activity,
ii) increased stability, iii) altered oligomerisation properties,
iv) substantially normal cellular protein accumulation properties, and
v) substantially normal subcellular targeting properties
relative to the first DGAT1, the second DGAT1, or both the first DGAT1 and the second DGAT1.

In one embodiment the chimeric DGAT1 protein when expressed in the plant has at least one of:
i) increased DGAT1 activity,
ii) increased stability,
iii) altered oligomerisation properties,
iv) substantially normal cellular protein accumulation properties, and
v) substantially normal subcellular targeting properties
relative to the first DGAT1.

In one embodiment the chimeric DGAT1 protein when expressed in the plant has at least one of:
i) increased DGAT1 activity,
ii) increased stability,
iii) altered oligomerisation properties,
iv) substantially normal cellular protein accumulation properties, and
v) substantially normal subcellular targeting properties
relative to the second DGAT1.

In one embodiment the chimeric DGAT1 protein when expressed in the plant has at least one of:
i) increased DGAT1 activity,
ii) increased stability,
iii) altered oligomerisation properties,
iv) substantially normal cellular protein accumulation properties, and
v) substantially normal subcellular targeting properties
relative to both the first DGAT1 and the second DGAT1.

In one embodiment the chimeric DGAT1 protein when expressed in the plant has at least one of:
i) increased DGAT1 activity,
ii) increased stability,
iii) altered oligomerisation properties,
iv) substantially normal cellular protein accumulation properties, and
v) substantially normal subcellular targeting properties
relative to both the first DGAT1 and the second DGAT1.

In a further embodiment the plant produces more lipid, in at least one of its tissues or parts, than does the equivalent tissue or part in a control plant.

In one embodiment the plant produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control cell.

In one embodiment the tissue is a vegetative tissue. In one embodiment the part is a leaf. In a further embodiment the part is a root. In a further embodiment the part is a tuber. In a further embodiment the part is a corm. In a further embodiment the part is a stalk. In a further embodiment the part is a stalk of a monoct plant. In a further embodiment the part is a stovum (stalk and leaf blade).

In a preferred embodiment the tissue is seed tissue. In a preferred embodiment the part is a seed. In a preferred embodiment the tissue is endosperm tissue.

In a further embodiment the plant as a whole produces more lipid than does the control plant as a whole.

In a further embodiment the plant has an altered lipid, in at least one of its tissues or parts, relative to a control plant.

In one embodiment the proportion of 16:0 in the triacylglycerol is altered relative to that in a control plant.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In one embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in a control plant.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In one embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control plant.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In one embodiment the altered lipid profile has a proportion of 18:1 in the triacylglycerol in the range 39% to 55%. In this embodiment the proportion of 18:1 in the triacylglycerol is altered within the range 39% to 55%.

In one embodiment the tissue is a vegetative tissue. In one embodiment the part is a leaf. In a further embodiment the part is a root. In a further embodiment the part is a tuber. In a further embodiment the part is a corm. In a further embodiment the part is a stalk. In a further embodiment the part is a stalk of a monoct plant. In a further embodiment the part is a stovum (stalk and leaf blade).

In a preferred embodiment the tissue is seed tissue. In a preferred embodiment the part is a seed. In a preferred embodiment the tissue is endosperm tissue.

In a further embodiment the plant as a whole has an altered lipid profile relative to the control plant as a whole.

The control plant may be any plant of the same type that is not transformed with the polynucleotide, or construct, of the invention to express the chimeric DGAT1.

In one embodiment the control plant is an untransformed plant. In a further embodiment the control plant is transformed plant to express the first DGAT1. In a further embodiment the control plant is transformed plant to express the second DGAT1.

Plant Also Transformed to Express an Oleosin

In one embodiment the plant is also transformed to express at least one of: an oleosin, steroleosin, caloleosin, polyoleosin, and an oleosin including at least one artificially introduced Cysteine (WO 2011/053169).

Polypeptide

In a further aspect the invention provides a chimeric DGAT1 protein that comprises:
  a) at its N-terminal end, an N-terminal portion of a first DGAT1 protein, and
  b) at its C-terminal end, a C-terminal portion of a second DGAT1 protein.

In one embodiment the chimeric DGAT1 protein has at least one of:
  i) increased DGAT1 activity
  ii) increased stability
  iii) altered oligomerisation properties
  iv) substantially normal cellular protein accumulation properties
  v) substantially normal cellular targeting properties
relative to the first DGAT1, the second DGAT1, or both the first DGAT1 and the second DGAT1.

In a further embodiment the chimeric DGAT1 protein has at least one of:
  i) increased DGAT1 activity
  ii) increased stability
  iii) altered oligomerisation properties
  iv) substantially normal cellular protein accumulation properties
  v) substantially normal cellular targeting properties
relative to the first DGAT1.

In a further embodiment the chimeric DGAT1 protein has at least one of:
  i) increased DGAT1 activity
  ii) increased stability
  iii) altered oligomerisation properties
  iv) substantially normal cellular protein accumulation properties
  v) substantially normal cellular targeting properties
relative to the second DGAT1.

In one embodiment the chimeric DGAT1 protein when expressed in the plant has at least one of:
  i) increased DGAT1 activity,
  ii) increased stability,
  iii) altered oligomerisation properties,
  iv) substantially normal cellular protein accumulation properties, and
  v) substantially normal subcellular targeting properties
relative to both the first DGAT1 and the second DGAT1.

In one embodiment the N-terminal portion of a first DGAT1 protein is the N-terminal cytoplasmic region of the first DGAT1 protein. In one embodiment the N-terminal cytoplasmic region of the first DGAT1 protein extends from the N-terminus of the first DGAT1 protein to the end of the acyl-CoA binding domain of the first DGAT1 protein. In a further embodiment the N-terminal cytoplasmic region of the first DGAT1 protein is the region upstream of the first transmembrane domain.

The position of the acyl-CoA binding domain and the first transmembrane domain, for a number of DGAT1 proteins, is shown in FIG. 3.

In one embodiment the junction between the N-terminal portion of a first DGAT1 protein and the C-terminal portion of a second DGAT1 protein is upstream of the first transmembrane domain.

In one embodiment the junction between the N-terminal portion of a first DGAT1 protein and the C-terminal portion of a second DGAT1 protein is in the acyl-CoA binding site of first and second DGAT1 protein.

In a further embodiment the junction between the N-terminal portion of a first DGAT1 protein and the C-terminal portion of a second DGAT1 protein is at a corresponding position in the acyl-CoA binding site of the first and second DGAT1 protein.

In one embodiment the junction between the N-terminal portion of a first DGAT1 protein and the C-terminal portion of a second DGAT1 protein is within the conserved LSS (Leu-Ser-Ser) in the acyl-CoA binding site of the first and second DGAT1 protein.

In a preferred embodiment the chimeric DGAT1 has an intact acyl-CoA binding site.

In one embodiment the acyl-CoA binding site in the chimeric DGAT1 is of the same length as the acyl-CoA binding site in the first DGAT1 protein.

In a further embodiment the acyl-CoA binding site in the chimeric DGAT1 is of the same length as the acyl-CoA binding site in the second DGAT1 protein.

In a preferred embodiment the acyl-CoA binding site in the chimeric DGAT1 is of the same length as the acyl-CoA binding site in the first and second DGAT1 protein.

Method for Producing an Chimeric DGAT1

In a further aspect the invention provides a method for producing a chimeric DGAT1 protein the method comprising combining:
  a) an N-terminal portion of a first DGAT1 protein, and
  b) a C-terminal portion of a second DGAT1 protein.

In a preferred embodiment chimeric DGAT1 protein comprises:
  a) at its N-terminal end, the N-terminal portion of a first DGAT1 protein, and
  b) at its C-terminal end, the C-terminal portion of a second DGAT1 protein.

In one embodiment the chimeric DGAT1 protein has at least one of:
  i) increased DGAT1 activity
  ii) increased stability
  iii) altered oligomerisation properties
  iv) substantially normal cellular protein accumulation properties
  v) substantially normal cellular targeting properties
relative to the first DGAT1, the second DGAT1, or both the first DGAT1 and the second DGAT1.

In a further embodiment the chimeric DGAT1 protein has at least one of:
  i) increased DGAT1 activity
  ii) increased stability
  iii) altered oligomerisation properties iv) substantially normal cellular protein accumulation properties
v) substantially normal cellular targeting properties
relative to the first DGAT1.

In a further embodiment the chimeric DGAT1 protein has at least one of:
i) increased DGAT1 activity
ii) increased stability
iii) altered oligomerisation properties
iv) substantially normal cellular protein accumulation properties
v) substantially normal cellular targeting properties
relative to the second DGAT1.

In a further embodiment the chimeric DGAT1 protein has at least one of:
i) increased DGAT1 activity
ii) increased stability
iii) altered oligomerisation properties
iv) substantially normal cellular protein accumulation properties
v) substantially normal cellular targeting properties
relative to both the first DGAT1 and the second DGAT1.

In a further embodiment the method comprises testing at least one of the
i) activity
ii) stability
iii) oligomerisation properties
iv) cellular protein accumulation properties
v) cellular targeting properties
of the chimeric DGAT1 protein.

In a further embodiment method comprises the step selecting a chimeric DGAT1 protein that has at least one of:
i) increased DGAT1 activity
ii) increased stability
iii) altered oligomerisation properties
iv) substantially normal cellular protein accumulation properties
v) substantially normal cellular targeting properties
relative to the first DGAT1, the second DGAT1, or both the first DGAT1 and the second DGAT1.

In a further embodiment method comprises the step of selecting a chimeric DGAT1 protein that has at least one of:
i) increased DGAT1 activity
ii) increased stability
iii) altered oligomerisation properties
iv) substantially normal cellular protein accumulation properties
v) substantially normal cellular targeting properties
relative to the first DGAT1 protein.

In a further embodiment method comprises the step of selecting a chimeric DGAT1 protein that has at least one of:
i) increased DGAT1 activity
ii) increased stability
iii) altered oligomerisation properties
iv) substantially normal cellular protein accumulation properties
v) substantially normal cellular targeting properties
relative to the second DGAT1 protein.

In a further embodiment method comprises the step of selecting a chimeric DGAT1 protein that has at least one of:
i) increased DGAT1 activity
ii) increased stability
iii) altered oligomerisation properties
iv) substantially normal cellular protein accumulation properties
v) substantially normal cellular targeting properties
relative to both the first DGAT1 and the second DGAT1.

In one embodiment the N-terminal portion of a first DGAT1 protein is the N-terminal cytoplasmic region of the first DGAT1 protein. In one embodiment the N-terminal cytoplasmic region of the first DGAT1 protein extends from the N-terminus of the first DGAT1 protein to the end of the acyl-CoA binding domain of the first DGAT1 protein. In a further embodiment the N-terminal cytoplasmic region of the first DGAT1 protein is the region upstream of the first transmembrane domain.

The position of the acyl-CoA binding domain and the first transmembrane domain, for a number of DGAT1 proteins, is shown in FIG. 3.

In one embodiment the junction between the N-terminal portion of a first DGAT1 protein and the C-terminal portion of a second DGAT1 protein is upstream of the first transmembrane domain.

In one embodiment the junction between the N-terminal portion of a first DGAT1 protein and the C-terminal portion of a second DGAT1 protein is in the acyl-CoA binding site of first and second DGAT1 protein.

In a further embodiment the junction between the N-terminal portion of a first DGAT1 protein and the C-terminal portion of a second DGAT1 protein is at a corresponding position in the acyl-CoA binding site of the first and second DGAT1 protein.

In one embodiment the junction between the N-terminal portion of a first DGAT1 protein and the C-terminal portion of a second DGAT1 protein is within the conserved LSS (Leu-Ser-Ser) in the acyl-CoA binding site of the first and second DGAT1 protein.

In a preferred embodiment the chimeric DGAT1 has an intact acyl-CoA binding site.

In one embodiment the acyl-CoA binding site in the chimeric DGAT1 is of the same length as the acyl-CoA binding site in the first DGAT1 protein.

In a further embodiment the acyl-CoA binding site in the chimeric DGAT1 is of the same length as the acyl-CoA binding site in the second DGAT1 protein.

In a preferred embodiment the acyl-CoA binding site in the chimeric DGAT1 is of the same length as the acyl-CoA binding site in the first and second DGAT1 protein.

Plant Parts

In a further embodiment the invention provides a part, propagule or progeny of a plant of the invention.

In a preferred embodiment the part, propagule or progeny comprises at least one of a polynucleotide, construct or polypeptide of the invention.

In a preferred embodiment the part, propagule or progeny expresses at least one of a polynucleotide, construct or polypeptide of the invention.

In a preferred embodiment the part, propagule or progeny expresses a chimeric DGAT1 protein of the invention.

In a further embodiment the part, propagule or progeny produces more lipid than does a control part, propagule or progeny, or part, propagule or progeny of a control plant.

In one embodiment the part, propagule or progeny produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control part, propagule or progeny, or part, propagule or progeny of a control plant.

In a further embodiment the part, propagule or progeny has an altered lipid profile relative to a control part, propagule or progeny, or part, propagule or progeny of a control plant.

In one embodiment the proportion of 16:0 in the triacylglycerol is altered relative to that in a control part, propagule or progeny, or part, propagule or progeny of a control plant.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control part, propagule or progeny, or part, propagule or progeny of a control plant.

In a further embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in a control part, propagule or progeny, or part, propagule or progeny of a control plant.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control part, propagule or progeny, or part, propagule or progeny of a control plant.

In a further embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control part, propagule or progeny, or part, propagule or progeny of a control plant.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control part, propagule or progeny, or part, propagule or progeny of a control plant.

In a further embodiment the altered lipid profile has a proportion of 18:1 in the triacylglycerol in the range 39% to 55%. In this embodiment the proportion of 18:1 in the triacylglycerol is altered within the range 39% to 55%.

The control plant may be any plant of the same type that is not transformed with the polynucleotide, or construct, of the invention to express the chimeric DGAT1.

In one embodiment the control plant is an untransformed plant. In a further embodiment the control plant is transformed plant to express the first DGAT1 protein. In a further embodiment the control plant is transformed plant to express the second DGAT1 protein.

Preferably the control the part, propagule or progeny is from a control plant as described above.

In one embodiment the part is from a vegetative tissue. In one embodiment the part is a leaf. In a further embodiment the part is a root. In a further embodiment the part is a tuber. In a further embodiment the part is a corm. In a further embodiment the part is a stalk. In a further embodiment the part is a stalk of a monocot plant. In a further embodiment the part is a stovum (stalk and leaf blade).

In a further embodiment the part is from a reproductive tissue. In a further embodiment the part is a seed. In a preferred embodiment the part is from or includes endosperm tissue.

Animal Feed

In a further aspect the invention provides an animal feedstock comprising at least one of a polynucleotide, construct, cell, plant cell, plant part, propagule and progeny of the invention.

Biofuel Feedstock

In a further aspect the invention provides a biofuel feedstock comprising at least one of a polynucleotide, construct, cell, plant cell, plant part, propagule and progeny of the invention.

Lipid

In one embodiment the lipid is an oil. In a further embodiment the lipid is triacylglycerol (TAG)

Methods for Producing Lipid

In a further aspect the invention provides a method for producing lipid, the method comprising expressing a chimeric DGAT1 protein of the invention in a plant.

In a preferred embodiment expressing the chimeric DGAT1 protein of the invention in the plant leads production of the lipid in the plant.

In one embodiment the method includes the step of transforming a plant cell or plant with a polynucleotide of the invention encoding the chimeric DGAT1 protein.

In a further embodiment the method includes the step of extracting the lipid from the cell, plant cell, or plant, or from a part, propagule or progeny of the plant.

In one embodiment the lipid is an oil. In a further embodiment the lipid is triacylglycerol (TAG)

In a further embodiment the lipid is processed into at least one of:
  a) a fuel,
  b) an oleochemical,
  c) a nutritional oil,
  d) a cosmetic oil,
  e) a polyunsaturated fatty acid (PUFA), and
  f) a combination of any of a) to e).

In a further aspect the invention provides a method for producing lipid, the method comprising extracting lipid from at least one of a cell, plant cell, plant, plant part, propagule and progeny of the invention.

In one embodiment the lipid is an oil. In a further embodiment the lipid is triacylglycerol (TAG)

In a further embodiment the lipid is processed into at least one of:
a) a fuel,
b) an oleochemical,
c) a nutritional oil,
d) a cosmetic oil,
e) a polyunsaturated fatty acid (PUFA), and
f) a combination of any of a) to e).

DETAILED DESCRIPTION OF THE INVENTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner. In some embodiments, the term "comprising" (and related terms such as "comprise and "comprises") can be replaced by "consisting of" (and related terms "consist" and "consists").

Definitions

The term "DGAT1" as used herein means acyl CoA: diacylglycerol acyltransferase (EC 2.3.1.20)

DGAT1 is typically the major TAG synthesising enzyme in both the seed and senescing leaf (Kaup et al., 2002, Plant Physiol. 129(4):1616-26; for reviews see Lung and Weselake 2006, Lipids. 41(12):1073-88; Cahoon et al., 2007, Current Opinion in Plant Biology. 10:236-244; and Li et al., 2010, Lipids. 45:145-157).

DGAT1 contains approximately 500 amino acids and has 10 predicted transmembrane domains whereas DGAT2 has only 320 amino acids and is predicted to contain only two transmembrane domains; both proteins were also predicted to have their N- and C-termini located in the cytoplasm (Shockey et al., 2006, Plant Cell 18:2294-2313). Both DGAT1 and DGAT2 have orthologues in animals and fungi and are transmembrane proteins located in the ER.

In most dicotyledonous plants DGAT1 & DGAT2 appear to be single copy genes whereas there are typically two versions of each in the grasses which presumably arose during the duplication of the grass genome (Salse et al., 2008, Plant Cell, 20:11-24).

The term "first DGAT1 protein" or "second DGAT1 protein" as used herein typically means a naturally occurring or native DGAT1. In some cases the DGAT1 sequence may have been assembled from sequences in the genome, but may not be expressed in plants. In one embodiment the first or second DGAT1 protein may therefore not be a DGAT1 that is isolated from nature.

In one embodiment the "first DGAT1 protein" or "second DGAT1 protein" has the sequence of any one of SEQ ID NO: 1 to 29 or a variant thereof. Preferably the variant has at least 70% identity to any one of SEQ ID NO: 1 to 29. In a further embodiment the "first DGAT1 protein" or "second DGAT1 protein" has the sequence of any one of SEQ ID NO: 1 to 29.

In one embodiment "first DGAT1 protein" or "second DGAT1 protein" is encoded by a polynucleotide comprising the sequence of any one of SEQ ID NO: 30 to 58 or a variant thereof. Preferably the variant has at least 70% identity to any one of SEQ ID NO: 30 to 58. In a further embodiment the "first DGAT1 protein" or "second DGAT1 protein" is encoded by a polynucleotide comprising the sequence of any one of SEQ ID NO: 30 to 58.

In one embodiment the chimeric DGAT1 sequences comprises the sequence of any SEQ ID NO: 59 to 94 or a variant thereof. Preferably the variant has at least 70% identity to any one of SEQ ID NO: 59 to 94. In a further embodiment the chimeric DGAT1 sequences the sequence of any one of SEQ ID NO: 59 to 94.

In a further embodiment the chimeric DGAT1 polypeptide sequences have the sequence of any SEQ ID NO: 59, 61, 66, 68, 70-72, 74-76, 78, 79, 82, 84-86, 88-90, 92 and 93 or a variant thereof. Preferably the variant has at least 70% identity to any one of SEQ ID NO: 59, 61, 66, 68, 70-72, 74-76, 78, 79, 82, 84-86, 88-90, 92 and 93. In a further embodiment the chimeric DGAT1 sequences have the sequence of any one of SEQ ID NO: 59, 61, 66, 68, 70-72, 74-76, 78, 79, 82, 84-86, 88-90, 92 and 93.

Although not preferred, the chimeric DGAT1 of the invention may include further modifications in at least one of:
a) the N-terminal portion of a first DGAT1 protein, and
b) the C-terminal portion of a second DGAT1 protein.

Preferably the chimeric DGAT1 of the invention includes a functional acyl-CoA binding site.

The terms upstream and downstream are according to normal convention to mean towards the N-terminus of a polypeptide, and towards the C-terminus of a polypeptide, respectively.

Acyl-CoA Binding Site

The position of the acyl-CoA binding site in a number of DGAT1 sequences is shown if FIG. 3.

Conserved Motif ESPLSS

In a preferred embodiment the acyl-CoA binding site comprises the conserved motif ESPLSS Acyl-CoA Binding Site General Formulae In a preferred embodiment the acyl-CoA binding site in the chimeric DGAT1 has the formula: XXXESPLSSXX-IFXXXHA (SEQ ID NO: 159), where X is any amino acid.

In a preferred embodiment the acyl-CoA binding site in the chimeric DGAT1 has the formula: XXXESPLSSXX-IFXXSHA (SEQ ID NO: 160), where X is any amino acid.

In a preferred embodiment the acyl-CoA binding site in the chimeric DGAT1 has the formula: $X_1X_2X_3ESPLSSX_4X_5IFX_6X_7X_8HA$ (SEQ ID NO: 161), where $X_1$=R, K, V, T, A, S or G; $X_2$=A, T, V, I, N, R, S or L; $X_3$=R or K; $X_4$=D or G; $X_5$=A, T, N, or L; $X_6$=K or R; $X_7$=Q or H; and $X_8$=S or is absent.

In a preferred embodiment the acyl-CoA binding site in the chimeric DGAT1 has the formula: $X_1X_2X_3ESPLSSX_4X_5IFX_6X_7SHA$ (SEQ ID NO: 162), where $X_1$=R, K, V, T, A, S or G; $X_2$=A, T, V, I, N, R, S or L; $X_3$=R or K; $X_4$=D or G; $X_5$=A, T, N, or L; $X_6$=K or R; and $X_7$=Q or H.

Methods for Producing Chimeric DGAT1 Proteins

Methods for producing chimeric proteins, or the polynucleotide sequences encoding them, are well known to those skilled in the art. A chimeric DGAT1 protein may be conveniently be produced by combining, using standard molecular biological techniques such as restriction digestion and ligation, sequences encoding DGAT1 proteins, and then expressing the chimeric DGAT1 protein. Alternatively polynucleotide sequences encoding the chimeric DGAT1 proteins may be conveniently synthesised, and the chimeric proteins expressed from the synthesised sequences. For making multiple chimeric DGAT1 proteins the encoding sequences can be synthesised to include restriction sites that do not alter the amino acid sequence of the expressed proteins. These restrictions sites can be utilised to combine sequences for production and expression of the chimeric proteins. These and similar methods for producing chimeric proteins are known to those skilled in the art.

The first and second DGAT1 protein sequences, and encoding polynucleotides, used to produce the chimeric DGAT1 proteins of the invention, may be selected from those disclosed herein. Alternatively further DGAT1 sequences can be identified by methods well known to those skilled in the art, including bioinformatic database searching, as well as physical cloning methods. The first and second DGAT1 protein sequences may be from any species, including plants, animals and microorganisms.

The phrase "increased DGAT1 activity" means increased specific activity relative to that of the first and/or DGAT1 protein.

An art skilled worker would know how to test the "specific activity" of the chimeric DGAT1. This may typically be done by isolating, enriching and quantifying the recombinant DGAT1 then using this material to determine either the rate of triacylglyceride formation and/or the disappearance of precursor substrates (including various forms of acyl-CoA and DAG) as per Xu et al., (2008), Plant Biotechnology Journal. 6:799-818.

The phrase "increased stability" means that the chimeric DGAT1 protein is more stable, when expressed in a cell, than the first and/or second DGAT1. This may lead to increased accumulation of active chimeric DGAT1 when it is expressed in cells, relative to when the first and/or second DGAT1 is expressed in cells.

Those skilled in the art know how to test the "stability" of the chimeric DGAT1. This would typically involve expressing the chimeric DGAT1 in a cell, or cells, and expressing the first or second DGAT1 in a separate cell, or cells of the same type. Accumulation of chimeric and the first or second DGAT1 protein in the respective cells can then be measured, for example by immunoblot and/or ELISA. A higher level of accumulation of the chimeric DGAT1 relative to the first or second DGAT1, at the same time point, indicates that the chimeric DGAT1 has increased stability. Alternatively, stability may also be determined by the formation of quaternary structure which can also be determined by immunoblot analysis.

The phrase "altered oligomerisation properties" means that the way in which, or the extent to which chimeric DGAT1 forms oligomers is altered relative to the first and/or second DGAT1.

Those skilled in the art know how to test the "oligomerisation properties" of the chimeric DGAT1. This may typically be done by immunoblot analysis or size exclusion chromatography.

The phrase "substantially normal cellular protein accumulation properties" means that the chimeric DGAT1 of the invention retains substantially the same protein accumulation when expressed in a cell, as does the first and/or second DGAT1. That is there is no less accumulation of chimeric DGAT1 than there is accumulation of first and/or second DGAT1, when either are separately expressed in the same cell type.

An art skilled worker would know how to test the "cellular protein accumulation properties" of the chimeric DGAT1. This would typically involve expressing the chimeric DGAT1 in a cell, or cells, and expressing the first or second DGAT1 in a separate cell, or cells of the same type. Accumulation of chimeric and the first or second DGAT1 protein in the respective cells can then be measured, for example by ELISA or immunoblot. A substantially similar level of accumulation of the chimeric DGAT1 relative to the first or second DGAT1, at the same time point, indicates that the chimeric DGAT1 has increased "substantially normal cellular protein accumulation properties".

The phrase "substantially normal subcellular targetting properties" means that the chimeric DGAT1 of the invention retains substantially the same subcellular targetting when expressed in a cell, as does the first and/or second DGAT1. That is the chimeric DGAT1 is targeted to the same subcellular compartment/s as the first and/or second DGAT1, when either are separately expressed in the same cell type.

An art skilled worker would know how to test the "subcellular targetting properties" of the chimeric DGAT1. This would typically involve expressing the chimeric DGAT1 in a cell, or cells, and expressing the first or second DGAT1 in a separate cell, or cells of the same type. Subcellular targetting of chimeric and the first or second DGAT1 protein in the respective cells can then be assessed, for example by using ultracentrifugation to separate and isolating individual subcellular fractions then determining the level of DGAT1 in each fraction. Substantially similar "subcellular targeting" of the chimeric DGAT1 relative to the first or second DGAT1, at the same time point, indicates that the chimeric DGAT1 has increased "substantially normal cellular protein has "substantially normal subcellular targetting properties".

Lipid

In one embodiment the lipid is an oil. In a further embodiment the oil is triacylglycerol (TAG)

Lipid Production

In certain embodiments the cell, cells, tissues, plants and plant parts of the invention produces more lipid than control cells, tissues, plants and plant parts.

Those skilled in the art are well aware of methods for measuring lipid production. This may typically be done by quantitative fatty acid methyl ester gas chromatography mass spectral analysis (FAMES GC-MS). Suitable methods are also described in the examples section of this specification.

Substrate Specificity

In certain embodiments, the polypeptides of the invention have altered substrate specificity relative to parent DGAT1 proteins. Plant DGAT1 proteins are relatively promiscuous in terms of the fatty acid substrates and DAG species they are capable of utilising to generate TAG. As such they can be considered to have relatively low substrate specificity. However, this can be modified such that certain fatty acids become a preferred substrate over others. This leads to an increase in the proportions of the preferred fatty acids in the TAG and decreases in the proportions of the non preferred fatty acid species. Substrate specificity can be determined by in vitro quantitative analysis of TAG production following the addition of specific and known quantities of purified substrates to known quantities of recombinant DGAT, as per Xu et al., (2008), Plant Biotechnology Journal. 6:799-818.

Lipid Profile

In a further embodiment the cell, cells, tissues, plants and plant parts of the invention have an altered lipid profile relative to the control cells, tissues, plants and plant parts.

Those skilled in the art are well aware of methods for assessing lipid profile. This may involve assessing the proportion or percentage of at least one of the 16:0, 16:1, 18:0, 18:1c9 fatty acid species present in the lipid. This may typically be done by fatty acid methyl ester (FAME) analysis (Browse et al., 1986, Anal. Biochem. 152, 141-145). Suitable methods are also described in the examples section of this specification.

Cells

The chimeric DGAT1 of the invention, or as used in the methods of the invention, may be expressed in any cell type.

In one embodiment the cell is a prokaryotic cell. In a further embodiment the cell is a eukaryotic cell. In one embodiment the cell is selected from a bacterial cell, a yeast cell, a fungal cell, an insect cell, algal cell, and a plant cell. In one embodiment the cell is a bacterial cell. In a further embodiment the cell is a yeast cell. In one embodiment the yeast cell is a *S. ceriviseae* cell. In further embodiment the cell is a fungal cell. In further embodiment the cell is an insect cell. In further embodiment the cell is an algal cell. In a further embodiment the cell is a plant cell.

In one embodiment the cell is a non-plant cell. In one embodiment the non-plant is selected from *E. coli, P. pastoris, S. ceriviseae, D. salina* and *C. reinhardtii*. In a further embodiment the non-plant is selected from *P. pastoris, S. ceriviseae, D. Salina* and *C. reinhardtii*.

In one embodiment the cell is a microbial cell. In another embodiment, the microbial cell is an algal cell of the division of Chlorophyta (green algae), Rhodophyta (red algae), Phaeophyceae (brown algae), Bacillariophycaeae (diatoms), or Dinoflagellata (dinoflagellates). In another embodiment, the microbial cell is an algal cell of the species *Chlamydomonas, Dunaliella, Botrycoccus, Chlorella, Cypthecodinium, Gracilaria, Sargassum, Pleurochrysis, Porpbyridium, Phaeodactylum, Haematococcus, Isochrysis, Scenedesmus, Monodus, Cyclotella, Nitzschia,* or *Parietochloris*. In another embodiment, the algal cell is *Chlamydomonas reinhardtii*. In yet another embodiment, the cell is from the genus *Yarrowia, Candida, Rhodotorula, Rhodosporidium, Cryptococcus, Trichosporon, Lipomyces, Pythium, Schizochytrium, Thraustochytrium,* or *Ulkenia*. In yet another embodiment, the cell is a bacterium of the genus *Rhodococcus, Escherichia,* or a cyanobacterium. In yet another embodiment, the cell is a yeast cell. In yet another embodiment, the cell is a synthetic cell.

Plants

The first and/or second DGAT1 sequences, from which the chimeric DGAT1 sequences are produced, may be naturally-occurring DGAT1 sequences. Preferably the first and/or DGAT1 sequences are from plants. In certain embodiments the cells into which the chimeric DGAT1 proteins are expressed are from plants. In other embodiments the chimeric DGAT1 proteins are expressed in plants.

The plant cells, from which the first and/or second DGAT1 proteins are derived, the plants from which the plant cells are derived, and the plants in which the chimeric DGAT1 proteins are expressed may be from any plant species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Other preferred plants are forage plant species from a group comprising but not limited to the following genera: *Zea, Lolium, Hordium, Miscanthus, Saccharum, Festuca, Dactylis, Bromus, Thinopyrum, Trifolium, Medicago, Pheleum, Phalaris, Holcus, Glycine, Lotus, Plantago* and *Cichorium*.

Other preferred plants are leguminous plants. The leguminous plant or part thereof may encompass any plant in the plant family Leguminosae or Fabaceae. For example, the plants may be selected from forage legumes including, alfalfa, clover; leucaena; grain legumes including, beans, lentils, lupins, peas, peanuts, soy bean; bloom legumes including lupin, pharmaceutical or industrial legumes; and fallow or green manure legume species.

A particularly preferred genus is *Trifolium*. Preferred *Trifolium* species include *Trifolium repens; Trifolium arvense; Trifolium affine*; and *Trifolium occidentale*. A particularly preferred *Trifolium* species is *Trifolium repens*.

Another preferred genus is *Medicago*. Preferred *Medicago* species include *Medicago sativa* and *Medicago truncatula*. A particularly preferred *Medicago* species is *Medicago sativa*, commonly known as alfalfa.

Another preferred genus is *Glycine*. Preferred *Glycine* species include *Glycine max* and *Glycine wightii* (also known as *Neonotonia wightii*). A particularly preferred *Glycine* species is *Glycine max*, commonly known as soy bean. A particularly preferred *Glycine* species is *Glycine wightii*, commonly known as perennial soybean.

Another preferred genus is *Vigna*. A particularly preferred *Vigna* species is *Vigna unguiculata* commonly known as cowpea.

Another preferred genus is *Mucana*. Preferred *Mucana* species include *Mucana pruniens*. A particularly preferred *Mucana* species is *Mucana pruniens* commonly known as velvetbean.

Another preferred genus is *Arachis*. A particularly preferred *Arachis* species is *Arachis glabrata* commonly known as perennial peanut.

Another preferred genus is *Pisum*. A preferred *Pisum* species is *Pisum sativum* commonly known as pea.

Another preferred genus is *Lotus*. Preferred *Lotus* species include *Lotus corniculatus, Lotus pedunculatus, Lotus glabar, Lotus tenuis* and *Lotus uliginosus*. A preferred *Lotus* species is *Lotus corniculatus* commonly known as Birdsfoot Trefoil. Another preferred *Lotus* species is *Lotus glabar* commonly known as Narrow-leaf Birdsfoot Trefoil. Another preferred *Lotus* species is *Lotus pedunculatus* commonly known as Big trefoil. Another preferred *Lotus* species is *Lotus tenuis* commonly known as Slender trefoil.

Another preferred genus is *Brassica*. A preferred *Brassica* species is *Brassica oleracea*, commonly known as forage kale and cabbage. A preferred *Brassica* genus is *Camelina*. A preferred *Camelina* species is *Camelina sativa*.

Other preferred species are oil seed crops including but not limited to the following genera: *Brassica, Carthamus, Helianthus, Zea* and *Sesamum*.

A preferred oil seed genera is *Brassica*. A preferred oil seed species is *Brassica napus*.

A preferred oil seed genera is *Brassica*. A preferred oil seed species is *Brassica oleraceae*.

A preferred oil seed genera is *Carthamus*. A preferred oil seed species is *Carthamus tinctorius*.

A preferred oil seed genera is *Helianthus*. A preferred oil seed species is *Helianthus annuus*.

A preferred oil seed genera is *Zea*. A preferred oil seed species is *Zea mays*.

A preferred oil seed genera is *Sesamum*. A preferred oil seed species is *Sesamum indicum*.

A preferred silage genera is *Zea*. A preferred silage species is *Zea mays*.

A preferred grain producing genera is *Hordeum*. A preferred grain producing species is *Hordeum vulgare*.

A preferred grazing genera is *Lolium*. A preferred grazing species is *Lolium perenne*.

A preferred grazing genera is *Lolium*. A preferred grazing species is *Lolium arundinaceum*.

A preferred grazing genera is *Trifolium*. A preferred grazing species is *Trifolium repens*.

A preferred grazing genera is *Hordeum*. A preferred grazing species is *Hordeum vulgare*.

Preferred plants also include forage, or animal feedstock plants. Such plants include but are not limited to the following genera: *Miscanthus, Saccharum, Panicum*.

A preferred biofuel genera is *Miscanthus*. A preferred biofuel species is *Miscanthus giganteus*.

A preferred biofuel genera is *Saccharum*. A preferred biofuel species is *Saccharum officinarum*.

A preferred biofuel genera is *Panicum*. A preferred biofuel species is *Panicum virgatum*.

Plant Parts, Propagues and Progeny

The term "plant" is intended to include a whole plant, any part of a plant, a seed, a fruit, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting progeny, comprising the polynucleotides or constructs of the invention, and/or expressing the chimeric DGAT1 sequences of the invention, also form an part of the present invention.

Preferably the plants, plant parts, propagules and progeny comprise a polynucleotide or construct of the invention, and/or express a chimeric DGAT1 sequence of the invention.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques.

A "fragment" of a polypeptide is a subsequence of the polypeptide that preferably performs a function of and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from the NCBI website on the World Wide Web at ftp<dot>ncbi<dot>nih<dot>gov/blast. The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from the World Wide Web at www<dot>hgmp<dot>mrc<dot>ac<dot>uk/Software/EMBOSS. The European Bioinformatics Institute server also provides the facility to perform EMBOSS-needle global alignments between two sequences on line at www<dot>ebi<dot>ac<dot>uk/emboss/align.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from the NCBI website on the World Wide Web at ftp<dot>ncbi<dot>nih<dot>gov/blast.

The similarity of polynucleotide sequences may be examined using the following unix command line parameters:

bl2seq nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention, or used in the methods of the invention, hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 by is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention, or used in the methods of the invention, also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from the NCBI website on the World Wide Web at ftp<dot>ncbi<dot>nih<dot>gov/blast via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from the NCBI website on the World Wide Web at ftp<dot>ncbi<dot>nih<dot>gov/blast. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at www<dot>ebi<dot>ac<dot>uk/emboss/align) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

Polypeptide variants of the present invention, or used in the methods of the invention, also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from the NCBI website on the World Wide Web at ftp<dot>ncbi<dot>nih<dot>gov/blast. The similarity of polypeptide sequences may be examined using the following unix command line parameters:

bl2seq -i peptideseq1 -j peptideseq2 -F F -p blastp

Variant polypeptide sequences preferably exhibit an E value of less than $1\times10$-6 more preferably less than $1\times10$-9, more preferably less than $1\times10$-12, more preferably less than $1\times10$-15, more preferably less than $1\times10$-18, more preferably less than $1\times10$-21, more preferably less than $1\times10$-30, more preferably less than $1\times10$-40, more preferably less than $1\times10$-50, more preferably less than $1\times10$-60, more preferably less than $1\times10$-70, more preferably less than $1\times10$-80, more preferably less than $1\times10$-90 and most preferably $1\times10$-100 when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence may, in some cases, identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination, mRNA stability, and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors. Introns within coding sequences can also regulate transcription and influence post-transcriptional processing (including splicing, capping and polyadenylation).

A promoter may be homologous with respect to the polynucleotide to be expressed. This means that the promoter and polynucleotide are found operably linked in nature.

Alternatively the promoter may be heterologous with respect to the polynucleotide to be expressed. This means that the promoter and the polynucleotide are not found operably linked in nature.

In certain embodiments the chimeric DGAT1 polynucleotides/polypeptides of the invention may be advantageously expressed under the control of selected promoter sequences as described below.

Vegetative Tissue Specific Promoters

An example of a vegetative specific promoter is found in U.S. Pat. No. 6,229,067; and U.S. Pat. No. 7,629,454; and U.S. Pat. No. 7,153,953; and U.S. Pat. No. 6,228,643.

Pollen Specific Promoters

An example of a pollen specific promoter is found in U.S. Pat. No. 7,141,424; and U.S. Pat. No. 5,545,546; and U.S. Pat. No. 5,412,085; and U.S. Pat. No. 5,086,169; and U.S. Pat. No. 7,667,097.

Seed Specific Promoters

An example of a seed specific promoter is found in U.S. Pat. No. 6,342,657; and U.S. Pat. No. 7,081,565; and U.S. Pat. No. 7,405,345; and U.S. Pat. No. 7,642,346; and U.S. Pat. No. 7,371,928. A preferred seed specific promoter is the napin promoter of *Brassica napus* (Josefsson et al., 1987, J Biol Chem. 262(25):12196-201; Ellerström et al., 1996, Plant Molecular Biology, Volume 32, Issue 6, pp 1019-1027).

Fruit Specific Promoters

An example of a fruit specific promoter is found in U.S. Pat. No. 5,536,653; and U.S. Pat. No. 6,127,179; and U.S. Pat. No. 5,608,150; and U.S. Pat. No. 4,943,674.

Non Photosynthetic Tissue Preferred Promoters

Non-photosynthetic tissue preferred promoters include those preferentially expressed in non-photosynthetic tissues/organs of the plant.

Non-photosynthetic tissue preferred promoters may also include light repressed promoters.

Light Repressed Promoters

An example of a light repressed promoter is found in U.S. Pat. No. 5,639,952 and in U.S. Pat. No. 5,656,496.

Root Specific Promoters

An example of a root specific promoter is found in U.S. Pat. No. 5,837,848; and US 2004/0067506 and US 2001/0047525.

Tuber Specific Promoters

An example of a tuber specific promoter is found in U.S. Pat. No. 6,184,443.

Bulb Specific Promoters

An example of a bulb specific promoter is found in Smeets et al., (1997) Plant Physiol. 113:765-771.

Rhizome Preferred Promoters

An example of a rhizome preferred promoter is found Seong Jang et al., (2006) Plant Physiol. 142:1148-1159.

Endosperm Specific Promoters

An example of an endosperm specific promoter is found in U.S. Pat. No. 7,745,697.

Corm Promoters

An example of a promoter capable of driving expression in a corm is found in Schenk et al., (2001) Plant Molecular Biology, 47:399-412.

Photosynthetic Tissue Preferred Promoters

Photosynthetic tissue preferred promoters include those that are preferentially expressed in photosynthetic tissues of the plants. Photosynthetic tissues of the plant include leaves, stems, shoots and above ground parts of the plant. Photosynthetic tissue preferred promoters include light regulated promoters.

Light Regulated Promoters

Numerous light regulated promoters are known to those skilled in the art and include for example chlorophyll a/b (Cab) binding protein promoters and Rubisco Small Subunit (SSU) promoters. An example of a light regulated promoter is found in U.S. Pat. No. 5,750,385. Light regulated in this context means light inducible or light induced.

A "transgene" is a polynucleotide that is taken from one organism and introduced into a different organism by transformation. The transgene may be derived from the same species or from a different species as the species of the organism into which the transgene is introduced.

Host Cells

Host cells may be derived from, for example, bacterial, fungal, yeast, insect, mammalian, algal or plant organisms. Host cells may also be synthetic cells. Preferred host cells are eukaryotic cells. A particularly preferred host cell is a plant cell, particularly a plant cell in a vegetative tissue of a plant.

A "transgenic plant" refers to a plant which contains new genetic material as a result of genetic manipulation or transformation. The new genetic material may be derived from a plant of the same species as the resulting transgenic plant or from a different species.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrive and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp<dot>ncbi<dot>nih<dot>gov/blast) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database.

BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, www-igbmc<dot>u-strasbg<dot>fr/BioInfo/ClustalW/Top<dot>html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www<dot>expasy<dot>org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, 1990, Ed, Methods in Enzymology, Vol. 182, Guide to Protein Purification,).

Alternatively the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Helens R P, et al., (2000) Plant Mol Biol 42: 819-32, Helens R et al., Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detect presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues respond to internal developmental signals or external abiotic or biotic stresses are described in the scientific literature. Exemplary promoters are described, e.g., in WO 02/00894 and WO2011/053169, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463, 174 and 5,750,871); cereals (U.S. Pat. No. 6,074,877); pear (Matsuda et al., 2005, Plant Cell Rep. 24(1):45-51); Prunus (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), Rubus (Graham et al., 1995 Methods Mol Biol. 1995; 44:129-33), tomato (Dan et al., 2006, Plant Cell Reports V25:432-441), apple (Yao et al., 1995, Plant Cell Rep. 14, 407-412), Canola (*Brassica napus* L.). (Cardoza and Stewart, 2006 Methods Mol Biol. 343:257-66), safflower (Orlikowska et al, 1995, Plant Cell Tissue and Organ Culture 40:85-91), ryegrass (Altpeter et al, 2004 Developments in Plant Breeding 11(7):255-250), rice (Christou et al, 1991 Nature Biotech. 9:957-962), maize (Wang et al., 2009 In: Handbook of Maize pp. 609-639) and *Actinidia eriantha* (Wang et al., 2006, Plant Cell Rep. 25, 5: 425-31). Transformation of other species is also contemplated by the invention. Suitable methods and protocols are available in the scientific literature.

BRIEF DESCRIPTION OF THE FIGURES

FIG. 1 shows the nucleic acid sequence and three frame translation of the *Arabidopsis thaliana* DGAT1 transcribed region (SEQ ID NO:128). Exon coding sequences are shown in bold face, underlined, grey blocks.

FIG. 2 shows the nucleic acid sequence and three frame translation of the Zea mays short DGAT1 transcribed region (SEQ ID NO:129). This genomic sequence has F469 deleted and Q67 added compared to the cDNA (EU039830) and peptide (ABV91586) sequences actually used in this patent. Exon coding sequences are shown in bold face, underlined, grey blocks.

FIG. 3 shows the peptide sequence of the N-terminal cytoplasmic region of a number of plant DGAT1s including both long and short versions from the grasses as well as examples from dicotyledonous species. Left hand box represents acyl-CoA binding site (Nykiforuk et al., 2002, Biochimica et Biophysica Acta 1580:95-109). Right hand box represents first transmembrane region (McFie et al., 2010, JBC., 285:37377-37387). Left hand arrow represents boundary between exon 1 and exon 2. Right hand arrow represents boundary between exon 2 and exon 3. The sequences are AtDGAT1 (SEQ ID NO:130), BjDGAT1 (SEQ ID NO:131), BnDGAT1-AF (SEQ ID NO:132), BjDGAT1 (SEQ ID NO:133), TmajusDGAT1 (SEQ ID NO:134), EpDGAT1 (SEQ ID NO:135), VgDGAT1 (SEQ ID NO:136), NtDGAT1 (SEQ ID NO:137), PfDGAT1 (SEQ ID NO:138), ZmL (SEQ ID NO:139), SbDGAT1 (SEQ ID NO:140), OsL (SEQ ID NO:141), OsS (SEQ ID NO:142), SbDGAT1 (SEQ ID NO:143), ZmS (SEQ ID NO:144), PpDGAT1 (SEQ ID NO:145), SmDGAT1 (SEQ ID NO:146), EaDGAT1 (SEQ ID NO:147), VvDGAT1 (SEQ ID NO:148), GmDGAT1 (SEQ ID NO:149), GmDGAT1 (SEQ ID NO:150), LjDGAT1 (SEQ ID NO:151), MtDGAT1 (SEQ ID NO:152), JcDGAT1 (SEQ ID NO:153), VfDGAT1 (SEQ ID NO:154), RcDGAT1 (SEQ ID NO:155), PtDGAT1 (SEQ ID NO:156), Pt DGAT1 (SEQ ID NO:157).

EXAMPLES

Figure 4:
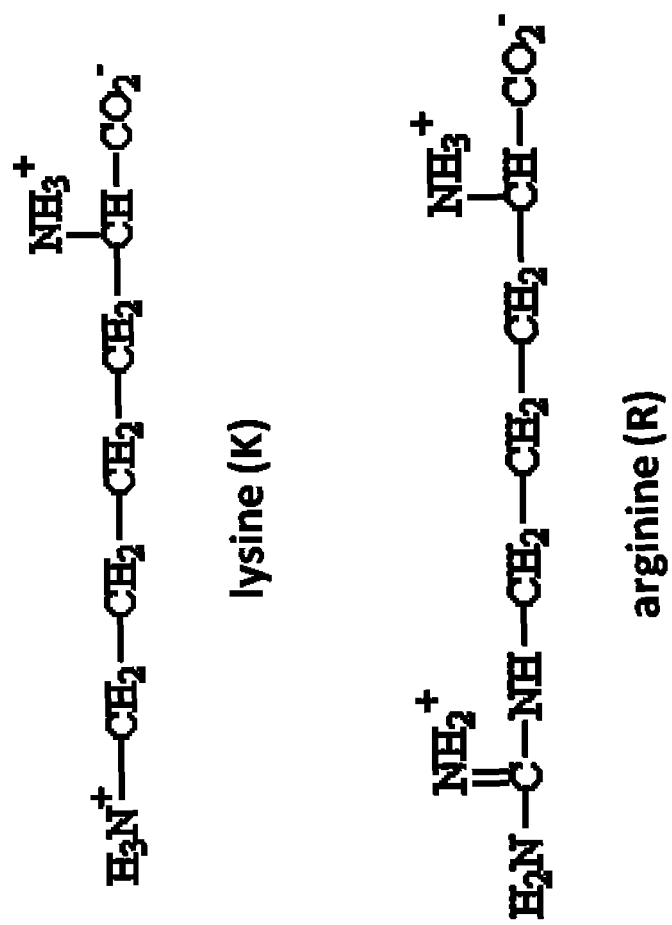
FIG. 4 shows the line-bond structures of the amino acid residues lysine (K) and arginine (R).

Example 1: Plant DGAT1 Sequence Selection and Splice Site Prediction

The majority of nucleic acid sequences and peptide sequences for the plant type 1 DGATs can be found by accession number in public domain libraries (Table 1). For creating initial alignments we used ClustalW (Thompson et al., 1994, Nucleic Acids Res., 22, 4673-4680); these were manually edited and used to create the models to search the DGAT sequences, using the HMMER2 package (HMMER 2.3.2 (October 2003) Copyright © 1992-2003 HHMI/Washington University School of Medicine, available from the World Wide Web at http: hmmer<dot>org). Initial matching of protein sequences against genomic DNA with splice prediction was performed with the GeneWise package (Birney et al., 2004, Genome Res. 14: 988-995). Some of the sequences retrieved appeared to have errors; in particular incorrectly predicted splice sites which would result in internal deletions that would likely result in non-functional proteins. While both dicotyledonous and monocotyledonous type 1 DGATs have 16 exons there are some differences in the position of the splicing. Exon 8 in the dicotylendonous DGAT1 gene corresponds to exons 8 and 9 in the monocotyledonous DGAT1 gene, while exon 14 in the monocotyledonous gene corresponds to exons 13 and 14 in the dicotyledonous gene. We have found that the most accurate method for determining the likely genuine coding sequence from genomic data has been to use Vector NTI Advance™ 11.0 (© 2008 Invitrogen Corporation) to translate the genome in the three forward reading frames and align these with demonstrated functional DGAT1s from dicotyledonous or monocotyledous species as appropriate (for example A. thaliana cDNA NM_127503, protein NP_179535 and Z. mays cDNA EU039830, protein ABV91586). The genomic sequence and corresponding exon/intron boundary positions for Arabidopsis thaliana encoding NP_179535 and Zea mays encoding ABV91586 that can be used as a template for determining other plant DGAT coding regions are shown in FIG. 1 and FIG. 2, respectively. An example of this template use is shown for the determination of Z. mays DGAT1 SEQ ID NO: 10 and SEQ ID NO: 39.

TABLE 1

| DGAT1 Species Source | DNA accession #s & BAC # | SEQ ID NO: | PROTEIN accession #s & BAC # | SEQ ID NO: |
|---|---|---|---|---|
| A. thaliana | NM_127503 | 1 | NP_179535 | 30 |
| B. juncea | AF164434 | 2 | AAY40784 | 31 |
| B. napus | AF164434_1 | 3 | AAD45536.1 | 32 |
| B. juncea | DQ016107 | 4 | AAY40785 | 33 |
| T. majus | AY084052 | 5 | AAM03340 | 34 |
| E. pitardii | FJ226588 | 6 | ACO55635 | 35 |
| V. galamensis | EF653276 | 7 | ABV21945 | 36 |
| N. tabacum | AF129003_1 | 8 | AAF19345.1 | 37 |
| P. frutescens | AF298815_1 | 9 | AAG23696.1 | 38 |
| Z. mays | From: CHORI-201 Maize B73 BAC | 10 | From: CHORI-201 Maize B73 BAC | 39 |
| S. bicolor | XM_002439374 | 11 | XP_002439419 | 40 |
| O. sativa | Os05g0196800 | 12 | NP_001054869 | 41 |
| O. sativa | From: AP003714.1 | 13 | From: AP003714.1 | 42 |
| S. bicolor | XM_002437120.1 | 14 | XP_002437165 | 43 |
| Z. mays | EU039830 | 15 | ABV91586 | 44 |
| P. patens | XM_001770877.1 | 16 | XP_001770929 | 45 |
| S. moellendorffii | XM_002964119 | 17 | XP_002964165 | 46 |
| E. alatus | AY751297 | 18 | AAV31083 | 47 |
| V. vinifera | XM_002279309 | 19 | XP_002279345 | 48 |
| G. max | AY496439 | 20 | AAS78662 | 49 |
| G. max | AB257590 | 21 | BAE93461 | 50 |
| L. japonicus | AY859489 | 22 | AAW51456 | 51 |
| M. truncatula | AC174465.2 | 23 | ABN09107 | 52 |
| J. curcas | DQ278448.1 | 24 | ABB84383 | 53 |
| V. fordii | DQ356680.1 | 25 | ABC94472 | 54 |
| V. galamensis | EF653276.1 | 26 | ABV21945 | 55 |
| R. communis | XM_002514086.1 | 27 | XP_002514132 | 56 |
| P. trichocarpa | XM_002308242.1 | 28 | XP_002308278 | 57 |
| P. trichocarpa | XM_002330474.1 | 29 | XP_002330510 | 58 |

Example 2: Production of Chimeric DGAT1 Proteins for Expression in Cells

Nucleic acid constructs encoding the amino acid sequences, SEQ ID NO: 30, 34, 39, 41, 42 and 44 (Table 1) were optimised for expression in Saccharomyces cerevisiae by GeneArt AG (Germany). These were engineered to have an internal XhoI site within exon 1 encoding the conserved N-terminal acyl-Co binding region (identified by Weselake 2006) without altering the amino acid sequence leucine-serine-serine (LSS).

FIG. 3 shows alignment of a number of DGAT1 sequences from plants. The left box shows the position of the Acyl-CoA binding site.

An EcoRI site was engineered upstream of the 5' coding sequence while an XbaI site was placed downstream of the 3' stop codon. The internal XhoI and flanking EcoRI and XbaI sites were used to generate chimeras between each of the original DGAT1 clones; essentially this fused the N-terminal reputed cytoplasmic region (based on Weselake et al 2006 and McFie et al, 2010) from one DGAT1 with the C-terminal ER luminal region of a different DGAT1. In some combinations this resulted in one amino acid change in the remaining cytoplasmic region downstream of the engineered XhoI site. The putative acyl-Co binding region the *A. thaliana* DGAT1, *T. majus* DGAT1, *Z. mays*-L DGAT1 and *O. sativa*-L DGAT1 have an identical amino acid sequence down stream of the XhoI site (LSSDAIFKQSHA) (SEQ ID NO: 163). While in the *Z. mays*-S DGAT1 and *O. sativa*-S DGAT1 the lysine (K) residue is replaced by an arginine (R) residue (LSSDAIFRQSHA) (SEQ ID NO: 164). Since the position of this residue is located 3' to the Xho I site encoded by LLS then chimeras deriving from one parent containing the lysine and one parent containing the arginine residue will effectively result in a substitution of this residue. This was considered to be a minimal disruption since both lysine and arginine are large, positively charged, hydrophilic, basic amino acids containing a free amine or guanidinium group, respectively at the end of an aliphatic side chain (FIG. 4). The complete list of N-terminal region/C-terminal region domain swapping constructs are found in Table 2, with the corresponding SEQ ID NO: 59-94.

TABLE 2

| DGAT1 N-terminal parent | DGAT1 C-terminal parent | C-terminal Tail Fusion | SEQ ID NO: |
|---|---|---|---|
| A. thaliana | A. thaliana | V5-6xHis | 59 |
| A. thaliana | O. sativa-S | V5-6xHis | 60 |
| A. thaliana | O. sativa-L | V5-6xHis | 61 |
| A. thaliana | Z. mays-S | V5-6xHis | 62 |
| A. thaliana | Z. mays-L | V5-6xHis | 63 |
| A. thaliana | T. majus | V5-6xHis | 64 |
| O. sativa-S | O. sativa-S | V5-6xHis | 65 |
| O. sativa-S | A. thaliana | V5-6xHis | 66 |
| O. sativa-S | O. sativa-L | V5-6xHis | 67 |
| O. sativa-S | Z. mays-S | V5-6xHis | 68 |
| O. sativa-S | Z. mays-L | V5-6xHis | 69 |
| O. sativa-S | T. majus | V5-6xHis | 70 |
| O. sativa-L | O. sativa-L | V5-6xHis | 71 |
| O. sativa-L | A. thaliana | V5-6xHis | 72 |
| O. sativa-L | O. sativa-S | V5-6xHis | 73 |
| O. sativa-L | Z. mays-S | V5-6xHis | 74 |
| O. sativa-L | Z. mays-L | V5-6xHis | 75 |
| O. sativa-L | T. majus | V5-6xHis | 76 |
| Z. mays-S | Z. mays-S | V5-6xHis | 77 |
| Z. mays-S | A. thaliana | V5-6xHis | 78 |
| Z. mays-S | O. sativa-S | V5-6xHis | 79 |
| Z. mays-S | O. sativa-L | V5-6xHis | 80 |
| Z. mays-S | Z. mays-L | V5-6xHis | 81 |
| Z. mays-S | T. majus | V5-6xHis | 82 |
| Z. mays-L | Z. mays-L | V5-6xHis | 83 |
| Z. mays-L | A. thaliana | V5-6xHis | 84 |
| Z. mays-L | O. sativa-S | V5-6xHis | 85 |
| Z. mays-L | O. sativa-L | V5-6xHis | 86 |
| Z. mays-L | Z. mays-S | V5-6xHis | 87 |
| Z. mays-L | T. majus | V5-6xHis | 88 |
| T. majus | T. majus | V5-6xHis | 89 |
| T. majus | A. thaliana | V5-6xHis | 90 |
| T. majus | O. sativa-S | V5-6xHis | 91 |
| T. majus | O. sativa-L | V5-6xHis | 92 |
| T. majus | Z. mays-S | V5-6xHis | 93 |
| T. majus | Z. mays-L | V5-6xHis | 94 |

Sequences were synthesised either by GENEART AG (Germany) or GeneScript (USA). Sequences were optimised for expression in *Saccharomyces cerevisiae* and flanked with appropriate incorporated appropriate restriction sites to facilitate the cloning into the pYES2.1 vector (Invitrogen).

Example 3: Expression of Chimeric DGAT1 Sequences in Cells

Expression of Constructs in *S. cerevisiae*

The parent DGAT1 constructs and chimeric DGAT1 constructs were placed into the galactose-inducible yeast expression vector pYES2.1/V5-His TOPO® (Invitrogen). This resulted in the addition of an inframe C-terminal V5 epitope and 6x histidine tag. The name of the chimeric constructs and the number of their corresponding peptide sequences are shown in Table 2.

The *Saccharomyces cerevisiae* quadruple mutant (H1246) in which all four neutral lipid biosynthesis genes have been disrupted (Sandager et al., 2002, The Journal of Biological Chemistry, 277:6478-6482) was transformed as per Elble (1992, BioTechniques 13, 18-20) and selected by the ability to grow in the absence of uracil. Routinely, yeast cells were grown aerobically overnight in a synthetic medium with 0.67% YNB, without uracil (SC-U) and containing 2% glucose. Cells from overnight culture were used to inoculate 200 mL of induction medium (SC-U containing 2% galactose and 1% raffinose) to an initial $OD_{600}$ of 0.4. Cells were allowed to further grow at 30° C., with shaking at 200 rpm until late stationary phase, normally 48 h. Cells were harvested by centrifugation at 1500xg for 5 min, then cell pellets were washed with distilled water and either used immediately for subsequent analysis or kept in −80° C. until required. Cell pellets for neutral lipid extraction were freeze-dried for 48 h and stored in −20° C. freezer until required.

Lipid Analysis of *S. cerevisiae*

Approximately 10 mg of freeze-dried yeast cell material was accurately weighed then disrupted using glass beads by vortexing for 1 minute. This lysate was extracted in hot methanolic HCL for fatty acid methyl ester (FAME) analysis (Browse et al., 1986, Anal. Biochem. 152, 141-145).

For FA profile analysis approximately 50 mg freeze dried yeast was placed in a 13-mm screw cap tube, and an equal volume of glass beads added before vortexing at high speed in 3x1 min bursts. Following addition of 50 µg of 19:0 TAG internal standard, 2.4 mL of 0.17 M NaCl in MeOH was added and the mixture vortexed for 15 sec followed by the addition of then 4.8 mL of heptane and the entire contents mixed.

The solution was then incubated in 80° C. water bath for 2 h without shaking. After incubation, the solution was cooled to room temperature. After cooling, the upper phase (lipidic phase) was transferred to fresh screw-cap tube and evaporated to dryness under stream of nitrogen gas. The dried residue was then dissolved in 1 mL heptane and mixed thoroughly for TAG SPE separation using Strata Si-1 Silica column (Phenomenwx, 8B-S012-EAK).

After preconditioning with methanol and equilibrating the Silica column with heptanes the 1 mL TAG extract (including 50 µg 17:0 TAG Internal Standard was passed through the pre-equilibrated column, followed by 1.2 mL of heptane and then 2 mL of chloroform:heptane (1:9 v/v/) and the eluate collected. The total eluate collected was evaporated to dryness under the stream of N gas and the residue used for FAMEs extraction.

FAMEs of Extracted TAG

To the TAG residue above 10 µL of internal standard 15:0 FA (4 mg/mL dissolved in heptane) and 1 mL of methanolic HCl (1N) reagent containing 5% of 2,2-dimeethoxypropane (as water scavenger) were added.

The tube was then flushed with N gas, then sealed immediately with Teflon-lined cap, and heated at 80° C. in a water bath for 1 h. After cooling down, 0.6 mL heptane and 1.0 mL of 0.9% (w/v) NaCl was added, the mixture vortexed then spun at 500 rpm for 1 min.

From the top heptane layer, 100 μL was collected and transferred to a flat-bottom glass insert fitted into a vial for FAMES GC/MS analysis.

Protein Extraction and Trypsin Digestion

Yeast cell pellets were washed with lysis buffer (50 mM sodium phosphate, pH 7.4, 1 mM EDTA, 5% glycerol, 1 mM PMSF) then resuspended in 500 μL lysis buffer, glass beads were added and cells disrupted by vortexing 2× at medium speed for 30 seconds. Cell debris was pelleted by centrifugation at 1000×g for 5 min, the supernatant transferred to fresh tubes and total cellular membranes pelleted by ultracentrifugation at 100,000×g for 1 h. Membrane proteins were resuspended in lysis buffer with or without detergent (1% Dodecyl maltoside) and quantified in a Qubit Fluorometer using the Qubit IT Quantitation Kit.

Trypsin was added to give a final concentration of 25 μg/mL to 50 μL of protein extract and the mixture incubated at 30° C. for 30 min. The reaction was terminated by addition of Trypsin inhibitor from *Glycine max* (Sigma-Aldrich catalogue # T6414) to a final concentration of 0.4 μg/μL. After addition of trypsin inhibitor, 4×SDS loading dye and 10× reducing agent (Invitrogen) were added, and the protein incubated at 70° C. for 10 min prior to SDS-PAGE followed by immunoblotting. The blot was probed with either Anti V5-HRP antibody (Cat #R96125, Invitrogen) at 1:2500 dilution, or anti Kar2 (y-115) antibody produced in rabbit (SC-33630, Santa Cruz Biotechnology) at 1:200 dilution. Anti Kar2 was used to detect the yeast protein Kar2, an ER luminaly-located protein (Rose et al., 1989, Cell 57, 1211-1221) which serves as a control to demonstrate the presence of intact microsomes.

Example 4: Expression of Chimeric DGAT1 in *Brassica napus*

The same strategy, as described in Example 2, was used to generate a variety of chimeric DGAT1 constructs for expression in the seeds of *Brassica napus*. This included the parent DGAT1s of *T. majus* DGAT1, *Z. mays*-L DGAT1 and *Z. mays*-S DGAT1 (amino acid SEQ ID NO: 34, 39 and 44 respectively, Table 1) optimised for expression in *Brassica napus* by GeneArt AG. The *T. majus* construct was engineered to contain a single point mutation $S_{197}A$ (Xu et al., 2008, Plant Biotechnology Journal, 6:799-818). All constructs were engineered to have an optimised Kozak, *Arabidopsis thaliana* UBQ10 intron, and tetranucleotide stop codon as per Scott et al., (2010, Plant Biotechnology Journal, 8:912-917) as indicated in Table 3 below.

TABLE 3

| DGAT1 Parent Species | Kozak, intron, stop codon | Residue modification | SEQ ID NO: |
|---|---|---|---|
| T. majus | yes | S197A | 95 |
| Z. mays-S | yes | none | 96 |
| Z. mays-L | yes | none | 97 |

The same digestion pattern used to generate the chimeras for expression in *S. cerevisiae* (Example 2) were used on the *B. Napus*-optimised constructs to generate the chimeras Tm-ZmS; Tm-ZmL; ZmS-Tm(S170A); ZmL-Tm(S189A); resulting in the peptide sequences listed in Table 4 (Region 1 DGAT1 chimeras for expression in *Brassica napus*).

TABLE 4

| DGAT1 N-terminal parent | DGAT1 C-terminal parent | Residue modification | SEQ ID NO: |
|---|---|---|---|
| T. majus | T. majus | S197A | 98 |
| Z. mays-S | Z. mays-S | none | 99 |
| Z. mays-L | Z. mays-L | none | 100 |
| T. majus | Z. mays-S | none | 101 |
| T. majus | Z. mays-L | none | 102 |
| Z. mays-S | T. majus | S170A | 103 |
| Z. mays-L | T. majus | S189A | 104 |

The parent DGATs and their chimeras were transferred into the Gateway®-compatible binary vector pMD107 (courtesy of Dr Mark Smith, NRC Saskatoon, SK, Canada, S7N 0W9) which placed them under the control of the seed-specific napin promoter (Ellerström et al., 1996, Plant Molecular Biology, Volume 32, Issue 6, pp 1019-1027).

Plant Transformation

*B. napus* (cv. DH12075) was transformed via *Agrobacterium tumefaciens* (GV3101) using the cotyledon co-cultivation method (adapted from that of Maloney et al., 1989, Plant Cell Rep. 8, 238-242). Control lines contained an empty-vector, and when identified, null sibling lines were subsequently used as true controls.

Approximately 200 $T_0$ transformed lines were produced and their corresponding $T_1$ selfed seeds were analysed for oil content by GC. Approximately 50 individual transgenic lines (including control lines) were selected for the next generation (10 plants/line) based on their oil content, or seed weight (8 lines).

A total of approximately $T_1$ plants were grown and screened by PCR for copy number and identification of null sibing lines. $T_2$ seeds were analysed in triplicate for oil content by NMR.

Example 5: Expression of Chimeric DGAT1 in *Camelina sativa*

The strategy above can also be used to generate a variety of chimeric DGAT1 constructs for expression in the seeds of *Camelina sativa* and other plants.

Sequences with modifications were synthesised either by GENEART AG (Germany) or GeneScript (USA). Sequences were optimised for expression in *Brassica* species and included an intron (SEQ ID NO:105) from *Arabidopsis thaliana* DGAT1-intron 3. Each sequence was flanked with appropriate attL recombination sites to enable the cloning Gateway® adapted vectors.

TABLE 5

| DGAT1 N-terminal parent | DGAT1 C-terminal parent | Residue modification | C-terminal mod | Additional information | Type of sequence | SEQ ID NO: |
|---|---|---|---|---|---|---|
| T. majus | T. majus | S197A | V5-His tag | +intron | NUCLEIC | 106 |
| T. majus | T. majus | S197A | V5-His tag | ORF only | NUCLEIC | 107 |
| T. majus | T. majus | S197A | V5-His tag | | PEPTIDE | 108 |
| Z. mays-L | Z. mays-L | None | V5-His tag | +intron | NUCLEIC | 109 |
| Z. mays-L | Z. mays-L | None | V5-His tag | ORF only | NUCLEIC | 110 |
| Z. mays-L | Z. mays-L | None | V5-His tag | | PEPTIDE | 111 |
| T. majus | Z. mays-L | None | V5-His tag | +intron | NUCLEIC | 112 |
| T. majus | Z. mays-L | None | V5-His tag | ORF only | NUCLEIC | 113 |
| T. majus | Z. mays-L | None | V5-His tag | | PEPTIDE | 114 |
| Z. mays-L | T. majus | S189A | V5-His tag | +intron | NUCLEIC | 115 |
| Z. mays-L | T. majus | S189A | V5-His tag | ORF only | NUCLEIC | 116 |
| Z. mays-L | T. majus | S189A | V5-His tag | | PEPTIDE | 117 |
| Z. mays-S | Z. mays-S | None | V5-His tag | +intron | NUCLEIC | 118 |
| Z. mays-S | Z. mays-S | None | V5-His tag | ORF only | NUCLEIC | 119 |
| Z. mays-S | Z. mays-S | None | V5-His tag | | PEPTIDE | 120 |
| Z. mays-S | T. majus | S170A | V5-His tag | +intron | NUCLEIC | 121 |
| Z. mays-S | T. majus | S170A | V5-His tag | ORF only | NUCLEIC | 122 |
| Z. mays-S | T. majus | S170A | V5-His tag | | PEPTIDE | 123 |
| T. majus | Z. mays-S | None | V5-His tag | +intron | NUCLEIC | 124 |
| T. majus | Z. mays-S | None | V5-His tag | ORF only | NUCLEIC | 125 |
| T. majus | Z. mays-S | None | V5-His tag | | PEPTIDE | 126 |

The parent DGATs and their modified forms were transferred into the Gateway®-compatible binary pRSh1 Gateway adapted binary vector (Winichayakul et al., 2009, Biotechnol. Appl. Biochem. 53, 111-122) modified by replacement of the CaMV35S promoter replaced with the Brassica napes Napin promoter (SEQ ID NO:127).

Camelina sativa Transformation

C. sativa (cf. Calena) were transformed via Agrobacterium tumefaciens (GV3101) using the floral dip method (adapted from that of Clough and Bent, 1998, Plant J. 16(6):735-745). Essentially seeds were sown in potting mix in 10 cm pots in a controlled environment, approximately 6 weeks after planting the flowers were dipped for 5-14 minutes under vacuum (70-80 inch Hg) in an overnight culture of appropriated Agrobacterium GV3101 cells re-suspended in a floral dip buffer. After vacuum-transformation, plants were kept for 24 h under low light conditions by partly covering with a black plastic sheet. Vacuum transformations can be repeated three times at approximately 10-12 days intervals, corresponding to the flowering duration. Plants were grown in potting mix in a controlled environment (16-h day length, 21-24° C., 65-70% relative humidity).

The $T_1$ seeds produced can be collected and screened for transformants by germinating and growing seedlings at 22° C. with continuous light on a half-strength MS medium (pH 5.6) selection plate containing 1% (w/v) sucrose, 300 mg/L Timentin, and 25 mg/L DL-phosphinothricin to select for herbicide resistance. $T_2$ selfed seed populations can also be screened by immuno blot for the presence of the V5 eptiope.

$T_2$ selfed seeds may be analysed for oil content by GC. Approximately 50 individual transgenic lines (including control lines) may be selected for the next generation (10 plants/line) based on their oil content, or seed weight. $T_2$ plants may be grown and screened by PCR for copy number and identification of null sibing lines. $T_2$ seeds may be analysed in triplicate for oil content by NMR or GC/MS.

Results

Swapping the N-Terminal Region of Plant DGAT1 s Enhances Lipid Production in Saccharomyces cerevisiae The N-terminal cytoplasmic region can be swapped between different plant DGAT1s to raise the lipid yield. Tables 5-11 show the lipid yields of a variety of chimeric DGAT1s in which the N-terminal cytoplasmic region has been derived from one plant DGAT1 while the remainder of the protein has been derived from another plant DGAT1. The lipid yields are presented either as grams of lipid produced per liter (which therefore compensates for any differences in growth rate) or have been normalised as a percentage of the lipid yield of the corresponding unmodified parent DGAT1.

A comparison of parent DGAT1s and chimeric DGAT1s made using one donor parent for the N-terminal region, and a different donor parent for the N-terminal region are shown in Table 5. The lipid yields at 32 hr have been normalised against the highest lipid-producing parent (Z. mays-L) and are presented in ascending order.

A comparison of T. majus parent DGAT1s and chimeric DGAT1s made using either T. majus as the donor parent for the N-terminal region or using T. majus as the donor parent for the C-terminal region are shown in Table 6. The lipid yields at 32 hr have been normalised against the lipid yield from the parent DGAT1 of the C-terminal region.

A comparison of O. Sativa-L parent DGAT1s and chimeric DGAT1s made using either O. Sativa-L as the donor parent for the N-terminal region or using O. Sativa-L as the donor parent for the C-terminal region are shown in Table 7. The lipid yields at 32 hr have been normalised against the lipid yield from the parent DGAT1 of the C-terminal region. NA=not available.

A comparison of Z. mays-L parent DGAT1s and chimeric DGAT1s made using either Z. mays-L as the donor parent for the N-terminal region or using Z. mays-L as the donor parent for the C-terminal region are shown in Table 8. The lipid yields at 32 hr have been normalised against the lipid yield from the parent DGAT1 of regions 2-4. NA=not available.

A comparison of O. sativa-S parent DGAT1s and chimeric DGAT1s made using either O. sativa-S as the donor parent for the N-terminal region or using O. sativa-S as the donor parent for the C-terminal region are shown in Table 9. The lipid yields at 32 hr have been normalised against the lipid yield from the parent DGAT1 of the C-terminal region. NA=not available.

A comparison of Z. mays-S parent DGAT1s and chimeric DGAT1s made using either Z. mays-S as the donor parent for the N-terminal region or using *Z. mays*-S as the donor parent for the C-terminal region are shown in Table 10. Lipid yields at 32 hr have been normalised against the lipid yield from the parent DGAT1 of the C-terminal region. NA=not available.

A comparison of *A. thaliana* parent DGAT1s and chimeric DGAT1s made using either *A. thaliana* as the donor parent for the N-terminal region or using *A. thaliana* as the donor parent for the C-terminal region are shown in Table 11. The lipid yields at 32 hr have been normalised against the lipid yield from the parent DGAT1 of the C-terminal region. NA=not available.

TABLE 5

| N-terminal region DGAT1 Parent | C-terminal region DGAT1 parent | SEQ ID NO: | Lipid yield as % Z. *mays*-L |
|---|---|---|---|
| Vector only | Vector only | N/A | 31.96 |
| A. thaliana | O. sativa-L | 61 | 37.93 |
| A. thaliana | Z. mays-L | 63 | 38.28 |
| A. thaliana | Z. mays-S | 62 | 50.67 |
| A. thaliana | T. majus | 64 | 52.86 |
| A. thaliana | O. sativa-S | 60 | 56.28 |
| A. thaliana | A. thaliana | 59 | 64.69 |
| T. majus | Z. mays-S | 93 | 75.96 |
| T. majus | O. sativa-L | 92 | 76.34 |
| T. majus | T. majus | 89 | 77.62 |
| Z. mays-S | Z. mays-S | 77 | 81.79 |
| Z. mays-L | T. majus | 88 | 83.39 |
| Z. mays-S | T. majus | 82 | 83.58 |
| O. sativa-S | O. sativa-S | 65 | 84.76 |
| T. majus | O. sativa-S | 91 | 86.45 |
| Z. mays-S | A. thaliana | 78 | 87.64 |
| O. sativa-L | O. sativa-L | 71 | 88.33 |
| T. majus | A. thaliana | 90 | 88.69 |
| Z. mays-S | O. sativa-L | 80 | 88.91 |
| O. sativa-S | Z. mays-S | 68 | 89.11 |
| O. sativa-L | A. thaliana | 72 | 93.02 |
| Z. mays-S | O. sativa-S | 79 | 94.15 |
| O. sativa-L | Z. mays-S | 74 | 94.51 |
| O. sativa-S | Z. mays-L | 69 | 95.81 |
| Z. mays-L | O. sativa-L | 86 | 96.17 |
| Z. mays-L | A. thaliana | 84 | 97.53 |
| O. sativa-S | T. majus | 70 | 98.52 |
| Z. mays-L | Z. mays-L | 83 | 100.00 |
| T. majus | Z. mays-L | 94 | 100.71 |
| O. sativa-L | T. majus | 76 | 102.78 |
| O. sativa-L | Z. mays-L | 75 | 104.29 |
| Z. mays-L | O. sativa-S | 85 | 105.02 |
| O. sativa-S | A. thaliana | 66 | 105.96 |

TABLE 6

| N-terminal region DGAT1 Parent | the C-terminal region DGAT1 parent | SEQ ID NO: | Lipid yield as % of the parent of the C-terminal region |
|---|---|---|---|
| T. majus | T. majus | 89 | 100 |
| T. majus | A. thaliana | 90 | 153.03 |
| T. majus | Z. mays-L | 94 | 100.61 |
| T. majus | O. sativa-L | 92 | 75.43 |
| T. majus | O. sativa-S | 91 | 95.41 |
| T. majus | Z. mays-S | 93 | 86.46 |
| A. thaliana | T. majus | 64 | 71.85 |
| O. sativa-L | T. majus | 76 | 135.21 |
| Z. mays-S | T. majus | 82 | 112.92 |
| O. sativa-S | T. majus | 70 | 142.91 |
| Z. mays-L | T. majus | 88 | 108.92 |

TABLE 7

| N-terminal region DGAT1 Parent | C-terminal region DGAT1 parent | SEQ ID NO: | Lipid yield as % of the parent of C-terminal region |
|---|---|---|---|
| O. sativa-L | O. sativa-L | 71 | 100 |
| O. sativa-L | T. majus | 76 | 135.21 |
| O. sativa-L | A. thaliana | 72 | 164.50 |
| O. sativa-L | Z. mays-L | 75 | 104.29 |
| O. sativa-L | Z. mays-S | 74 | 111.64 |
| O. sativa-L | O. sativa-S | 73 | N/A |
| A. thaliana | O. sativa-L | 61 | 43.43 |
| T. majus | O. sativa-L | 92 | 75.43 |
| Z. mays-S | O. sativa-L | 79 | 100.79 |
| O. sativa-S | O. sativa-L | 67 | N/A |
| Z. mays-L | O. sativa-L | 86 | 112.03 |

TABLE 8

| N-terminal region DGAT1 Parent | C-terminal region DGAT1 parent | SEQ ID NO: | Lipid yield as % of the parent of C-terminal region |
|---|---|---|---|
| Z. mays-L | Z. mays-L | 83 | 100 |
| Z. mays-L | T. majus | 88 | 108.65 |
| Z. mays-L | A. thaliana | 84 | 189.61 |
| Z. mays-L | O. sativa-L | 86 | 112.03 |
| Z. mays-L | Z. mays-S | 87 | N/A |
| Z. mays-L | O. sativa-S | 85 | 135.81 |
| A. thaliana | Z. mays-L | 63 | 38.28 |
| T. majus | Z. mays-L | 94 | 100.61 |
| Z. mays-S | Z. mays-L | 81 | N/A |
| O. sativa-S | Z. mays-L | 69 | 101.42 |
| O. sativa-L | Z. mays-L | 75 | 104.29 |

TABLE 9

| N-terminal region DGAT1 Parent | C-terminal region DGAT1 parent | SEQ ID NO: | Lipid yield as % of the parent of C-terminal region |
|---|---|---|---|
| O. sativa-S | O. sativa-S | 65 | 100 |
| O. sativa-S | T. majus | 70 | 142.91 |
| O. sativa-S | A. thaliana | 66 | 178.00 |
| O. sativa-S | O. sativa-L | 67 | N/A |
| O. sativa-S | Z. mays-S | 68 | 128.84 |
| O. sativa-S | Z. mays-L | 69 | 101.42 or 90.21 |
| A. thaliana | O. sativa-S | 60 | 65.19 |
| T. majus | O. sativa-S | 91 | 95.41 |
| Z. mays-S | O. sativa-S | 79 | 125.26 |
| Z. mays-L | O. sativa-S | 85 | 135.81 |
| O. sativa-L | O. sativa-S | 73 | N/A |

TABLE 10

| N-terminal region DGAT1 Parent | C-terminal region DGAT1 parent | SEQ ID NO: | Lipid yield as % of the parent of C-terminal region |
|---|---|---|---|
| Z. mays-S | Z. mays-S | 77 | 100 |
| Z. mays-S | Z. mays-L | 81 | N/A |
| Z. mays-S | O. sativa-L | 80 | 100.79 |
| Z. mays-S | O. sativa-S | 79 | 125.26 |
| Z. mays-S | T. majus | 82 | 112.92 |
| Z. mays-S | A. thaliana | 78 | 170.39 |
| T. majus | Z. mays-S | 93 | 105.30 |
| O. sativa-L | Z. mays-S | 74 | 129.16 |
| A. thaliana | Z. mays-S | 62 | 67.52 |
| O. sativa-S | Z. mays-S | 68 | 128.84 |
| Z. mays-L | Z. mays-S | 87 | N/A |

TABLE 11

| N-terminal region DGAT1 Parent | C-terminal region DGAT1 parent | SEQ ID NO: | Lipid yield as % of the parent of C-terminal region |
|---|---|---|---|
| A. thaliana | A. thaliana | 59 | 100 |
| A. thaliana | Z. mays-L | 63 | 38.28 |
| A. thaliana | O. sativa-L | 61 | 43.43 |
| A. thaliana | O. sativa-S | 60 | 65.19 |
| A. thaliana | Z. mays-S | 62 | 67.52 |
| A. thaliana | T. majus | 64 | 71.52 |
| T. majus | A. thaliana | 90 | 153.03 |
| O. sativa-L | A. thaliana | 72 | 164.50 |
| Z. mays-S | A. thaliana | 78 | 170.39 |
| O. sativa-S | A. thaliana | 66 | 178.00 |
| Z. mays-L | A. thaliana | 84 | 189.61 |

Swapping the N-Terminal Region of Plant DGAT1 s Alters Substrate Specificity

The ability to change substrate specificity of the plant DGAT1s through swapping the N-terminal regions is shown in Table 12 which demonstrates that the lipid profile of the TAG extracted from *Saccharomyces cerevisiae* cells overexpressing plant DGAT1's is determined predominantly by which the donor of the N-terminal region. In the examples given this is specifically seen as a relatively high level of 16:0 and 18:0 but low level of 18:1c9 in the TAG extracted from cells expressing DGAT1s in which the N-terminal region was derived from *Arabidopsis thaliana*. In contrast the TAG from cells expressing DGAT1s in which the N-terminal region was derived from *O. sativa*-L have relatively low levels of 16:0 and 18:0 but high levels of 18:1c9. While the TAG from cells expressing DGAT1s in which the N-terminal regions was derived from *T. majus* have intermediate levels of 16:0, 18:0 and 18:1c9.

TABLE 12

| N-teminal DGAT1 Parent | C-teminal DGAT1 parent | SEQ ID NO: | FATTY ACID SPECIES AS A PERCENTAGE OF TOTAL FATTY ACIDS IN TAG | | | |
|---|---|---|---|---|---|---|
| | | | 16:0 | 16:1 | 18:0 | 18:1c9 |
| A. thaliana | A. thaliana | 59 | 16.11 | 28.92 | 15.61 | 39.35 |
| T. majus | T. majus | 89 | 9.29 | 35.22 | 10.63 | 44.86 |
| O. sativa-L | O. sativa-L | 71 | 6.26 | 31.21 | 7.03 | 55.50 |
| A. thaliana | O. sativa-L | 61 | 13.98 | 33.91 | 12.82 | 39.29 |
| O. sativa-L | A. thaliana | 72 | 6.68 | 33.19 | 7.43 | 52.70 |
| T. majus | O. sativa-L | 92 | 12.43 | 30.70 | 12.22 | 44.65 |
| O. sativa-L | T. majus | 76 | 8.22 | 32.85 | 9.08 | 49.85 |

Swapping the N-Terminal Region of Plant DGAT1 s Enhances Lipid Production in *Brassica napus*

The N-terminal region can be swapped between different plant DGAT1s to raise the oil content in *Brassica napus* seeds. Tables 13-14 show the seed oil contents from a variety of transgenic plants containing chimeric DGAT1s in which the N-terminal region has been derived from one plant DGAT1 while the remainder of the protein (the C-terminal region) has been derived from another plant DGAT1. In Table 13 the seed oil contents are presented both as a % of Dry Matter (DM) and as a normalised percentage of the seed oil content of the corresponding unmodified DGAT1 parents.

TABLE 13

| Construct description | Transgenic plant ID # | Seed Oil as % DM | Oil Increase as % of Vector Control | Oil Increase as % of N-terminal DGAT1 Parent | Oil Increase as % of C-terminal DGAT1 Parent |
|---|---|---|---|---|---|
| Vector control | CV | 37.99 | 0.00 | N/A | N/A |
| T. majus | N2 | 39.07 | 2.84 | N/A | N/A |
| Z. mays-S | N3 | 40.25 | 5.95 | N/A | N/A |
| Z. mays-L | N6 | 38.96 | 2.55 | N/A | N/A |
| Tm-ZmS | 182-38-4 | 44.66 | 17.56 | 14.31 | 10.96 |
| Tm-ZmS | 182-38-9 | 43.05 | 13.32 | 10.19 | 6.96 |
| Tm-ZmS | 182-52-5 | 46.20 | 21.61 | 18.25 | 14.78 |
| Tm-ZmS | 182-52-9 | 43.37 | 14.16 | 11.01 | 7.75 |
| Tm-ZmS | 182-52-10 | 43.30 | 13.98 | 10.83 | 7.58 |
| Tm-ZmL | 183-17-10 | 43.80 | 15.29 | 12.11 | 12.42 |
| Tm-ZmL | 183-60-6 | 44.47 | 17.06 | 13.82 | 14.14 |
| ZmS-Tm | 184-17-1 | 43.38 | 14.19 | 7.78 | 11.03 |
| ZmS-Tm | 184-26-10 | 43.94 | 15.66 | 9.17 | 12.46 |
| ZmL-Tm | 185-24-5 | 45.27 | 19.16 | 16.20 | 15.87 |
| ZmL-Tm | 185-24-9 | 45.14 | 18.82 | 15.86 | 15.54 |
| ZmL-Tm | 185-22-1 | 44.23 | 16.43 | 13.53 | 13.21 |
| ZmL-Tm | 185-22-4 | 43.20 | 13.71 | 10.88 | 10.57 |
| ZmL-Tm | 185-22-9 | 43.49 | 14.48 | 11.63 | 11.31 |
| ZmL-Tm | 185-14-10 | 44.77 | 17.85 | 14.91 | 14.59 |
| ZmL-Tm | 185-9-9 | 43.73 | 15.11 | 12.24 | 11.93 |
| ZmL-Tm | 185-8-4 | 44.02 | 15.87 | 12.99 | 12.67 |
| ZmL-Tm | 185-8-7 | 45.11 | 18.74 | 15.79 | 15.46 |
| ZmL-Tm | 185-8-8 | 44.62 | 17.45 | 14.53 | 14.21 |
| ZmL-Tm | 185-8-9 | 43.48 | 14.45 | 11.60 | 11.29 |

In Table 14 the oil contents are presented both on a % of DM basis and as a normalised percentage of the seed oil content of the corresponding segregating null sibling.

TABLE 14

| Construct description | Transgenic ID # | Seed Oil as % DM | Oil Increase as % of Null Sibling |
|---|---|---|---|
| Tm-ZmS | 182-38-4 | 44.66 | 34.03 |
| Tm-ZmS | 182-38-9 | 43.05 | 29.20 |
| Tm-ZmS | 182-38-10 | 33.32 | N/A |
| Null Sib | | | |
| Tm-ZmL | 183-17-10 | 43.8 | 29.43 |
| Tm-ZmL | 183-17-4 | 33.84 | N/A |
| Null Sib | | | |
| ZmS-Tm | 184-17-1 | 43.38 | 30.39 |
| ZmS-Tm | 184-17-5 | 33.27 | N/A |
| Null Sib | | | |
| ZmS-Tm | 184-17-1 | 43.38 | 24.55 |
| ZmS-Tm | 184-17-7 | 34.83 | N/A |
| Null Sib | | | |
| ZmS-Tm | 184-26-10 | 43.94 | 15.66 |
| ZmS-Tm | 184-26-2 | 37.99 | N/A |
| Null Sib | | | |
| ZmS-Tm | 184-26-10 | 43.94 | 31.99 |
| ZmS-Tm | 184-26-6 | 33.29 | N/A |
| Null Sib | | | |
| ZmL-Tm | 185-24-5 | 45.27 | 19.41 |
| ZmL-Tm | 185-24-9 | 45.14 | 19.07 |
| ZmL-Tm | 185-24-10 | 37.91 | N/A |
| Null Sib | | | |
| ZmL-Tm | 185-22-1 | 44.23 | 30.09 |
| ZmL-Tm | 185-22-4 | 43.2 | 27.06 |
| ZmL-Tm | 185-22-9 | 43.49 | 27.91 |
| ZmL-Tm | 185-22-2 | 34 | N/A |
| Null Sib | | | |
| ZmL-Tm | 185-9-9 | 43.73 | 15.60 |
| ZmL-Tm | 185-9-8 | 37.83 | N/A |
| Null Sib | | | |

DISCUSSION

The applicants have thus shown that the chimeric DGAT1 proteins of the invention can be used to manipulate cellular lipid accumulation and cellular lipid profile. More specifically they can be used to achieve higher levels of lipid accumulation in eukaryotic cells than can be achieved using unaltered DGAT1 proteins. They have also shown that by selecting to express specific chimeric DGAT1 proteins they can not only increase the lipid content of the eukaryotic cell but also alter the lipid profile within the accumulating TAG.

There is discussion of producing chimeric plant DGAT1s in US 2012/0156360 A1. In Example 11, the authors describe two chimeras using the N-terminus from a maize DGAT1 and the C-terminus from a hazelnut DGAT1. However, the junction of the chimeras is in the putative transmembrane domain which is further downstream from the junction of the chimeras described by the present applicants. Furthermore, there is no data presented with respect to the activity of the chimeric plant DGAT1s in US 2012/0156360 A1. Thus there is no disclosure in US 2012/0156360 A1 of the chimeric DGAT1 molecules presented herein, or the altered activities specified, or use of the chimeras of the invention to produce the effects described herein.

The invention claimed is:

1. An isolated polynucleotide encoding a chimeric DGAT1 protein that comprises:
   a) at its N-terminal end, an N-terminal portion of a first DGAT1 protein, and
   b) at its C-terminal end, a C-terminal portion of a second DGAT1 protein,
wherein the junction between the N-terminal portion of a first DGAT1 protein and the C-terminal portion of a second DGAT1 protein is upstream of the first transmembrane domain, and wherein the chimeric protein increases the production of lipid when it is expressed in a cell relative to that in a control cell.

2. The polynucleotide of claim 1 wherein the chimeric DGAT1 protein has at least one of:
   i) increased DGAT1 activity
   ii) increased stability
   iii) altered oligomerisation properties
   iv) substantially normal cellular protein accumulation properties
   v) substantially normal cellular targeting properties
relative to the first DGAT1, the second DGAT1, or both the first DGAT1 and the second DGAT1.

3. The polynucleotide of claim 1 wherein the N-terminal portion of a first DGAT1 protein is the N-terminal cytoplasmic region of the first DGAT1 protein.

4. The polynucleotide of claim 1 wherein the N-terminal portion of the first DGAT1 protein extends from the N-terminus of the first DGAT1 protein to the end of the acyl-CoA binding domain of the first DGAT1 protein.

5. The polynucleotide of claim 1 wherein the N-terminal portion of the first DGAT1 protein is the region upstream of the first transmembrane domain.

6. The polynucleotide of claim 1 wherein the junction between the N-terminal portion of a first DGAT1 protein and the C-terminal portion of a second DGAT1 protein is in the acyl-CoA binding site of first and second DGAT1 protein.

7. The polynucleotide of claim 1 wherein the N-terminal portion of a first DGAT1 protein and the C-terminal portion of a second DGAT1 protein is at a corresponding position in the acyl-CoA binding site of the first and second DGAT1 protein.

8. The polynucleotide of claim 1 wherein the junction between the N-terminal portion of a first DGAT1 protein and the C-terminal portion of a second DGAT1 protein is within the conserved LSS (Leu-Ser-Ser) in the acyl-CoA binding site of the first and second DGAT1 protein.

9. The polynucleotide of claim 1 wherein the chimeric DGAT1 has an intact acyl-CoA binding site.

10. The polynucleotide of claim 1 wherein the acyl-CoA binding site in the chimeric DGAT1 is of the same length as the acyl-CoA binding site in the first DGAT1 protein.

11. The polynucleotide of claim 1 wherein the acyl-CoA binding site in the chimeric DGAT1 is of the same length as the acyl-CoA binding site in the second DGAT1 protein.

12. The polynucleotide of claim 1 wherein the acyl-CoA binding site in the chimeric DGAT1 is of the same length as the acyl-CoA binding site in the first and second DGAT1 protein.

13. The polynucleotide of claim 1 wherein the chimeric DGAT1 protein, when expressed in a cell, has altered substrate specificity relative to at least one of the first and second DGAT1 proteins.

14. A genetic construct comprising a polynucleotide of claim 1.

15. A cell comprising a polynucleotide of claim 1.

16. The cell of claim 15 that expresses the chimeric DGAT1.

17. The cell of claim 15 wherein the chimeric DGAT1 protein has at least one of: i) increased DGAT1 activity,
  ii) increased stability,
  iii) altered oligomerisation properties,
  iv) substantially normal cellular protein accumulation properties, and
  v) substantially normal subcellular targeting properties
relative to the first DGAT1, the second DGAT1, or both the first DGAT1 and the second DGAT1.

18. The cell of claim 15 which produces more lipid than does a control cell.

19. The cell of claim 15 which has an altered lipid profile relative to a control cell.

20. The cell of claim 15 which is also transformed to express at least one of: an oleosin, steroleosin, caloleosin, polyoleosin, and an oleosin including at least one artificially introduced cysteine.

21. A plant comprising the polynucleotide of claim 1.

22. The plant of claim 21 that expresses the chimeric DGAT1.

23. The plant of claim 21 wherein the chimeric DGAT1 protein when expressed in the plant has at least one of:
  i) increased DGAT1 activity,
  ii) increased stability,
  iii) altered oligomerisation properties,
  iv) substantially normal cellular protein accumulation properties and
  v) substantially normal subcellular targeting properties
relative to the first DGAT1, the second DGAT1, or both the first DGAT1 and the second DGAT1.

24. The plant of claim 21 that produces more lipid, in at least one of its tissues or parts, or as a whole, than does a control plant.

25. The plant of claim 21 that has an altered lipid profile, in at least one of its tissues or parts, or as a whole, relative to a control plant.

26. The plant of claim 21 that is also transformed to express at least one of: an oleosin, steroleosin, caloleosin, polyoleosin, and an oleosin including at least one artificially introduced cysteine.

27. A chimeric DGAT1 protein that comprises:
  a) at its N-terminal end, an N-terminal portion of a first DGAT1 protein, and
  b) at its C-terminal end, a C-terminal portion of a second DGAT1 protein,
wherein the junction between the N-terminal portion of a first DGAT1 protein and the C-terminal portion of a second DGAT1 protein is upstream of the first transmembrane domain, and wherein the chimeric protein increases the production of lipid when it is expressed in a cell relative to that in a control cell.

28. The chimeric DGAT1 protein of claim 27 that has at least one of:
  i) increased DGAT1 activity
  ii) increased stability
  iii) altered oligomerisation properties
  iv) substantially normal cellular protein accumulation properties
  v) substantially normal cellular targeting properties
relative to the first DGAT1, the second DGAT1, or both the first DGAT1 and the second DGAT1.

29. A method for producing a chimeric DGAT1 protein the method comprising combining:
  a) an N-terminal portion of a first DGAT1 protein, and
  b) a C-terminal portion of a second DGAT1 protein,
wherein the junction between the N-terminal portion of a first DGAT1 protein and the C-terminal portion of a second DGAT1 protein is upstream of the first transmembrane domain, and wherein the chimeric protein increases the production of lipid when it is expressed in a cell relative to that in a control cell.

30. The method of claim 29 wherein the chimeric DGAT1 protein produced comprises:
  a) at its N-terminal end, the N-terminal portion of a first DGAT1 protein, and
  b) at its C-terminal end, the C-terminal portion of a second DGAT1 protein.

31. The method of claim 29 wherein the chimeric DGAT1 protein has at least one of:
  i) increased DGAT1 activity
  ii) increased stability
  iii) altered oligomerisation properties
  iv) substantially normal cellular protein accumulation properties
  v) substantially normal cellular targeting properties
relative to the first DGAT1, the second DGAT1, or both the first DGAT1 and the second DGAT1.

32. The method of claim 29 wherein the method comprises the step of testing at least one of the
  i) activity
  ii) stability
  iii) oligomerisation properties
  iv) cellular protein accumulation properties
cellular targeting properties of the chimeric DGAT1 protein.

33. The method of claim 29 wherein method comprises the step selecting a chimeric DGAT1 protein that has at least one of:
  i) increased DGAT1 activity
  ii) increased stability
  iii) altered oligomerisation properties
  iv) substantially normal cellular protein accumulation properties
  v) substantially normal cellular targeting properties
relative to the first DGAT1, the second DGAT1, or both the first DGAT1 and the second DGAT1.

34. A part, propagule or progeny of the plant of claim 21 that comprises of the polynucleotide.

35. The part, propagule or progeny of claim 34 that produces more lipid than does a control part, propagule or progeny, or pad, propagule or progeny of a control plant.

36. The part, propagule or progeny of claim 34 that has an altered lipid profile relative to a control part, propagule or progeny, or part, propagule or progeny of a control plant.

37. An animal feedstock, or biofuel feedstock comprising the polynucleotide of claim 1.

38. An animal feedstock, or biofuel feedstock comprising the chimeric DGAT1 protein of claim 27.

39. A method for producing lipid, the method comprising expressing a chimeric DGAT1 protein of claim 27 in a plant.

40. The method of claim 39 wherein expressing the chimeric DGAT1 protein of the invention in a plant leads to production of the lipid in the plant.

41. The method of claim 39 wherein the method includes the step of transforming a plant cell or plant with a polynucleotide encoding the chimeric DGAT1 protein.

42. The method of claim 39 which includes the step of extracting the lipid from the plant, or from a part, propagule or progeny of the plant.

43. A method for producing lipid, the method comprising extracting lipid from at least one cell of claim 15.

44. The method of claim 42 wherein the lipid is processed into at least one of:
 a) a fuel,
 b) an oleochemical,
 c) a nutritional oil,
 d) a cosmetic oil,
 e) a polyunsaturated fatty acid (PUFA), and
a combination of any of a) to e).

* * * * *

SEQUENCE LISTING

<160> NUMBER OF SEQ ID NOS: 157

<210> SEQ ID NO 1
<211> LENGTH: 2074
<212> TYPE: DNA
<213> ORGANISM: Arabidopsis thaliana

<400> SEQUENCE: 1

```
tgaatccttt ttcctttctt cttcttcttc tcttcagaga aaactttgct tctctttcta      60
taaggaacca gacacgaatc ccattcccac cgatttctta gcttcttcct tcaatccgct     120
ctttccctct ccattagatt ctgtttcctc tttcaatttc ttctgcatgc ttctcgattc     180
tctctgacgc ctcttttctc ccgacgctgt ttcgtcaaac gcttttcgaa atggcgattt     240
tggattctgc tggcgttact acggtgacgg agaacggtgg cggagagttc gtcgatcttg     300
ataggcttcg tcgacggaaa tcgagatcgg attcttctaa cggacttctt ctctctggtt     360
ccgataataa ttctccttcg gatgatgttg gagctcccgc cgacgttagg gatcggattg     420
attccgttgt taacgatgac gctcagggaa cagccaattt ggccggagat aataacggtg     480
gtggcgataa taacggtggt ggaagaggcg gcggagaagg aagaggaaac gccgatgcta     540
cgtttacgta tcgaccgtcg gttccagctc atcggagggc gagagagagt ccacttagct     600
ccgacgcaat cttcaaacag agccatgccg gattattcaa cctctgtgta gtagttctta     660
ttgctgtaaa cagtagactc atcatcgaaa atcttatgaa gtatggttgg ttgatcagaa     720
cggatttctg gtttagttca agatcgctgc gagattggcc gcttttcatg tgttgtatat     780 cccttttcgat ctttccttkg gctgccttta cggttgagaa attggtactt cagaaataca     840
tatcagaacc tgttgtcatc tttcttcata ttattatcac catgacagag gttttgtatc     900
cagtttacgt caccctaagg tgtgattctg cttttttatc aggtgtcact ttgatgctcc     960
tcacttgcat tgtgtggcta aagttggttt cttatgctca tactagctat gacataagat    1020
ccctagccaa tgcagctgat aaggccaatc ctgaagtctc ctactacgtt agcttgaaga    1080
gcttggcata tttcatggtc gctcccacat tgtgttatca gccaagttat ccacgttctg    1140
catgtatacg gaagggttgg gtggctcgtc aatttgcaaa actggtcata ttcaccggat    1200
tcatgggatt tataatagaa caatatataa atcctattgt caggaactca aagcatcctt    1260
tgaaaggcga tcttctatat gctattgaaa gagtgttgaa gctttcagtt ccaaatttat    1320
atgtgtggct ctgcatgttc tactgcttct tccacctttg gttaaacata ttggcagagc    1380
ttctctgctt cggggatcgt gaattctaca aagattggtg gaatgcaaaa agtgtgggag    1440
attactggag aatgtggaat atgcctgttc ataaatggat ggttcgacat atatacttcc    1500
cgtgcttgcg cagcaagata ccaaagacac tcgccattat cattgctttc ctagtctctg    1560
```

```
cagtctttca tgagctatgc atcgcagttc cttgtcgtct cttcaagcta tgggcttttc    1620
ttgggattat gtttcaggtg cctttggtct tcatcacaaa ctatctacag gaaaggtttg    1680
gctcaacggt ggggaacatg atcttctggt tcatcttctg cattttcgga caaccgatgt    1740
gtgtgcttct ttattaccac gacctgatga accgaaaagg atcgatgtca tgaaacaact    1800
gttcaaaaaa tgactttctt caaacatcta tggcctcgtt ggatctccgt tgatgttgtg    1860
gtggttctga tgctaaaacg acaaatagtg ttataaccat tgaagaagaa aagaaaatta    1920
gagttgttgt atctgcaaaa attttggtag agacacgcga acccgtttgg attttgttat    1980
ggtgtaaaga aatttcaatc aaaaaactgt tgtaataatt gttaccaaaa agaaatgctt    2040
ttctggaaac gagggaaaa atagtagttt tgtt                                 2074

<210> SEQ ID NO 2
<211> LENGTH: 1512
<212> TYPE: DNA
<213> ORGANISM: Brassica juncea

<400> SEQUENCE: 2
atggcgattt tggattctgg aggcgtcgct gtaccgccga cggagaacgg cgtcgcggat      60
ctcgacaggc tccaccgtcg taaatcgagt tcggattctt ccaacggact cctctccgat     120
acttccccgt cggacgatgt tggagctgcg gcggccgaaa gggatcgggt tgattccgct     180
gccgaggagg aggctcaggg aacagcgaat ttagctggcg gagatgccga aactagggaa     240
tccgccggag gcgatgtaag gtttacgtat cgaccgtcgg ttccagctca tcggaggacg     300
agggagagtc ctctcagctc cgacgctatc ttcaaacaaa gccatgcagg attgttcaac     360
ctctgtgtag ttgttcttgt tgctgttaac agtagactca tcatcgaaaa cctcatgaag     420
tatggttggt tgatcagaac tgattttttgg tttagttcta catccttacg agactggccg     480
cttttcatgt gttgtctttc actttcggtc tttcctttgg ctgccttcac ggtcgagaaa     540
atggtacttc agaaattcat atctgagcct gttgccatca ttcttcatgt cattataacc     600
atgacagagg tcttgtatcc agtctacgtc acactgaggt gtgattctgc cttcttgtca     660
ggtgtcacgt tgatgctgct cacttgcatt gtgtggctga agttggtttc ttacgctcat     720
actagctacg acataagaac cctggccaat tcagctgata aggtcgatcc tgaaatctcc     780
tactatgtta gcttgaagag cttggcgtat ttcatggttg ctcccacact gtgttatcag     840
ccaagctatc cacgttctcc atgtatccgg aagggttggg tggctcgtca acttgcaaaa     900
ctggtcatat tcactggact catgggattt ataatagagc aatatataaa tcctattgtt     960
aggaactcaa agcatcctct gaaagggggac cttctatatg ctattgaaag agtgttgaag    1020
ctttcagttc caaatctata tgtgtggctc tgcatgttct actgcttctt ccacctttgg    1080
ttaaacatat tggcagagct cctctgcttc ggggaccgtg aattctacaa agattggtgg    1140
aatgcaaaaa gcgttggaga ttattggaga atgtggaata tgcctgttca caaatggatg    1200
gttcgacatg tatactttcc gtgcctgcgc atcaagatac caaaagtacc cgccattatc    1260 attgcttttct tagtctctgc agtctttcat gagttatgca tcgcagttcc ttgccgtctc    1320
ttcaatctat gggctttcat gggaattatg tttcaggtcc ctttggtctt tatcacaaac    1380
tttttacaag aaaggtttgg ctccatggtg ggaaacatga tctttggttc agcttcttgc    1440
attttcggac aaccgatgtg tgggcttctt tattaccatg acctgatgaa ccgcaaagga    1500
tccatgtcct ga                                                        1512
```

<210> SEQ ID NO 3
<211> LENGTH: 1512
<212> TYPE: DNA
<213> ORGANISM: Brassica napus

<400> SEQUENCE: 3

```
atggcgattt tggattctgg aggcgtcgct gtaccgccga cggagaacgg cgtcgcggat      60
ctcgacaggc tccaccgtcg taaatcgagt tcggattctt ccaacggact cctctccgat     120
acttccccgt cggacgatgt tggagctgcg gcggccgaaa gggatcgggt tgattccgct     180
gccgaggagg aggctcaggg aacagcgaat ttagctggcg agatgccga aactagggaa      240 tccgccggag gcgatgtaag gtttacgtat cgaccgtcgg ttccagctca tcggaggacg     300
agggagagtc ctctcagctc cgacgctatc ttcaaacaaa gccatgcagg attgttcaac     360
ctctgtgtag ttgttcttgt tgctgttaac agtagactca tcatcgaaaa cctcatgaag     420
tatggttggt tgatcagaac tgattttgg tttagttcta catccttacg agactggccg      480
cttttcatgt gttgtctttc actttcggtc tttcctttgg ctgccttcac ggtcgagaaa     540
atggtacttc agaaattcat atctgagcct gttgccatca ttcttcatgt cattataacc     600
atgacagagg tcttgtatcc agtctacgtc acactgaggt gtgattctgc cttcttgtca     660
ggtgtcacgt tgatgctgct cacttgcatt gtgtggctga agttggtttc ttacgctcat     720
actagctacg acataagaac cctggccaat tcagctgata aggtcgatcc tgaaatctcc     780
tactatgtta gcttgaagag cttggcgtat ttcatggttg ctcccacact gtgttatcag     840
ccaagctatc cacgttctcc atgtatccgg aagggttggg tggctcgtca acttgcaaaa     900
ctggtcatat tcactggact catgggattt ataatagagc aatatataaa tcctattgtt     960
aggaactcaa agcatcctct gaaagggac cttctatatg ctattgaaag agtgttgaag     1020 cttttcagttc caaatctata tgtgtggctc tgcatgttct actgcttctt ccacctttgg    1080
ttaaacatat tggcagagct cctctgcttc ggggaccgtg aattctacaa agattggtgg    1140
aatgcaaaaa gcgttggaga ttattggaga atgtggaata tgcctgttca caatggatg    1200 gttcgacatg tatactttcc gtgcctgcgc atcaagatac caaaagtacc cgccattatc    1260
attgctttct tagtctctgc agtctttcat gagttatgca tcgcagttcc ttgccgtctc    1320
ttcaatctat gggctttcat gggaattatg tttcaggtcc cttggtctt tatcacaaac    1380 tttttacaag aaaggttggg ctccatggtg ggaaacatga tctttggttc agcttcttgc    1440
attttcggac aaccgatgtg tgggcttctt tattaccatg acctgatgaa ccgcaaagga    1500
tccatgtcct ga                                                        1512
```

<210> SEQ ID NO 4
<211> LENGTH: 1510
<212> TYPE: DNA
<213> ORGANISM: Brassica juncea

<400> SEQUENCE: 4

```
atggcgattt tggattctgg aactgtcacg atggcgacgg agaacggtgt cgcggatctc      60
gatatgcttc gtcgtcgtaa atcgagatcg gattcttcca acggacttct ctccgagact    120
tccccatcgg atgatgctgg agctccggcc gacgtggagg atcgggttga ttcagctgct    180
cagggaacag cgaatttagc tggagatacg gaaactaggg aatccggtgg aggaggagga    240
ggaggaaacg gcgaggtaag gtttacgtat cgaccgtcgg ttccagctca tcggaggacg    300
agggagagtc cactcagctc cgacgctatc ttcaaacaaa gccatgcagg attgttcaac    360
```

```
ctctgtgtag ttgttcttgt tgctgttaac agtagactca tcatcgaaaa tctcatgaag    420
tacggttggt tgatcagaac tgatttctgg tttagttcta catccctccg agattggccg    480
cttttcatgt gttgtctttc actttcaatc tttcctttgg ctgcctttac cgtcgagaaa    540
ttggtactcc agaaattcat atctgaacct gttgtcatca ttcttcatat tattatcacc    600
atgactgagg tcttgtatcc agtctacgtc accctaaggt gtgattcggc tttcttatca    660
ggtgtcacat tgatgctact cacttgcatt gtgtggctga agttggtttc ttacgctcat    720
actaattacg acataagaac cgtagctaat tcagctgata aggtcgatcc tgaagtctcc    780
tactatgtta gcttgaagag cttggcgtat ttcatggttg ctcccacatt gtgttatcag    840
ccaagctatc cacgttctcc gggtatccgg aagggttggg tggctcgtca atttgcgaaa    900
ctggtcatat tcactggact catgggtttt ataatagagc aatatataaa tcctattgtg    960
aggaactcaa agcatccttt gaaagggat cttctatacg ctattgaaag agtgttgaag   1020
ctttcagttc caaatctata tgtgtggctc tgcatgttct actgcttctt ccacctttgg   1080
ttaaatatat tggcagagct cctttgcttc ggggatcgtg aattctacaa agattggtgg   1140
aatgcaaaaa gcgtaggaga ttattggaga atgtggaata tgcctgttca taaatggatg   1200
gttcgacatg tatactttcc atgcctgcgc ataaagatac cgaaagtacc cgccattatc   1260
attgctttct tagtctctgc agttttccat gagctgtgca ttgcagttcc ttgccgtctc   1320
tttaatttat gggctttcat aggaatcatg tttcaggtgc ctttggtctt tatcacaaac   1380
tatttacaag aaaggtttgg ctccatggtg ggaaacatga tcttctggtt cagcttctgc   1440
attttcggac aaccgatgtg tgtgcttctt tattaccatg acctcatgaa ccgcaaagga   1500
tccatgtcct                                                           1510
```

<210> SEQ ID NO 5
<211> LENGTH: 2090
<212> TYPE: DNA
<213> ORGANISM: Tropaeolum majus

<400> SEQUENCE: 5

```
acgcggggag ttttcaaaat catattatgc ttttcttca ctactgcatg aactttcttt     60
ctacttcttg caactgatt gtaatcctta cacatgtttc tagttttctc catataaaaa   120
aaatattctc tgagcttctc gattctctag agagagaagg ccaaaaaaaa atggcggtgg   180
cagagtcgtc acagaacacg acaaccatga gtggtcacgg cgactcggat ctcaacaatt   240
tccgtagaag gaaaccgagt tcctccgtga ttgaaccttc gtcgtccggt tttacatcca   300
ccaatggcgt accggcgact ggccacgtgg ctgagaatcg tgaccaggat cgggtagggg   360
ctatggagaa cgcaacagga tcggtcaact taattggaaa tggtggaggc gtggttatcg   420
ggaatgaaga gaaacaggta ggggagactg atatacgatt cacttaccgg ccttcgtttc   480
cggctcatcg gagggtgagg gagagtcctc ttagctctga tgcaatcttc aaacagagcc   540
atgcgggttt attcaacttg tgtatagtag tgctcattgc agtaaacagt aggcttatca   600
tcgaaaatct tatgaagtat ggttggttga tcgatactgg tttctggttt agctcaagat   660
cactgggtga ttggtccatc tttatgtgct gtcttacact cccaattttc ccacttgctg   720
cttttattgt tgaaaagctg gtgcagcgaa atcatatatc tgaacttgtt gctgttctcc   780
ttcatgtaat cgtttctacc gctgcagttt tatatccagt tattgtgatc ttaacgtgtg   840
attcggtgta tatgtctggt gtggtattga tgctctttgg ttgcattatg tggttgaagc   900
tggtgtcata tgcacatact agttctgata ttagaacact ggccaaatct ggctataagg   960
```

```
gggatgcgca ccccaattca accattgtga gttgctcata tgatgttagc ttgaagagtt    1020
tggcatactt catggttgct ccgacattat gttaccagcc tagctatcct cgttcgtcgt    1080
gtatccgcaa gggttgggtt gttcgtcaat ttgtcaaact aatagttttc ataggactca    1140
tggggttcat tatagaacaa tatattaatc ctatcgttcg aaattccaaa cacccattga    1200
aaggagattt tttatatgca atagaaagag ttttgaagct ttcagttcca aatctatatg    1260
tttggctttg catgttctac tctttttcc acctctggtt gaacatactg gctgagcttc     1320
ttcgctttgg tgatcgtgaa ttctacaaag attggtggaa tgcaaaaact gttgcggagt    1380
attggaaaat gtggaatatg cctgttcata gatggatggt tcgtcatcta tattttccct    1440
gtttgaggaa tgggataccc aaggaaggtg ccattattat cgcgttctta gtttctggtg    1500
ctttccatga gctctgcatt gcagttcctt gccacgtatt caagttatgg gcctttatag    1560
gcattatgtt tcaggttccc ttggtattga ttacgaatta tctacaagaa aagttcagta    1620
attctatggt gggcaatatg atcttctggt tcatcttctg catacttggc caacctatgt    1680
gtgtccttct atattaccat gacctgataa atctaaagga aaagtgaaaa atggaagtt    1740 gcctatgctc agagtattcc tatcccaatg cacacattat atggttctgt acaatctgtg    1800 ccccttcat cctttacacg tacccatgct ggttcctgca cgatgatttg ccttttgttt     1860
gtaagcaata tttggagaga gtccaattta ggaagtgact agtgtggctt atatcttgta    1920 tactacctt agtcatgggg gggttttat attactagta ccaaagtca agttgtatat       1980 gatttacggt ttagtttctt tcatgttttt tgttttgtg taaatatacg tttcatatat     2040
cactgttttt tcaaagtaaa atcaataata ccccatagat gttgaaactg                2090

<210> SEQ ID NO 6
<211> LENGTH: 1494
<212> TYPE: DNA
<213> ORGANISM: Echium pitardii

<400> SEQUENCE: 6
cacaaatgac aatatgggag tcgccggaga tcataagctc cgatgaagca gcagcggcgt      60
tgaggcggag aggcggcgcc aaggaggttg cggaacagag attggatagt gaagaagaga     120
agaagaagga ggaggaaaat ggaaaactga agtatactta tcgagcttcc gctccggctc     180 accgagaat caaggagagt cctcttagct ccgacgccat tttcaaacaa agtcatgcag      240
gcctcttcaa tctttgcatt gtggtgcttg ttgctgtaaa cagtcggctt atcattgaga     300
atttgatgaa gtatggttgg ctaattagct cagggttttg gttaagttca acatcattaa     360
gcgactggcc acttctaata tgttgtctca gtctgccgat attccctctg gcttcttttg     420
tggttgaaaa gttgtctcaa caggaattta tatctgagca gtggtgatc actcttcatg      480 cactcataac aacgactgtg attatgtatc cagtaattgt catcctcaga tgtgatcccg     540
ccgttctatc aggtgtgata ttgatgcttt tcacgtgtat tgtgtggttg aagctggtat     600
cttatgcaca tacaaactat gatatgcgag cactagcaaa ggactgtgat aagttacagg     660
cactatcagg ctcttcaatg gaagattgtt cttttgaagt caacttccaa gctttggtat     720
acttcatggt tgctccgaca ttatgttatc agctaaggta tccgcgtacc ccctgcattc     780
gttggggttg ggttacacgt catctcatca gttaatcat atttactgga ctgatgggat      840
tcattattga gcagtatatt aatccaattg tgaaaaattc acaacatcca ttgaagggga    900
acctgttgta tgctatagag agggtcttga agctttcagt tccaaatata tatgtctggc    960
```

```
tctgcatgtt ttattgtctc ttccatcttt ggttaaatat actagccgaa cttctgtgtt    1020
ttggggatcg tgagttctac aaagattggt ggaatgctca aacgatagag gagtattgga    1080
ggatgtggaa catgcctgta cataaatgga tggttcgtca tatatatttc ccttgcttgc    1140
ggaatgggat gcctaaggag ttggctattt tgattgcgtt cctaatatct gcaatcttcc    1200
atgagctgtg cattgctgtg ccgtgtcaca tctttaagtt ctgggctttt atcggaataa    1260
tgtttcaggt cccttggtc cttctgacaa atgttttggt aaaaagttc caaaattcaa     1320 tggttggcaa tatgatattc tggtgcttct tctgcattct tggtcaaccc atgagtctgc    1380
tgctctatta ccatgatgtc ttgaataaa aagttaatgc aaactgatac tacagatatc    1440
ttgaaaatgt catcacaaag agtgtgaagg atcgataggt ttcgctcaac agga          1494
```

<210> SEQ ID NO 7
<211> LENGTH: 1828
<212> TYPE: DNA
<213> ORGANISM: Vernonia galamensis

<400> SEQUENCE: 7

```
tctgagctca aatcaaattt ctgcgactca tacaggattc aactcaatac tttcttgatc      60
ggttctgctg ttcatttact tgtaatttct acttctgctt tgctttcatt tcaagctttt    120
ttccttaata tggcgttat tagatacgcc tcagattgga gaaataacga ccaccgccac     180
cacaactata agacggcgga ccactgtcaa gcctgatgct ggaatcggag atggattgtt    240
tgattcttcg tcgtcttcca aaaccaactc atccttcgag gatggtgaca gtttgaatgg    300
tgatttcaat gacaaattta aggaacagat cggagctggt gatgaatcca aggacgactc    360 caagggggaac ggacagaaga tagatcacgg aggagttaaa aagggacgtg aaacgactgt    420
ggtgcattat gcttatcggc cttcttctcc ggctcatcgg agaattaaag aatctccgct    480
tagctctgac gccatcttca agcagagtca tgcaggcctc tttaaccttt gcatagtggt    540
gcttgttgca gtaaatggta ggctcatcat tgagaatctg atgaagtatg gactattgat    600
caattccaac ttttggttca gttcgagatc attgagagac tggccacttc tgatgtgctg    660
cctcactcct tctgactttc cacttgctgc ctacattgtt gagaaattgg catggaaaaa    720
acgtatatcc gaccctgttg taatcacact ccatgttata ataactacaa ctgcaattct    780
ttatccggtc ttcatgattc tgaggttcga ttcagttgtt ctatcaggcg tctcgttgat    840
gctgtgtgct tgcattaatt ggttgaagtt ggtatctttt gtgcatacaa attatgacat    900
gcggtcgctt tgaactcaa ctgataaggg agaagtggaa cccatgtctt caaatatgga    960
ttatttttat gatgtcaact tcaaaagctt ggtttatttc atggttgctc caactttgtg    1020
ttaccagata agctatcctc gcactgcatt tattcgaaag ggttgggtgt tacggcaact    1080
gatcaagcta gtaatattta cagggttcat gggattcatc attgaacaat atatcaatcc    1140
gattgtcaaa aattctcgtc atccattgaa aggagacttt ttatatgcga ttgagcgggt    1200
tttaaagctt tcagttccga atttatatgt gtggctctgt atgttctact gcttttttca    1260
cctttggtta aatatacttg ctgagcttct tgttttggg gatcgtgaat tttataaaga     1320
ttggtggaat gcacaaacta ttgaagagta ttggaggcta tggaatatgc ctgttcataa    1380
atggattgtt aggcaccttt attttccatg cttgcgtaat gggataccta agggtgctgc    1440
catattggtt gcattttca tgtctgccgt gttccatgag ctttgtattg ctgttccctg     1500
ccacattttc aagttttggg cttttatcgg gatcatgttt caggtcccgt tggtcctact    1560
cacaaaatta cttgcagcaca agtttcaaaa ctcgatggtg ggaaatatga tcttctggtg    1620
```

-continued

```
cttttttcagc attttttggtc aacccatgtg tgtattactt tactaccatg atgtcatgaa      1680
tcaaaagggg aaaagcaaat aaaaagatgt gattgtgttg ctccatttga tctcatagca      1740
tgactggact aaacaaaccc aagggacaca ttttagtcct taaaggaaaa ttttttgtagg     1800 aaaaaaaaaa aaaaaaaaaa aaaaaaaa                                         1828

<210> SEQ ID NO 8
<211> LENGTH: 2099
<212> TYPE: DNA
<213> ORGANISM: Nicotiana tabacum

<400> SEQUENCE: 8
ggcacgagcg aaatcttacc caatcctccg ttgcttttct tttagatcct cttttttctgt      60 cattctcttt ttcccaataa caacaactca ttgcatgtga aggttgattt tgattttttgt    120 gtttattcaa actctctctt cacgattttc ttactctttc tagaagtatc cattactttt     180
tagtctgtga ttcggcgaaa gtaagcaatg gtgatcatgg aattgccgga gagcgtcgaa    240
atgacgacga cgacgacgac ttcgggtatt gagaacctca actccgatct taatcactcg    300
gttcggagga gacgtggcag taatggtttt gaggcggcta gtgcaattaa cagttcggat    360
gcgaatatga gcgaagatag aagagatgtg tgtggcagcg gtgctggatt ggaaacggtg    420
aatgagcgga gtaaatcggt tggtgagtcc agtgatgtaa ttcgaaagga ggacgacagg    480
aatgataatg ttgcgaatgg tgaggaaagc aaatcaacgg aaacaacaac gacgccgttt    540
aaatttgctt acagggcgtc ggcaccagct caccggcgaa tcaaggagag tcctctcagc    600
tccgacgcca ttttcaaaca gagtcacgca ggcctgttca atctctgtgt ggtggtgctg    660
attgctgtta acagcaggct gattatcgag aacttgatga agtatggcct tttaattagg    720
gctggctttt ggtttagctc gaagtcgttg agggattggc cgcttctaat gtgctgtctc    780
agtctccaaa ttttgccgct cgctgctttt cttgtggaga agttggcaca gcagaggcat    840
ttgactgagc gtgcggtggt tactcttcac ataactataa caacagctgc cattttgtat    900
ccagttctgg tcattcttgg gtgtgattct gcttttctgt ttggtgtcat attgatgctg    960
gttgcttgca ttgtgtggat gaagctggtt tcttacgcac atacaaatca tgatatgaga   1020
cagctcgcaa agtctacgga caaggatgaa acttcagatg gggatttctc ttatgatgtt   1080
agcttcaaga gtttggctta cttcatggtt gcgccaacat tatgttatca gcttagctat   1140
ccccacactc catgcattcg caaaggttgg gtggcacgcc aattcatcaa gctggtaata   1200
tttacaggat tgatgggatt tatcatagaa cagtacatta acccaattgt gcaaaactca   1260
caacatcctt tgaaaggaaa ccttttatat gccatcgaga gggtattgaa gctttcggtt   1320
ccaaatttat atgtctggct ctgcatgttt tactgcttct ttcatctttg gctaaatata   1380
cttgcggaac tactatgttt tggtgatcgt gagttctaca aggattggtg gaatgccaaa   1440
acaattgatg agtactggag gatgtggaat atgcctgttc ataagtggat ggttcgtcac   1500
atttatttcc cttgcttaag aaacggaatt ccaaaggggg tcgcaatact gattgctttc   1560
cttgtatctg ctgttttcca cgagctgtgt attgctgttc catgtcgcct tttcaagtgg   1620
tgggcattca tgggaattat gttccaggtt cctttggtca tactcacaaa cttcttacaa   1680
aacaagttcc aaagctcgat ggtgggcaat atgatgttct ggtgcttttt ctgcattctt   1740
ggtcagccaa tgtgtgtgct tctgtattac cacgatgtga tgaatagaaa aagcagtgca   1800
cgttaagctt catccaggga tgaattgttg tatgagcaag tatttttaagt tttggatccc   1860
```

```
aagctctatt ctactgtttc tggcaaggca ttcctgctat ttccttcatc agttccaaca    1920
atattcagat gatacgaaat atctgtttgg aatgcacaac acaagccacg gccagagatg    1980
ctgatgtctc acattttatt gtgttcttca tgtcggagaa atgtaaaata ctatcttgag    2040
ataactctca tgttagtaaa tacctttttg cctctaaaaa aaaaaaaaaa aaaaaaaa      2099
```

<210> SEQ ID NO 9
<211> LENGTH: 1964
<212> TYPE: DNA
<213> ORGANISM: Perilla frutescens

<400> SEQUENCE: 9

```
tttagaacca aactattctc cgttaagttc tgagttcgat ttctttcttt tctcaaattt      60
tccgtgcgat ggcgatcttg gactcgccgg agatcctgga cacgacgtcg tccagtgccg     120
acaacggcgc cgcacatcac accactcttc gccggagaca agtgcgcgc tccgttccgc      180 ctcttctcga ctccgattcc aactctctgg aggcagagag cgcaatcaat gattccgaaa     240
atgttcgaaa cgacgctaat ttgatcgaaa atctccgcgg cggagccgtg aatccgaga      300 acgaaaaaca ggagagttat ggtaaggagg aggggcgaa agtgaaggag aatggagaaa      360
ctagtaatgg caacggaact gatgttatgg ccgtcaaatt cacattcagg ccggcggcgc     420
ctgctcaccg caaaaataag gagagtcctc ttagctccga cgccatcttc aaacagagcc     480
atgcaggcct cttcaacctt tgtatagtgg tgcttgttgc tgtaaatagc agactaataa     540
ttgagaattt aatgaagtat gggtggctga tcaaatcagg attttggttt agttcaacat     600
cgcttaggga ttggccactg ctaatgtgtt gtcttagtct tccagttttt gcactcgctt     660
catttcttgt cgagaagttg gtgaaactaa attatatacc tgagtgggtc gcagtctttc     720
ttcatgttac aatcacaaca gtggaaatct tgtttccagt tgttgtcatt cttaggtgtg     780
attctgctgt tctatcaggt gtcacgctaa tgctctttgc ttgcactgta tggttgaagc     840
tcgtttccta cgcacataca aactatgatt tgagagtact tgcaaaatca cttgataagt     900
gggaagctat gtccaggtac tggaacctcg actacgctta tgatgtaagc tttaagagtc     960
tggcatactt catggttgct cctacattgt gttaccagcc aagctaccct cggacagctt    1020
gcattcggaa gggttgggtg gtaaggcaac taattaagct ggtaatattc acaggactca    1080
tgggatttat tatagaacag tacataaacc cgatcgttca aaattctcaa catcctctga    1140
aaggaaacct tttatatgcc attgagaggg tcttgaagct ttctgttcca aatttatatg    1200
tgtggctctg catgttttat tgttttttcc acctctggct aaatatactt gctgaacttc    1260
tgtgctttgg ggaccgtgag ttttataagg attggtggaa tgcgaggaca gtggaggagt    1320
actggagaat gtggaatatg cctgtccata aatggatggt tcggcatata tactgtccat    1380
gcttacaaaa tggaatacca aagatagtgg cagttttgat cgcgtttctt gtgtctgcga    1440
tttttcatga gctgtgcgtt gcagtcccctt gccaaatatt caagttttgg gcgttctcgg    1500
gtatcatgct tcaggttcct ctcgtaatcg tgactaatta cttgcaagaa aagttcaaaa    1560
actcaatggt gggcaatatg atgttctggt gcttcttctg tatctttggt caacctatgt    1620
gtgtgttgct gtactaccac gacttgatga atcgaaaagc tagtgcaagg tagggatgtg    1680
attcatcttc tgagtagaaa tctaaagctc accagcccca acccacccga aaacaaaaa     1740 ggagcaagga tcctgattgt gagctggtag ataatttgct acaactatgt ttcttaaata    1800
gctgggagta gtttgttatc tgccttcacc taggacgacg ttatgatctg ttgtgatggg    1860
ggtaaggggg catgcaaatt ttgtctattt ttcaaggaat acagaaatgg tgaaaatttg    1920
```

```
atgaagcata cccctcgttt actgacaaaa aaaaaaaaaa aaaa            1964
```

<210> SEQ ID NO 10
<211> LENGTH: 1539
<212> TYPE: DNA
<213> ORGANISM: Zea mays

<400> SEQUENCE: 10

```
atggcggact ccgaagacgc gccgccagcc gtgcaccgcc gcccaccgcg ccccgctcgc     60
ggtgctgctg cagcccaggg cttcgcggcc gcgttgcgcc gccggctgag atccggcgct    120
gcggtggcgg cacgcgccag cttttgccgca gactccgggg acgagtctgg ccccggcgag   180
ccctcttcgt ctcgccgccg cgacaacagc gggggcgcct cgtccgccgc cggcggccgg    240
gccggggcag gggacttctc cgcgttcacc ttccgcgccg cggcgcctgt ccaccggaaa    300
gccaaggaga gccctctgag ctccgacgcc atcttcaagc agagtcatgc aggccttttc    360
aacctatgta ttgttgttct ggttgcggtg aatagcaggc tcattattga gaacctgatg    420
aagtatggct tattaataag atctggcttt tggtttaatg ctacatcatt gcgagactgg    480
ccactgctaa tgtgttgcct tagtctaccc atatttcccc ttggtgcatt tgcagtcgaa    540
aagttggcat tcaacaatct cattagtgat cctgctacta cctgttttca catccttttt    600
acaacatttg aaattgtata tccagtgctc gtgattctta agtgtgattc tgcagtttta    660
tcaggctttg tgttgatgtt tattgcctgc attgtttggc tgaagcttgt atcttttgca    720
catacaaacc atgatataag aaaactgatc acaagcggca agaaggttga taatgaactg    780
accgcggctg gcatagataa tttacaagct ccaactcttg ggagtctaac atacttcatg    840
atggctccga cactctgtta tcagccaagt tatcctcgaa caccttatgt tagaaaaggt    900
tggctggtcc gtcaagttat tctatacttg atatttactg gtctccaagg attcattatt    960
gagcaataca taaatcctat tgttgtgaac tctcaacatc cattgatggg aggattactg   1020
aatgctgtag agactgtttt gaagctctca ttaccaaatg tctacctgtg gctttgcatg   1080
ttttattgcc ttttccatct gtggttaaac atacttgctg agattcttcg atttggtgac   1140
cgagaattct acaaagactg gtggaatgca agacaattga tgagtactg gagaaaatgg    1200
aacatgcctg tgcataaatg gattgttcgt catatatatt tcccttgcat gcgaaatggt   1260
atatcaaagg aagttgctgt ttttatatcg ttctttgttt ctgctgtact tcatgagtta   1320
tgtgttgctg ttccctgcca catactcaag ttctgggctt tcttaggaat catgcttcag   1380
attcccctca tcatattgac atcatacctc aaaaataaat tcagtgacac aatggttggc   1440
aatatgatct tttggttttt tttctgcata tacgggcagc caatgtgtgt tctattgtat   1500
taccatgatg tgatgaaccg gactgagaag gcaaaataa                          1539
```

<210> SEQ ID NO 11
<211> LENGTH: 1548
<212> TYPE: DNA
<213> ORGANISM: Sorghum bicolor

<400> SEQUENCE: 11

```
atggcggaca ccgacgacgc gccgccggcc ccggccgtgc accgccgccc accgcgcccc     60
gcccgcggtg ctgccgctgc ccagggcttc gcggccaagt tgcgccgacg gctcagctcc    120
ggcgccgcgg cggcggcgcg cgccagcttc gcggcagact ccggggacga gtccggcccc    180
ggggagccct cttcgtcccg ccgccgcgac aacggcgggg acgcctcgtc cgccgccgac    240
```

```
ggcggccggg gcggggcagg ggacttctcc gctttcacgt tccgcgccgc ggcgcctgtc      300
caccggaaag ccaaggagag cccctcagc tccgacgcta tcttcaagca gagtcatgca       360
ggccttttca acctatgtat tgttgttctg gttgcagtga atagcaggct cattattgag      420
aacctgatga agtatggctt attaataagg tctggctttt ggtttaatgc tacatcattg      480
cgagactggc cactgctaat gtgttgcctt agtctacctg tgtttcccct tggtgcattt      540
gcagttgaaa agttggcatt caacaatctc attactgatg ctgccgctac ctgttttcac      600
atctttctta caacacttga aattgtatat ccagtgcttg tgattcttaa gtgtgattct      660
gcagttttat caggctttgt gttgatgttt attgcctgca ttgttggct gaagcttgta       720 tcttttgcac atacaaacca tgatataaga aaactgatca caagcggcaa gaaggttgat     780
aatgaactga ccgtggctga catagataat ttacaagctc caactcttgg gagtctaaca     840
tacttcatga tggctccgac actctgttat cagccaagtt atcctcgaac accttatgtt    900
agaaaaggtt ggctggttcg tcaagttatt ctatacttga tatttactgg ctccaagga    960 ttcattattg agcaatacat aaatcctatt gttgtgaact ctcaacatcc attgaaggga   1020
ggattactga atgctgtaga gactgttttg aagctctcat taccaaatgt ctacctgtgg    1080
ctttgcatgt tctattgcct tttccatcta tggttaaaca tacttgctga gattcttcga    1140
tttggtgacc gtgaattcta caaagactgg tggaatgcaa aaacaattga tgagtactgg    1200
agaaaatgga acatgcctgt gcataaatgg atgcttcgtc atatatattt tccttgcata   1260
cgaaatggta tatcaaagga agttgctgct tttatagcgt tcttgtttc tgctgtattt    1320 catgagttat gtgttgctgt tccctgccac atactcaagt tctgggcttt cttaggaatc    1380
atgcttcaga ttccctcat catactgaca tcatacctca aaataaatt caatgacaca      1440 atggttggca atatgatctt ttggttcttt tctgcattt acgggcagcc aatgtgcgtt     1500
ctattgtatt accatgatgt gatgaaccgg actgagaaga caaaataa                 1548
```

<210> SEQ ID NO 12
<211> LENGTH: 2103
<212> TYPE: DNA
<213> ORGANISM: Oryza sativa

<400> SEQUENCE: 12

```
gtcgtcccgc gtctctcctc acctctcgtc tccctcgcga cgtctcccct tctccctcca      60
cccctccaat ggtgggctcc gatggcgacg gcgacggcgg cggaggggaa gcacacgcgc     120
cggcggcgcc cgcgcaccac caccgccggc ccccgcgccc gcggggaggc agcggggcca    180
tcgtcgaggg cttcgcggcg gcgctccgtc gcaggatccg ctcggggggcc gcggcggccg    240 cgcgggccag cttcggggggc gactccgggg acgaggccgc ctccggggag ccctcctcgt    300
cctcgtcctc gtccccgtcc cgccgccgtg gcggcgactc caacgggggcg gaggcgtcct   360 ccgccgccgg gggcggtggt ggccgtggcg gcggtgggga cttctccgcg ttcacgttcc    420
gcgcggcggc gccggtgcac cgcaaggcca aggagagccc cctcagctcc gacgccatct    480
tcaagcagag tcatgcaggc ctttttcaacc tatgcattgt tgttctagtt gcagtgaaca    540
gcaggcttat tatcgagaac ttaatgaagt atggcttatt aataagagct gggttttggt    600
ttaatgataa atcattgcgg gactggccac ttctaatgtg ttgtcttagt ctgcctgctt    660
tccccctggg tgcatttgca gttgaaaagt tggcatttaa caatgttatt actgatgctg    720
ttgctacctg cctccatatc ttccttttcaa caaccgaaat tgtatatcca gtgcttgtga    780
ttcttaagtg tgattctgca gttttgtctg gcttttttgtt gatatttatt gcctgtattg    840
```

```
tttggctgaa gcttgtatct tttgcacata caaaccatga tataaggcaa ctgaccatgg      900
gcggcaagaa ggttgataat gaactaagca cagttgacat ggataattta caacctccaa      960
ctttagggaa tctaatatac ttcatgatgg ctcctacact ctgttatcag ccaagctatc     1020
cccgaacttc atgtgttaga aaaggttggc tgattcgtca aattattctg tacttgatct     1080
ttactggtct tcaaggcttc attattgagc aatacataaa tccaattgtt gtgaattctc     1140
agcatccatt gaaaggagga ctcctaaatg ctgtagagac tgttttgaaa ctctcattac     1200
caaatgttta cctgtggctt tgcatgttct atgctttttt ccatctctgg ttaagtatac     1260
ttgctgagat tcttcgattt ggtgaccgtg aattctacaa agattggtgg aatgcaaaaa     1320
caattgatga gtattggaga aaatggaata tgcctgtaca taaatgggtt gttcgccata     1380
tttactttcc ttgcatgcga aatggtatat caaaggaagt tgctgtcttg atatcattcc     1440
ttgtttctgc cgtactccat gagatatgtg tcgctgttcc ctgccgcatt ctcaagttct     1500
gggcattctt aggaataatg ctacagatcc cccttatcgt attgacagca tacctcaaaa     1560
gtaaattcag agatacaatg gttggcaaca tgatattttg gttcttttc tgcatctatg      1620 ggcagccaat gtgccttctc ctgtactatc atgatgtgat gaacaggatt gagaaggcaa     1680
gataaatgcg tgttgccatc ttttcctct gtttcatttt gtaccagcag aagcacaagc      1740
aataatccac atgctagcca taaaacagca tgattcccaa cggtgtggta cagccaacct     1800
tcctgttatt ctatttctt ggctgtggtg tagatttagt ttttaacttg tggctaaccg      1860
caggaatgcc tgtagataag catctgtcat tctgtctggc gacgttctcc ttattaatgt     1920
gtagatgtag aactgtttcc gaaaactata tatcttgaat ctgttatgcc tcgacgaaca     1980
taatcctttt gttaagctta gttggtacag tctagaaagg ataagagtcg tggatgtacg     2040
atttcgtctg ccatatatca cgctcatatt ggcacaggta actttgtcgc taccttctat     2100
ctc                                                                   2103

<210> SEQ ID NO 13
<211> LENGTH: 1473
<212> TYPE: DNA
<213> ORGANISM: Oryza sativa

<400> SEQUENCE: 13
atggccccgc cccctcgct cgcccccgat cgcggcggcg gcgaacccga cgacgccctc        60
cgcctgcggg cccgcgccgc cgccgccgcc ggtgacgctc ccgctccgca gcagcagcag      120
gagcagaggc atcaggagca gcagcagcag ctgctctggt accgcgcgtc ggcgcccgcc      180
caccgccgcg tcagggagag ccccctcagc tccgacgcca tcttccgcca gagccatgca      240
ggccttctga acctatgcat tgttgtgctg gttgctgtga acagcagact tattattgag      300
aatttaatga agtatggcct actaattaga gctggatttt ggtttagtgg aacatcgctg      360
gcagattggc ctcttctcat gtgctgtctc acttaccaa cttcccgct tgctgcactt       420 atggttgaga agttggctca agaaaaactt attagtaaac atgtggttat tcttctccat      480
atcgttatta caacatctgt ccttgtctat ccagttgttg tgattctaaa gtgtgattcg      540
gcagtattat ctggatttgt gttgatgttt cttgcaagca ttatttggtt gaagcttgtt      600
tcttttgctc atacaaatta tgatataaga atgctgtcca aaagtattga aaagggcgtg      660
acacatgaca tttctataga tccggagaac attaaatggc caacctttaa aaggctatcc      720
tacttcatgt tggccccaac actttgttac cagccaagtt atccccgaac tacatatatt      780
```

-continued

```
agaaaaggtt gggtggtccg acaactgata aaatgccttg tttttacagg cttgatgggt    840
tttataattg agcaatacat aaatccaatt gtgaagaatt cgaagcatcc attgaaaggg    900
aatttcttga atgctataga gagagtattg aaattatcag tgccaacatt atatgtctgg    960
ctttgcatgt tctactgttt tttccatctc tggttgaata ttcttgctga gctcctctgt   1020
tttggtgatc gtgaattcta caaggactgg tggaatgcca aaacagttga agagtattgg   1080
agaatgtgga atatgcctgt tcacaagtgg gtcattcgac atatatattt tccatgcata   1140
aggaatggtt tttcaaaggg tgttgctatc ctaatctcgt tcctggtttc agctgcattt   1200
catgagatat gtattattta tttcattgtc cttatcgatt gcagctatg tgttgctgtt    1260 ccatgccaca ttttaaatt ctgggcattt attgggatca tgtttcagat tccctggta    1320 ttcttgacga ataccttca agataaattc aataacacaa tggtgggcaa catgatattt   1380
tggttcttct tcagcatcct ggggcaacca atgtgtgttc tcttatacta ccatgatgtc   1440
atgaacaggc aacaagccca acaaatagaa tag                                1473
```

<210> SEQ ID NO 14
<211> LENGTH: 1590
<212> TYPE: DNA
<213> ORGANISM: Sorghum bicolor

<400> SEQUENCE: 14

```
atggccccgc cccctccat ggccgccgcc tccgatcgcg ccgtccccgg cgccgacgcg      60
accgaggcgt cctccctccg cctccgccgc gcccctcag ccgacgccgg cgaccttgcc     120
gacgattcct caggagaccg gcgggagaac ggcgagccgc aaccgccgca ggagcagcag    180
cagcagcacg agatgctgta ctaccgcgcg tcggcgcccg cccaccgccg cgtcaaggag    240 agcccctca gctccgacgc catcttccgg cagagccatg ctggtcttct gaatctatgc     300
atcgttgttc tgattgcagt gaacagcaga ctcattattg agaatttaat gaagtatggc    360
ctattgataa gagctggatt ttggtttagt gcaagatcgc tgggtgactg ccccttcta    420 atgtgctgcc tcactttacc agttttccca cttgttgccc tcatggctga agctgatt     480 agaagaaagc tcattggtga acatgtggtt attctactcc atatcattat tacaacatct    540
gtcattgtct atccagttgt tgtgactctt aagtgcgact cagcagtgct atctggattc    600
ttgctaatgt ttcttgcgag catcatgtgg atgaagcttg tctcttatgc acatacaat    660 tatgatataa gggcattgtc caaaagtact gaaaagggtg ctgcatatgg aaattatgtc    720
gatcctgaga gtatgaaaga tccaaccttt aaaagtctag tgtacttcat gttggcccca    780
acactttgtt accagccaac ttatccccga actacatgta ttaggaaggg ttgggtgacc    840
cgacaactta taaagtgcct ggtttttaca ggcttgatgg gcttcataat tgagcaatat    900
ataaacccaa ttgtgaagaa ttccaaacat ccactgaaag ggaatttctt gaatgctata    960
gaaagagtct taaactctc agtgccaaca ttatatgtat ggctttgcat gttctattgc   1020
ttttttcatt tatggctgaa cattctagct gaactcctct gtttcggtga ccgtgaattc   1080
tacaaggact ggtggaatgc caaaactgtt gaagagtact ggaggatgtg aacatgcct    1140 gttcataaat ggatcatcag acacatatat tttccatgta taggaaagg cttttccagg    1200 ggtgtagcta ttctagtctc gtttctggtt tcagctgtat ttcatgagat atgtattgcg    1260
gtgccgtgcc acattttcaa attctgggca ttttctggga tcatgtttca gataccgttg   1320
gtattcttga caagatatct ccaggctacg ttcaagaata taatggtggg caacatgata   1380
ttttggttct tcttcagtat agtcgggcag ccgatgtgtg tcctttata ctaccatgat    1440
```

| | | |
|---|---|---|
| gtcatgaaca ggcaggccca gcaagtagat aattcggcag aaacatgtac tttaagacaa | 1500 | |
| gttatcagaa gcagactgga gcgacgcagc aggaagcagc agcagcagca ggccagcagc | 1560 | |
| cccccttttgc cattgttacc agctagctag | 1590 | |

<210> SEQ ID NO 15
<211> LENGTH: 1485
<212> TYPE: DNA
<213> ORGANISM: Zea mays

<400> SEQUENCE: 15

| | |
|---|---|
| atggccccgc cccctccat gcctgccgcc tccgatcgcg ccggccctgg ccgcgacgcg | 60 |
| ggcgactcgt cctcccttcg cctccgccgc gcccctcag ccgacgccgg cgaccttgcc | 120 |
| ggcgattcct cgggaggctt gcgggagaac ggcgagccgc aatcgccgac gaatccgccg | 180 |
| ccgcaggagc agcagcagca cgagatgcta tactaccgcg cgtcggcgcc cgcccaccgc | 240 |
| cgcgtcaagg agagccccct cagctctgac gccatcttcc ggcagagcca tgctggtctt | 300 |
| ctgaatctat gcattgttgt tctgatcgca gtgaacagca gactcattat tgagaattta | 360 |
| atgaagtatg gcctgttgat aagagctgga ttttggttta gtgcaagatc gctgggtgac | 420 |
| tggccccttc taatgtgctg cctcactcta ccagttttcc cactagttgc actcatggct | 480 |
| gagaagctga tcacaagaaa gctcattggt gaacatgtgg ttattctact ccatatcatt | 540 |
| attacaacat ctgccattgt ctatccagtt gttgtgactc ttaagtgtga ctcagcagta | 600 |
| ctatctggat ttgtgctaat gtttcttgcg agcatcatgt ggatgaagct tgtctcttat | 660 |
| gcacatacaa attatgatat aagggtattg tccaaaagta ctgaaaaggg tgctgcatat | 720 |
| ggaaattatg tcgatcctga gaatatgaaa gatccaaacct ttaaaagtct agtgtacttt | 780 |
| atgttggccc caacactttg ttaccagcca acttatcctc aaactacatg tattagaaag | 840 |
| ggttgggtga cccagcaact cataaagtgc gtggttttta caggcttgat gggcttcata | 900 |
| attgagcaat atataaaccc aattgtgaag aattccaaac atccactgaa agggaatttt | 960 |
| ttgaatgcta tagaaagagt cttaaaaactc tcagtgccaa cattatatgt atggctttgc | 1020 |
| atgttctatt gctttttttca tttatggctg aacattgtag ctgaactcct ctgtttcggt | 1080 |
| gaccgtgaat tctataagga ctggtggaat gccaaaactg ttgaagagta ctggaggatg | 1140 |
| tggaacatgc ctgttcataa gtggatcatc agacacatat attttccatg tataaggaaa | 1200 |
| ggcttttcca ggggtgtagc tattctaatc tcgtttctgg tttcagctgt atttcatgag | 1260 |
| atatgtattg cggtgccttg ccacattttc aaattctggg cattttctgg gatcatgttt | 1320 |
| cagatacct tggtattctt gacaagatat ctccatgcta cgttcaagca tgtaatggtg | 1380 |
| ggcaacatga tatttggtt cttcttcagt atagtcggac agccgatgtg tgtccttcta | 1440 |
| tactaccatg acgtcatgaa caggcaggcc aggcaagta gatag | 1485 |

<210> SEQ ID NO 16
<211> LENGTH: 1912
<212> TYPE: DNA
<213> ORGANISM: Physcomitrella patens

<400> SEQUENCE: 16

| | |
|---|---|
| atgcctgtga agagtagcaa tctggcgggg gagagggctg ccaccagcca tattaatgcc | 60 |
| aacacgaaat tcgacctgcg ggggtgtacg cctgcgcatc gcgttaggag ggaaagcccg | 120 |
| cttagttcag acgcaatttt tcatcagagt catgctgggt tgttcaatct ctgtattgtt | 180 |

-continued

| | |
|---|---|
| gttttgatag ctgttaacag ccggcttatt attgagaact taatgaagta tggactactc | 240 |
| attagaactg gtttctggtt tagctccaag tctgcacgcg attggccact cttgatgtgc | 300 |
| ggtttgagtt taccgacttt tcccttttgca gcgttactag tggaaaaact atgctggaaa | 360 |
| aatgaaaacg ggaaatggtt gatttttcgta ctacacctca taatcagcac tgtagggata | 420 |
| ctgtatcctg gatatgttat acacagggtg caatccgcac tgctgcctgg tcttgtattg | 480 |
| atactcattg cagtgactgg gtggatgaag cttatatctt acgctcatgt caacaaggac | 540 |
| atgcgagaac ttttgagagc caaagaaaag ctacctgagg caccacagta cgcagataaa | 600 |
| atagaggttc cggaccacct tacgatccaa aatattgctt atttcatgct cgcgcccaca | 660 |
| ctttgctacc agttgagcta ccctcgttcg acacaattc gaaaagttg ggtgttacgg | 720 |
| caagccggga aattggttgt gttcttgggt tagggggat tcatcattga gcagtacata | 780 |
| aatcccactg tgaagaattc acagcacccg ctcagggca actatcttca agcactggag | 840 |
| agggttttaa agctttcgtt gccagttctt tatgtttggc tgtgcttgtt ctactgttta | 900 |
| tttcatcttt ggttgaatat tgtggcggag ctacttcgct ttggggacag ggaattttat | 960 |
| aaggactggt ggaatgctca aacagttgaa gagtattggc gaatgtggaa catgcctgtg | 1020 |
| cacaagtgga tggtgcggca tatttatttt ccctccattc gagctggctt atcaaagaaa | 1080 |
| gcagcagtac tactggtgtt tgcaatttca gctttgtttc atgaggttat cattggtgtt | 1140 |
| ccgtgtcata tgcttcgatg ctgggctttt cttggtatca tgatgcaggt tccgttggtg | 1200 |
| tacttgacaa acgtgataaa agagcggtac catagctcta tggttggaaa tatggtattt | 1260 |
| tggttcttct tttgcattgt cgggcaaccc atgtgcttgc ttctctacta ccacgacgtt | 1320 |
| ttcaacaact ttcccagtac ctgaactgag atcacccatt cgtgcagttg ttaatcttgt | 1380 |
| gaatagcact cctcatctgt accttgttat ggcttccact tctcgagaat cgactaaacc | 1440 |
| gcaactcata tgtttgtcaa taacgattca ttcgtaggcg ggttggtgtg agattacaag | 1500 |
| agaggaaact ttcgtcgtaa gccagcagtg tagatacagt ccaggtagga gtgtaacggg | 1560 |
| cacttgcttc aagggcagat ccttgtcaac gcaagctttt gttggagctt gttggagctt | 1620 |
| gtttcgcact tagtattctt ttctagctgt agtttttaggt gacgttagtc tattcttggt | 1680 |
| cccatcatcc atcctgtaag atgctgggcg tgctcacgtg cagaagctgc ctcgaatcct | 1740 |
| acgttacaat ttcatgttgg ataccgcgtg gatgtccgct tcagaatctg cgtcatgatg | 1800 |
| atgcacacca tttttttcta ttggaaactg aacagagggt agtgatacgt aagaacattt | 1860 |
| tgggaaccgt gcctgaaaat cgtcggagca ataatgatg tggttttgca gc | 1912 |

<210> SEQ ID NO 17
<211> LENGTH: 1278
<212> TYPE: DNA
<213> ORGANISM: Selaginella moellendorffii

<400> SEQUENCE: 17

| | |
|---|---|
| atgcggcccct cgctcccggc gcaccggcgg agcaaggaga gcccgctcag ctccgacgcc | 60 |
| atcttcacgc agagccacgc cggcctcttc aacctctgca tcgtcgtgct ggtggcggtg | 120 |
| aacagccggc tcatcatcga gaatctcatg aagtatggcc tcctcatcca ggccgaggtc | 180 |
| ctcttcagct ccaagtcgct caaggactgg ccgctcctca tgtgtggcct ctcgctgctg | 240 |
| atcttccccc tcgccgccta tgtcatcgag aagatcaagg cccgccgccc cgccaccgcc | 300 |
| gtggcgccgc tccacttgat caacctcgcc gccgcgctgc tctacccgat ctacgtgatc | 360 |
| gagatgttcc agtcggatct cctctcgggg ctggttctca tgctcatcgc cgtcaccggc | 420 |

```
tggctcaagc tcgtctccta cgcgcacacc aacgccgaca tccgcgcggt gaagaaggac      480
ggtggcaaga tcgagctccc cgccgaggcg ccggcgatcg actacccgga caacatctcg      540
ctcaagaaca tcgcctactt catggcagcg ccgacgctgt gctaccagct gagctacccg      600
cgctcgccgc ggattagaac cgggtgggtg ctccggcagc tgggcaagtg gatcgtcttc      660
aacggattca tgggcttcat catcgggcag tacatgaatc cgatcatccg gaactcgacg      720
cacccgctca gggggaacta cctctacgcg atcgagcgcg tgctcaagct gtccatcccc      780
acgctctacg tctggctcgg cttcttctac tgcttcttcc acctgtggct caacatcgtg      840
gcggagatcc tgtgcttcgg cgaccgcgag ttctacaagg actggtggaa cgccaagtcg      900
gtggacgagt actggcggct gtggaacatg cccgtccacc gctggctcgt ccgccacgtc      960
tacttcccgt gcctccggct gggcctccac aagcagttcg ccattttggt ggtgttcgtc     1020
atctccggga tctttcacga gatttgcatc gcggtgccgt gccacatgct gcggggctgg     1080
gcgtttctgg ggatcatgtt ccaggtgccg ctggttctgg tgaccaacgt cctccagcgc     1140
aagttccaga gctccatggt cggcaacatg atcttctggt tcttcttttg catcgtcggg     1200
cagccgatgt gcgtgctgct ctactatcac gacgttgtca acaggcagca gctccagcta     1260
gctgggcggt ccaaataa                                                  1278

<210> SEQ ID NO 18
<211> LENGTH: 1524
<212> TYPE: DNA
<213> ORGANISM: Euonymus alatus

<400> SEQUENCE: 18
atggctgcta acttgaacga agcctcggat cttaattttt cgcttcggag gagaactggt       60
ggcatctcaa gtacgactgt gcctgattct agttccgaga caagttcgtc ggaggcggac      120
tatttggacg gaggcaaagg tgccgcggac gtcaaagatc gtggggatgg tgcggtggag      180
tttcagaatt cgatgaagaa cgtggagagg attgagaaac atgagagccg agtaggattg      240
gattcgagat tcacgtatag gccatcggtc ccggctcatc gcacaataaa ggagagcccg      300
cttagctcgg acgcaatatt caaacagagt cacgcaggtc tcttcaatct ctgtatagta      360
gttctggttg ctgtgaacag caggctgatc attgaaaatc taatgaagta tggatggtta      420
ataaggagtg ggttttggtt cagctcaaga tcattgagag actggcccct ttttatgtgt      480
tgtctcacac taccagtatt ccctcttgct gcttttctgt ttgagaagtt ggctcaaaaa      540
aatttaatat ctgaacctgt tgttgttttg cttcatatag taaacactac agctgccgtt      600 ttatacccctg ttttggtgat tctaaggtgt gattctgcct ttatgtctgg ggttacgttg      660
atgctctttg cttgtattgt gtggttaaag ttggtatctt atgctcatac caactatgat      720
atgagagccc tcaccaagtc tgttgaaaag ggggacacgc cgttgagctc tcagaacatg      780
gattactcgt ttgatgtcaa tatcaagagt ttggcatatt ttatggttgc tcccacatta      840
tgttaccaga ttagctatcc tcgtacccca tatgttcgca agggttgggt ggttcgtcaa      900
tttgtcaagt taataatatt tactggactt atgggattta taattgaaca atatatcaat      960
cctattgtcc agaattcaca acacccttg aaaggaaact ttttgtatgc cattgagaga     1020
gttttgaagc tttcagtccc aaacctttat gtttggctct gcatgttcta ctgccttttt     1080
catctctggt taaacactac tgctgaactt cttgttttg tgatcgtga ttctacaag       1140 gattggtgga acgctaaaac tgttgaggag tactggagaa tgtggaacat gcctgttcat     1200
```

```
aagtggatgg ttcgtcatat ctacttccca tgcttgagga acgggatacc caagggtgtt   1260
gcttttgtca tttccttctt agtttctgcc gtcttccatg agctatgcat tgctgttccc   1320
tgccacatct tcaagttatg ggctttcttt ggaataatgc ttcaggttcc cttggtgttg   1380
atcacaagtt atctgcaaaa taagttcaga agctcaatgg tgggaaatat gatgttttgg   1440
ttctctttct gcattttggg tcaacctatg tgcttacttc tatattacca tgatttgatg   1500
aatcgcaatg ggaagatgga gtag                                          1524

<210> SEQ ID NO 19
<211> LENGTH: 1557
<212> TYPE: DNA
<213> ORGANISM: Vitis vinifera

<400> SEQUENCE: 19
atggcgatct gcaactcgcc tgtcagtgtg accacgtcgt catcaagctc tcacgccgat     60
tcagatctcg acttttccat tcggaagagg ttcggcggga aggggaaggc cgtggcggat    120
tcgtcgctgg agacggagac ggaggcggcg gcggcggcg tgctcgaagc agagaagtcg     180
gtgggcgagg tggggagtgg cggtgatcga ggggaatcgg ggagtcaggt ggtgaggaat    240
ggggagaacg gagtggctga ggttgccgcg aaattcgcgt accggccgtg tgcgccggct    300
caccggaaag tgaaggaaag tcctctcagt tctgacgcca ttttcagaca gagtcatgcg    360
ggtctcttca acctctgtat agtagtgctt gtagctgtaa acagccggct tatcattgag    420
aatcttatga agtatggttg gttaatcagg gctggttttt ggtttagttc aaaatcattg    480
agagattggc cactctttat gtgctgttta accctcccaa tctttccact tgctgctttt    540
gtggttgaaa agttggctca acaaaagtat atctctgagc aggttgttgt ctctcttcac    600
atcataatta ctacagctgc agttttgttt ccagttttgg tgattctaag gtgtgattca    660
gctgttctct ctggtgtcac actaatgctc tttgcttgca ttgtgtggtt aaaattggta    720
tcttttgcac atacaaatta tgacatgaga gcagttgcca agttaattga taaggggat    780 gacttgtcca cttcattgaa tatggattac ccttatgatg tcaacttcaa gagtttggca    840
tacttcatgg ttgcccccac gctatgttac cagccaagct atcctcgcag cacatgcatt    900
cggaagggtt gggtctttcg ccaatttgtc aagttggcaa tatttacagg tgttatggga    960
tttataatag aacagtatat taatccaatt gttcagaatt ctcagcaccc tttgaagggg   1020 aattttttt atgcattgga gaggattttg aagctttctg ttccaaattt atatgtgtgg   1080
ctctgcatgt tctactgctt tttccacctc tggttaaata tacttgctga gcttcttcgt   1140
tttggggacc gtgagttcta taagattgg tggaatgcaa aaacagttga ggagtattgg   1200
agaatgtgga atatgcctgt tcataaatgg atggttcgcc atctctattt tccatgtcta   1260
cggaatggga tatctaaggg agtttctgtg gtgattgcct tgccatatc tgccatattc   1320 catgagctat gcattgctgt accttgtcac atgtttaagc tttgggcttt cattggaatt   1380
atgttccagg ttcccttggt tttggtcaca aattacttgc aaaataagtt cagaaattct   1440
atggtgggaa atatgatctt ctggctgttt ttcagcattc ttggtcagcc aatgtgtgtg   1500
cttctatatt accatgactt gatgaatcga aaagagacaa ctgaatcaag cctctga     1557

<210> SEQ ID NO 20
<211> LENGTH: 1880
<212> TYPE: DNA
<213> ORGANISM: Glycine max
<220> FEATURE:
<221> NAME/KEY: misc_feature
```

<222> LOCATION: (1798)..(1798)
<223> OTHER INFORMATION: n is a, c, g, or t

<400> SEQUENCE: 20

```
gaagagaaga ctgagttagt aaacacgctc gctcggtctt cttttccaat ggcgatttcc      60
gatgagcctg aaactgtagc cactgctctc aaccactctt ccctgcgccg ccgtcccacc     120
gccgctggcc tcttcaattc gcccgagacg accaccgaca gttccggtga tgacttggcc     180
aaggattccg gttccgacga ctccatcagc agcgacgccg ccaattcgca accgcaacaa     240
aaacaagaca ctgatttctc cgtcctcaaa ttcgcctacc gtccttccgt ccccgctcat     300
cgcaaagtga aggaaagtcc gctcagctcc gacaccattt ccgtcagag tcacgcgggc      360
ctcttcaacc tctgtatagt agtccttgtt gctgtgaata gccgactcat cattgagaat     420
ttaatgaagt atggttggtt gatcaaatct ggcttttggt ttagctcaaa gtcattgaga     480
gactggcccc tcttcatgtg ttgtctttct cttgtggtat ttccttttgc tgcatttata     540
gtggagaagt tggcacagca gaagtgtata cccgaaccag ttgttgttgt acttcatata     600
atcattacct cagcttcact tttctatcca gttttagtaa ttctcaggtg tgattctgct     660
tttctatcag gtgttacgtt aatgctattt gcttgtgttg tatggttaaa attggtgtct     720
tatgcacata caaactatga tatgagagca cttaccaaat cagttgaaaa gggagaagct     780
ctgcccgata ctctgaacat ggactatcct tacaatgtaa gcttcaagag cttagcatat     840
ttcctggttg cccctacatt atgttaccag ccaagctatc ctcgcacacc ttatattcga     900
aagggttggc tgtttcgcca acttgtcaag ctgataatat ttacaggagt tatgggattt     960
ataatagaac aatacattaa tcccattgta caaaattcac agcatcctct caagggaaac    1020
cttctttacg ccatcgagag agttctgaag ctttctgttc caaatttata tgtgtggctc    1080
tgcatgttct attgcttttt ccacctttgg ttaaatatat tggcagagct tcttcgattt    1140
ggtgatcgtg aattctacca ggattggtgg aatgccaaaa ctgttgaaga ttattggagg    1200
atgtggaata tgcctgttca caaatggatg atccgccacc tatattttcc atgtttaagg    1260
cacggtatac caaaggccgt tgctctttta attgccttcc tggtttctgc tttattccat    1320
gagctgtgca tcgctgttcc ttgccacata ttcaagttgt gggctttcgg tggaattatg    1380
tttcaggttc ctttggtctt catcactaat tatctgcaaa ataaattcag aaactcgatg    1440
gttggaaata tgatttttg gttcatattc agtattcttg gtcaacctat gtgcgtactg     1500
ctatattacc atgacttaat gaataggaaa ggcaaacttg actgaaggtg cacgtggata    1560
agcttttctg tttttggagt gtataattga tgtcgatatg ttgatcaata ttggtttcca    1620
cgagtacttt catctaccat ggcagtggct gctctgaagg atttccacct gatataccag    1680
gtcgcgaggc taattcatct tgatctatgt acttaatcaa ctctcctctg gcaattgtat    1740
cgatatatgc aattttgaga gccatacact ggcattgata actgccaagg aacagtgnta    1800
gctgttttc tgttaaatgt taattagtag agagctagat gtaaataaat ttatgctcaa     1860
aaaaaaaaaa aaaaaaaaa                                                  1880
```

<210> SEQ ID NO 21
<211> LENGTH: 1960
<212> TYPE: DNA
<213> ORGANISM: Glycine max

<400> SEQUENCE: 21

```
acgcgggggg agaagagaag actgagttag aaaacacgct cggtcttctt ctccaatggc      60
```

-continued

```
gatttccgat gagcctgaaa gtgtagccac tgctctcaac cactcttccc tgcgccgccg      120
tccctccgcc acctccaccg ccggcctctt caattcgcct gagacaacca ccgacagttc      180
cggtgatgac ttggccaagg attctggttc cgacgactcc atcaacagcg acgacgccgc      240
cgtcaattcc caacagcaaa acgaaaaaca agacactgat ttctccgtcc tcaaattcgc      300
ctaccgtcct tccgtccccg ctcaccgcaa agtgaaggaa agtccgctca gctccgacac      360
tattttccgt cagagtcacg cgggcctctt caacctttgt atagtagtcc ttgttgctgt      420
gaatagccga ctcatcattg agaatttaat gaagtatggt tggttgatca aatctggctt      480
ttggtttagc tcaaagtcat tgagagactg gccccttttc atgtgttgtc tttctcttgt      540
ggtatttcct ttcgctgcct ttatagtgga gaagttggca caacggaagt gtatacccga      600
accagttgtt gttgtacttc atataatcat tacctcaact tcgcttttct atccagtttt      660
agttattctc aggtgtgatt ctgcttttgt atcaggtgtc acgttaatgc tgttttcttg      720
tgttgtatgg ttaaaattgg tgtcttatgc acatacaaac tatgatatga gagcacttac      780
caaattagtt gaaaagggag aagcactgct cgatactctg aacatggact atccttacaa      840
cgtaagcttc aagagcttgg catatttcct ggttgcccct acattatgtt accagccaag      900
ctatcctcgc acaccttata ttcgaaaggg ttggttgttt cgccaacttg tcaagctgat      960
aatatttaca ggagtatgg gatttataat agaacaatat attaatccca tagtacaaaa     1020
ttcacagcat cctctcaagg gaaaccttct ttacgccacc gagagagttc tgaagctttc     1080
tgttccaaat ttatatgtgt ggctctgcat gttctattgc ttttttccacc tttggttaaa     1140 tatcctggca gagcttcttc gatttggtga tcgtgaattc tacaaggatt ggtggaatgc     1200
caaaactgtc gaagattatt ggaggatgtg gaatatgcct gttcacaaat ggatgatccg     1260
ccacctatat tatccatgtt taaggcacgg tctcccaaag gctgctgctc ttttaattgc     1320
cttcctggtt tctgctttat tccatgagct gtgcattgct gttccttgcc acatattcaa     1380
gttgtgggct ttcggtggaa ttatgtttca ggttcctttg gtcttgatca ctaattatct     1440
gcaaaataaa ttcagaaact caatggttgg aaatatgatt ttttggttca tattcagtat     1500
ccttggtcaa cctatgtgtg tactgctata ctaccatgac ttgatgaata ggaaaggcaa     1560
acttgactga agctacggcc attacatttt aaaggtgcac atggatgagc ttttcagttt     1620
tcagattgta aaattgatgt ggatatgttg gtcaatattg ttttctacga atgctttcat     1680
ctaccatggc attggctgct ctgaaggaat tccacgggat atgccagttc acgaggctaa     1740
ttcattatct tgatctatgt acttaccaac tctcctctgg caattgtatc aaaatatgca     1800
attttgagag ccatacactg gcattgataa ctgccaagga acactctaac tgttttctgt     1860
tagctgttaa ttagtagagg gctagatgta aatggtttat gctcaatata tttatttcct     1920
cctagtcttc aagttccaaa aaaaaaaaaa aaaaaaaaa                            1960
```

<210> SEQ ID NO 22
<211> LENGTH: 1536
<212> TYPE: DNA
<213> ORGANISM: Lotus japonicus

<400> SEQUENCE: 22

```
atggcgattt ccgaagactc tgaatctcta ttcgccgccg ccgccgcttc ctccgtcatc       60
caaagcggct cttccgtacg ccgcaggccc agcgctatct ccgccgtcgc gacagtcgaa      120
gacgagagtt cgagtgaaga gccggtgccg gtgagggatt ctggttccga cgtcgacgac      180
tccgtaagca gcgagcaaca cgtctccccc gccaccgcca atcgagagaa gaatcaggtg      240
```

```
catgacatct cagccaccaa attcgcctac cgtccttccg ccccgctca tcgcagagtc      300 aaggagagcc ccctcagctc cgacaacatt ttccgtcatc atgcgggtct cttcaacctt      360
tgtatagttg tgcttgttgc agtgaatagc agacttatca ttgagaattt gatgaagtat      420
ggttggttga ttaggactgg cttttggttt agttcaaaat cattgaggga ttggccactc      480
ttcatgtgtt gtctcagtct tgcaatattt ccttttgccg cctttgtagt cgagaagttg      540
gtgcaacaga agtgtatttc tgaaccagtt gttgttcttc atatattcat ttcaacagct      600
gcagttgtct atccagtttt agtaatcctc aggactgatt ctgcttttcc atcaggcgtc      660
acattaatgt tatttgcttg cattgtatgg ctaaaactgg tgtcttatgc acatacgaac      720
tatgatatga gagaacttac caaatcaatt gaaaagggag aagcacttcc caatactctg      780
aatatggact attcttatga tgtgagcttc aagagcttgg catactttat gattgctcct      840
acattatgtt accagccaag atatcctcgc agtccttcta tccggaaagg ttgggtgctt      900
cgtcaacttg tcaagctgat aatatttaca ggagtaatgg gatttataat agaacaatat      960
attaatccta tagttcaaaa ttcacagcat cctttgaagg gaaacctact atatgccatt     1020
gaaagagttc tgaagctgtc tgttccaaac ttatatgtgt ggctctgcat gttctactgc     1080 ttttccacc tttggttaaa tattctcgca gagcttctta gatttggtga tcgcgagttc     1140
tacaaggatt ggtggaatgc caaaactttt gaagagtatt ggaggatgtg gaatatgcct     1200
gttcacaaat ggatgatccg acacctatat tttccatgtt taagaaatgg tatacccaag     1260
ggtgttgcta ttttaattgc cttcctggtt tctgcattgt tccatgagct gtgcattgct     1320
gttccttgcc acatttcaa gttgtgggct tttggtggaa ttatgtttca ggttcctttg     1380
atcttgataa caattatct gcaaaataag ttcagaaact caatggttgg aaacatgatt     1440
ttttggttca tattcagtat tcttggtcaa ccaatggccg tactgctata ctaccacgat     1500
ttgatgaatc ggaaaagcaa acttgaccaa agctag                               1536
```

<210> SEQ ID NO 23
<211> LENGTH: 1620
<212> TYPE: DNA
<213> ORGANISM: Medicago truncatula

<400> SEQUENCE: 23

```
atggcaattt ccgatacacc ggaaaccact gcaaccgcca cagccaccgt aacaaccatc       60
gaaaccgaca cagatctcaa acgctcttca ctccgacgac gaccgagcgc cacatcaacc      120
gccggtggtc tcttcgacgc ggaaagtgca gctgcagatg ccgttcgaga ttcaggctcc      180
gatgattcgt tgaacggtaa gatcaacaac gaagaagagg ttaaagatcg aaaaacggat      240
catgcagaag gaattgttga cgatgatgat gataatgcgg ttaagaagaa tggtggtaat      300
gacgtcatca atgatcgtga aaatgttgct gtcgatttca aattcactta tcgtccttca      360
gttcccgctc accggagaag caagaaagt cctcttagct ccgcaatat ttttagacag       420 agtcatgcag gactgttcaa tctctgtatt gtggtgcttg ttgcagtgaa tagtaggctt      480
attattgaaa atctgatgaa gtatggatgg ttgattcgat ctggcttttg gtttagttca      540
aaatcgctta gagattggcc cctcttcatg tgttgtctta gtcttgcaat atttccactt      600
gctgcctttg tagtcgaaaa gttggcccaa caaaaacgta tttctgaacc agttattgtt      660
ctccttcata ttgtaattac aactgttata tcttatggat ccatggcctt gctgtgcagg      720
tgcgattctg ctttttatc tggttccacg ttaatgctat tgacttgcat agtgtggtta      780
```

| | |
|---|---|
| aaattggtgt catatgcaca tacaacctat gatatgagag cgcttgctgt ttcaaatgaa | 840 |
| aagggagaaa caatgcccga tactttcaat atggaggagt acccacacaa tgtgagcttc | 900 |
| cagagtttag catacttcat ggttgctcct acattatgct accagccaag ctatcctcgc | 960 |
| acaccttcgg ttcgaaaggg ttgggtctgt cgacaacttc tcaagctggt catatttaca | 1020 |
| ggagttatgg gatttataat agaacaatat atgaatccta ttgtccagaa ttcacaacat | 1080 |
| ccattgaagg gaaaccttct atatgccatt gagagagttc tgaagctttc tgttccaaat | 1140 |
| gtttatgtgt ggctgtgcat gttctattgc ttttttccatc tttggttaaa tatacttgcg | 1200 |
| gagcttctcc ggtttggtga tcgtgagttc tacaaagatt ggtggaatgc ccaaacggtt | 1260 |
| gaagagtatt ggaggatgtg gaatatgcct gtgcacaaat ggatggttcg tcacgtgtat | 1320 |
| tttccctgca taaggtttgg tatacccaag ggtgctgctg ctttgactgc ttttcctggtt | 1380 |
| tctgctgtgt tccatgagtt atgcattgct gttccttgcc gcatgttcaa gttgtgggct | 1440 |
| tttattggaa ttatgttcca ggttcctttg gtcttgatca ccaattacct gaaaaataaa | 1500 |
| tacagaaact caatggttgg aaatatgatt ttttggttca tattttgtat tcttggtcaa | 1560 |
| cctatgtgtg tactactata ctatcatgac ttgatgaata ggaaaggtga aattgactga | 1620 |

<210> SEQ ID NO 24
<211> LENGTH: 1566
<212> TYPE: DNA
<213> ORGANISM: Jatropha curcas

<400> SEQUENCE: 24

| | |
|---|---|
| atgacgattt tggagaccac tactagcgga ggtgatggtg ttgctgagtc gtcttccgat | 60 |
| cttaacgtat cgcttcgacg gagacggaaa ggcaccagct cggatggagc tttgccggaa | 120 |
| ttgacttcga atattgttga attggaatct gaaagcggtg gccaggtgat gatggatcca | 180 |
| ggtatggtga cggaaccgga gacagagaaa attaatggaa aagattgcgg cggtgacaag | 240 |
| gataagattg acaatcgcga gaatcgtggg aggtcggata ttaaattcac gtaccggcca | 300 |
| tcggtgccgg ctcatcgagc gctcagggag agtccgctta gctctgatgc tatatttaaa | 360 |
| caaagtcatg caggtctgtt caacctctgt atagtagtgc ttgttgctgt taacagcagg | 420 |
| cttatcattg aaaatctaat gaagtatggt tggttaatta aaacgggggtt ttggtttagt | 480 |
| tcaagatcgt tgagagattg gccccttctt atgtgctgtc ttaccctccc tatattctct | 540 |
| cttgccgcct atctagttga aagttggca tatcgaaaat atatatctgc acctattgtt | 600 |
| attttctttc atatgctcat taccacaaca gcagttttgt acccagtttc tgtgattctc | 660 |
| agttgtgggt ctgctgttct gtctggtgtt gcattgatgc tctttgcttg tatcgtgtgg | 720 |
| ttgaaattag tatcttatgc acatacaaac tatgacatga gagccattgc caactcagct | 780 |
| gacaagggag atgcactatc cgatacttca ggtgcagatt cttcacgtga tgttagcttc | 840 |
| aagagtttgg tctacttcat ggttgctcct acgctatgtt accagccaag ttatcctcga | 900 |
| acagattcag ttagaaaggg ttgggtggtt cgtcaatttg tcaagttaat aatatttaca | 960 |
| ggattcatgg gatttatcat agaacaatat atcaatccta ttgtccagaa ttcacaacac | 1020 |
| cccttaaagg gggatctatt tatgccatt gaaagggttt tgaagctctc agttccaaac | 1080 |
| ttatatgtgt ggctctgcat gttctactgc ttttttcatc tatggttaaa tatacttgct | 1140 |
| gagctccttc ggtttggtga cagagagttc tataaagatt ggtggaatgc aaggacagtt | 1200 |
| gaggagtact ggagaatgtg gaatatgcct gttcataagt ggatggttcg ccatatctac | 1260 |
| tttccatgct tgcggcataa aataccaagg ggggtagcct tgttaattgc tttcttcgtt | 1320 |

```
tcagctgtat tcatgagtt gtgcattgct gttccttgcc acatgttcaa gctctgggct    1380
tttattggaa ttatgtttca gattccattg gtcgggatca ctaattacct ccagaacaag    1440
ttcagaagct ccatggtggg aaatatgatc ttttggttca ttttctgcat tcttggtcaa    1500
cccatgtgtg tgctattgta ttatcatgac ctaatgaatc ggaaaggcaa tgctgaatta    1560
agatga                                                                1566
```

<210> SEQ ID NO 25
<211> LENGTH: 2084
<212> TYPE: DNA
<213> ORGANISM: Vernicia fordii

<400> SEQUENCE: 25

```
tctctctctc tttgctttac gtgtacatcg accaccacca cagccatctt gcgactgttc      60
aattatccta taagtaccac cgcattcatc accgccaatc cttaactcta atttgctata     120
ctaaacactt gctttatatg cgcttttcta tttactcttc actgtaattt cttattggta     180
ttcaaagtgt tttcaatgac aatccctgaa cgccggata attccacgga tgctaccacc      240
agtggcggtg ctgagtcctc ttccgatctt aacctttctc ttcgacggag gaggactgct     300
tcaaactccg atggagctgt cgcggaattg gcttccaaga ttgatgagtt ggaatctgat     360
gccggaggag gccaggtgat taaggatccg ggagcagaaa tggattcggg gactttgaaa     420
agtaatggaa aagattgcgg aaccgttaag gataggattg aaaatcgtga aatcgtgga      480 ggatcggatg ttaaattcac gtatcggccg tcggtgccgg ctcaccgggc gctcaaggag     540
agtccgctta gctctgataa tatatttaaa caaagtcatg caggtctctt caatctctgt     600
atagtagtgc ttgtagcggt taacagtcgg cttatcattg aaaacataat gaagtatggt     660
tggttaatta agactgggtt tggtttagt tcaagatcgt tgagagactg gccacttctt      720
atgtgctgtc ttaccctccc aatattttct cttgctgcct atctagttga aagttggcc      780 tgtcggaagt atatatctgc acccactgtt gttttttcttc atattctttt ctcctcaaca     840
gcagttttat accctgtttc tgtgattctc agttgtgaat ctgctgtttt gtccggtgtc     900
gcattgatgc tctttgcttg tatcgtgtgg ttgaaattgg tatcttatgc acatacaaac     960
tttgatatga gagcaattgc taactcagtt gataagggag atgcgctatc caatgcttcg    1020
agtgcagagt cctctcatga tgttagcttc aagagtttgg ttatttcat ggttgctccc     1080 acattgtgtt accagccaag ttatcctcga actgcatcca ttcgaaaggg ttgggtggtt    1140
cgtcaatttg ttaagttaat aatatttaca ggattcatgg gatttatcat agaacaatat    1200
atcaatccta tcgttcagaa ttcacaacat cctttaaaag gggatctctt atatgccatt    1260
gagagggttt tgaagctctc agttccgaat ttatatgtct ggctttgcat gttctactgc    1320 tttttttcacc tatggttaaa tatacttgct gagctccttc gctttggtga tagagagttc    1380
tataaagatt ggtggaatgc aaggacagtt gaggagtatt ggagaatgtg aaatatgcct    1440
gttcataagt ggatggttcg ccatatctac tttccatgct gcggcataa aataccaagg     1500 gggtggcct tattaattac tttcttcgtt tcagcagtat ttcatgagtt gtgcattgct     1560
gttccttgcc acatattcaa gctctgggct tttattggaa taatgtttca gattcctttg    1620
gtcgggatca caaattacct tcaaaacaag ttcagaagct caatggtggg aacatgatc     1680 ttctggttca ttttctgcat tcttggtcaa ccatgtgct tgctgttgta ttaccatgac     1740
ctaatgaatc gaaaagggac taccgaatca agatgacact aactcatcgt gtggtagact    1800
```

| | | |
|---|---|---|
| ctatatatat | acatagactt accagagatg ggttgcttcc aacatattgt gcacaagagg | 1860 |
| caattgttgt | tctcatcaga agagtgggtt aattaattaa ttaatgtaca agcaattttg | 1920 |
| aaagtataat | cactggcagg gactagtgcc cgactgtagt actgagatta tagaggtatt | 1980 |
| atcaatcgtt | agtggaaaat tgtaaatgta taaagttcaa tctttgtatt gtttcttttc | 2040 |
| taatatcata | ttttttttta ttgctcatca aaaaaaaaaa aaaa | 2084 |

<210> SEQ ID NO 26
<211> LENGTH: 1828
<212> TYPE: DNA
<213> ORGANISM: Vernonia galamensis

<400> SEQUENCE: 26

| | | |
|---|---|---|
| tctgagctca | aatcaaattt ctgcgactca tacaggattc aactcaatac tttcttgatc | 60 |
| ggttctgctg | ttcatttact tgtaatttct acttctgctt tgctttcatt tcaagctttt | 120 |
| ttccttaata | atggcgttat tagatacgcc tcagattgga gaaataacga ccaccgccac | 180 |
| cacaactata | agacggcgga ccactgtcaa gcctgatgct ggaatcggag atggattgtt | 240 |
| tgattcttcg | tcgtcttcca aaaccaactc atccttcgag gatggtgaca gtttgaatgg | 300 |
| tgatttcaat | gacaaattta aggaacagat cggagctggt gatgaatcca aggacgactc | 360 |
| caaggggaac | ggacagaaga tagatcacgg aggagttaaa aagggacgtg aaacgactgt | 420 |
| ggtgcattat | gcttatcggc cttcttctcc ggctcatcgg agaattaaag aatctccgct | 480 |
| tagctctgac | gccatcttca agcagagtca tgcaggcctc tttaaccttt gcatagtggt | 540 |
| gcttgttgca | gtaaatggta ggctcatcat tgagaatctg atgaagtatg gactattgat | 600 |
| caattccaac | ttttggttca gttcgagatc attgagagac tggccacttc tgatgtgctg | 660 |
| cctcactcct | tctgactttc cacttgctgc ctacattgtt gagaaattgg catggaaaaa | 720 |
| acgtatatcc | gaccctgttg taatcacact ccatgttata ataactacaa ctgcaattct | 780 |
| ttatccggtc | ttcatgattc tgaggttcga ttcagttgtt ctatcaggcg tctcgttgat | 840 |
| gctgtgtgct | tgcattaatt ggttgaagtt ggtatctttt gtgcatacaa attatgacat | 900 |
| gcggtcgctt | tgaactcaa ctgataaggg agaagtggaa cccatgtctt caaatatgga | 960 |
| ttatttttat | gatgtcaact tcaaaagctt ggtttatttc atggttgctc aactttgtg | 1020 |
| ttaccagata | agctatcctc gcactgcatt tattcgaaag ggttgggtgt tacggcaact | 1080 |
| gatcaagcta | gtaatattta cagggttcat gggattcatc attgaacaat atatcaatcc | 1140 |
| gattgtcaaa | aattctcgtc atccattgaa aggagacttt ttatatgcga ttgagcgggt | 1200 |
| tttaaagctt | tcagttccga atttatatgt gtggctctgt atgttctact gctttttttca | 1260 |
| cctttggtta | aatatacttg ctgagcttct ttgttttggg gatcgtgaat tttataaaga | 1320 |
| ttggtggaat | gcacaaacta ttgaagagta ttggaggcta tggaatatgc ctgttcataa | 1380 |
| atggattgtt | aggcacccttt attttccatg cttgcgtaat gggataccta agggtgctgc | 1440 |
| catattggtt | gcatttttca tgtctgccgt gttccatgag ctttgtattg ctgttccctg | 1500 |
| ccacatttc | aagtttgggg cttttatcgg gatcatgttt caggtcccgt tggtcctact | 1560 |
| cacaaattac | ttgcagcaca agtttcaaaa ctcgatggtg ggaaatatga tcttctggtg | 1620 |
| cttttttcagc | atttttggtc aacccatgtg tgtattactt tactaccatg atgtcatgaa | 1680 |
| tcaaaggggg | aaaagcaaat aaaaagatgt gattgtgttg ctccatttga tctcatagca | 1740 |
| tgactggact | aaacaaaccc aagggacaca ttttagtcct taaaggaaaa ttttttgtagg | 1800 |
| aaaaaaaaaa | aaaaaaaaa aaaaaaaa | 1828 |

<210> SEQ ID NO 27
<211> LENGTH: 2020
<212> TYPE: DNA
<213> ORGANISM: Ricinus communis

<400> SEQUENCE: 27

```
cttcttcttc tgctgctgtt cctctctcct ccaccgccac gctcacctct ctttgcatga      60
cataatacta ttgttcttat tatcattttc actctttaaa tacaaacatc aattattcct     120
tttctatcaa acacatgtat tctattctct cgtcgtctag attctcatct tcattgaatc     180
ctccttctta gcgtgtcttt gtccacttct tttgggcacc gacgttttta atctccatga     240
cgattctcga aacgccagaa actcttggcg tcatctcctc ctccgccact tccgatctca     300
acctctctct ccgacgtaga cggacctcaa atgactccga tggtgcactt gctgatttgg     360
cttcgaagtt tgatgatgat gacgacgtaa gatcggaaga ttctgctgaa aatattatcg     420
aagatcctgt agcagcggtt actgaattgg cgacagcaaa gagtaacgga aaagactgtg     480
ttgccaatag taataaggat aaaattgata gccatggagg atcatcggat tttaaacttg     540
catataggcc ttcggttcca gctcaccggt cacttaagga gagtccgctt agctctgatt     600
taatatttaa acaaagtcat gcaggtctgt ttaacctttg tatagtagtg ctcgtagctg     660
ttaacagcag gctcatcatt gagaatttaa tgaagtatgg ctggttaatt aagacgggct     720
tttggtttag ttcaagatca ttgagagatt ggccgctttt tatgtgctgt ctttctctcc     780
cagtattccc ccttgctgcc tatctagttg agaaggccgc atatcgaaaa tatatatctc     840
cgcctattgt tattttcctt catgtgatca tcacctcagc agctgttttg tacccagctt     900
ctgtaattct cagttgtgaa tctgcttttt tatctggtgt cacattgatg gaacttgctt     960
gtatggtatg gttgaaattg gtatcctatg cacatacaaa ctatgatatg agagcgatcg    1020
ctgacaccat tcataaggaa gatgcatcca attcttctag tacagagtat tgtcatgatg    1080
tgagctttaa gactttggcg tacttcatgg tcgcacccac attatgttac cagccaagtt    1140
atcctcgcac agcatttatt agaaagggct gggtgttccg tcaatttgtc aaactaataa    1200
tttttacagg attcatggga tttatcatag aacaatacac caatcctatc gtccagaatt    1260
ctcaacaccc tttaaaaggg gatctcttat atgccattga gagggttctg aagctctcag    1320
ttccgaattt atatgtgtgg ctctgcttgt tctactgctt ttttcacctg tggttgaata    1380
tagttgctga gctccttcgc ttcggtgacc gggagttcta caaagattgg tggaatgcaa    1440
aaactgttga ggagtactgg aggatgtgga atatgcctgt tcacaagtgg atggttcgcc    1500
atatctactt cccatgccta cgtcgtaaaa taccaagggg ggtagcaata gttattgctt    1560
tcttcgtttc agctgtattt catgagttgt gcattgctgt tccttgccac atgttcaaac    1620
tttgggcttt ttttggaata atgtttcaga ttcctttagt tgtgatcact aattattttc    1680
aaaggaagtt cagaagctca atggtgggaa atatgatctt ctggttcttt ttctgcattc    1740
tcggccaacc tatgtgtgta ctgttgtatt accatgacct aatgaatcgc gatgggaact    1800
gaaccatggg ctcagtccag atatgggtac accttccaag atgttatttt cgtgagtgaa    1860
gactgcacca cagtgttgtt cttgttacac aatccccatt gacagagtag gttaatcgtc    1920
agtttcagga gataagacac aattttgaaa gtacagcaga ggctgctatt aatgtatcat    1980
gttgagtttc tgttatgtta tgttattctt ttttaatctc                          2020
```

<210> SEQ ID NO 28

<211> LENGTH: 1444
<212> TYPE: DNA
<213> ORGANISM: Populus trichocarpa

<400> SEQUENCE: 28

```
aaatcatggc ggcgttagag tctccggaga atcatatacg acgtcggatc ttaacttctc    60
cgttcgacgg aggtctacta ctgtcacgga ttcgccttcg acggagatga tggaatcgga   120
ggatttgaaa agtaatggta agaatgcgaa taaggttacg aatgagaatc gatcggatat   180
taaattcaat tatcggcctt caatgcctgc tcatcgtggt gttagagaga gtcctcttag   240
ttctgatgct attttaaac aaagtcatgc aggtctcttc aatctctgta tagttgtgct   300
tgtggctata aacagcaggc ttatcattga aaatataatc aagtatggtt ggttaattaa   360
cggtggattt tggtttagtt caaaatcatt aagagactgg cccctgttta tgtgctgtct   420
tagccttcca gcattccctt cgcggccta tcttgttgag aagttggcat atcaaaatta    480
tttacctcaa cttgttgttg ttttccttca tacaatcatc accacaggat cacttttata   540
tccagtttta gtaattctca ggtgtgattc tgcttttcta tctggtgtca cgttgatgct   600
cttttcttgc attgtgtggc taaaattggt atcttatgct catacaaact ctgatttgag   660
agcaattgcc aagtcaatag atagggaaga tgtcccatcc atttctcctt atgtgggtaa   720
tccttatgat acttacttta agagtttggt ctacttcatg gtggctccca cattatgtta   780
ccagtcaagc tatcctcgca ctgaatctgt tcgaaaggga tgggtggttc aacaatttgt   840
caagttaata atatttactg gattcatggg atttatcata gaacaatata tcaatcctat   900
tgttaagaat tcacagcacc cttttaaagg aaatctcttg tatgccattg agagggtctt   960
gaagctctca gttcctaatt tatatgtatg gctttgcatg ttctactgct ttttccacct  1020
gtggttaaat atacttgccg agctcctttg ctttggtgat cgggagttct acaaggattg  1080
gtggaatgca agaactgttg aagaatattg gagaatgtgg aatatgccag ttcataagtg  1140
gatggttcgc catatctatt ttccatgcct acggaataaa ataccgaagg ggttagctat  1200
acttattgcc ttcttagttt cagctgtatt tcacgagctg tgcattgctg ttccctgcca  1260
cgtgttcaag ctctgggcat ttattggaat tatgttacag gttcccttag tggtgatcac  1320
aaaatttctc caaaataagt tcagaagctc catggtggga aacatgatct tctggttgtt  1380
tttcagcatt cttggtcaac caatgtgtgt gcttctgtat taccatgact tgatgaatcg  1440
gaag                                                                1444
```

<210> SEQ ID NO 29
<211> LENGTH: 1816
<212> TYPE: DNA
<213> ORGANISM: Populus trichocarpa

<400> SEQUENCE: 29

```
aacatatttta aatcatggcg gagtcagagt caccggagaa tcgtatagcg gcaatggaaa    60
gtacatcttc ctcgacgtca gatctcaact tctctattcg acggaggtct acagtcatgg   120
actcggcttc gacggaaatg atgggatcgg agggtttgaa agtagtggt aaagcatgcg    180
ataaggttaa gattgagaag caatcagata tgaaattcaa ttatcggcca tcaatgcccg   240
ctcatagtgg tgttagagag agtcctctta gttctgatgc tatttttaaa caaagtcatg   300
caggtctctt caatctctgt atagtagtgc ttgtggctgt aaacagcagg cttatcattg   360
aaaatttaat caagtacggc tggttaatca attcaggatt tggtttagt tcaaaatcat    420
taagagactg gcccctgttt atgtgctgtc ttagtcttcc agcattccct ctcgcggcct    480
```

```
atctcgttga gaagttggca tatcgaaatt gtatatctga acttgttgtt gttttccttc    540
atataatcat caccacagca tcacttttgt atccagtttt agtaattctc aggtgtgatt    600
ctgctttact atctggtggc acattgatgc tctttgcttg cattgtgtgg ttgaaattgg    660
tatcttttgc acatacaagc tctgatatga gagcaattgc caagtcaatt gataaggaaa    720
ataccccatc catttcttcg aaagcagata attcttatga tgctaacttt aagagtttgg    780
tctacttcat ggtggctccc acattatgtt accagtcaag ctatcctcgt tctgcatctg    840
ttcgaaaggg ttgggtggtt cgacaatttg tcaagttaat aatatttact ggattcatgg    900
gatttatcat agaacaatat atcaatccta ttgttcagaa ctcgcagcac cctttgaaag    960
gaaatctctt gtatgccatt gagagggtct tgaagctctc agttcctaat ttatatgttt   1020
ggctctgcat gttctactgc ttttTccact tgtggttaaa tatacttgcc gagctccttc   1080
gctttggtga tcgggagttc tacaaggatt ggtggaatgc aagaactgtt gaagagtact   1140
ggagaatgtg gaatatgcca gttcataagt ggatggttcg ccatatctat tttccatgtt   1200
tacggaataa aataccaaag tgggcagcct tacttattgc cttctttgtc tcagctgtat   1260
ttcatgagtt gtgtattgct gttccttgcc acatgttcaa gctctgggca tttattggaa   1320
ttatgtttca ggttccctta gtggtgatca caaaattcct tcaaaataag ttcaaaagct   1380
caatggtggg caatatgatc ttctggttat ttttcagcat tcttggtcaa cctatgtgtg   1440
tgcttctata ttaccatgac ttgatgaatc ggaaagggaa aactgaacga agatgacaaa   1500
tgcggtatgg tagagatcgt caagatgaac aaaatgcacg ttatgatag tagagcaggc   1560
attaggtgtg ccttttctta tgtattctgc aggagaaatt gactcgattt tgttgagtcg   1620
agagatggtc tcttcaggac ttttattttt atgtatctca attgacgtgc aagcaatttt   1680
ggaagtacaa gcactggcaa ttaaaatgcc aatgcaacag tggatctgtt gtgttggtta   1740
atcatttcca gaaatttgta aatgtttctt gttccgtctt ttgcttcaaa ggaaataaaa   1800
aaagaagaaa atttct                                                  1816
```

<210> SEQ ID NO 30
<211> LENGTH: 520
<212> TYPE: PRT
<213> ORGANISM: Arabidopsis thaliana

<400> SEQUENCE: 30

```
Met Ala Ile Leu Asp Ser Ala Gly Val Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125
```

```
Lys Gln Ser His Ala Gly Leu Phe Asn Leu Cys Val Val Leu Ile
        130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
                180                 185                 190

Phe Thr Val Glu Lys Leu Val Leu Gln Lys Tyr Ile Ser Glu Pro Val
                195                 200                 205

Val Ile Phe Leu His Ile Ile Ile Thr Met Thr Glu Val Leu Tyr Pro
210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
                260                 265                 270

Asn Pro Glu Val Ser Tyr Tyr Val Ser Leu Lys Ser Leu Ala Tyr Phe
                275                 280                 285

Met Val Ala Pro Thr Leu Cys Tyr Gln Pro Ser Tyr Pro Arg Ser Ala
290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
                340                 345                 350

Glu Arg Val Leu Lys Leu Ser Val Pro Asn Leu Tyr Val Trp Leu Cys
                355                 360                 365

Met Phe Tyr Cys Phe Phe His Leu Trp Leu Asn Ile Leu Ala Glu Leu
                370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
                420                 425                 430

Thr Leu Ala Ile Ile Ile Ala Phe Leu Val Ser Ala Val Phe His Glu
                435                 440                 445

Leu Cys Ile Ala Val Pro Cys Arg Leu Phe Lys Leu Trp Ala Phe Leu
450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
                500                 505                 510

Met Asn Arg Lys Gly Ser Met Ser
                515                 520

<210> SEQ ID NO 31
<211> LENGTH: 503
<212> TYPE: PRT
```

<213> ORGANISM: Brassica juncea

<400> SEQUENCE: 31

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Arg Ser Asp
                20                  25                  30

Ser Ser Asn Gly Leu Leu Ser Asp Thr Ser Pro Ser Asp Asp Val Gly
            35                  40                  45

Ala Ala Ala Ala Glu Arg Asp Arg Val Asp Ser Ala Ala Glu Glu Glu
        50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
                100                 105                 110

Gln Ser His Ala Gly Leu Phe Asn Leu Cys Val Val Leu Val Ala
            115                 120                 125

Val Asn Ser Arg Pro Ile Ile Glu Asn Leu Met Lys Tyr Gly Trp Leu
    130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175

Thr Val Glu Lys Met Val Leu Gln Lys Phe Ile Ser Glu Pro Val Ala
                180                 185                 190

Ile Ile Leu His Val Ile Ile Thr Leu Thr Glu Val Leu Tyr Pro Val
            195                 200                 205

Tyr Val Thr Leu Arg Cys Asp Ser Ala Phe Leu Ser Gly Val Thr Leu
    210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                245                 250                 255

Pro Glu Ile Ser Tyr Tyr Val Ser Leu Lys Ser Leu Ala Tyr Phe Met
                260                 265                 270

Val Ala Pro Thr Leu Cys Tyr Gln Pro Ser Tyr Pro Arg Ser Pro Cys
            275                 280                 285

Ile Arg Lys Gly Trp Val Ala Arg Gln Phe Ala Lys Leu Val Ile Phe
    290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Cys Phe Gly Asp Arg Glu Phe Tyr Lys Asp Trp Trp Asn Ala Lys Ser
    370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
            405                 410                 415

Pro Ala Ile Ile Ile Ala Phe Leu Val Ser Ala Val Phe His Glu Leu
        420                 425                 430

Cys Ile Ala Val Pro Cys Arg Leu Phe Asn Leu Trp Ala Phe Met Gly
        435                 440                 445

Ile Met Phe Gln Val Pro Leu Val Phe Ile Thr Asn Phe Leu Gln Glu
    450                 455                 460

Arg Phe Gly Ser Met Val Gly Asn Met Ile Phe Trp Phe Ser Phe Cys
465                 470                 475                 480

Ile Phe Gly Gln Pro Met Cys Val Leu Leu Tyr Tyr His Asp Leu Met
            485                 490                 495

Asn Arg Lys Gly Ser Met Ser
            500

<210> SEQ ID NO 32
<211> LENGTH: 503
<212> TYPE: PRT
<213> ORGANISM: Brassica napus

<400> SEQUENCE: 32

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Leu Val Ala
        115                 120                 125

Val Asn Ser Arg Leu Ile Ile Glu Asn Leu Met Lys Tyr Gly Trp Leu
    130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175

Thr Val Glu Lys Met Val Leu Gln Lys Phe Ile Ser Glu Pro Val Ala
            180                 185                 190

Ile Ile Leu His Val Ile Ile Thr Met Thr Glu Val Leu Tyr Pro Val
        195                 200                 205

Tyr Val Thr Leu Arg Cys Asp Ser Ala Phe Leu Ser Gly Val Thr Leu
    210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                245                 250                 255

Pro Glu Ile Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Cys
            275                 280                 285

Ile Arg Lys Gly Trp Val Ala Arg Gln Leu Ala Lys Leu Val Ile Phe
290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
            325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
            355                 360                 365

Cys Phe Gly Asp Arg Glu Phe Tyr Lys Asp Trp Asn Ala Lys Ser
            370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
            405                 410                 415

Pro Ala Ile Ile Ile Ala Phe Leu Val Ser Ala Val Phe His Glu Leu
            420                 425                 430

Cys Ile Ala Val Pro Cys Arg Leu Phe Asn Leu Trp Ala Phe Met Gly
            435                 440                 445

Ile Met Phe Gln Val Pro Leu Val Phe Ile Thr Asn Phe Leu Gln Glu
450                 455                 460

Arg Phe Gly Ser Met Val Gly Asn Met Ile Phe Gly Ser Ala Ser Cys
465                 470                 475                 480

Ile Phe Gly Gln Pro Met Cys Gly Leu Leu Tyr Tyr His Asp Leu Met
            485                 490                 495

Asn Arg Lys Gly Ser Met Ser
            500

<210> SEQ ID NO 33
<211> LENGTH: 503
<212> TYPE: PRT
<213> ORGANISM: Brassica juncea

<400> SEQUENCE: 33

Met Ala Ile Leu Asp Ser Gly Thr Val Thr Met Ala Thr Glu Asn Gly
1               5                   10                  15

Val Ala Asp Leu Asp Met Leu Arg Arg Arg Lys Ser Arg Ser Asp Ser
            20                  25                  30

Ser Asn Gly Leu Leu Ser Glu Thr Ser Pro Ser Asp Asp Ala Gly Ala
            35                  40                  45

Pro Ala Asp Val Glu Asp Arg Val Asp Ser Ala Ala Gln Gly Thr Ala
    50                  55                  60

Asn Leu Ala Gly Asp Thr Glu Arg Glu Ser Gly Gly Gly Gly
65                  70                  75                  80

Gly Gly Asn Gly Glu Val Arg Phe Thr Tyr Arg Pro Ser Val Pro Ala
            85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Leu Val Ala
            115                 120                 125

Val Asn Ser Arg Leu Ile Ile Glu Asn Leu Met Lys Tyr Gly Trp Leu

```
            130                 135                 140
Ile Arg Thr Asp Phe Trp Phe Ser Ser Thr Ser Leu Arg Asp Trp Pro
145                 150                 155                 160

Leu Phe Met Cys Cys Leu Ser Leu Ser Ile Phe Pro Leu Ala Ala Phe
                165                 170                 175

Thr Val Glu Lys Leu Val Leu Gln Lys Phe Ile Ser Glu Pro Val Val
                180                 185                 190

Ile Ile Leu His Ile Ile Ile Thr Met Thr Glu Val Leu Tyr Pro Val
                195                 200                 205

Tyr Val Thr Leu Arg Cys Asp Ser Ala Phe Leu Ser Gly Val Thr Leu
                210                 215                 220

Met Leu Leu Thr Cys Ile Val Trp Leu Lys Leu Val Ser Tyr Ala His
225                 230                 235                 240

Thr Asn Tyr Asp Ile Arg Thr Val Ala Asn Ser Ala Asp Lys Val Asp
                245                 250                 255

Pro Glu Val Ser Tyr Tyr Val Ser Leu Lys Ser Leu Ala Tyr Phe Met
                260                 265                 270

Val Ala Pro Thr Leu Cys Tyr Gln Pro Ser Tyr Pro Arg Ser Pro Gly
                275                 280                 285

Ile Arg Lys Gly Trp Val Ala Arg Gln Phe Ala Lys Leu Val Ile Phe
                290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
                340                 345                 350

Phe Tyr Cys Phe His Leu Trp Leu Asn Ile Leu Ala Glu Leu Leu
                355                 360                 365

Cys Phe Gly Asp Arg Glu Phe Tyr Lys Asp Trp Trp Asn Ala Lys Ser
                370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
                420                 425                 430

Cys Ile Ala Val Pro Cys Arg Leu Phe Asn Leu Trp Ala Phe Ile Gly
                435                 440                 445

Ile Met Phe Gln Val Pro Leu Val Phe Ile Thr Asn Tyr Leu Gln Glu
                450                 455                 460

Arg Phe Gly Ser Met Val Gly Asn Met Ile Phe Trp Phe Ser Phe Cys
465                 470                 475                 480

Ile Phe Gly Gln Pro Met Cys Val Leu Leu Tyr Tyr His Asp Leu Met
                485                 490                 495

Asn Arg Lys Gly Ser Met Ser
                500

<210> SEQ ID NO 34
<211> LENGTH: 518
<212> TYPE: PRT
<213> ORGANISM: Tropaeolum majus

<400> SEQUENCE: 34
```

-continued

```
Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
            115                 120                 125

Asn Leu Cys Ile Val Val Leu Ile Ala Val Asn Ser Arg Leu Ile Ile
            130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
            195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
            275                 280                 285

Val Ala Pro Thr Leu Cys Tyr Gln Pro Ser Tyr Pro Arg Ser Ser Cys
    290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
            355                 360                 365

Phe Tyr Ser Phe Phe His Leu Trp Leu Asn Ile Leu Ala Glu Leu Leu
    370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
```

```
                420             425            430
Gly Ala Ile Ile Ile Ala Phe Leu Val Ser Gly Ala Phe His Glu Leu
            435                 440             445

Cys Ile Ala Val Pro Cys His Val Phe Lys Leu Trp Ala Phe Ile Gly
            450                 455             460

Ile Met Phe Gln Val Pro Leu Val Leu Ile Thr Asn Tyr Leu Gln Glu
465             470             475                 480

Lys Phe Ser Asn Ser Met Val Gly Asn Met Ile Phe Trp Phe Ile Phe
            485                 490             495

Cys Ile Leu Gly Gln Pro Met Cys Val Leu Tyr Tyr His Asp Leu
            500                 505             510

Ile Asn Leu Lys Glu Lys
            515

<210> SEQ ID NO 35
<211> LENGTH: 473
<212> TYPE: PRT
<213> ORGANISM: Echium pitardii

<400> SEQUENCE: 35

Met Thr Ile Trp Glu Ser Pro Glu Ile Ile Ser Ser Asp Glu Ala Ala
1               5                   10                  15

Ala Ala Leu Arg Arg Arg Gly Gly Ala Lys Glu Val Ala Glu Gln Arg
            20                  25                  30

Leu Asp Ser Glu Glu Glu Lys Lys Glu Glu Glu Asn Gly Lys Leu
        35                  40                  45

Lys Tyr Thr Tyr Arg Ala Ser Ala Pro Ala His Arg Arg Ile Lys Glu
50                  55                  60

Ser Pro Leu Ser Ser Asp Ala Ile Phe Lys Gln Ser His Ala Gly Leu
65                  70                  75                  80

Phe Asn Leu Cys Ile Val Val Leu Val Ala Val Asn Ser Arg Leu Ile
                85                  90                  95

Ile Glu Asn Leu Met Lys Tyr Gly Trp Leu Ile Ser Ser Gly Phe Trp
            100                 105                 110

Leu Ser Ser Thr Ser Leu Ser Asp Trp Pro Leu Leu Ile Cys Cys Leu
            115                 120                 125

Ser Leu Pro Ile Phe Pro Leu Ala Ser Phe Val Val Glu Lys Leu Ser
130                 135                 140

Gln Gln Glu Phe Ile Ser Glu Gln Val Val Ile Thr Leu His Ala Leu
145                 150                 155                 160

Ile Thr Thr Thr Val Ile Met Tyr Pro Val Ile Val Leu Arg Cys
                165                 170                 175

Asp Pro Ala Val Leu Ser Gly Val Ile Leu Met Leu Phe Thr Cys Ile
            180                 185                 190

Val Trp Leu Lys Leu Val Ser Tyr Ala His Thr Asn Tyr Asp Met Arg
            195                 200                 205

Ala Leu Ala Lys Asp Cys Asp Lys Leu Gln Ala Leu Ser Gly Ser Ser
            210                 215                 220

Met Glu Asp Cys Ser Phe Glu Val Asn Phe Gln Ala Leu Val Tyr Phe
225                 230                 235                 240

Met Val Ala Pro Thr Leu Cys Tyr Gln Leu Arg Tyr Pro Arg Thr Pro
                245                 250                 255

Cys Ile Arg Trp Gly Trp Val Thr Arg His Leu Ile Lys Leu Ile Ile
            260                 265                 270
```

```
Phe Thr Gly Leu Met Gly Phe Ile Ile Glu Gln Tyr Ile Asn Pro Ile
            275                 280                 285

Val Lys Asn Ser Gln His Pro Leu Lys Gly Asn Leu Leu Tyr Ala Ile
290                 295                 300

Glu Arg Val Leu Lys Leu Ser Val Pro Asn Ile Tyr Val Trp Leu Cys
305                 310                 315                 320

Met Phe Tyr Cys Phe Phe His Leu Trp Leu Asn Ile Leu Ala Glu Leu
                325                 330                 335

Leu Cys Phe Gly Asp Arg Glu Phe Tyr Lys Asp Trp Asn Ala Gln
                340                 345                 350

Thr Ile Glu Glu Tyr Trp Arg Met Trp Asn Met Pro Val His Lys Trp
            355                 360                 365

Met Val Arg His Ile Tyr Phe Pro Cys Leu Arg Asn Gly Met Pro Lys
370                 375                 380

Glu Leu Ala Ile Leu Ile Ala Phe Leu Ile Ser Ala Ile Phe His Glu
385                 390                 395                 400

Leu Cys Ile Ala Val Pro Cys His Ile Phe Lys Phe Trp Ala Phe Ile
                405                 410                 415

Gly Ile Met Phe Gln Val Pro Leu Val Leu Thr Asn Val Leu Val
                420                 425                 430

Lys Lys Phe Gln Asn Ser Met Val Gly Asn Met Ile Phe Trp Cys Phe
            435                 440                 445

Phe Cys Ile Leu Gly Gln Pro Met Ser Leu Leu Leu Tyr Tyr His Asp
                450                 455                 460

Val Leu Asn Arg Lys Val Asn Ala Asn
465                 470

<210> SEQ ID NO 36
<211> LENGTH: 523
<212> TYPE: PRT
<213> ORGANISM: Vernonia galamensis

<400> SEQUENCE: 36

Met Ala Leu Leu Asp Thr Pro Gln Ile Gly Glu Ile Thr Thr Thr Ala
1               5                   10                  15

Thr Thr Thr Ile Arg Arg Arg Thr Thr Val Lys Pro Asp Ala Gly Ile
                20                  25                  30

Gly Asp Gly Leu Phe Asp Ser Ser Ser Ser Lys Thr Asn Ser Ser
            35                  40                  45

Phe Glu Asp Gly Asp Ser Leu Asn Gly Asp Phe Asn Asp Lys Phe Lys
    50                  55                  60

Glu Gln Ile Gly Ala Gly Asp Glu Ser Lys Asp Ser Lys Gly Asn
65                  70                  75                  80

Gly Gln Lys Ile Asp His Gly Gly Val Lys Lys Gly Arg Glu Thr Thr
                85                  90                  95

Val Val His Tyr Ala Tyr Arg Pro Ser Ser Pro Ala His Arg Arg Ile
                100                 105                 110

Lys Glu Ser Pro Leu Ser Ser Asp Ala Ile Phe Lys Gln Ser His Ala
            115                 120                 125

Gly Leu Phe Asn Leu Cys Ile Val Val Leu Val Ala Val Asn Gly Arg
130                 135                 140

Leu Ile Ile Glu Asn Leu Met Lys Tyr Gly Leu Leu Ile Asn Ser Asn
145                 150                 155                 160

Phe Trp Phe Ser Ser Arg Ser Leu Arg Asp Trp Pro Leu Leu Met Cys
                165                 170                 175
```

Cys Leu Thr Pro Ser Asp Phe Pro Leu Ala Ala Tyr Ile Val Glu Lys
            180                 185                 190

Leu Ala Trp Lys Lys Arg Ile Ser Asp Pro Val Val Ile Thr Leu His
        195                 200                 205

Val Ile Ile Thr Thr Ala Ile Leu Tyr Pro Val Phe Met Ile Leu
210                 215                 220

Arg Phe Asp Ser Val Val Leu Ser Gly Val Ser Leu Met Leu Cys Ala
225                 230                 235                 240

Cys Ile Asn Trp Leu Lys Leu Val Ser Phe Val His Thr Asn Tyr Asp
            245                 250                 255

Met Arg Ser Leu Leu Asn Ser Thr Asp Lys Gly Glu Val Glu Pro Met
        260                 265                 270

Ser Ser Asn Met Asp Tyr Phe Tyr Asp Val Asn Phe Lys Ser Leu Val
        275                 280                 285

Tyr Phe Met Val Ala Pro Thr Leu Cys Tyr Gln Ile Ser Tyr Pro Arg
        290                 295                 300

Thr Ala Phe Ile Arg Lys Gly Trp Val Leu Arg Gln Leu Ile Lys Leu
305                 310                 315                 320

Val Ile Phe Thr Gly Phe Met Gly Phe Ile Ile Glu Gln Tyr Ile Asn
                325                 330                 335

Pro Ile Val Lys Asn Ser Arg His Pro Leu Lys Gly Asp Phe Leu Tyr
            340                 345                 350

Ala Ile Glu Arg Val Leu Lys Leu Ser Val Pro Asn Leu Tyr Val Trp
        355                 360                 365

Leu Cys Met Phe Tyr Cys Phe Phe His Leu Trp Leu Asn Ile Leu Ala
370                 375                 380

Glu Leu Leu Cys Phe Gly Asp Arg Glu Phe Tyr Lys Asp Trp Trp Asn
385                 390                 395                 400

Ala Gln Thr Ile Glu Glu Tyr Trp Arg Leu Trp Asn Met Pro Val His
                405                 410                 415

Lys Trp Ile Val Arg His Leu Tyr Phe Pro Cys Leu Arg Asn Gly Ile
            420                 425                 430

Pro Lys Gly Ala Ala Ile Leu Val Ala Phe Phe Met Ser Ala Val Phe
        435                 440                 445

His Glu Leu Cys Ile Ala Val Pro Cys His Ile Phe Lys Phe Trp Ala
        450                 455                 460

Phe Ile Gly Ile Met Phe Gln Val Pro Leu Val Leu Leu Thr Asn Tyr
465                 470                 475                 480

Leu Gln His Lys Phe Gln Asn Ser Met Val Gly Asn Met Ile Phe Trp
                485                 490                 495

Cys Phe Phe Ser Ile Phe Gly Gln Pro Met Cys Val Leu Leu Tyr Tyr
            500                 505                 510

His Asp Val Met Asn Gln Lys Gly Lys Ser Lys
        515                 520

<210> SEQ ID NO 37
<211> LENGTH: 532
<212> TYPE: PRT
<213> ORGANISM: Nicotiana tabacum

<400> SEQUENCE: 37

Met Val Ile Met Glu Leu Pro Glu Ser Val Glu Met Thr Thr Thr Thr
1               5                   10                  15

Thr Thr Ser Gly Ile Glu Asn Leu Asn Ser Asp Leu Asn His Ser Val

-continued

```
                20                  25                  30
Arg Arg Arg Arg Gly Ser Asn Gly Phe Glu Ala Ala Ser Ala Ile Asn
                35                  40                  45
Ser Ser Asp Ala Asn Met Ser Glu Asp Arg Arg Asp Val Cys Gly Ser
 50                  55                  60
Gly Ala Gly Leu Glu Thr Val Asn Glu Arg Ser Lys Ser Val Gly Glu
 65                  70                  75                  80
Ser Ser Asp Val Ile Arg Lys Glu Asp Arg Asn Asp Asn Val Ala
                85                  90                  95
Asn Gly Glu Glu Ser Lys Ser Thr Glu Thr Thr Thr Pro Phe Lys
                100                 105                 110
Phe Ala Tyr Arg Ala Ser Ala Pro Ala His Arg Arg Ile Lys Glu Ser
                115                 120                 125
Pro Leu Ser Ser Asp Ala Ile Phe Lys Gln Ser His Ala Gly Leu Phe
                130                 135                 140
Asn Leu Cys Val Val Val Leu Ile Ala Val Asn Ser Arg Leu Ile Ile
145                 150                 155                 160
Glu Asn Leu Met Lys Tyr Gly Leu Leu Ile Arg Ala Gly Phe Trp Phe
                165                 170                 175
Ser Ser Lys Ser Leu Arg Asp Trp Pro Leu Leu Met Cys Cys Leu Ser
                180                 185                 190
Leu Gln Ile Leu Pro Leu Ala Ala Phe Leu Val Glu Lys Leu Ala Gln
                195                 200                 205
Gln Arg His Leu Thr Glu Arg Ala Val Val Thr Leu His Ile Thr Ile
                210                 215                 220
Thr Thr Ala Ala Ile Leu Tyr Pro Val Leu Val Ile Leu Gly Cys Asp
225                 230                 235                 240
Ser Ala Phe Leu Phe Gly Val Ile Leu Met Leu Val Ala Cys Ile Val
                245                 250                 255
Trp Met Lys Leu Val Ser Tyr Ala His Thr Asn His Asp Met Arg Gln
                260                 265                 270
Leu Ala Lys Ser Thr Asp Lys Asp Glu Thr Ser Asp Gly Asp Phe Ser
                275                 280                 285
Tyr Asp Val Ser Phe Lys Ser Leu Ala Tyr Phe Met Val Ala Pro Thr
                290                 295                 300
Leu Cys Tyr Gln Leu Ser Tyr Pro His Thr Pro Cys Ile Arg Lys Gly
305                 310                 315                 320
Trp Val Ala Arg Gln Phe Ile Lys Leu Val Ile Phe Thr Gly Leu Met
                325                 330                 335
Gly Phe Ile Ile Glu Gln Tyr Ile Asn Pro Ile Val Gln Asn Ser Gln
                340                 345                 350
His Pro Leu Lys Gly Asn Leu Leu Tyr Ala Ile Glu Arg Val Leu Lys
                355                 360                 365
Leu Ser Val Pro Asn Leu Tyr Val Trp Leu Cys Met Phe Tyr Cys Phe
                370                 375                 380
Phe His Leu Trp Leu Asn Ile Leu Ala Glu Leu Leu Cys Phe Gly Asp
385                 390                 395                 400
Arg Glu Phe Tyr Lys Asp Trp Trp Asn Ala Lys Thr Ile Asp Glu Tyr
                405                 410                 415
Trp Arg Met Trp Asn Met Pro Val His Lys Trp Met Val Arg His Ile
                420                 425                 430
Tyr Phe Pro Cys Leu Arg Asn Gly Ile Pro Lys Gly Val Ala Ile Leu
                435                 440                 445
```

```
Ile Ala Phe Leu Val Ser Ala Val Phe His Glu Leu Cys Ile Ala Val
        450                 455                 460

Pro Cys Arg Leu Phe Lys Trp Trp Ala Phe Met Gly Ile Met Phe Gln
465                 470                 475                 480

Val Pro Leu Val Ile Leu Thr Asn Phe Leu Gln Asn Lys Phe Gln Ser
                485                 490                 495

Ser Met Val Gly Asn Met Met Phe Trp Cys Phe Phe Cys Ile Leu Gly
                500                 505                 510

Gln Pro Met Cys Val Leu Leu Tyr Tyr His Asp Val Met Asn Arg Lys
                515                 520                 525

Ser Ser Ala Arg
        530

<210> SEQ ID NO 38
<211> LENGTH: 534
<212> TYPE: PRT
<213> ORGANISM: Perilla frutescens

<400> SEQUENCE: 38

Met Ala Ile Leu Asp Ser Pro Glu Ile Leu Asp Thr Thr Ser Ser Ser
1                   5                   10                  15

Ala Asp Asn Gly Ala Ala His His Thr Thr Leu Arg Arg Arg Gln Ser
                20                  25                  30

Ala Arg Ser Val Pro Pro Leu Leu Asp Ser Asp Ser Asn Ser Leu Glu
            35                  40                  45

Ala Glu Ser Ala Ile Asn Asp Ser Glu Asn Val Arg Asn Asp Ala Asn
        50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Gly Ala Lys Val Lys Glu Asn Gly
                85                  90                  95

Glu Thr Ser Asn Gly Asn Gly Thr Asp Val Met Ala Val Lys Phe Thr
                100                 105                 110

Phe Arg Pro Ala Ala Pro Ala His Arg Lys Asn Lys Glu Ser Pro Leu
            115                 120                 125

Ser Ser Asp Ala Ile Phe Lys Gln Ser His Ala Gly Leu Phe Asn Leu
        130                 135                 140

Cys Ile Val Val Leu Val Ala Val Asn Ser Arg Leu Ile Ile Glu Asn
145                 150                 155                 160

Leu Met Lys Tyr Gly Trp Leu Ile Lys Ser Gly Phe Trp Phe Ser Ser
                165                 170                 175

Thr Ser Leu Arg Asp Trp Pro Leu Leu Met Cys Cys Leu Ser Leu Pro
            180                 185                 190

Val Phe Ala Leu Ala Ser Phe Leu Val Glu Lys Leu Val Lys Leu Asn
        195                 200                 205

Tyr Ile Pro Glu Trp Val Ala Val Phe Leu His Val Thr Ile Thr Thr
        210                 215                 220

Val Glu Ile Leu Phe Pro Val Val Ile Leu Arg Cys Asp Ser Ala
225                 230                 235                 240

Val Leu Ser Gly Val Thr Leu Met Leu Phe Ala Cys Thr Val Trp Leu
                245                 250                 255

Lys Leu Val Ser Tyr Ala His Thr Asn Tyr Asp Leu Arg Val Leu Ala
            260                 265                 270

Lys Ser Leu Asp Lys Trp Glu Ala Met Ser Arg Tyr Trp Asn Leu Asp
```

```
            275                 280                 285
Tyr Ala Tyr Asp Val Ser Phe Lys Ser Leu Ala Tyr Phe Met Val Ala
    290                 295                 300
Pro Thr Leu Cys Tyr Gln Pro Ser Tyr Pro Arg Thr Ala Cys Ile Arg
305                 310                 315                 320
Lys Gly Trp Val Val Arg Gln Leu Ile Lys Leu Val Ile Phe Thr Gly
                325                 330                 335
Leu Met Gly Phe Ile Ile Glu Gln Tyr Ile Asn Pro Ile Val Gln Asn
            340                 345                 350
Ser Gln His Pro Leu Lys Gly Asn Leu Leu Tyr Ala Ile Glu Arg Val
        355                 360                 365
Leu Lys Leu Ser Val Pro Asn Leu Tyr Val Trp Leu Cys Met Phe Tyr
    370                 375                 380
Cys Phe Phe His Leu Trp Leu Asn Ile Leu Ala Glu Leu Leu Cys Phe
385                 390                 395                 400
Gly Asp Arg Glu Phe Tyr Lys Asp Trp Trp Asn Ala Arg Thr Val Glu
                405                 410                 415
Glu Tyr Trp Arg Met Trp Asn Met Pro Val His Lys Trp Met Val Arg
            420                 425                 430
His Ile Tyr Cys Pro Cys Leu Gln Asn Gly Ile Pro Lys Ile Val Ala
        435                 440                 445
Val Leu Ile Ala Phe Leu Val Ser Ala Ile Phe His Glu Leu Cys Val
    450                 455                 460
Ala Val Pro Cys Gln Ile Phe Lys Phe Trp Ala Phe Ser Gly Ile Met
465                 470                 475                 480
Leu Gln Val Pro Leu Val Ile Val Thr Asn Tyr Leu Gln Glu Lys Phe
                485                 490                 495
Lys Asn Ser Met Val Gly Asn Met Met Phe Trp Cys Phe Phe Cys Ile
            500                 505                 510
Phe Gly Gln Pro Met Cys Val Leu Leu Tyr Tyr His Asp Leu Met Asn
        515                 520                 525
Arg Lys Ala Ser Ala Arg
    530

<210> SEQ ID NO 39
<211> LENGTH: 512
<212> TYPE: PRT
<213> ORGANISM: Zea mays

<400> SEQUENCE: 39

Met Ala Asp Ser Glu Asp Ala Pro Pro Ala Val His Arg Arg Pro Pro
1               5                   10                  15
Arg Pro Ala Arg Gly Ala Ala Ala Gln Gly Phe Ala Ala Ala Ala Leu
            20                  25                  30
Arg Arg Arg Leu Arg Ser Gly Ala Ala Val Ala Ala Arg Ala Ser Phe
        35                  40                  45
Ala Ala Asp Ser Gly Asp Glu Ser Gly Pro Gly Glu Pro Ser Ser Ser
    50                  55                  60
Arg Arg Arg Asp Asn Ser Gly Gly Ala Ser Ser Ala Ala Gly Gly Arg
65                  70                  75                  80
Ala Gly Ala Gly Asp Phe Ser Ala Phe Thr Phe Arg Ala Ala Ala Pro
                85                  90                  95
Val His Arg Lys Ala Lys Glu Ser Pro Leu Ser Ser Asp Ala Ile Phe
            100                 105                 110
```

```
Lys Gln Ser His Ala Gly Leu Phe Asn Leu Cys Ile Val Val Leu Val
            115                 120                 125

Ala Val Asn Ser Arg Leu Ile Ile Glu Asn Leu Met Lys Tyr Gly Leu
        130                 135                 140

Leu Ile Arg Ser Gly Phe Trp Phe Asn Ala Thr Ser Leu Arg Asp Trp
145                 150                 155                 160

Pro Leu Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
            180                 185                 190

Thr Thr Cys Phe His Ile Leu Phe Thr Thr Phe Glu Ile Val Tyr Pro
        195                 200                 205

Val Leu Val Ile Leu Lys Cys Asp Ser Ala Val Leu Ser Gly Phe Val
    210                 215                 220

Leu Met Phe Ile Ala Cys Ile Val Trp Leu Lys Leu Val Ser Phe Ala
225                 230                 235                 240

His Thr Asn His Asp Ile Arg Lys Leu Ile Thr Ser Gly Lys Lys Val
                245                 250                 255

Asp Asn Glu Leu Thr Ala Ala Gly Ile Asp Asn Leu Gln Ala Pro Thr
            260                 265                 270

Leu Gly Ser Leu Thr Tyr Phe Met Met Ala Pro Thr Leu Cys Tyr Gln
        275                 280                 285

Pro Ser Tyr Pro Arg Thr Pro Tyr Val Arg Lys Gly Trp Leu Val Arg
    290                 295                 300

Gln Val Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Met
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Cys Leu Phe His Leu Trp
        355                 360                 365

Leu Asn Ile Leu Ala Glu Ile Leu Arg Phe Gly Asp Arg Glu Phe Tyr
370                 375                 380

Lys Asp Trp Trp Asn Ala Lys Thr Ile Asp Glu Tyr Trp Arg Lys Trp
385                 390                 395                 400

Asn Met Pro Val His Lys Trp Ile Val Arg His Ile Tyr Phe Pro Cys
                405                 410                 415

Met Arg Asn Gly Ile Ser Lys Gly Val Ala Val Phe Ile Ser Phe Phe
            420                 425                 430

Val Ser Ala Val Leu His Glu Leu Cys Val Ala Val Pro Cys His Ile
        435                 440                 445

Leu Lys Phe Trp Ala Phe Leu Gly Ile Met Leu Gln Ile Pro Leu Ile
    450                 455                 460

Ile Leu Thr Ser Tyr Leu Lys Asn Lys Phe Ser Asp Thr Met Val Gly
465                 470                 475                 480

Asn Met Ile Phe Trp Phe Phe Phe Cys Ile Tyr Gly Gln Pro Met Cys
                485                 490                 495

Val Leu Leu Tyr Tyr His Asp Val Met Asn Arg Thr Glu Lys Ala Lys
            500                 505                 510

<210> SEQ ID NO 40
<211> LENGTH: 515
<212> TYPE: PRT
```

<213> ORGANISM: Sorghum bicolor

<400> SEQUENCE: 40

```
Met Ala Asp Thr Asp Ala Pro Pro Ala Val His Arg Arg
1               5                   10                  15

Pro Pro Arg Pro Ala Arg Gly Ala Ala Ala Gln Gly Phe Ala Ala
            20                  25                  30

Lys Leu Arg Arg Arg Leu Ser Ser Gly Ala Ala Ala Ala Arg Ala
            35                  40                  45

Ser Phe Ala Ala Asp Ser Gly Asp Glu Ser Gly Pro Gly Glu Pro Ser
        50                  55                  60

Ser Ser Arg Arg Arg Asp Asn Gly Gly Asp Ala Ser Ser Ala Ala Asp
65                  70                  75                  80

Gly Gly Arg Gly Gly Ala Gly Asp Phe Ser Ala Phe Thr Phe Arg Ala
                85                  90                  95

Ala Ala Pro Val His Arg Lys Ala Lys Glu Ser Pro Leu Ser Ser Asp
                100                 105                 110

Ala Ile Phe Lys Gln Ser His Ala Gly Leu Phe Asn Leu Cys Ile Val
            115                 120                 125

Val Leu Val Ala Val Asn Ser Arg Leu Ile Ile Glu Asn Leu Met Lys
130                 135                 140

Tyr Gly Leu Leu Ile Arg Ser Gly Phe Trp Phe Asn Ala Thr Ser Leu
145                 150                 155                 160

Arg Asp Trp Pro Leu Leu Met Cys Cys Leu Ser Leu Pro Val Phe Pro
                165                 170                 175

Leu Gly Ala Phe Ala Val Glu Lys Leu Ala Phe Asn Asn Leu Ile Thr
            180                 185                 190

Asp Ala Ala Ala Thr Cys Phe His Ile Phe Leu Thr Thr Leu Glu Ile
            195                 200                 205

Val Tyr Pro Val Leu Val Ile Leu Lys Cys Asp Ser Ala Val Leu Ser
210                 215                 220

Gly Phe Val Leu Met Phe Ile Ala Cys Ile Val Trp Leu Lys Leu Val
225                 230                 235                 240

Ser Phe Ala His Thr Asn His Asp Ile Arg Lys Leu Ile Thr Ser Gly
                245                 250                 255

Lys Lys Val Asp Asn Glu Leu Thr Val Ala Asp Ile Asp Asn Leu Gln
            260                 265                 270

Ala Pro Thr Leu Gly Ser Leu Thr Tyr Phe Met Met Ala Pro Thr Leu
            275                 280                 285

Cys Tyr Gln Pro Ser Tyr Pro Arg Thr Pro Tyr Val Arg Lys Gly Trp
            290                 295                 300

Leu Val Arg Gln Val Ile Leu Tyr Leu Ile Phe Thr Gly Leu Gln Gly
305                 310                 315                 320

Phe Ile Ile Glu Gln Tyr Ile Asn Pro Ile Val Val Asn Ser Gln His
                325                 330                 335

Pro Leu Lys Gly Gly Leu Leu Asn Ala Val Glu Thr Val Leu Lys Leu
            340                 345                 350

Ser Leu Pro Asn Val Tyr Leu Trp Leu Cys Met Phe Tyr Cys Leu Phe
            355                 360                 365

His Leu Trp Leu Asn Ile Leu Ala Glu Ile Leu Arg Phe Gly Asp Arg
        370                 375                 380

Glu Phe Tyr Lys Asp Trp Trp Asn Ala Lys Thr Ile Asp Glu Tyr Trp
385                 390                 395                 400
```

```
Arg Lys Trp Asn Met Pro Val His Lys Trp Met Leu Arg His Ile Tyr
                405                 410                 415

Phe Pro Cys Ile Arg Asn Gly Ile Ser Lys Glu Val Ala Ala Phe Ile
            420                 425                 430

Ala Phe Phe Val Ser Ala Val Phe His Glu Leu Cys Val Ala Val Pro
        435                 440                 445

Cys His Ile Leu Lys Phe Trp Ala Phe Leu Gly Ile Met Leu Gln Ile
    450                 455                 460

Pro Leu Ile Ile Leu Thr Ser Tyr Leu Lys Asn Lys Phe Asn Asp Thr
465                 470                 475                 480

Met Val Gly Asn Met Ile Phe Trp Phe Phe Cys Ile Tyr Gly Gln
                485                 490                 495

Pro Met Cys Val Leu Leu Tyr Tyr His Asp Val Met Asn Arg Thr Glu
                500                 505                 510

Lys Thr Lys
        515

<210> SEQ ID NO 41
<211> LENGTH: 538
<212> TYPE: PRT
<213> ORGANISM: Oryza sativa

<400> SEQUENCE: 41

Met Val Gly Ser Asp Gly Asp Gly Gly Gly Gly Glu Ala His
1               5                   10                  15

Ala Pro Ala Ala Pro Ala His His Arg Arg Pro Arg Pro Arg
            20                  25                  30

Gly Gly Ser Gly Ala Ile Val Glu Gly Phe Ala Ala Leu Arg Arg
        35                  40                  45

Arg Ile Arg Ser Gly Ala Ala Ala Ala Arg Ala Ser Phe Gly Gly
    50                  55                  60

Asp Ser Gly Asp Glu Ala Ala Ser Gly Glu Pro Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Arg Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Leu Ile Arg Ala Gly Phe
                165                 170                 175

Trp Phe Asn Asp Lys Ser Leu Arg Asp Trp Pro Leu Leu Met Cys Cys
            180                 185                 190

Leu Ser Leu Pro Ala Phe Pro Leu Gly Ala Phe Ala Val Glu Lys Leu
        195                 200                 205

Ala Phe Asn Asn Val Ile Thr Asp Ala Val Ala Thr Cys Leu His Ile
    210                 215                 220

Phe Leu Ser Thr Thr Glu Ile Val Tyr Pro Val Leu Val Ile Leu Lys
225                 230                 235                 240

Cys Asp Ser Ala Val Leu Ser Gly Phe Leu Leu Ile Phe Ile Ala Cys
                245                 250                 255
```

Ile Val Trp Leu Lys Leu Val Ser Phe Ala His Thr Asn His Asp Ile
                260                 265                 270

Arg Gln Leu Thr Met Gly Gly Lys Val Asp Asn Glu Leu Ser Thr
            275                 280                 285

Val Asp Met Asp Asn Leu Gln Pro Pro Thr Leu Gly Asn Leu Ile Tyr
290                 295                 300

Phe Met Met Ala Pro Thr Leu Cys Tyr Gln Pro Ser Tyr Pro Arg Thr
305                 310                 315                 320

Ser Cys Val Arg Lys Gly Trp Leu Ile Arg Gln Ile Ile Leu Tyr Leu
                325                 330                 335

Ile Phe Thr Gly Leu Gln Gly Phe Ile Ile Glu Gln Tyr Ile Asn Pro
            340                 345                 350

Ile Val Val Asn Ser Gln His Pro Leu Lys Gly Gly Leu Leu Asn Ala
        355                 360                 365

Val Glu Thr Val Leu Lys Leu Ser Leu Pro Asn Val Tyr Leu Trp Leu
370                 375                 380

Cys Met Phe Tyr Ala Phe Phe His Leu Trp Leu Ser Ile Leu Ala Glu
385                 390                 395                 400

Ile Leu Arg Phe Gly Asp Arg Glu Phe Tyr Lys Asp Trp Trp Asn Ala
                405                 410                 415

Lys Thr Ile Asp Glu Tyr Trp Arg Lys Trp Asn Met Pro Val His Lys
            420                 425                 430

Trp Val Arg His Ile Tyr Phe Pro Cys Met Arg Asn Gly Ile Ser
        435                 440                 445

Lys Glu Val Ala Val Leu Ile Ser Phe Leu Val Ser Ala Val Leu His
    450                 455                 460

Glu Ile Cys Val Ala Val Pro Cys Arg Ile Leu Lys Phe Trp Ala Phe
465                 470                 475                 480

Leu Gly Ile Met Leu Gln Ile Pro Leu Ile Val Leu Thr Ala Tyr Leu
                485                 490                 495

Lys Ser Lys Phe Arg Asp Thr Met Val Gly Asn Met Ile Phe Trp Phe
            500                 505                 510

Phe Phe Cys Ile Tyr Gly Gln Pro Met Cys Leu Leu Leu Tyr Tyr His
        515                 520                 525

Asp Val Met Asn Arg Ile Glu Lys Ala Arg
    530                 535

<210> SEQ ID NO 42
<211> LENGTH: 477
<212> TYPE: PRT
<213> ORGANISM: Oryza sativa

<400> SEQUENCE: 42

Met Ala Pro Pro Ser Leu Ala Pro Asp Arg Gly Gly Gly Glu Pro
1               5                   10                  15

Asp Asp Ala Leu Arg Leu Arg Ala Arg Ala Ala Ala Gly Asp
            20                  25                  30

Ala Pro Ala Pro Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg

```
                85                  90                  95
Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
            115                 120                 125

Cys Leu Thr Leu Pro Thr Phe Pro Leu Ala Ala Leu Met Val Glu Lys
            130                 135                 140

Leu Ala Gln Arg Lys Leu Ile Ser Lys His Val Val Ile Leu Leu His
145                 150                 155                 160

Ile Val Ile Thr Thr Ser Val Leu Val Tyr Pro Val Val Ile Leu
                165                 170                 175

Lys Cys Asp Ser Ala Val Leu Ser Gly Phe Val Leu Met Phe Leu Ala
                180                 185                 190

Ser Ile Ile Trp Leu Lys Leu Val Ser Phe Ala His Thr Asn Tyr Asp
            195                 200                 205

Ile Arg Met Leu Ser Lys Ser Ile Glu Lys Gly Val Thr His Asp Ile
            210                 215                 220

Ser Ile Asp Pro Glu Asn Ile Lys Trp Pro Thr Phe Lys Arg Leu Ser
225                 230                 235                 240

Tyr Phe Met Leu Ala Pro Thr Leu Cys Tyr Gln Pro Ser Tyr Pro Arg
                245                 250                 255

Thr Thr Tyr Ile Arg Lys Gly Trp Val Val Arg Gln Leu Ile Lys Cys
                260                 265                 270

Leu Val Phe Thr Gly Leu Met Gly Phe Ile Ile Glu Gln Tyr Ile Asn
                275                 280                 285

Pro Ile Val Lys Asn Ser Lys His Pro Leu Lys Gly Asn Phe Leu Asn
290                 295                 300

Ala Ile Glu Arg Val Leu Lys Leu Ser Val Pro Thr Leu Tyr Val Trp
305                 310                 315                 320

Leu Cys Met Phe Tyr Cys Phe Phe His Leu Trp Leu Asn Ile Leu Ala
                325                 330                 335

Glu Leu Leu Cys Phe Gly Asp Arg Glu Phe Tyr Lys Asp Trp Trp Asn
                340                 345                 350

Ala Lys Thr Val Glu Glu Tyr Trp Arg Met Trp Asn Met Pro Val His
                355                 360                 365

Lys Trp Val Ile Arg His Ile Tyr Phe Pro Cys Ile Arg Asn Gly Phe
370                 375                 380

Ser Lys Gly Val Ala Ile Leu Ile Ser Phe Leu Val Ser Ala Ala Phe
385                 390                 395                 400

His Glu Leu Cys Val Ala Val Pro Cys His Ile Phe Lys Phe Trp Ala
                405                 410                 415

Phe Ile Gly Ile Met Phe Gln Ile Pro Leu Val Phe Leu Thr Lys Tyr
                420                 425                 430

Leu Gln Asp Lys Phe Asn Asn Thr Met Val Gly Asn Met Ile Phe Trp
                435                 440                 445

Phe Phe Phe Ser Ile Leu Gly Gln Pro Met Cys Val Leu Leu Tyr Tyr
                450                 455                 460

His Asp Val Met Asn Arg Gln Gln Ala Gln Thr Asn Arg
465                 470                 475

<210> SEQ ID NO 43
<211> LENGTH: 529
<212> TYPE: PRT
<213> ORGANISM: Sorghum bicolor
```

<400> SEQUENCE: 43

Met Ala Pro Pro Pro Ser Met Ala Ala Ser Asp Arg Ala Val Pro
1               5                   10                  15

Gly Ala Asp Ala Thr Glu Ala Ser Ser Leu Arg Leu Arg Arg Ala Pro
            20                  25                  30

Ser Ala Asp Ala Gly Asp Leu Ala Asp Asp Ser Ser Gly Asp Arg Arg
            35                  40                  45

Glu Asn Gly Glu Pro Gln Pro Pro Gln Glu Gln Gln Gln Gln His Glu
        50                  55                  60

Met Leu Tyr Tyr Arg Ala Ser Ala Pro Ala His Arg Arg Val Lys Glu
65                  70                  75                  80

Ser Pro Leu Ser Ser Asp Ala Ile Phe Arg Gln Ser His Ala Gly Leu
                85                  90                  95

Leu Asn Leu Cys Ile Val Val Leu Ile Ala Val Asn Ser Arg Leu Ile
                100                 105                 110

Ile Glu Asn Leu Met Lys Tyr Gly Leu Ile Arg Ala Gly Phe Trp
            115                 120                 125

Phe Ser Ala Arg Ser Leu Gly Asp Trp Pro Leu Leu Met Cys Cys Leu
130                 135                 140

Thr Leu Pro Val Phe Pro Leu Val Ala Leu Met Ala Glu Lys Leu Ile
145                 150                 155                 160

Arg Arg Lys Leu Ile Gly Glu His Val Val Ile Leu His Ile Ile
                165                 170                 175

Ile Thr Thr Ser Val Ile Val Tyr Pro Val Val Thr Leu Lys Cys
            180                 185                 190

Asp Ser Ala Val Leu Ser Gly Phe Leu Leu Met Phe Leu Ala Ser Ile
            195                 200                 205

Met Trp Met Lys Leu Val Ser Tyr Ala His Thr Asn Tyr Asp Ile Arg
    210                 215                 220

Ala Leu Ser Lys Ser Thr Glu Lys Gly Ala Ala Tyr Gly Asn Tyr Val
225                 230                 235                 240

Asp Pro Glu Ser Met Lys Asp Pro Thr Phe Lys Ser Leu Val Tyr Phe
            245                 250                 255

Met Leu Ala Pro Thr Leu Cys Tyr Gln Pro Thr Tyr Pro Arg Thr Thr
            260                 265                 270

Cys Ile Arg Lys Gly Trp Val Thr Arg Gln Leu Ile Lys Cys Leu Val
            275                 280                 285

Phe Thr Gly Leu Met Gly Phe Ile Ile Glu Gln Tyr Ile Asn Pro Ile
            290                 295                 300

Val Lys Asn Ser Lys His Pro Leu Lys Gly Asn Phe Leu Asn Ala Ile
305                 310                 315                 320

Glu Arg Val Leu Lys Leu Ser Val Pro Thr Leu Tyr Val Trp Leu Cys
                325                 330                 335

Met Phe Tyr Cys Phe Phe His Leu Trp Leu Asn Ile Leu Ala Glu Leu
            340                 345                 350

Leu Cys Phe Gly Asp Arg Glu Phe Tyr Lys Asp Trp Trp Asn Ala Lys
        355                 360                 365

Thr Val Glu Glu Tyr Trp Arg Met Trp Asn Met Pro Val His Lys Trp
        370                 375                 380

Ile Ile Arg His Ile Tyr Phe Pro Cys Ile Arg Lys Gly Phe Ser Arg
385                 390                 395                 400

Gly Val Ala Ile Leu Val Ser Phe Leu Val Ser Ala Val Phe His Glu

```
                    405                 410                 415
Ile Cys Ile Ala Val Pro Cys His Ile Phe Lys Phe Trp Ala Phe Ser
                420                 425                 430

Gly Ile Met Phe Gln Ile Pro Leu Val Phe Leu Thr Arg Tyr Leu Gln
            435                 440                 445

Ala Thr Phe Lys Asn Ile Met Val Gly Asn Met Ile Phe Trp Phe Phe
450                 455                 460

Phe Ser Ile Val Gly Gln Pro Met Cys Val Leu Leu Tyr Tyr His Asp
465                 470                 475                 480

Val Met Asn Arg Gln Ala Gln Gln Val Asp Asn Ser Ala Glu Thr Cys
                485                 490                 495

Thr Leu Arg Gln Val Ile Arg Ser Arg Leu Glu Arg Arg Ser Arg Lys
                500                 505                 510

Gln Gln Gln Gln Gln Ala Ser Ser Pro Pro Leu Pro Leu Leu Pro Ala
            515                 520                 525

Ser

<210> SEQ ID NO 44
<211> LENGTH: 494
<212> TYPE: PRT
<213> ORGANISM: Zea mays

<400> SEQUENCE: 44

Met Ala Pro Pro Pro Ser Met Pro Ala Ala Ser Asp Arg Ala Gly Pro
1               5                   10                  15

Gly Arg Asp Ala Gly Asp Ser Ser Leu Arg Leu Arg Ala Pro
            20                  25                  30

Ser Ala Asp Ala Gly Asp Leu Ala Gly Asp Ser Ser Gly Gly Leu Arg
            35                  40                  45

Glu Asn Gly Glu Pro Gln Ser Pro Thr Asn Pro Pro Gln Glu Gln
50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
            115                 120                 125

Ala Gly Phe Trp Phe Ser Ala Arg Ser Leu Gly Asp Trp Pro Leu Leu
        130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
            180                 185                 190

Thr Leu Lys Cys Asp Ser Ala Val Leu Ser Gly Phe Val Leu Met Phe
            195                 200                 205

Leu Ala Ser Ile Met Trp Met Lys Leu Val Ser Tyr Ala His Thr Asn
        210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
```

```
                       245                 250                 255
Leu Val Tyr Phe Met Leu Ala Pro Thr Leu Cys Tyr Gln Pro Thr Tyr
                260                 265                 270

Pro Gln Thr Thr Cys Ile Arg Lys Gly Trp Val Thr Gln Gln Leu Ile
            275                 280                 285

Lys Cys Val Val Phe Thr Gly Leu Met Gly Phe Ile Ile Glu Gln Tyr
        290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
                340                 345                 350

Val Ala Glu Leu Leu Cys Phe Gly Asp Arg Glu Phe Tyr Lys Asp Trp
            355                 360                 365

Trp Asn Ala Lys Thr Val Glu Glu Tyr Trp Arg Met Trp Asn Met Pro
        370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
                420                 425                 430

Trp Ala Phe Ser Gly Ile Met Phe Gln Ile Pro Leu Val Phe Leu Thr
            435                 440                 445

Arg Tyr Leu His Ala Thr Phe Lys His Val Met Val Gly Asn Met Ile
        450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg
                485                 490

<210> SEQ ID NO 45
<211> LENGTH: 447
<212> TYPE: PRT
<213> ORGANISM: Physcomitrella patens

<400> SEQUENCE: 45

Met Pro Val Lys Ser Ser Asn Leu Ala Gly Glu Arg Ala Ala Thr Ser
1               5                   10                  15

His Ile Asn Ala Asn Thr Lys Phe Asp Leu Arg Gly Cys Thr Pro Ala
            20                  25                  30

His Arg Val Arg Arg Glu Ser Pro Leu Ser Ser Asp Ala Ile Phe His
        35                  40                  45

Gln Ser His Ala Gly Leu Phe Asn Leu Cys Ile Val Val Leu Ile Ala
    50                  55                  60

Val Asn Ser Arg Leu Ile Ile Glu Asn Leu Met Lys Tyr Gly Leu Leu
65                  70                  75                  80

Ile Arg Thr Gly Phe Trp Phe Ser Ser Lys Ser Ala Arg Asp Trp Pro
                85                  90                  95

Leu Leu Met Cys Gly Leu Ser Leu Pro Thr Phe Pro Phe Ala Ala Leu
            100                 105                 110

Leu Val Glu Lys Leu Cys Trp Lys Asn Glu Asn Gly Lys Trp Leu Ile
        115                 120                 125
```

```
Phe Val Leu His Leu Ile Ile Ser Thr Val Gly Ile Leu Tyr Pro Gly
        130                 135                 140

Tyr Val Ile His Arg Val Gln Ser Ala Leu Leu Pro Gly Leu Val Leu
145                 150                 155                 160

Ile Leu Ile Ala Val Thr Gly Trp Met Lys Leu Ile Ser Tyr Ala His
            165                 170                 175

Val Asn Lys Asp Met Arg Glu Leu Leu Arg Ala Lys Glu Lys Leu Pro
        180                 185                 190

Glu Ala Pro Gln Tyr Ala Asp Lys Ile Glu Val Pro Asp His Leu Thr
    195                 200                 205

Ile Gln Asn Ile Ala Tyr Phe Met Leu Ala Pro Thr Leu Cys Tyr Gln
210                 215                 220

Leu Ser Tyr Pro Arg Ser Asp Thr Ile Arg Lys Ser Trp Val Leu Arg
225                 230                 235                 240

Gln Ala Gly Lys Leu Val Val Phe Leu Gly Leu Gly Phe Ile Ile
                245                 250                 255

Glu Gln Tyr Ile Asn Pro Thr Val Lys Asn Ser Gln His Pro Leu Arg
            260                 265                 270

Gly Asn Tyr Leu Gln Ala Leu Glu Arg Val Leu Lys Leu Ser Leu Pro
    275                 280                 285

Val Leu Tyr Val Trp Leu Cys Leu Phe Tyr Cys Leu Phe His Leu Trp
290                 295                 300

Leu Asn Ile Val Ala Glu Leu Leu Arg Phe Gly Asp Arg Glu Phe Tyr
305                 310                 315                 320

Lys Asp Trp Trp Asn Ala Gln Thr Val Glu Glu Tyr Trp Arg Met Trp
                325                 330                 335

Asn Met Pro Val His Lys Trp Met Val Arg His Ile Tyr Phe Pro Ser
            340                 345                 350

Ile Arg Ala Gly Leu Ser Lys Lys Ala Ala Val Leu Leu Val Phe Ala
    355                 360                 365

Ile Ser Ala Leu Phe His Glu Val Ile Ile Gly Val Pro Cys His Met
370                 375                 380

Leu Arg Cys Trp Ala Phe Leu Gly Ile Met Met Gln Val Pro Leu Val
385                 390                 395                 400

Tyr Leu Thr Asn Val Ile Lys Glu Arg Tyr His Ser Ser Met Val Gly
                405                 410                 415

Asn Met Val Phe Trp Phe Phe Cys Ile Val Gly Gln Pro Met Cys
            420                 425                 430

Leu Leu Leu Tyr Tyr His Asp Val Phe Asn Asn Phe Pro Ser Thr
    435                 440                 445

<210> SEQ ID NO 46
<211> LENGTH: 425
<212> TYPE: PRT
<213> ORGANISM: Selaginella moellendorffii

<400> SEQUENCE: 46

Met Arg Pro Ser Leu Pro Ala His Arg Arg Ser Lys Glu Ser Pro Leu
1               5                   10                  15

Ser Ser Asp Ala Ile Phe Thr Gln Ser His Ala Gly Leu Phe Asn Leu
            20                  25                  30

Cys Ile Val Val Leu Val Ala Val Asn Ser Arg Leu Ile Ile Glu Asn
        35                  40                  45

Leu Met Lys Tyr Gly Leu Leu Ile Gln Ala Glu Val Leu Phe Ser Ser
    50                  55                  60
```

```
Lys Ser Leu Lys Asp Trp Pro Leu Leu Met Cys Gly Leu Ser Leu Leu
 65                  70                  75                  80

Ile Phe Pro Leu Ala Ala Tyr Val Ile Glu Lys Ile Lys Ala Arg Arg
                 85                  90                  95

Pro Ala Thr Ala Val Ala Pro Leu His Leu Ile Asn Leu Ala Ala Ala
            100                 105                 110

Leu Leu Tyr Pro Ile Tyr Val Ile Glu Met Phe Gln Ser Asp Leu Leu
            115                 120                 125

Ser Gly Leu Val Leu Met Leu Ile Ala Val Thr Gly Trp Leu Lys Leu
        130                 135                 140

Val Ser Tyr Ala His Thr Asn Ala Asp Ile Arg Ala Val Lys Lys Asp
145                 150                 155                 160

Gly Gly Lys Ile Glu Leu Pro Ala Glu Ala Pro Ala Ile Asp Tyr Pro
                165                 170                 175

Asp Asn Ile Ser Leu Lys Asn Ile Ala Tyr Phe Met Ala Ala Pro Thr
            180                 185                 190

Leu Cys Tyr Gln Leu Ser Tyr Pro Arg Ser Pro Arg Ile Arg Thr Gly
        195                 200                 205

Trp Val Leu Arg Gln Leu Gly Lys Trp Ile Val Phe Asn Gly Phe Met
210                 215                 220

Gly Phe Ile Ile Gly Gln Tyr Met Asn Pro Ile Ile Arg Asn Ser Thr
225                 230                 235                 240

His Pro Leu Lys Gly Asn Tyr Leu Tyr Ala Ile Glu Arg Val Leu Lys
                245                 250                 255

Leu Ser Ile Pro Thr Leu Tyr Val Trp Leu Gly Phe Phe Tyr Cys Phe
            260                 265                 270

Phe His Leu Trp Leu Asn Ile Val Ala Glu Ile Leu Cys Phe Gly Asp
        275                 280                 285

Arg Glu Phe Tyr Lys Asp Trp Trp Asn Ala Lys Ser Val Asp Glu Tyr
    290                 295                 300

Trp Arg Leu Trp Asn Met Pro Val His Arg Trp Leu Val Arg His Val
305                 310                 315                 320

Tyr Phe Pro Cys Leu Arg Leu Gly Leu His Lys Gln Phe Ala Ile Leu
                325                 330                 335

Val Val Phe Val Ile Ser Gly Ile Phe His Glu Ile Cys Ile Ala Val
            340                 345                 350

Pro Cys His Met Leu Arg Gly Trp Ala Phe Leu Gly Ile Met Phe Gln
        355                 360                 365

Val Pro Leu Val Leu Val Thr Asn Val Leu Gln Arg Lys Phe Gln Ser
    370                 375                 380

Ser Met Val Gly Asn Met Ile Phe Trp Phe Phe Phe Cys Ile Val Gly
385                 390                 395                 400

Gln Pro Met Cys Val Leu Leu Tyr Tyr His Asp Val Val Asn Arg Gln
                405                 410                 415

Gln Leu Gln Leu Ala Gly Arg Ser Lys
            420                 425
```

<210> SEQ ID NO 47
<211> LENGTH: 507
<212> TYPE: PRT
<213> ORGANISM: Euonymus alatus

<400> SEQUENCE: 47

Met Ala Ala Asn Leu Asn Glu Ala Ser Asp Leu Asn Phe Ser Leu Arg

-continued

```
  1               5                  10                 15
Arg Arg Thr Gly Gly Ile Ser Ser Thr Thr Val Pro Asp Ser Ser Ser
              20                 25                 30
Glu Thr Ser Ser Ser Glu Ala Asp Tyr Leu Asp Gly Gly Lys Gly Ala
              35                 40                 45
Ala Asp Val Lys Asp Arg Gly Asp Gly Ala Val Glu Phe Gln Asn Ser
 50                 55                 60
Met Lys Asn Val Glu Arg Ile Glu Lys His Glu Ser Arg Val Gly Leu
 65                 70                 75                 80
Asp Ser Arg Phe Thr Tyr Arg Pro Ser Val Pro Ala His Arg Thr Ile
              85                 90                 95
Lys Glu Ser Pro Leu Ser Ser Asp Ala Ile Phe Lys Gln Ser His Ala
             100                105                110
Gly Leu Phe Asn Leu Cys Ile Val Val Leu Val Ala Val Asn Ser Arg
             115                120                125
Leu Ile Ile Glu Asn Leu Met Lys Tyr Gly Trp Leu Ile Arg Ser Gly
             130                135                140
Phe Trp Phe Ser Ser Arg Ser Leu Arg Asp Trp Pro Leu Phe Met Cys
145                150                155                160
Cys Leu Thr Leu Pro Val Phe Pro Leu Ala Ala Phe Leu Phe Glu Lys
             165                170                175
Leu Ala Gln Lys Asn Leu Ile Ser Glu Pro Val Val Leu Leu His
             180                185                190
Ile Val Asn Thr Thr Ala Ala Val Leu Tyr Pro Val Leu Val Ile Leu
             195                200                205
Arg Cys Asp Ser Ala Phe Met Ser Gly Val Thr Leu Met Leu Phe Ala
             210                215                220
Cys Ile Val Trp Leu Lys Leu Val Ser Tyr Ala His Thr Asn Tyr Asp
225                230                235                240
Met Arg Ala Leu Thr Lys Ser Val Glu Lys Gly Asp Thr Pro Leu Ser
             245                250                255
Ser Gln Asn Met Asp Tyr Ser Phe Asp Val Asn Ile Lys Ser Leu Ala
             260                265                270
Tyr Phe Met Val Ala Pro Thr Leu Cys Tyr Gln Ile Ser Tyr Pro Arg
             275                280                285
Thr Pro Tyr Val Arg Lys Gly Trp Val Val Arg Gln Phe Val Lys Leu
             290                295                300
Ile Ile Phe Thr Gly Leu Met Gly Phe Ile Ile Glu Gln Tyr Ile Asn
305                310                315                320
Pro Ile Val Gln Asn Ser Gln His Pro Leu Lys Gly Asn Phe Leu Tyr
             325                330                335
Ala Ile Glu Arg Val Leu Lys Leu Ser Val Pro Asn Leu Tyr Val Trp
             340                345                350
Leu Cys Met Phe Tyr Cys Leu Phe His Leu Trp Leu Asn Ile Leu Ala
             355                360                365
Glu Leu Leu Cys Phe Gly Asp Arg Glu Phe Tyr Lys Asp Trp Trp Asn
             370                375                380
Ala Lys Thr Val Glu Glu Tyr Trp Arg Met Trp Asn Met Pro Val His
385                390                395                400
Lys Trp Met Val Arg His Ile Tyr Phe Pro Cys Leu Arg Asn Gly Ile
             405                410                415
Pro Lys Gly Val Ala Phe Val Ile Ser Phe Leu Val Ser Ala Val Phe
             420                425                430
```

```
His Glu Leu Cys Ile Ala Val Pro Cys His Ile Phe Lys Leu Trp Ala
            435                 440                 445

Phe Phe Gly Ile Met Leu Gln Val Pro Leu Val Leu Ile Thr Ser Tyr
        450                 455                 460

Leu Gln Asn Lys Phe Arg Ser Ser Met Val Gly Asn Met Met Phe Trp
465                 470                 475                 480

Phe Ser Phe Cys Ile Phe Gly Gln Pro Met Cys Leu Leu Tyr Tyr
                485                 490                 495

His Asp Leu Met Asn Arg Asn Gly Lys Met Glu
            500                 505

<210> SEQ ID NO 48
<211> LENGTH: 518
<212> TYPE: PRT
<213> ORGANISM: Vitis vinifera

<400> SEQUENCE: 48

Met Ala Ile Cys Asn Ser Pro Val Ser Val Thr Thr Ser Ser Ser Ser
1               5                   10                  15

Ser His Ala Asp Ser Asp Leu Asp Phe Ser Ile Arg Lys Arg Phe Gly
            20                  25                  30

Gly Lys Gly Lys Ala Val Ala Asp Ser Ser Leu Glu Thr Glu Thr Glu
        35                  40                  45

Ala Ala Ala Ala Val Leu Glu Ala Glu Lys Ser Val Gly Glu Val
    50                  55                  60

Gly Ser Gly Gly Asp Arg Gly Glu Ser Gly Ser Gln Val Val Arg Asn
65                  70                  75                  80

Gly Glu Asn Gly Val Ala Glu Val Ala Ala Lys Phe Ala Tyr Arg Pro
                85                  90                  95

Cys Ala Pro Ala His Arg Lys Val Lys Glu Ser Pro Leu Ser Ser Asp
            100                 105                 110

Ala Ile Phe Arg Gln Ser His Ala Gly Leu Phe Asn Leu Cys Ile Val
        115                 120                 125

Val Leu Val Ala Val Asn Ser Arg Leu Ile Ile Glu Asn Leu Met Lys
130                 135                 140

Tyr Gly Trp Leu Ile Arg Ala Gly Phe Trp Phe Ser Ser Lys Ser Leu
145                 150                 155                 160

Arg Asp Trp Pro Leu Phe Met Cys Cys Leu Thr Leu Pro Ile Phe Pro
                165                 170                 175

Leu Ala Ala Phe Val Val Glu Lys Leu Ala Gln Gln Lys Tyr Ile Ser
            180                 185                 190

Glu Gln Val Val Val Ser Leu His Ile Ile Thr Thr Ala Ala Val
        195                 200                 205

Leu Phe Pro Val Leu Val Ile Leu Arg Cys Asp Ser Ala Val Leu Ser
210                 215                 220

Gly Val Thr Leu Met Leu Phe Ala Cys Ile Val Trp Leu Lys Leu Val
225                 230                 235                 240

Ser Phe Ala His Thr Asn Tyr Asp Met Arg Ala Val Ala Lys Leu Ile
                245                 250                 255

Asp Lys Gly Asp Asp Leu Ser Thr Ser Leu Asn Met Asp Tyr Pro Tyr
            260                 265                 270

Asp Val Asn Phe Lys Ser Leu Ala Tyr Phe Met Val Ala Pro Thr Leu
        275                 280                 285

Cys Tyr Gln Pro Ser Tyr Pro Arg Ser Thr Cys Ile Arg Lys Gly Trp
```

```
                  290                 295                 300
Val Phe Arg Gln Phe Val Lys Leu Ala Ile Phe Thr Gly Val Met Gly
305                 310                 315                 320

Phe Ile Ile Glu Gln Tyr Ile Asn Pro Ile Val Gln Asn Ser Gln His
                325                 330                 335

Pro Leu Lys Gly Asn Phe Phe Tyr Ala Leu Glu Arg Ile Leu Lys Leu
            340                 345                 350

Ser Val Pro Asn Leu Tyr Val Trp Leu Cys Met Phe Tyr Cys Phe Phe
            355                 360                 365

His Leu Trp Leu Asn Ile Leu Ala Glu Leu Leu Arg Phe Gly Asp Arg
        370                 375                 380

Glu Phe Tyr Lys Asp Trp Trp Asn Ala Lys Thr Val Glu Glu Tyr Trp
385                 390                 395                 400

Arg Met Trp Asn Met Pro Val His Lys Trp Met Val Arg His Leu Tyr
                405                 410                 415

Phe Pro Cys Leu Arg Asn Gly Ile Ser Lys Gly Val Ser Val Val Ile
            420                 425                 430

Ala Phe Ala Ile Ser Ala Ile Phe His Glu Leu Cys Ile Ala Val Pro
        435                 440                 445

Cys His Met Phe Lys Leu Trp Ala Phe Ile Gly Ile Met Phe Gln Val
    450                 455                 460

Pro Leu Val Leu Val Thr Asn Tyr Leu Gln Asn Lys Phe Arg Asn Ser
465                 470                 475                 480

Met Val Gly Asn Met Ile Phe Trp Leu Phe Phe Ser Ile Leu Gly Gln
                485                 490                 495

Pro Met Cys Val Leu Leu Tyr Tyr His Asp Leu Met Asn Arg Lys Glu
            500                 505                 510

Thr Thr Glu Ser Ser Leu
            515

<210> SEQ ID NO 49
<211> LENGTH: 498
<212> TYPE: PRT
<213> ORGANISM: Glycine max

<400> SEQUENCE: 49

Met Ala Ile Ser Asp Glu Pro Glu Thr Val Ala Thr Ala Leu Asn His
1               5                   10                  15

Ser Ser Leu Arg Arg Pro Thr Ala Ala Gly Leu Phe Asn Ser Pro
            20                  25                  30

Glu Thr Thr Thr Asp Ser Ser Gly Asp Asp Leu Ala Lys Asp Ser Gly
            35                  40                  45

Ser Asp Asp Ser Ile Ser Ser Asp Ala Ala Asn Ser Gln Pro Gln Gln
        50                  55                  60

Lys Gln Asp Thr Asp Phe Ser Val Leu Lys Phe Ala Tyr Arg Pro Ser
65                  70                  75                  80

Val Pro Ala His Arg Lys Val Lys Glu Ser Pro Leu Ser Ser Asp Thr
                85                  90                  95

Ile Phe Arg Gln Ser His Ala Gly Leu Phe Asn Leu Cys Ile Val Val
            100                 105                 110

Leu Val Ala Val Asn Ser Arg Leu Ile Ile Glu Asn Leu Met Lys Tyr
        115                 120                 125

Gly Trp Leu Ile Lys Ser Gly Phe Trp Phe Ser Ser Lys Ser Leu Arg
    130                 135                 140
```

Asp Trp Pro Leu Phe Met Cys Cys Leu Ser Leu Val Val Phe Pro Phe
145                 150                 155                 160

Ala Ala Phe Ile Val Glu Lys Leu Ala Gln Gln Lys Cys Ile Pro Glu
            165                 170                 175

Pro Val Val Val Leu His Ile Ile Ile Thr Ser Ala Ser Leu Phe
        180                 185                 190

Tyr Pro Val Leu Val Ile Leu Arg Cys Asp Ser Ala Phe Leu Ser Gly
        195                 200                 205

Val Thr Leu Met Leu Phe Ala Cys Val Val Trp Leu Lys Leu Val Ser
210                 215                 220

Tyr Ala His Thr Asn Tyr Asp Met Arg Ala Leu Thr Lys Ser Val Glu
225                 230                 235                 240

Lys Gly Glu Ala Leu Pro Asp Thr Leu Asn Met Asp Tyr Pro Tyr Asn
            245                 250                 255

Val Ser Phe Lys Ser Leu Ala Tyr Phe Leu Val Ala Pro Thr Leu Cys
            260                 265                 270

Tyr Gln Pro Ser Tyr Pro Arg Thr Pro Tyr Ile Arg Lys Gly Trp Leu
            275                 280                 285

Phe Arg Gln Leu Val Lys Leu Ile Ile Phe Thr Gly Val Met Gly Phe
290                 295                 300

Ile Ile Glu Gln Tyr Ile Asn Pro Ile Val Gln Asn Ser Gln His Pro
305                 310                 315                 320

Leu Lys Gly Asn Leu Leu Tyr Ala Ile Glu Arg Val Leu Lys Leu Ser
            325                 330                 335

Val Pro Asn Leu Tyr Val Trp Leu Cys Met Phe Tyr Cys Phe Phe His
            340                 345                 350

Leu Trp Leu Asn Ile Leu Ala Glu Leu Leu Arg Phe Gly Asp Arg Glu
            355                 360                 365

Phe Tyr Gln Asp Trp Trp Asn Ala Lys Thr Val Glu Asp Tyr Trp Arg
            370                 375                 380

Met Trp Asn Met Pro Val His Lys Trp Met Ile Arg His Leu Tyr Phe
385                 390                 395                 400

Pro Cys Leu Arg His Gly Ile Pro Lys Ala Val Ala Leu Leu Ile Ala
            405                 410                 415

Phe Leu Val Ser Ala Leu Phe His Glu Leu Cys Ile Ala Val Pro Cys
            420                 425                 430

His Ile Phe Lys Leu Trp Ala Phe Gly Gly Ile Met Phe Gln Val Pro
            435                 440                 445

Leu Val Phe Ile Thr Asn Tyr Leu Gln Asn Lys Phe Arg Asn Ser Met
            450                 455                 460

Val Gly Asn Met Ile Phe Trp Phe Ile Phe Ser Ile Leu Gly Gln Pro
465                 470                 475                 480

Met Cys Val Leu Leu Tyr Tyr His Asp Leu Met Asn Arg Lys Gly Lys
            485                 490                 495

Leu Asp

<210> SEQ ID NO 50
<211> LENGTH: 504
<212> TYPE: PRT
<213> ORGANISM: Glycine max

<400> SEQUENCE: 50

Met Ala Ile Ser Asp Glu Pro Glu Ser Val Ala Thr Ala Leu Asn His
1               5                   10                  15

-continued

```
Ser Ser Leu Arg Arg Pro Ser Ala Thr Ser Thr Ala Gly Leu Phe
         20                  25                  30

Asn Ser Pro Glu Thr Thr Thr Asp Ser Ser Gly Asp Asp Leu Ala Lys
     35                  40                  45

Asp Ser Gly Ser Asp Asp Ser Ile Asn Ser Asp Asp Ala Ala Val Asn
 50                      55                  60

Ser Gln Gln Gln Asn Glu Lys Gln Asp Thr Asp Phe Ser Val Leu Lys
 65                  70                  75                  80

Phe Ala Tyr Arg Pro Ser Val Pro Ala His Arg Lys Val Lys Glu Ser
             85                      90                  95

Pro Leu Ser Ser Asp Thr Ile Phe Arg Gln Ser His Ala Gly Leu Phe
                 100                 105                 110

Asn Leu Cys Ile Val Val Leu Val Ala Val Asn Ser Arg Leu Ile Ile
             115                 120                 125

Glu Asn Leu Met Lys Tyr Gly Trp Leu Ile Lys Ser Gly Phe Trp Phe
         130                 135                 140

Ser Ser Lys Ser Leu Arg Asp Trp Pro Leu Phe Met Cys Cys Leu Ser
145                 150                 155                 160

Leu Val Val Phe Pro Phe Ala Ala Phe Ile Val Glu Lys Leu Ala Gln
                 165                 170                 175

Arg Lys Cys Ile Pro Glu Pro Val Val Val Leu His Ile Ile Ile
             180                 185                 190

Thr Ser Thr Ser Leu Phe Tyr Pro Val Leu Val Ile Leu Arg Cys Asp
             195                 200                 205

Ser Ala Phe Val Ser Gly Val Thr Leu Met Leu Phe Ser Cys Val Val
 210                 215                 220

Trp Leu Lys Leu Val Ser Tyr Ala His Thr Asn Tyr Asp Met Arg Ala
225                 230                 235                 240

Leu Thr Lys Leu Val Glu Lys Gly Glu Ala Leu Leu Asp Thr Leu Asn
                 245                 250                 255

Met Asp Tyr Pro Tyr Asn Val Ser Phe Lys Ser Leu Ala Tyr Phe Leu
             260                 265                 270

Val Ala Pro Thr Leu Cys Tyr Gln Pro Ser Tyr Pro Arg Thr Pro Tyr
                 275                 280                 285

Ile Arg Lys Gly Trp Leu Phe Arg Gln Leu Val Lys Leu Ile Ile Phe
 290                 295                 300

Thr Gly Val Met Gly Phe Ile Ile Glu Gln Tyr Ile Asn Pro Ile Val
305                 310                 315                 320

Gln Asn Ser Gln His Pro Leu Lys Gly Asn Leu Leu Tyr Ala Thr Glu
                 325                 330                 335

Arg Val Leu Lys Leu Ser Val Pro Asn Leu Tyr Val Trp Leu Cys Met
             340                 345                 350

Phe Tyr Cys Phe Phe His Leu Trp Leu Asn Ile Leu Ala Glu Leu Leu
         355                 360                 365

Arg Phe Gly Asp Arg Glu Phe Tyr Lys Asp Trp Asn Ala Lys Thr
     370                 375                 380

Val Glu Asp Tyr Trp Arg Met Trp Asn Met Pro Val His Lys Trp Met
385                 390                 395                 400

Ile Arg His Leu Tyr Tyr Pro Cys Leu Arg His Gly Leu Pro Lys Ala
                 405                 410                 415

Ala Ala Leu Leu Ile Ala Phe Leu Val Ser Ala Leu Phe His Glu Leu
             420                 425                 430

Cys Ile Ala Val Pro Cys His Ile Phe Lys Leu Trp Ala Phe Gly Gly
```

```
                   435                 440                 445
Ile Met Phe Gln Val Pro Leu Val Leu Ile Thr Asn Tyr Leu Gln Asn
450                 455                 460

Lys Phe Arg Asn Ser Met Val Gly Asn Met Ile Phe Trp Phe Ile Phe
465                 470                 475                 480

Ser Ile Leu Gly Gln Pro Met Cys Val Leu Leu Tyr Tyr His Asp Leu
                485                 490                 495

Met Asn Arg Lys Gly Lys Leu Asp
                500

<210> SEQ ID NO 51
<211> LENGTH: 511
<212> TYPE: PRT
<213> ORGANISM: Lotus japonicus

<400> SEQUENCE: 51

Met Ala Ile Ser Glu Asp Ser Glu Ser Leu Phe Ala Ala Ala Ala Ala
1               5                   10                  15

Ser Ser Val Ile Gln Ser Gly Ser Ser Val Arg Arg Pro Ser Ala
                20                  25                  30

Ile Ser Ala Val Ala Thr Val Glu Asp Glu Ser Ser Glu Glu Pro
            35                  40                  45

Val Pro Val Arg Asp Ser Gly Ser Asp Val Asp Ser Val Ser Ser
50                  55                  60

Glu Gln His Val Ser Pro Ala Thr Ala Asn Arg Glu Lys Asn Gln Val
65              70                  75                  80

His Asp Ile Ser Ala Thr Lys Phe Ala Tyr Arg Pro Ser Ala Pro Ala
                85                  90                  95

His Arg Arg Val Lys Glu Ser Pro Leu Ser Ser Asp Asn Ile Phe Arg
            100                 105                 110

His His Ala Gly Leu Phe Asn Leu Cys Ile Val Val Leu Val Ala Val
        115                 120                 125

Asn Ser Arg Leu Ile Ile Glu Asn Leu Met Lys Tyr Gly Trp Leu Ile
130                 135                 140

Arg Thr Gly Phe Trp Phe Ser Lys Ser Leu Arg Asp Trp Pro Leu
145                 150                 155             160

Phe Met Cys Cys Leu Ser Leu Ala Ile Phe Pro Phe Ala Ala Phe Val
                165                 170                 175

Val Glu Lys Leu Val Gln Gln Lys Cys Ile Ser Glu Pro Val Val Val
            180                 185                 190

Leu His Ile Phe Ile Ser Thr Ala Val Val Tyr Pro Val Leu Val
        195                 200                 205

Ile Leu Arg Thr Asp Ser Ala Phe Pro Ser Gly Val Thr Leu Met Leu
210                 215                 220

Phe Ala Cys Ile Val Trp Leu Lys Leu Val Ser Tyr Ala His Thr Asn
225                 230                 235                 240

Tyr Asp Met Arg Glu Leu Thr Lys Ser Ile Glu Lys Gly Glu Ala Leu
                245                 250                 255

Pro Asn Thr Leu Asn Met Asp Tyr Ser Tyr Asp Val Ser Phe Lys Ser
            260                 265                 270

Leu Ala Tyr Phe Met Ile Ala Pro Thr Leu Cys Tyr Gln Pro Arg Tyr
        275                 280                 285

Pro Arg Ser Pro Ser Ile Arg Lys Gly Trp Val Leu Arg Gln Leu Val
    290                 295                 300
```

```
Lys Leu Ile Ile Phe Thr Gly Val Met Gly Phe Ile Glu Gln Tyr
305                 310                 315                 320

Ile Asn Pro Ile Val Gln Asn Ser Gln His Pro Leu Lys Gly Asn Leu
            325                 330                 335

Leu Tyr Ala Ile Glu Arg Val Leu Lys Leu Ser Val Pro Asn Leu Tyr
            340                 345                 350

Val Trp Leu Cys Met Phe Tyr Cys Phe Phe His Leu Trp Leu Asn Ile
            355                 360                 365

Leu Ala Glu Leu Leu Arg Phe Gly Asp Arg Gly Phe Tyr Lys Asp Trp
370                 375                 380

Trp Asn Ala Lys Thr Phe Glu Glu Tyr Trp Arg Met Trp Asn Met Pro
385                 390                 395                 400

Val His Lys Trp Met Ile Arg His Leu Tyr Phe Pro Cys Leu Arg Asn
            405                 410                 415

Gly Ile Pro Lys Gly Val Ala Ile Leu Ile Ala Phe Leu Val Ser Ala
            420                 425                 430

Leu Phe His Glu Leu Cys Ile Ala Val Pro Cys His Ile Phe Lys Leu
            435                 440                 445

Trp Ala Phe Gly Gly Ile Met Phe Gln Val Pro Leu Ile Leu Ile Thr
450                 455                 460

Asn Tyr Leu Gln Asn Lys Phe Arg Asn Ser Met Val Gly Asn Met Ile
465                 470                 475                 480

Phe Trp Phe Ile Phe Ser Ile Leu Gly Gln Pro Met Ala Val Leu Leu
            485                 490                 495

Tyr Tyr His Asp Leu Met Asn Arg Lys Ser Lys Leu Asp Gln Ser
            500                 505                 510

<210> SEQ ID NO 52
<211> LENGTH: 539
<212> TYPE: PRT
<213> ORGANISM: Medicago truncatula

<400> SEQUENCE: 52

Met Ala Ile Ser Asp Thr Pro Glu Thr Thr Ala Thr Ala Thr Ala Thr
1               5                   10                  15

Val Thr Thr Ile Glu Thr Asp Thr Asp Leu Lys Arg Ser Ser Leu Arg
            20                  25                  30

Arg Arg Pro Ser Ala Thr Ser Thr Ala Gly Gly Leu Phe Asp Ala Glu
        35                  40                  45

Ser Ala Ala Ala Asp Ala Val Arg Asp Ser Gly Ser Asp Asp Ser Leu
    50                  55                  60

Asn Gly Lys Ile Asn Asn Glu Glu Val Lys Asp Arg Lys Thr Asp
65                  70                  75                  80

His Ala Glu Gly Ile Val Asp Asp Asp Asp Asn Ala Val Lys Lys
            85                  90                  95

Asn Gly Gly Asn Asp Val Ile Asn Asp Arg Glu Asn Val Ala Val Asp
            100                 105                 110

Phe Lys Phe Thr Tyr Arg Pro Ser Val Pro Ala His Arg Arg Ser Lys
            115                 120                 125

Glu Ser Pro Leu Ser Ser Gly Asn Ile Phe Arg Gln Ser His Ala Gly
        130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Trp Leu Ile Arg Ser Gly Phe
                165                 170                 175
```

Trp Phe Ser Ser Lys Ser Leu Arg Asp Trp Pro Leu Phe Met Cys Cys
              180                 185                 190

Leu Ser Leu Ala Ile Phe Pro Leu Ala Ala Phe Val Glu Lys Leu
        195                 200                 205

Ala Gln Gln Lys Arg Ile Ser Glu Pro Val Ile Val Leu Leu His Ile
    210                 215                 220

Val Ile Thr Thr Val Ala Ile Ile Tyr Pro Val Leu Val Ile Leu Trp
225                 230                 235                 240

Cys Asp Ser Ala Phe Leu Ser Gly Ser Thr Leu Met Leu Leu Thr Cys
                245                 250                 255

Ile Val Trp Leu Lys Leu Val Ser Tyr Ala His Thr Thr Tyr Asp Met
        260                 265                 270

Arg Ala Leu Ala Val Ser Asn Glu Lys Gly Glu Thr Met Pro Asp Thr
    275                 280                 285

Phe Asn Met Glu Glu Tyr Pro His Asn Val Ser Phe Gln Ser Leu Ala
290                 295                 300

Tyr Phe Met Val Ala Pro Thr Leu Cys Tyr Gln Pro Ser Tyr Pro Arg
305                 310                 315                 320

Thr Pro Ser Val Arg Lys Gly Trp Val Cys Arg Gln Leu Leu Lys Leu
                325                 330                 335

Val Ile Phe Thr Gly Val Met Gly Phe Ile Ile Glu Gln Tyr Met Asn
        340                 345                 350

Pro Ile Val Gln Asn Ser Gln His Pro Leu Lys Gly Asn Leu Leu Tyr
    355                 360                 365

Ala Ile Glu Arg Val Leu Lys Leu Ser Val Pro Asn Val Tyr Val Trp
370                 375                 380

Leu Cys Met Phe Tyr Cys Phe Phe His Leu Trp Leu Asn Ile Leu Ala
385                 390                 395                 400

Glu Leu Leu Arg Phe Gly Asp Arg Glu Phe Tyr Lys Asp Trp Trp Asn
                405                 410                 415

Ala Gln Thr Val Glu Glu Tyr Trp Arg Met Trp Asn Met Pro Val His
        420                 425                 430

Lys Trp Met Val Arg His Val Tyr Phe Pro Cys Ile Arg Phe Gly Ile
    435                 440                 445

Pro Lys Gly Ala Ala Ala Leu Thr Ala Phe Leu Val Ser Ala Val Phe
450                 455                 460

His Glu Leu Cys Ile Ala Val Pro Cys Arg Met Phe Lys Leu Trp Ala
465                 470                 475                 480

Phe Ile Gly Ile Met Phe Gln Val Pro Leu Val Leu Ile Thr Asn Tyr
                485                 490                 495

Leu Lys Asn Lys Tyr Arg Asn Ser Met Val Gly Asn Met Ile Phe Trp
        500                 505                 510

Phe Ile Phe Cys Ile Leu Gly Gln Pro Met Cys Val Leu Leu Tyr Tyr
    515                 520                 525

His Asp Leu Met Asn Arg Lys Gly Glu Ile Asp
530                 535

<210> SEQ ID NO 53
<211> LENGTH: 521
<212> TYPE: PRT
<213> ORGANISM: Jatropha curcas

<400> SEQUENCE: 53

Met Thr Ile Leu Glu Thr Thr Thr Ser Gly Gly Asp Gly Val Ala Glu

```
1               5                   10                  15
Ser Ser Ser Asp Leu Asn Val Ser Leu Arg Arg Arg Lys Gly Thr
            20                  25                  30

Ser Ser Asp Gly Ala Leu Pro Glu Leu Thr Ser Asn Ile Val Glu Leu
            35                  40                  45

Glu Ser Glu Ser Gly Gly Gln Val Met Met Asp Pro Gly Met Val Thr
50                      55                  60

Glu Pro Glu Thr Glu Lys Ile Asn Gly Lys Asp Cys Gly Gly Asp Lys
65                  70                  75                  80

Asp Lys Ile Asp Asn Arg Glu Asn Arg Gly Arg Ser Asp Ile Lys Phe
                85                  90                  95

Thr Tyr Arg Pro Ser Val Pro Ala His Arg Ala Leu Arg Glu Ser Pro
            100                 105                 110

Leu Ser Ser Asp Ala Ile Phe Lys Gln Ser His Ala Gly Leu Phe Asn
            115                 120                 125

Leu Cys Ile Val Val Leu Val Ala Val Asn Ser Arg Leu Ile Ile Glu
            130                 135                 140

Asn Leu Met Lys Tyr Gly Trp Leu Ile Lys Thr Gly Phe Trp Phe Ser
145                 150                 155                 160

Ser Arg Ser Leu Arg Asp Trp Pro Leu Leu Met Cys Cys Leu Thr Leu
                165                 170                 175

Pro Ile Phe Ser Leu Ala Ala Tyr Leu Val Glu Lys Leu Ala Tyr Arg
            180                 185                 190

Lys Tyr Ile Ser Ala Pro Ile Val Ile Phe Phe His Met Leu Ile Thr
            195                 200                 205

Thr Thr Ala Val Leu Tyr Pro Val Ser Val Ile Leu Ser Cys Gly Ser
            210                 215                 220

Ala Val Leu Ser Gly Val Ala Leu Met Leu Phe Ala Cys Ile Val Trp
225                 230                 235                 240

Leu Lys Leu Val Ser Tyr Ala His Thr Asn Tyr Asp Met Arg Ala Ile
                245                 250                 255

Ala Asn Ser Ala Asp Lys Gly Asp Ala Leu Ser Asp Thr Ser Gly Ala
            260                 265                 270

Asp Ser Ser Arg Asp Val Ser Phe Lys Ser Leu Val Tyr Phe Met Val
            275                 280                 285

Ala Pro Thr Leu Cys Tyr Gln Pro Ser Tyr Pro Arg Thr Asp Ser Val
            290                 295                 300

Arg Lys Gly Trp Val Val Arg Gln Phe Val Lys Leu Ile Ile Phe Thr
305                 310                 315                 320

Gly Phe Met Gly Phe Ile Ile Glu Gln Tyr Ile Asn Pro Ile Val Gln
                325                 330                 335

Asn Ser Gln His Pro Leu Lys Gly Asp Leu Leu Tyr Ala Ile Glu Arg
            340                 345                 350

Val Leu Lys Leu Ser Val Pro Asn Leu Tyr Val Trp Leu Cys Met Phe
            355                 360                 365

Tyr Cys Phe Phe His Leu Trp Leu Asn Ile Leu Ala Glu Leu Leu Arg
            370                 375                 380

Phe Gly Asp Arg Glu Phe Tyr Lys Asp Trp Trp Asn Ala Arg Thr Val
385                 390                 395                 400

Glu Glu Tyr Trp Arg Met Trp Asn Met Pro Val His Lys Trp Met Val
                405                 410                 415

Arg His Ile Tyr Phe Pro Cys Leu Arg His Lys Ile Pro Arg Gly Val
            420                 425                 430
```

```
Ala Leu Leu Ile Ala Phe Phe Val Ser Ala Val Phe His Glu Leu Cys
            435                 440                 445

Ile Ala Val Pro Cys His Met Phe Lys Leu Trp Ala Phe Ile Gly Ile
    450                 455                 460

Met Phe Gln Ile Pro Leu Val Gly Ile Thr Asn Tyr Leu Gln Asn Lys
465                 470                 475                 480

Phe Arg Ser Ser Met Val Gly Asn Met Ile Phe Trp Phe Ile Phe Cys
                485                 490                 495

Ile Leu Gly Gln Pro Met Cys Val Leu Leu Tyr Tyr His Asp Leu Met
                500                 505                 510

Asn Arg Lys Gly Asn Ala Glu Leu Arg
            515                 520

<210> SEQ ID NO 54
<211> LENGTH: 526
<212> TYPE: PRT
<213> ORGANISM: Vernicia fordii

<400> SEQUENCE: 54

Met Thr Ile Pro Glu Thr Pro Asp Asn Ser Thr Asp Ala Thr Thr Ser
1               5                   10                  15

Gly Gly Ala Glu Ser Ser Ser Asp Leu Asn Leu Ser Leu Arg Arg Arg
            20                  25                  30

Arg Thr Ala Ser Asn Ser Asp Gly Ala Val Ala Glu Leu Ala Ser Lys
        35                  40                  45

Ile Asp Glu Leu Glu Ser Asp Ala Gly Gly Gln Val Ile Lys Asp
50                  55                  60

Pro Gly Ala Glu Met Asp Ser Gly Thr Leu Lys Ser Asn Gly Lys Asp
65                  70                  75                  80

Cys Gly Thr Val Lys Asp Arg Ile Glu Asn Arg Glu Asn Arg Gly Gly
                85                  90                  95

Ser Asp Val Lys Phe Thr Tyr Arg Pro Ser Val Pro Ala His Arg Ala
            100                 105                 110

Leu Lys Glu Ser Pro Leu Ser Ser Asp Asn Ile Phe Lys Gln Ser His
        115                 120                 125

Ala Gly Leu Phe Asn Leu Cys Ile Val Val Leu Val Ala Val Asn Ser
    130                 135                 140

Arg Leu Ile Ile Glu Asn Ile Met Lys Tyr Gly Trp Leu Ile Lys Thr
145                 150                 155                 160

Gly Phe Trp Phe Ser Ser Arg Ser Leu Arg Asp Trp Pro Leu Leu Met
                165                 170                 175

Cys Cys Leu Thr Leu Pro Ile Phe Ser Leu Ala Ala Tyr Leu Val Glu
                180                 185                 190

Lys Leu Ala Cys Arg Lys Tyr Ile Ser Ala Pro Thr Val Val Phe Leu
            195                 200                 205

His Ile Leu Phe Ser Ser Thr Ala Val Leu Tyr Pro Val Ser Val Ile
        210                 215                 220

Leu Ser Cys Glu Ser Ala Val Leu Ser Gly Val Ala Leu Met Leu Phe
225                 230                 235                 240

Ala Cys Ile Val Trp Leu Lys Leu Val Ser Tyr Ala His Thr Asn Phe
                245                 250                 255

Asp Met Arg Ala Ile Ala Asn Ser Val Asp Lys Gly Asp Ala Leu Ser
            260                 265                 270

Asn Ala Ser Ser Ala Glu Ser Ser His Asp Val Ser Phe Lys Ser Leu
```

```
                 275                 280                 285
Val Tyr Phe Met Val Ala Pro Thr Leu Cys Tyr Gln Pro Ser Tyr Pro
        290                 295                 300

Arg Thr Ala Ser Ile Arg Lys Gly Trp Val Val Arg Gln Phe Val Lys
305                 310                 315                 320

Leu Ile Ile Phe Thr Gly Phe Met Gly Phe Ile Ile Glu Gln Tyr Ile
                325                 330                 335

Asn Pro Ile Val Gln Asn Ser Gln His Pro Leu Lys Gly Asp Leu Leu
        340                 345                 350

Tyr Ala Ile Glu Arg Val Leu Lys Leu Ser Val Pro Asn Leu Tyr Val
            355                 360                 365

Trp Leu Cys Met Phe Tyr Cys Phe Phe His Leu Trp Leu Asn Ile Leu
    370                 375                 380

Ala Glu Leu Leu Arg Phe Gly Asp Arg Glu Phe Tyr Lys Asp Trp Trp
385                 390                 395                 400

Asn Ala Arg Thr Val Glu Glu Tyr Trp Arg Met Trp Asn Met Pro Val
                405                 410                 415

His Lys Trp Met Val Arg His Ile Tyr Phe Pro Cys Leu Arg His Lys
        420                 425                 430

Ile Pro Arg Gly Val Ala Leu Leu Ile Thr Phe Phe Val Ser Ala Val
            435                 440                 445

Phe His Glu Leu Cys Ile Ala Val Pro Cys His Ile Phe Lys Leu Trp
    450                 455                 460

Ala Phe Ile Gly Ile Met Phe Gln Ile Pro Leu Val Gly Ile Thr Asn
465                 470                 475                 480

Tyr Leu Gln Asn Lys Phe Arg Ser Ser Met Val Gly Asn Met Ile Phe
                485                 490                 495

Trp Phe Ile Phe Cys Ile Leu Gly Gln Pro Met Cys Leu Leu Leu Tyr
        500                 505                 510

Tyr His Asp Leu Met Asn Arg Lys Gly Thr Thr Glu Ser Arg
            515                 520                 525

<210> SEQ ID NO 55
<211> LENGTH: 523
<212> TYPE: PRT
<213> ORGANISM: Vernonia galamensis

<400> SEQUENCE: 55

Met Ala Leu Leu Asp Thr Pro Gln Ile Gly Glu Ile Thr Thr Thr Ala
1               5                   10                  15

Thr Thr Thr Ile Arg Arg Arg Thr Thr Val Lys Pro Asp Ala Gly Ile
                20                  25                  30

Gly Asp Gly Leu Phe Asp Ser Ser Ser Ser Lys Thr Asn Ser Ser
            35                  40                  45

Phe Glu Asp Gly Asp Ser Leu Asn Gly Asp Phe Asn Asp Lys Phe Lys
    50                  55                  60

Glu Gln Ile Gly Ala Gly Asp Glu Ser Lys Asp Ser Lys Gly Asn
65                  70                  75                  80

Gly Gln Lys Ile Asp His Gly Gly Val Lys Lys Gly Arg Glu Thr Thr
                85                  90                  95

Val Val His Tyr Ala Tyr Arg Pro Ser Ser Pro Ala His Arg Arg Ile
            100                 105                 110

Lys Glu Ser Pro Leu Ser Ser Asp Ala Ile Phe Lys Gln Ser His Ala
    115                 120                 125
```

```
Gly Leu Phe Asn Leu Cys Ile Val Leu Val Ala Val Asn Gly Arg
            130                 135                 140
Leu Ile Ile Glu Asn Leu Met Lys Tyr Gly Leu Leu Ile Asn Ser Asn
145                 150                 155                 160
Phe Trp Phe Ser Ser Arg Ser Leu Arg Asp Trp Pro Leu Leu Met Cys
                165                 170                 175
Cys Leu Thr Pro Ser Asp Phe Pro Leu Ala Ala Tyr Ile Val Glu Lys
            180                 185                 190
Leu Ala Trp Lys Lys Arg Ile Ser Asp Pro Val Val Ile Thr Leu His
            195                 200                 205
Val Ile Ile Thr Thr Thr Ala Ile Leu Tyr Pro Val Phe Met Ile Leu
210                 215                 220
Arg Phe Asp Ser Val Val Leu Ser Gly Val Ser Leu Met Leu Cys Ala
225                 230                 235                 240
Cys Ile Asn Trp Leu Lys Leu Val Ser Phe Val His Thr Asn Tyr Asp
                245                 250                 255
Met Arg Ser Leu Leu Asn Ser Thr Asp Lys Gly Glu Val Glu Pro Met
            260                 265                 270
Ser Ser Asn Met Asp Tyr Phe Tyr Asp Val Asn Phe Lys Ser Leu Val
            275                 280                 285
Tyr Phe Met Val Ala Pro Thr Leu Cys Tyr Gln Ile Ser Tyr Pro Arg
        290                 295                 300
Thr Ala Phe Ile Arg Lys Gly Trp Val Leu Arg Gln Leu Ile Lys Leu
305                 310                 315                 320
Val Ile Phe Thr Gly Phe Met Gly Phe Ile Ile Glu Gln Tyr Ile Asn
                325                 330                 335
Pro Ile Val Lys Asn Ser Arg His Pro Leu Lys Gly Asp Phe Leu Tyr
            340                 345                 350
Ala Ile Glu Arg Val Leu Lys Leu Ser Val Pro Asn Leu Tyr Val Trp
            355                 360                 365
Leu Cys Met Phe Tyr Cys Phe Phe His Leu Trp Leu Asn Ile Leu Ala
370                 375                 380
Glu Leu Leu Cys Phe Gly Asp Arg Glu Phe Tyr Lys Asp Trp Trp Asn
385                 390                 395                 400
Ala Gln Thr Ile Glu Glu Tyr Trp Arg Leu Trp Asn Met Pro Val His
                405                 410                 415
Lys Trp Ile Val Arg His Leu Tyr Phe Pro Cys Leu Arg Asn Gly Ile
            420                 425                 430
Pro Lys Gly Ala Ala Ile Leu Val Ala Phe Phe Met Ser Ala Val Phe
            435                 440                 445
His Glu Leu Cys Ile Ala Val Pro Cys His Ile Phe Lys Phe Trp Ala
        450                 455                 460
Phe Ile Gly Ile Met Phe Gln Val Pro Leu Val Leu Leu Thr Asn Tyr
465                 470                 475                 480
Leu Gln His Lys Phe Gln Asn Ser Met Val Gly Asn Met Ile Phe Trp
                485                 490                 495
Cys Phe Phe Ser Ile Phe Gly Gln Pro Met Cys Val Leu Leu Tyr Tyr
            500                 505                 510
His Asp Val Met Asn Gln Lys Gly Lys Ser Lys
            515                 520

<210> SEQ ID NO 56
<211> LENGTH: 521
<212> TYPE: PRT
```

<213> ORGANISM: Ricinus communis

<400> SEQUENCE: 56

```
Met Thr Ile Leu Glu Thr Pro Glu Thr Leu Gly Val Ile Ser Ser
1               5                   10                  15

Ala Thr Ser Asp Leu Asn Leu Ser Leu Arg Arg Arg Thr Ser Asn
            20                  25                  30

Asp Ser Asp Gly Ala Leu Ala Asp Leu Ala Ser Lys Phe Asp Asp
        35                  40                  45

Asp Asp Val Arg Ser Glu Asp Ser Ala Glu Asn Ile Ile Glu Asp Pro
    50                  55                  60

Val Ala Ala Val Thr Glu Leu Ala Thr Ala Lys Ser Asn Gly Lys Asp
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
            100                 105                 110

Leu Lys Glu Ser Pro Leu Ser Ser Asp Leu Ile Phe Lys Gln Ser His
        115                 120                 125

Ala Gly Leu Phe Asn Leu Cys Ile Val Val Leu Val Ala Val Asn Ser
    130                 135                 140

Arg Leu Ile Ile Glu Asn Leu Met Lys Tyr Gly Trp Leu Ile Lys Thr
145                 150                 155                 160

Gly Phe Trp Phe Ser Ser Arg Ser Leu Arg Asp Trp Pro Leu Phe Met
                165                 170                 175

Cys Cys Leu Ser Leu Pro Val Phe Pro Leu Ala Ala Tyr Leu Val Glu
            180                 185                 190

Lys Ala Ala Tyr Arg Lys Tyr Ile Ser Pro Pro Ile Val Ile Phe Leu
        195                 200                 205

His Val Ile Ile Thr Ser Ala Ala Val Leu Tyr Pro Ala Ser Val Ile
    210                 215                 220

Leu Ser Cys Glu Ser Ala Phe Leu Ser Gly Val Thr Leu Met Glu Leu
225                 230                 235                 240

Ala Cys Met Val Trp Leu Lys Leu Val Ser Tyr Ala His Thr Asn Tyr
                245                 250                 255

Asp Met Arg Ala Ile Ala Asp Thr Ile His Lys Glu Asp Ala Ser Asn
            260                 265                 270

Ser Ser Ser Thr Glu Tyr Cys His Asp Val Ser Phe Lys Thr Leu Ala
        275                 280                 285

Tyr Phe Met Val Ala Pro Thr Leu Cys Tyr Gln Pro Ser Tyr Pro Arg
    290                 295                 300

Thr Ala Phe Ile Arg Lys Gly Trp Val Phe Arg Gln Phe Val Lys Leu
305                 310                 315                 320

Ile Ile Phe Thr Gly Phe Met Gly Phe Ile Ile Glu Gln Tyr Ile Asn
                325                 330                 335

Pro Ile Val Gln Asn Ser Gln His Pro Leu Lys Gly Asp Leu Leu Tyr
            340                 345                 350

Ala Ile Glu Arg Val Leu Lys Leu Ser Val Pro Asn Leu Tyr Val Trp
        355                 360                 365

Leu Cys Leu Phe Tyr Cys Phe Phe His Leu Trp Leu Asn Ile Val Ala
    370                 375                 380

Glu Leu Leu Arg Phe Gly Asp Arg Glu Phe Tyr Lys Asp Trp Trp Asn
385                 390                 395                 400
```

```
Ala Lys Thr Val Glu Glu Tyr Trp Arg Met Trp Asn Met Pro Val His
            405                 410                 415

Lys Trp Met Val Arg His Ile Tyr Phe Pro Cys Leu Arg Lys Ile
        420                 425                 430

Pro Arg Gly Val Ala Ile Val Ile Ala Phe Phe Val Ser Ala Val Phe
            435                 440                 445

His Glu Leu Cys Ile Ala Val Pro Cys His Met Phe Lys Leu Trp Ala
    450                 455                 460

Phe Phe Gly Ile Met Phe Gln Ile Pro Leu Val Val Ile Thr Asn Tyr
465                 470                 475                 480

Phe Gln Arg Lys Phe Arg Ser Ser Met Val Gly Asn Met Ile Phe Trp
            485                 490                 495

Phe Phe Phe Cys Ile Leu Gly Gln Pro Met Cys Val Leu Leu Tyr Tyr
                500                 505                 510

His Asp Leu Met Asn Arg Asp Gly Asn
            515                 520

<210> SEQ ID NO 57
<211> LENGTH: 446
<212> TYPE: PRT
<213> ORGANISM: Populus trichocarpa

<400> SEQUENCE: 57

Met Met Glu Ser Glu Asp Leu Lys Ser Asn Gly Lys Glu Cys Asp Lys
1               5                   10                  15

Val Thr Asn Glu Asn Arg Ser Asp Ile Lys Phe Asn Tyr Arg Pro Ser
            20                  25                  30

Met Pro Ala His Arg Gly Val Arg Glu Ser Pro Leu Ser Ser Asp Ala
        35                  40                  45

Ile Phe Lys Gln Ser His Ala Gly Leu Phe Asn Leu Cys Ile Val Val
    50                  55                  60

Leu Val Ala Ile Asn Ser Arg Leu Ile Ile Glu Asn Ile Ile Lys Tyr
65                  70                  75                  80

Gly Trp Leu Ile Asn Gly Gly Phe Trp Phe Ser Ser Lys Ser Leu Arg
                85                  90                  95

Asp Trp Pro Leu Phe Met Cys Cys Leu Ser Leu Pro Ala Phe Pro Phe
            100                 105                 110

Ala Ala Tyr Leu Val Glu Lys Leu Ala Tyr Gln Asn Tyr Leu Pro Gln
        115                 120                 125

Leu Val Val Phe Leu His Thr Ile Thr Thr Gly Ser Leu Leu
    130                 135                 140

Tyr Pro Val Leu Val Ile Leu Arg Cys Asp Ser Ala Phe Leu Ser Gly
145                 150                 155                 160

Val Thr Leu Met Leu Phe Ser Cys Ile Val Trp Leu Lys Leu Val Ser
                165                 170                 175

Tyr Ala His Thr Asn Ser Asp Leu Arg Ala Ile Ala Lys Ser Ile Asp
            180                 185                 190

Arg Glu Asp Val Pro Ser Ile Ser Pro Tyr Val Gly Asn Pro Tyr Asp
        195                 200                 205

Thr Tyr Phe Lys Ser Leu Val Tyr Phe Met Val Ala Pro Thr Leu Cys
    210                 215                 220

Tyr Gln Ser Ser Tyr Pro Arg Thr Glu Ser Val Arg Lys Gly Trp Val
225                 230                 235                 240

Val Gln Gln Phe Val Lys Leu Ile Ile Phe Thr Gly Phe Met Gly Phe
                245                 250                 255
```

```
Ile Ile Glu Gln Tyr Ile Asn Pro Ile Val Lys Asn Ser Gln His Pro
            260                 265                 270

Phe Lys Gly Asn Leu Leu Tyr Ala Ile Glu Arg Val Leu Lys Leu Ser
            275                 280                 285

Val Pro Asn Leu Tyr Val Trp Leu Cys Met Phe Tyr Cys Phe Phe His
            290                 295                 300

Leu Trp Leu Asn Ile Leu Ala Glu Leu Leu Cys Phe Gly Asp Arg Glu
305                 310                 315                 320

Phe Tyr Lys Asp Trp Trp Asn Ala Arg Thr Val Glu Tyr Trp Arg
                325                 330                 335

Met Trp Asn Met Pro Val His Lys Trp Met Val Arg His Ile Tyr Phe
            340                 345                 350

Pro Cys Leu Arg Asn Lys Ile Pro Lys Gly Leu Ala Ile Leu Ile Ala
            355                 360                 365

Phe Leu Val Ser Ala Val Phe His Glu Leu Cys Ile Ala Val Pro Cys
            370                 375                 380

His Val Phe Lys Leu Trp Ala Phe Ile Gly Ile Met Leu Gln Val Pro
385                 390                 395                 400

Leu Val Val Ile Thr Lys Phe Leu Gln Asn Lys Phe Arg Ser Ser Met
                405                 410                 415

Val Gly Asn Met Ile Phe Trp Leu Phe Phe Ser Ile Leu Gly Gln Pro
            420                 425                 430

Met Cys Val Leu Leu Tyr Tyr His Asp Leu Met Asn Arg Lys
            435                 440                 445

<210> SEQ ID NO 58
<211> LENGTH: 493
<212> TYPE: PRT
<213> ORGANISM: Populus trichocarpa

<400> SEQUENCE: 58

Met Ala Glu Ser Glu Ser Pro Glu Asn Arg Ile Ala Ala Met Glu Ser
1               5                   10                  15

Thr Ser Ser Ser Thr Ser Asp Leu Asn Phe Ser Ile Arg Arg Arg Ser
            20                  25                  30

Thr Val Met Asp Ser Ala Ser Thr Glu Met Met Gly Ser Glu Gly Leu
        35                  40                  45

Lys Ser Ser Gly Lys Ala Cys Asp Lys Val Lys Ile Glu Lys Gln Ser
    50                  55                  60

Asp Met Lys Phe Asn Tyr Arg Pro Ser Met Pro Ala His Ser Gly Val
65                  70                  75                  80

Arg Glu Ser Pro Leu Ser Ser Asp Ala Ile Phe Lys Gln Ser His Ala
                85                  90                  95

Gly Leu Phe Asn Leu Cys Ile Val Val Leu Val Ala Val Asn Ser Arg
            100                 105                 110

Leu Ile Ile Glu Asn Leu Ile Lys Tyr Gly Trp Leu Ile Asn Ser Gly
            115                 120                 125

Phe Trp Phe Ser Ser Lys Ser Leu Arg Asp Trp Pro Leu Phe Met Cys
        130                 135                 140

Cys Leu Ser Leu Pro Ala Phe Pro Leu Ala Ala Tyr Leu Val Glu Lys
145                 150                 155                 160

Leu Ala Tyr Arg Asn Cys Ile Ser Glu Leu Val Val Val Phe Leu His
                165                 170                 175

Ile Ile Ile Thr Thr Ala Ser Leu Leu Tyr Pro Val Leu Val Ile Leu
```

```
            180                 185                 190
Arg Cys Asp Ser Ala Leu Leu Ser Gly Gly Thr Leu Met Leu Phe Ala
            195                 200                 205

Cys Ile Val Trp Leu Lys Leu Val Ser Phe Ala His Thr Ser Ser Asp
        210                 215                 220

Met Arg Ala Ile Ala Lys Ser Ile Asp Lys Glu Asn Thr Pro Ser Ile
225                 230                 235                 240

Ser Ser Lys Ala Asp Asn Ser Tyr Asp Ala Asn Phe Lys Ser Leu Val
                245                 250                 255

Tyr Phe Met Val Ala Pro Thr Leu Cys Tyr Gln Ser Ser Tyr Pro Arg
            260                 265                 270

Ser Ala Ser Val Arg Lys Gly Trp Val Val Arg Gln Phe Val Lys Leu
        275                 280                 285

Ile Ile Phe Thr Gly Phe Met Gly Phe Ile Ile Glu Gln Tyr Ile Asn
        290                 295                 300

Pro Ile Val Gln Asn Ser Gln His Pro Leu Lys Gly Asn Leu Leu Tyr
305                 310                 315                 320

Ala Ile Glu Arg Val Leu Lys Leu Ser Val Pro Asn Leu Tyr Val Trp
                325                 330                 335

Leu Cys Met Phe Tyr Cys Phe Phe His Leu Trp Leu Asn Ile Leu Ala
            340                 345                 350

Glu Leu Leu Arg Phe Gly Asp Arg Glu Phe Tyr Lys Asp Trp Trp Asn
            355                 360                 365

Ala Arg Thr Val Glu Glu Tyr Trp Arg Met Trp Asn Met Pro Val His
        370                 375                 380

Lys Trp Met Val Arg His Ile Tyr Phe Pro Cys Leu Arg Asn Lys Ile
385                 390                 395                 400

Pro Lys Trp Ala Ala Leu Leu Ile Ala Phe Phe Val Ser Ala Val Phe
                405                 410                 415

His Glu Leu Cys Ile Ala Val Pro Cys His Met Phe Lys Leu Trp Ala
            420                 425                 430

Phe Ile Gly Ile Met Phe Gln Val Pro Leu Val Val Ile Thr Lys Phe
            435                 440                 445

Leu Gln Asn Lys Phe Lys Ser Ser Met Val Gly Asn Met Ile Phe Trp
        450                 455                 460

Leu Phe Phe Ser Ile Leu Gly Gln Pro Met Cys Val Leu Leu Tyr Tyr
465                 470                 475                 480

His Asp Leu Met Asn Arg Lys Gly Lys Thr Glu Arg Arg
                485                 490

<210> SEQ ID NO 59
<211> LENGTH: 554
<212> TYPE: PRT
<213> ORGANISM: Artificial Sequence
<220> FEATURE:
<223> OTHER INFORMATION: A. thaliana

<400> SEQUENCE: 59

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
```

```
                50                  55                  60
    Ser Val Val Asn Asp Asp Ala Gln Gly Thr Ala Asn Leu Ala Gly Asp
    65                  70                  75                  80

Asn Asn Gly Gly Gly Asp Asn Gly Gly Arg Gly Gly Gly Glu
                    85                  90                  95

Gly Arg Gly Asn Ala Asp Ala Thr Phe Thr Tyr Arg Pro Ser Val Pro
                    100                 105                 110

Ala His Arg Arg Ala Arg Glu Ser Pro Leu Ser Ser Asp Ala Ile Phe
                    115                 120                 125

Lys Gln Ser His Ala Gly Leu Phe Asn Leu Cys Val Val Leu Ile
        130                 135                 140

Ala Val Asn Ser Arg Leu Ile Ile Glu Asn Leu Met Lys Tyr Gly Trp
    145                 150                 155                 160

Leu Ile Arg Thr Asp Phe Trp Phe Ser Ser Arg Ser Leu Arg Asp Trp
                    165                 170                 175

Pro Leu Phe Met Cys Cys Ile Ser Leu Ser Ile Phe Pro Leu Ala Ala
                    180                 185                 190

Phe Thr Val Glu Lys Leu Val Leu Gln Lys Tyr Ile Ser Glu Pro Val
                    195                 200                 205

Val Ile Phe Leu His Ile Ile Ile Thr Met Thr Glu Val Leu Tyr Pro
        210                 215                 220

Val Tyr Val Thr Leu Arg Cys Asp Ser Ala Phe Leu Ser Gly Val Thr
    225                 230                 235                 240

Leu Met Leu Leu Thr Cys Ile Val Trp Leu Lys Leu Val Ser Tyr Ala
                    245                 250                 255

His Thr Ser Tyr Asp Ile Arg Ser Leu Ala Asn Ala Ala Asp Lys Ala
                    260                 265                 270

Asn Pro Glu Val Ser Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
    305                 310                 315                 320

Phe Thr Gly Phe Met Gly Phe Ile Ile Glu Gln Tyr Ile Asn Pro Ile
                    325                 330                 335

Val Arg Asn Ser Lys His Pro Leu Lys Gly Asp Leu Leu Tyr Ala Ile
                    340                 345                 350

Glu Arg Val Leu Lys Leu Ser Val Pro Asn Leu Tyr Val Trp Leu Cys
                    355                 360                 365

Met Phe Tyr Cys Phe Phe His Leu Trp Leu Asn Ile Leu Ala Glu Leu
        370                 375                 380

Leu Cys Phe Gly Asp Arg Glu Phe Tyr Lys Asp Trp Trp Asn Ala Lys
    385                 390                 395                 400

Ser Val Gly Asp Tyr Trp Arg Met Trp Asn Met Pro Val His Lys Trp
                    405                 410                 415

Met Val Arg His Ile Tyr Phe Pro Cys Leu Arg Ser Lys Ile Pro Lys
                    420                 425                 430

Thr Leu Ala Ile Ile Ile Ala Phe Leu Val Ser Ala Val Phe His Glu
                    435                 440                 445

Leu Cys Ile Ala Val Pro Cys Arg Leu Phe Lys Leu Trp Ala Phe Leu
        450                 455                 460

Gly Ile Met Phe Gln Val Pro Leu Val Phe Ile Thr Asn Tyr Leu Gln
    465                 470                 475                 480
```

```
Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
                500                 505                 510

Met Asn Arg Lys Gly Ser Met Ser Ala Lys Gly Glu Leu Arg Gly His
            515                 520                 525

Pro Phe Glu Gly Lys Pro Ile Pro Asn Pro Leu Leu Gly Leu Asp Ser
        530                 535                 540

Thr Arg Thr Gly His His His His His His
545             550
```

<210> SEQ ID NO 60
<211> LENGTH: 564
<212> TYPE: PRT
<213> ORGANISM: Artificial Sequence
<220> FEATURE:
<223> OTHER INFORMATION: A. thaliana

<400> SEQUENCE: 60

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Arg Gln Ser His Ala Gly Leu Leu Asn Leu Cys Ile Val Val Leu Val
    130                 135                 140

Ala Val Asn Ser Arg Leu Ile Ile Glu Asn Leu Met Lys Tyr Gly Leu
145                 150                 155                 160

Leu Ile Arg Ala Gly Phe Trp Phe Ser Gly Thr Ser Leu Ala Asp Trp
                165                 170                 175

Pro Leu Leu Met Cys Cys Leu Thr Leu Pro Thr Phe Pro Leu Ala Ala
            180                 185                 190

Leu Met Val Glu Lys Leu Ala Gln Arg Lys Leu Ile Ser Lys His Val
        195                 200                 205

Val Ile Leu Leu His Ile Val Ile Thr Thr Ser Val Leu Val Tyr Pro
    210                 215                 220

Val Val Val Ile Leu Lys Cys Asp Ser Ala Val Leu Ser Gly Phe Val
225                 230                 235                 240

Leu Met Phe Leu Ala Ser Ile Ile Trp Leu Lys Leu Val Ser Phe Ala
                245                 250                 255

His Thr Asn Tyr Asp Ile Arg Met Leu Ser Lys Ser Ile Glu Lys Gly
            260                 265                 270

Val Thr His Asp Ile Ser Ile Asp Pro Glu Asn Ile Lys Trp Pro Thr
        275                 280                 285
```

```
Phe Lys Arg Leu Ser Tyr Phe Met Leu Ala Pro Thr Leu Cys Tyr Gln
            290                 295                 300

Pro Ser Tyr Pro Arg Thr Thr Tyr Ile Arg Lys Gly Trp Val Val Arg
305                 310                 315                 320

Gln Leu Ile Lys Cys Leu Val Phe Thr Gly Leu Met Gly Phe Ile Ile
                325                 330                 335

Glu Gln Tyr Ile Asn Pro Ile Val Lys Asn Ser Lys His Pro Leu Lys
            340                 345                 350

Gly Asn Phe Leu Asn Ala Ile Glu Arg Val Leu Lys Leu Ser Val Pro
        355                 360                 365

Thr Leu Tyr Val Trp Leu Cys Met Phe Tyr Cys Phe Phe His Leu Trp
    370                 375                 380

Leu Asn Ile Leu Ala Glu Leu Leu Cys Phe Gly Asp Arg Glu Phe Tyr
385                 390                 395                 400

Lys Asp Trp Trp Asn Ala Lys Thr Val Glu Glu Tyr Trp Arg Met Trp
                405                 410                 415

Asn Met Pro Val His Lys Trp Val Ile Arg His Ile Tyr Phe Pro Cys
            420                 425                 430

Ile Arg Asn Gly Phe Ser Lys Gly Val Ala Ile Leu Ile Ser Phe Leu
        435                 440                 445

Val Ser Ala Ala Phe His Glu Leu Cys Val Ala Val Pro Cys His Ile
    450                 455                 460

Phe Lys Phe Trp Ala Phe Ile Gly Ile Met Phe Gln Ile Pro Leu Val
465                 470                 475                 480

Phe Leu Thr Lys Tyr Leu Gln Asp Lys Phe Asn Asn Thr Met Val Gly
                485                 490                 495

Asn Met Ile Phe Trp Phe Phe Phe Ser Ile Leu Gly Gln Pro Met Cys
            500                 505                 510

Val Leu Leu Tyr Tyr His Asp Val Met Asn Arg Gln Gln Ala Gln Thr
        515                 520                 525

Asn Arg Ala Lys Gly Glu Leu Arg Gly His Pro Phe Glu Gly Lys Pro
    530                 535                 540

Ile Pro Asn Pro Leu Leu Gly Leu Asp Ser Thr Arg Thr Gly His His
545                 550                 555                 560

His His His His

<210> SEQ ID NO 61
<211> LENGTH: 562
<212> TYPE: PRT
<213> ORGANISM: Artificial Sequence
<220> FEATURE:
<223> OTHER INFORMATION: A. thaliana

<400> SEQUENCE: 61

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
                20                  25                  30

Ser Asp Ser Ser Asn Gly Leu Leu Leu Ser Gly Ser Asp Asn Asn Ser
            35                  40                  45

Pro Ser Asp Asp Val Gly Ala Pro Ala Asp Val Arg Asp Arg Ile Asp
        50                  55                  60

Ser Val Val Asn Asp Asp Ala Gln Gly Thr Ala Asn Leu Ala Gly Asp
65                  70                  75                  80
```

-continued

```
Asn Asn Gly Gly Gly Asp Asn Asn Gly Gly Gly Arg Gly Gly Glu
                85                  90                  95
Gly Arg Gly Asn Ala Asp Ala Thr Phe Thr Tyr Arg Pro Ser Val Pro
            100                 105                 110
Ala His Arg Arg Ala Arg Glu Ser Pro Leu Ser Ser Asp Ala Ile Phe
            115                 120                 125
Lys Gln Ser His Ala Gly Leu Phe Asn Leu Cys Ile Val Val Leu Val
            130                 135                 140
Ala Val Asn Ser Arg Leu Ile Ile Glu Asn Leu Met Lys Tyr Gly Leu
145                 150                 155                 160
Leu Ile Arg Ala Gly Phe Trp Phe Asn Asp Lys Ser Leu Arg Asp Trp
                165                 170                 175
Pro Leu Leu Met Cys Cys Leu Ser Leu Pro Ala Phe Pro Leu Gly Ala
                180                 185                 190
Phe Ala Val Glu Lys Leu Ala Phe Asn Asn Val Ile Thr Asp Ala Val
                195                 200                 205
Ala Thr Cys Leu His Ile Phe Leu Ser Thr Thr Glu Ile Val Tyr Pro
            210                 215                 220
Val Leu Val Ile Leu Lys Cys Asp Ser Ala Val Leu Ser Gly Phe Leu
225                 230                 235                 240
Leu Ile Phe Ile Ala Cys Ile Val Trp Leu Lys Leu Val Ser Phe Ala
                245                 250                 255
His Thr Asn His Asp Ile Arg Gln Leu Thr Met Gly Gly Lys Lys Val
                260                 265                 270
Asp Asn Glu Leu Ser Thr Val Asp Met Asp Asn Leu Gln Pro Pro Thr
            275                 280                 285
Leu Gly Asn Leu Ile Tyr Phe Met Met Ala Pro Thr Leu Cys Tyr Gln
            290                 295                 300
Pro Ser Tyr Pro Arg Thr Ser Cys Val Arg Lys Gly Trp Leu Ile Arg
305                 310                 315                 320
Gln Ile Ile Leu Tyr Leu Ile Phe Thr Gly Leu Gln Gly Phe Ile Ile
                325                 330                 335
Glu Gln Tyr Ile Asn Pro Ile Val Val Asn Ser Gln His Pro Leu Lys
            340                 345                 350
Gly Gly Leu Leu Asn Ala Val Glu Thr Val Leu Lys Leu Ser Leu Pro
            355                 360                 365
Asn Val Tyr Leu Trp Leu Cys Met Phe Tyr Ala Phe Phe His Leu Trp
            370                 375                 380
Leu Ser Ile Leu Ala Glu Ile Leu Arg Phe Gly Asp Arg Glu Phe Tyr
385                 390                 395                 400
Lys Asp Trp Trp Asn Ala Lys Thr Ile Asp Glu Tyr Trp Arg Lys Trp
                405                 410                 415
Asn Met Pro Val His Lys Trp Val Val Arg His Ile Tyr Phe Pro Cys
            420                 425                 430
Met Arg Asn Gly Ile Ser Lys Glu Val Ala Val Leu Ile Ser Phe Leu
            435                 440                 445
Val Ser Ala Val Leu His Glu Ile Cys Val Ala Val Pro Cys Arg Ile
            450                 455                 460
Leu Lys Phe Trp Ala Phe Leu Gly Ile Met Leu Gln Ile Pro Leu Ile
465                 470                 475                 480
Val Leu Thr Ala Tyr Leu Lys Ser Lys Phe Arg Asp Thr Met Val Gly
                485                 490                 495
Asn Met Ile Phe Trp Phe Phe Phe Cys Ile Tyr Gly Gln Pro Met Cys
```

```
                500               505               510
Leu Leu Leu Tyr Tyr His Asp Val Met Asn Arg Ile Glu Lys Ala Arg
            515               520               525

Ala Lys Gly Glu Leu Arg Gly His Pro Phe Glu Gly Lys Pro Ile Pro
        530               535               540

Asn Pro Leu Leu Gly Leu Asp Ser Thr Arg Thr Gly His His His His
545               550               555               560

His His

<210> SEQ ID NO 62
<211> LENGTH: 563
<212> TYPE: PRT
<213> ORGANISM: Artificial Sequence
<220> FEATURE:
<223> OTHER INFORMATION: A. thaliana

<400> SEQUENCE: 62

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Arg Gln Ser His Ala Gly Leu Leu Asn Leu Cys Ile Val Val Leu Ile
130                 135                 140

Ala Val Asn Ser Arg Leu Ile Ile Glu Asn Leu Met Lys Tyr Gly Leu
145                 150                 155                 160

Leu Ile Arg Ala Gly Phe Trp Phe Ser Ala Arg Ser Leu Gly Asp Trp
                165                 170                 175

Pro Leu Leu Met Cys Cys Leu Thr Leu Pro Val Phe Pro Leu Val Ala
            180                 185                 190

Leu Met Ala Glu Lys Leu Ile Thr Arg Lys Leu Ile Gly Glu His Val
        195                 200                 205

Val Ile Leu Leu His Ile Ile Ile Thr Thr Ser Ala Ile Val Tyr Pro
210                 215                 220

Val Val Val Thr Leu Lys Cys Asp Ser Ala Val Leu Ser Gly Phe Val
225                 230                 235                 240

Leu Met Phe Leu Ala Ser Ile Met Trp Met Lys Leu Val Ser Tyr Ala
                245                 250                 255

His Thr Asn Tyr Asp Ile Arg Val Leu Ser Lys Ser Thr Glu Lys Gly
            260                 265                 270

Ala Ala Tyr Gly Asn Tyr Val Asp Pro Glu Asn Met Lys Asp Pro Thr
        275                 280                 285

Phe Lys Ser Leu Val Tyr Phe Met Leu Ala Pro Thr Leu Cys Tyr Gln
290                 295                 300
```

```
Pro Thr Tyr Pro Gln Thr Thr Cys Ile Arg Lys Gly Trp Val Thr Gln
305                 310                 315                 320

Gln Leu Ile Lys Cys Val Val Phe Thr Gly Leu Met Gly Phe Ile Ile
            325                 330                 335

Glu Gln Tyr Ile Asn Pro Ile Val Lys Asn Ser Lys His Pro Leu Lys
            340                 345                 350

Gly Asn Phe Leu Asn Ala Ile Glu Arg Val Leu Lys Leu Ser Val Pro
            355                 360                 365

Thr Leu Tyr Val Trp Leu Cys Met Phe Tyr Cys Phe Phe His Leu Trp
    370                 375                 380

Leu Asn Ile Val Ala Glu Leu Leu Cys Phe Gly Asp Arg Glu Phe Tyr
385                 390                 395                 400

Lys Asp Trp Trp Asn Ala Lys Thr Val Glu Glu Tyr Trp Arg Met Trp
                405                 410                 415

Asn Met Pro Val His Lys Trp Ile Ile Arg His Ile Tyr Phe Pro Cys
            420                 425                 430

Ile Arg Lys Gly Phe Ser Arg Gly Val Ala Ile Leu Ile Ser Phe Leu
            435                 440                 445

Val Ser Ala Val Phe His Glu Ile Cys Ile Ala Val Pro Cys His Ile
    450                 455                 460

Phe Lys Phe Trp Ala Phe Ser Gly Ile Met Phe Gln Ile Pro Leu Val
465                 470                 475                 480

Phe Leu Thr Arg Tyr Leu His Ala Thr Phe Lys His Val Met Val Gly
                485                 490                 495

Asn Met Ile Phe Trp Phe Phe Ser Ile Val Gly Gln Pro Met Cys
            500                 505                 510

Val Leu Leu Tyr Tyr His Asp Val Met Asn Arg Gln Ala Gln Ala Ser
            515                 520                 525

Arg Ala Lys Gly Glu Leu Arg Gly His Pro Phe Glu Gly Lys Pro Ile
    530                 535                 540

Pro Asn Pro Leu Leu Gly Leu Asp Ser Thr Arg Thr Gly His His His
545                 550                 555                 560

His His His

<210> SEQ ID NO 63
<211> LENGTH: 562
<212> TYPE: PRT
<213> ORGANISM: Artificial Sequence
<220> FEATURE:
<223> OTHER INFORMATION: A. thaliana

<400> SEQUENCE: 63

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Glu
            85                  90                  95
```

```
Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Ile Val Val Leu Val
    130                 135                 140

Ala Val Asn Ser Arg Leu Ile Ile Glu Asn Leu Met Lys Tyr Gly Leu
145                 150                 155                 160

Leu Ile Arg Ser Gly Phe Trp Phe Asn Ala Thr Ser Leu Arg Asp Trp
                165                 170                 175

Pro Leu Leu Met Cys Cys Leu Ser Leu Pro Ile Phe Pro Leu Gly Ala
            180                 185                 190

Phe Ala Val Glu Lys Leu Ala Phe Asn Asn Leu Ile Ser Asp Pro Ala
        195                 200                 205

Thr Thr Cys Phe His Ile Leu Phe Thr Thr Phe Glu Ile Val Tyr Pro
210                 215                 220

Val Leu Val Ile Leu Lys Cys Asp Ser Ala Val Leu Ser Gly Phe Val
225                 230                 235                 240

Leu Met Phe Ile Ala Cys Ile Val Trp Leu Lys Leu Val Ser Phe Ala
                245                 250                 255

His Thr Asn His Asp Ile Arg Lys Leu Ile Thr Ser Gly Lys Lys Val
            260                 265                 270

Asp Asn Glu Leu Thr Ala Ala Gly Ile Asp Asn Leu Gln Ala Pro Thr
        275                 280                 285

Leu Gly Ser Leu Thr Tyr Phe Met Met Ala Pro Thr Leu Cys Tyr Gln
290                 295                 300

Pro Ser Tyr Pro Arg Thr Pro Tyr Val Arg Lys Gly Trp Leu Val Arg
305                 310                 315                 320

Gln Val Ile Leu Tyr Leu Ile Phe Thr Gly Leu Gln Gly Phe Ile Ile
                325                 330                 335

Glu Gln Tyr Ile Asn Pro Ile Val Val Asn Ser Gln His Pro Leu Met
            340                 345                 350

Gly Gly Leu Leu Asn Ala Val Glu Thr Val Leu Lys Leu Ser Leu Pro
        355                 360                 365

Asn Val Tyr Leu Trp Leu Cys Met Phe Tyr Cys Leu Phe His Leu Trp
370                 375                 380

Leu Asn Ile Leu Ala Glu Ile Leu Arg Phe Gly Asp Arg Glu Phe Tyr
385                 390                 395                 400

Lys Asp Trp Trp Asn Ala Lys Thr Ile Asp Glu Tyr Trp Arg Lys Trp
                405                 410                 415

Asn Met Pro Val His Lys Trp Ile Val Arg His Ile Tyr Phe Pro Cys
            420                 425                 430

Met Arg Asn Gly Ile Ser Lys Glu Val Ala Val Phe Ile Ser Phe Phe
        435                 440                 445

Val Ser Ala Val Leu His Glu Leu Cys Val Ala Val Pro Cys His Ile
450                 455                 460

Leu Lys Phe Trp Ala Phe Leu Gly Ile Met Leu Gln Ile Pro Leu Ile
465                 470                 475                 480

Ile Leu Thr Ser Tyr Leu Lys Asn Lys Phe Ser Asp Thr Met Val Gly
                485                 490                 495

Asn Met Ile Phe Trp Phe Phe Phe Cys Ile Tyr Gly Gln Pro Met Cys
            500                 505                 510

Val Leu Leu Tyr Tyr His Asp Val Met Asn Arg Thr Glu Lys Ala Lys
```

```
              515                 520                 525
Ala Lys Gly Glu Leu Arg Gly His Pro Phe Glu Gly Lys Pro Ile Pro
        530                 535                 540

Asn Pro Leu Leu Gly Leu Asp Ser Thr Arg Thr Gly His His His His
545                 550                 555                 560

His His
```

<210> SEQ ID NO 64
<211> LENGTH: 560
<212> TYPE: PRT
<213> ORGANISM: Artificial Sequence
<220> FEATURE:
<223> OTHER INFORMATION: A. thaliana

<400> SEQUENCE: 64

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Ile Val Val Leu Ile
    130                 135                 140

Ala Val Asn Ser Arg Leu Ile Ile Glu Asn Leu Met Lys Tyr Gly Trp
145                 150                 155                 160

Leu Ile Asp Thr Gly Phe Trp Phe Ser Ser Arg Ser Leu Gly Asp Trp
                165                 170                 175

Ser Ile Phe Met Cys Cys Leu Thr Leu Pro Ile Phe Pro Leu Ala Ala
            180                 185                 190

Phe Ile Val Glu Lys Leu Val Gln Arg Asn His Ile Ser Glu Leu Val
        195                 200                 205

Ala Val Leu Leu His Val Ile Val Ser Thr Ala Ala Val Leu Tyr Pro
    210                 215                 220

Val Ile Val Ile Leu Thr Cys Asp Ser Val Tyr Met Ser Gly Val Val
225                 230                 235                 240

Leu Met Leu Phe Gly Cys Ile Met Trp Leu Lys Leu Val Ser Tyr Ala
                245                 250                 255

His Thr Ser Ser Asp Ile Arg Thr Leu Ala Lys Ser Gly Tyr Lys Gly
            260                 265                 270

Asp Ala His Pro Asn Ser Thr Ile Val Ser Cys Ser Tyr Asp Val Ser
        275                 280                 285

Leu Lys Ser Leu Ala Tyr Phe Met Val Ala Pro Thr Leu Cys Tyr Gln
    290                 295                 300

Pro Ser Tyr Pro Arg Ser Ser Cys Ile Arg Lys Gly Trp Val Val Arg
305                 310                 315                 320
```

```
Gln Phe Val Lys Leu Ile Val Phe Ile Gly Leu Met Gly Phe Ile Ile
                325                 330                 335

Glu Gln Tyr Ile Asn Pro Ile Val Arg Asn Ser Lys His Pro Leu Lys
            340                 345                 350

Gly Asp Phe Leu Tyr Ala Ile Glu Arg Val Leu Lys Leu Ser Val Pro
        355                 360                 365

Asn Leu Tyr Val Trp Leu Cys Met Phe Tyr Ser Phe Phe His Leu Trp
    370                 375                 380

Leu Asn Ile Leu Ala Glu Leu Leu Arg Phe Gly Asp Arg Glu Phe Tyr
385                 390                 395                 400

Lys Asp Trp Trp Asn Ala Lys Thr Val Ala Glu Tyr Trp Lys Met Trp
                405                 410                 415

Asn Met Pro Val His Arg Trp Met Val Arg His Leu Tyr Phe Pro Cys
            420                 425                 430

Leu Arg Asn Gly Ile Pro Lys Glu Gly Ala Ile Ile Ile Ala Phe Leu
        435                 440                 445

Val Ser Gly Ala Phe His Glu Leu Cys Ile Ala Val Pro Cys His Val
    450                 455                 460

Phe Lys Leu Trp Ala Phe Ile Gly Ile Met Phe Gln Val Pro Leu Val
465                 470                 475                 480

Leu Ile Thr Asn Tyr Leu Gln Glu Lys Phe Ser Asn Ser Met Val Gly
                485                 490                 495

Asn Met Ile Phe Trp Phe Ile Phe Cys Ile Leu Gly Gln Pro Met Cys
            500                 505                 510

Val Leu Leu Tyr Tyr His Asp Leu Ile Asn Leu Lys Glu Lys Ala Lys
        515                 520                 525

Gly Glu Leu Arg Gly His Pro Phe Glu Gly Lys Pro Ile Pro Asn Pro
    530                 535                 540

Leu Leu Gly Leu Asp Ser Thr Arg Thr Gly His His His His His His
545                 550                 555                 560

<210> SEQ ID NO 65
<211> LENGTH: 511
<212> TYPE: PRT
<213> ORGANISM: Artificial Sequence
<220> FEATURE:
<223> OTHER INFORMATION: O. sativa-S

<400> SEQUENCE: 65

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
        115                 120                 125
```

-continued

```
Cys Leu Thr Leu Pro Thr Phe Pro Leu Ala Ala Leu Met Val Glu Lys
            130                 135                 140
Leu Ala Gln Arg Lys Leu Ile Ser Lys His Val Val Ile Leu Leu His
145                 150                 155                 160
Ile Val Ile Thr Thr Ser Val Leu Val Tyr Pro Val Val Ile Leu
                    165                 170                 175
Lys Cys Asp Ser Ala Val Leu Ser Gly Phe Val Leu Met Phe Leu Ala
                180                 185                 190
Ser Ile Ile Trp Leu Lys Leu Val Ser Phe Ala His Thr Asn Tyr Asp
            195                 200                 205
Ile Arg Met Leu Ser Lys Ser Ile Glu Lys Gly Val Thr His Asp Ile
210                 215                 220
Ser Ile Asp Pro Glu Asn Ile Lys Trp Pro Thr Phe Lys Arg Leu Ser
225                 230                 235                 240
Tyr Phe Met Leu Ala Pro Thr Leu Cys Tyr Gln Pro Ser Tyr Pro Arg
                    245                 250                 255
Thr Thr Tyr Ile Arg Lys Gly Trp Val Val Arg Gln Leu Ile Lys Cys
                260                 265                 270
Leu Val Phe Thr Gly Leu Met Gly Phe Ile Ile Glu Gln Tyr Ile Asn
            275                 280                 285
Pro Ile Val Lys Asn Ser Lys His Pro Leu Lys Gly Asn Phe Leu Asn
290                 295                 300
Ala Ile Glu Arg Val Leu Lys Leu Ser Val Pro Thr Leu Tyr Val Trp
305                 310                 315                 320
Leu Cys Met Phe Tyr Cys Phe His Leu Trp Leu Asn Ile Leu Ala
                    325                 330                 335
Glu Leu Leu Cys Phe Gly Asp Arg Glu Phe Tyr Lys Asp Trp Trp Asn
                340                 345                 350
Ala Lys Thr Val Glu Glu Tyr Trp Arg Met Trp Asn Met Pro Val His
            355                 360                 365
Lys Trp Val Ile Arg His Ile Tyr Phe Pro Cys Ile Arg Asn Gly Phe
370                 375                 380
Ser Lys Gly Val Ala Ile Leu Ile Ser Phe Leu Val Ser Ala Ala Phe
385                 390                 395                 400
His Glu Leu Cys Val Ala Val Pro Cys His Ile Phe Lys Phe Trp Ala
                    405                 410                 415
Phe Ile Gly Ile Met Phe Gln Ile Pro Leu Val Phe Leu Thr Lys Tyr
                420                 425                 430
Leu Gln Asp Lys Phe Asn Asn Thr Met Val Gly Asn Met Ile Phe Trp
            435                 440                 445
Phe Phe Phe Ser Ile Leu Gly Gln Pro Met Cys Val Leu Leu Tyr Tyr
450                 455                 460
His Asp Val Met Asn Arg Gln Gln Ala Gln Thr Asn Arg Ala Lys Gly
465                 470                 475                 480
Glu Leu Arg Gly His Pro Phe Glu Gly Lys Pro Ile Pro Asn Pro Leu
                    485                 490                 495
Leu Gly Leu Asp Ser Thr Arg Thr Gly His His His His His
                500                 505                 510

<210> SEQ ID NO 66
<211> LENGTH: 501
<212> TYPE: PRT
<213> ORGANISM: Artificial Sequence
<220> FEATURE:
```

<223> OTHER INFORMATION: O. sativa-S

<400> SEQUENCE: 66

```
Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Lys Gln Ser His Ala
65                  70                  75                  80

Gly Leu Phe Asn Leu Cys Val Val Leu Ile Ala Val Asn Ser Arg
                85                  90                  95

Leu Ile Ile Glu Asn Leu Met Lys Tyr Gly Trp Leu Ile Arg Thr Asp
                100                 105                 110

Phe Trp Phe Ser Ser Arg Ser Leu Arg Asp Trp Pro Leu Phe Met Cys
            115                 120                 125

Cys Ile Ser Leu Ser Ile Phe Pro Leu Ala Ala Phe Thr Val Glu Lys
130                 135                 140

Leu Val Leu Gln Lys Tyr Ile Ser Glu Pro Val Val Ile Phe Leu His
145                 150                 155                 160

Ile Ile Ile Thr Met Thr Glu Val Leu Tyr Pro Val Tyr Val Thr Leu
                165                 170                 175

Arg Cys Asp Ser Ala Phe Leu Ser Gly Val Thr Leu Met Leu Leu Thr
            180                 185                 190

Cys Ile Val Trp Leu Lys Leu Val Ser Tyr Ala His Thr Ser Tyr Asp
            195                 200                 205

Ile Arg Ser Leu Ala Asn Ala Ala Asp Lys Ala Asn Pro Glu Val Ser
210                 215                 220

Tyr Tyr Val Ser Leu Lys Ser Leu Ala Tyr Phe Met Val Ala Pro Thr
225                 230                 235                 240

Leu Cys Tyr Gln Pro Ser Tyr Pro Arg Ser Ala Cys Ile Arg Lys Gly
                245                 250                 255

Trp Val Ala Arg Gln Phe Ala Lys Leu Val Ile Phe Thr Gly Phe Met
            260                 265                 270

Gly Phe Ile Ile Glu Gln Tyr Ile Asn Pro Ile Val Arg Asn Ser Lys
            275                 280                 285

His Pro Leu Lys Gly Asp Leu Tyr Ala Ile Glu Arg Val Leu Lys
            290                 295                 300

Leu Ser Val Pro Asn Leu Tyr Val Trp Leu Cys Met Phe Tyr Cys Phe
305                 310                 315                 320

Phe His Leu Trp Leu Asn Ile Leu Ala Glu Leu Leu Cys Phe Gly Asp
                325                 330                 335

Arg Glu Phe Tyr Lys Asp Trp Trp Asn Ala Lys Ser Val Gly Asp Tyr
            340                 345                 350

Trp Arg Met Trp Asn Met Pro Val His Lys Trp Met Val Arg His Ile
            355                 360                 365

Tyr Phe Pro Cys Leu Arg Ser Lys Ile Pro Lys Thr Leu Ala Ile Ile
            370                 375                 380

Ile Ala Phe Leu Val Ser Ala Val Phe His Glu Leu Cys Ile Ala Val
385                 390                 395                 400
```

```
Pro Cys Arg Leu Phe Lys Leu Trp Ala Phe Leu Gly Ile Met Phe Gln
                405                 410                 415

Val Pro Leu Val Phe Ile Thr Asn Tyr Leu Gln Glu Arg Phe Gly Ser
            420                 425                 430

Thr Val Gly Asn Met Ile Phe Trp Phe Ile Phe Cys Ile Phe Gly Gln
        435                 440                 445

Pro Met Cys Val Leu Leu Tyr Tyr His Asp Leu Met Asn Arg Lys Gly
    450                 455                 460

Ser Met Ser Ala Lys Gly Glu Leu Arg Gly His Pro Phe Glu Gly Lys
465                 470                 475                 480

Pro Ile Pro Asn Pro Leu Leu Gly Leu Asp Ser Thr Arg Thr Gly His
                485                 490                 495

His His His His His
            500

<210> SEQ ID NO 67
<211> LENGTH: 509
<212> TYPE: PRT
<213> ORGANISM: Artificial Sequence
<220> FEATURE:
<223> OTHER INFORMATION: O. sativa-S

<400> SEQUENCE: 67

Met Ala Pro Pro Ser Leu Ala Pro Asp Arg Gly Gly Glu Pro
1               5                   10                  15

Asp Ala Leu Arg Leu Arg Ala Arg Ala Ala Ala Gly Asp Asp
                20                  25                  30

Ala Pro Ala Pro Gln Gln Gln Glu Gln Arg His Gln Glu Gln Gln
            35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Lys Gln Ser His Ala
65                  70                  75                  80

Gly Leu Phe Asn Leu Cys Ile Val Val Leu Ala Val Asn Ser Arg
                85                  90                  95

Leu Ile Ile Glu Asn Leu Met Lys Tyr Gly Leu Leu Ile Arg Ala Gly
                100                 105                 110

Phe Trp Phe Asn Asp Lys Ser Leu Arg Asp Trp Pro Leu Leu Met Cys
            115                 120                 125

Cys Leu Ser Leu Pro Ala Phe Pro Leu Gly Ala Phe Ala Val Glu Lys
        130                 135                 140

Leu Ala Phe Asn Asn Val Ile Thr Asp Ala Val Ala Thr Cys Leu His
145                 150                 155                 160

Ile Phe Leu Ser Thr Thr Glu Ile Val Tyr Pro Val Leu Val Ile Leu
                165                 170                 175

Lys Cys Asp Ser Ala Val Leu Ser Gly Phe Leu Leu Ile Phe Ile Ala
            180                 185                 190

Cys Ile Val Trp Leu Lys Leu Val Ser Phe Ala His Thr Asn His Asp
        195                 200                 205

Ile Arg Gln Leu Thr Met Gly Gly Lys Lys Val Asp Asn Glu Leu Ser
    210                 215                 220

Thr Val Asp Met Asp Asn Leu Gln Pro Pro Thr Leu Gly Asn Leu Ile
225                 230                 235                 240

Tyr Phe Met Met Ala Pro Thr Leu Cys Tyr Gln Pro Ser Tyr Pro Arg
                245                 250                 255
```

```
Thr Ser Cys Val Arg Lys Gly Trp Leu Ile Arg Gln Ile Ile Leu Tyr
            260                 265                 270

Leu Ile Phe Thr Gly Leu Gln Gly Phe Ile Ile Glu Gln Tyr Ile Asn
            275                 280                 285

Pro Ile Val Val Asn Ser Gln His Pro Leu Lys Gly Gly Leu Leu Asn
            290                 295                 300

Ala Val Glu Thr Val Leu Lys Leu Ser Leu Pro Asn Val Tyr Leu Trp
305                 310                 315                 320

Leu Cys Met Phe Tyr Ala Phe Phe His Leu Trp Leu Ser Ile Leu Ala
                325                 330                 335

Glu Ile Leu Arg Phe Gly Asp Arg Glu Phe Tyr Lys Asp Trp Trp Asn
                340                 345                 350

Ala Lys Thr Ile Asp Glu Tyr Trp Arg Lys Trp Asn Met Pro Val His
                355                 360                 365

Lys Trp Val Val Arg His Ile Tyr Phe Pro Cys Met Arg Asn Gly Ile
                370                 375                 380

Ser Lys Glu Val Ala Val Leu Ile Ser Phe Leu Val Ser Ala Val Leu
385                 390                 395                 400

His Glu Ile Cys Val Ala Val Pro Cys Arg Ile Leu Lys Phe Trp Ala
                405                 410                 415

Phe Leu Gly Ile Met Leu Gln Ile Pro Leu Ile Val Leu Thr Ala Tyr
                420                 425                 430

Leu Lys Ser Lys Phe Arg Asp Thr Met Val Gly Asn Met Ile Phe Trp
                435                 440                 445

Phe Phe Phe Cys Ile Tyr Gly Gln Pro Met Cys Leu Leu Leu Tyr Tyr
450                 455                 460

His Asp Val Met Asn Arg Ile Glu Lys Ala Arg Ala Lys Gly Glu Leu
465                 470                 475                 480

Arg Gly His Pro Phe Glu Gly Lys Pro Ile Pro Asn Pro Leu Leu Gly
                485                 490                 495

Leu Asp Ser Thr Arg Thr Gly His His His His His
                500                 505

<210> SEQ ID NO 68
<211> LENGTH: 510
<212> TYPE: PRT
<213> ORGANISM: Artificial Sequence
<220> FEATURE:
<223> OTHER INFORMATION: O. sativa-S

<400> SEQUENCE: 68

Met Ala Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
                20                  25                  30

Ala Pro Ala Pro Gln Gln Gln Glu Gln Arg His Gln Glu Gln Gln
                35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Ile Ala Val Asn Ser Arg
                85                  90                  95

Leu Ile Ile Glu Asn Leu Met Lys Tyr Gly Leu Leu Ile Arg Ala Gly
                100                 105                 110
```

Phe Trp Phe Ser Ala Arg Ser Leu Gly Asp Trp Pro Leu Met Cys
            115                 120                 125

Cys Leu Thr Leu Pro Val Phe Pro Leu Val Ala Leu Met Ala Glu Lys
130                 135                 140

Leu Ile Thr Arg Lys Leu Ile Gly Glu His Val Val Ile Leu Leu His
145                 150                 155                 160

Ile Ile Ile Thr Thr Ser Ala Ile Val Tyr Pro Val Val Thr Leu
                165                 170                 175

Lys Cys Asp Ser Ala Val Leu Ser Gly Phe Val Leu Met Phe Leu Ala
            180                 185                 190

Ser Ile Met Trp Met Lys Leu Val Ser Tyr Ala His Thr Asn Tyr Asp
            195                 200                 205

Ile Arg Val Leu Ser Lys Ser Thr Glu Lys Gly Ala Ala Tyr Gly Asn
            210                 215                 220

Tyr Val Asp Pro Glu Asn Met Lys Asp Pro Thr Phe Lys Ser Leu Val
225                 230                 235                 240

Tyr Phe Met Leu Ala Pro Thr Leu Cys Tyr Gln Pro Thr Tyr Pro Gln
                245                 250                 255

Thr Thr Cys Ile Arg Lys Gly Trp Val Thr Gln Gln Leu Ile Lys Cys
            260                 265                 270

Val Val Phe Thr Gly Leu Met Gly Phe Ile Ile Glu Gln Tyr Ile Asn
            275                 280                 285

Pro Ile Val Lys Asn Ser Lys His Pro Leu Lys Gly Asn Phe Leu Asn
            290                 295                 300

Ala Ile Glu Arg Val Leu Lys Leu Ser Val Pro Thr Leu Tyr Val Trp
305                 310                 315                 320

Leu Cys Met Phe Tyr Cys Phe His Leu Trp Leu Asn Ile Val Ala
                325                 330                 335

Glu Leu Leu Cys Phe Gly Asp Arg Glu Phe Tyr Lys Asp Trp Trp Asn
            340                 345                 350

Ala Lys Thr Val Glu Glu Tyr Trp Arg Met Trp Asn Met Pro Val His
            355                 360                 365

Lys Trp Ile Ile Arg His Ile Tyr Phe Pro Cys Ile Arg Lys Gly Phe
370                 375                 380

Ser Arg Gly Val Ala Ile Leu Ile Ser Phe Leu Val Ser Ala Val Phe
385                 390                 395                 400

His Glu Ile Cys Ile Ala Val Pro Cys His Ile Phe Lys Phe Trp Ala
                405                 410                 415

Phe Ser Gly Ile Met Phe Gln Ile Pro Leu Val Phe Leu Thr Arg Tyr
            420                 425                 430

Leu His Ala Thr Phe Lys His Val Met Val Gly Asn Met Ile Phe Trp
            435                 440                 445

Phe Phe Phe Ser Ile Val Gly Gln Pro Met Cys Val Leu Leu Tyr Tyr
450                 455                 460

His Asp Val Met Asn Arg Gln Ala Gln Ala Ser Arg Ala Lys Gly Glu
465                 470                 475                 480

Leu Arg Gly His Pro Phe Glu Gly Lys Pro Ile Pro Asn Pro Leu Leu
                485                 490                 495

Gly Leu Asp Ser Thr Arg Thr Gly His His His His His
            500                 505                 510

<210> SEQ ID NO 69
<211> LENGTH: 509
<212> TYPE: PRT

<213> ORGANISM: Artificial Sequence
<220> FEATURE:
<223> OTHER INFORMATION: O. sativa-S

<400> SEQUENCE: 69

```
Met Ala Pro Pro Pro Ser Leu Ala Pro Asp Arg Gly Gly Glu Pro
1               5                   10                  15

Asp Asp Ala Leu Arg Leu Arg Ala Arg Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
50                  55                  60

Arg Glu Ser Pro Leu Ser Ser Asp Ala Ile Phe Lys Gln Ser His Ala
65                  70                  75                  80

Gly Leu Phe Asn Leu Cys Ile Val Val Leu Val Ala Val Asn Ser Arg
                85                  90                  95

Leu Ile Ile Glu Asn Leu Met Lys Tyr Gly Leu Leu Ile Arg Ser Gly
            100                 105                 110

Phe Trp Phe Asn Ala Thr Ser Leu Arg Asp Trp Pro Leu Leu Met Cys
        115                 120                 125

Cys Leu Ser Leu Pro Ile Phe Pro Leu Gly Ala Phe Ala Val Glu Lys
        130                 135                 140

Leu Ala Phe Asn Asn Leu Ile Ser Asp Pro Ala Thr Thr Cys Phe His
145                 150                 155                 160

Ile Leu Phe Thr Thr Phe Glu Ile Val Tyr Pro Val Leu Val Ile Leu
                165                 170                 175

Lys Cys Asp Ser Ala Val Leu Ser Gly Phe Val Leu Met Phe Ile Ala
            180                 185                 190

Cys Ile Val Trp Leu Lys Leu Val Ser Phe Ala His Thr Asn His Asp
        195                 200                 205

Ile Arg Lys Leu Ile Thr Ser Gly Lys Lys Val Asp Asn Glu Leu Thr
        210                 215                 220

Ala Ala Gly Ile Asp Asn Leu Gln Ala Pro Thr Leu Gly Ser Leu Thr
225                 230                 235                 240

Tyr Phe Met Met Ala Pro Thr Leu Cys Tyr Gln Pro Ser Tyr Pro Arg
                245                 250                 255

Thr Pro Tyr Val Arg Lys Gly Trp Leu Val Arg Gln Val Ile Leu Tyr
            260                 265                 270

Leu Ile Phe Thr Gly Leu Gln Gly Phe Ile Ile Glu Gln Tyr Ile Asn
        275                 280                 285

Pro Ile Val Val Asn Ser Gln His Pro Leu Met Gly Gly Leu Leu Asn
        290                 295                 300

Ala Val Glu Thr Val Leu Lys Leu Ser Leu Pro Asn Val Tyr Leu Trp
305                 310                 315                 320

Leu Cys Met Phe Tyr Cys Leu Phe His Leu Trp Leu Asn Ile Leu Ala
                325                 330                 335

Glu Ile Leu Arg Phe Gly Asp Arg Glu Phe Tyr Lys Asp Trp Trp Asn
            340                 345                 350

Ala Lys Thr Ile Asp Glu Tyr Trp Arg Lys Trp Asn Met Pro Val His
        355                 360                 365

Lys Trp Ile Val Arg His Ile Tyr Phe Pro Cys Met Arg Asn Gly Ile
        370                 375                 380

Ser Lys Glu Val Ala Val Phe Ile Ser Phe Phe Val Ser Ala Val Leu
```

```
385                 390                 395                 400
His Glu Leu Cys Val Ala Val Pro Cys His Ile Leu Lys Phe Trp Ala
                405                 410                 415

Phe Leu Gly Ile Met Leu Gln Ile Pro Leu Ile Ile Leu Thr Ser Tyr
                420                 425                 430

Leu Lys Asn Lys Phe Ser Asp Thr Met Val Gly Asn Met Ile Phe Trp
                435                 440                 445

Phe Phe Phe Cys Ile Tyr Gly Gln Pro Met Cys Val Leu Leu Tyr Tyr
                450                 455                 460

His Asp Val Met Asn Arg Thr Glu Lys Ala Lys Ala Lys Gly Glu Leu
465                 470                 475                 480

Arg Gly His Pro Phe Glu Gly Lys Pro Ile Pro Asn Pro Leu Leu Gly
                485                 490                 495

Leu Asp Ser Thr Arg Thr Gly His His His His His
                500                 505

<210> SEQ ID NO 70
<211> LENGTH: 507
<212> TYPE: PRT
<213> ORGANISM: Artificial Sequence
<220> FEATURE:
<223> OTHER INFORMATION: O. sativa-S

<400> SEQUENCE: 70

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Gly Asp
                20                  25                  30

Ala Pro Ala Pro Gln Gln Gln Gln Glu Gln Arg His Gln Glu Gln Gln
                35                  40                  45

Gln Gln Leu Leu Trp Tyr Arg Ala Ser Ala Pro Ala His Arg Arg Val
        50                  55                  60

Arg Glu Ser Pro Leu Ser Ser Asp Ala Ile Phe Lys Gln Ser His Ala
65                  70                  75                  80

Gly Leu Phe Asn Leu Cys Ile Val Val Leu Ile Ala Val Asn Ser Arg
                85                  90                  95

Leu Ile Ile Glu Asn Leu Met Lys Tyr Gly Trp Leu Ile Asp Thr Gly
                100                 105                 110

Phe Trp Phe Ser Ser Arg Ser Leu Gly Asp Trp Ser Ile Phe Met Cys
                115                 120                 125

Cys Leu Thr Leu Pro Ile Phe Pro Leu Ala Ala Phe Ile Val Glu Lys
                130                 135                 140

Leu Val Gln Arg Asn His Ile Ser Glu Leu Val Ala Val Leu Leu His
145                 150                 155                 160

Val Ile Val Ser Thr Ala Ala Val Leu Tyr Pro Val Ile Val Ile Leu
                165                 170                 175

Thr Cys Asp Ser Val Tyr Met Ser Gly Val Val Leu Met Leu Phe Gly
                180                 185                 190

Cys Ile Met Trp Leu Lys Leu Val Ser Tyr Ala His Thr Ser Ser Asp
                195                 200                 205

Ile Arg Thr Leu Ala Lys Ser Gly Tyr Lys Gly Asp Ala His Pro Asn
                210                 215                 220

Ser Thr Ile Val Ser Cys Ser Tyr Asp Val Ser Leu Lys Ser Leu Ala
225                 230                 235                 240

Tyr Phe Met Val Ala Pro Thr Leu Cys Tyr Gln Pro Ser Tyr Pro Arg
```

```
            245                 250                 255
Ser Ser Cys Ile Arg Lys Gly Trp Val Val Arg Gln Phe Val Lys Leu
            260                 265                 270

Ile Val Phe Ile Gly Leu Met Gly Phe Ile Ile Glu Gln Tyr Ile Asn
            275                 280                 285

Pro Ile Val Arg Asn Ser Lys His Pro Leu Lys Gly Asp Phe Leu Tyr
290                 295                 300

Ala Ile Glu Arg Val Leu Lys Leu Ser Val Pro Asn Leu Tyr Val Trp
305                 310                 315                 320

Leu Cys Met Phe Tyr Ser Phe Phe His Leu Trp Leu Asn Ile Leu Ala
                325                 330                 335

Glu Leu Leu Arg Phe Gly Asp Arg Glu Phe Tyr Lys Asp Trp Trp Asn
                340                 345                 350

Ala Lys Thr Val Ala Glu Tyr Trp Lys Met Trp Asn Met Pro Val His
                355                 360                 365

Arg Trp Met Val Arg His Leu Tyr Phe Pro Cys Leu Arg Asn Gly Ile
            370                 375                 380

Pro Lys Glu Gly Ala Ile Ile Ala Phe Leu Val Ser Gly Ala Phe
385                 390                 395                 400

His Glu Leu Cys Ile Ala Val Pro Cys His Val Phe Lys Leu Trp Ala
                405                 410                 415

Phe Ile Gly Ile Met Phe Gln Val Pro Leu Val Leu Ile Thr Asn Tyr
            420                 425                 430

Leu Gln Glu Lys Phe Ser Asn Ser Met Val Gly Asn Met Ile Phe Trp
                435                 440                 445

Phe Ile Phe Cys Ile Leu Gly Gln Pro Met Cys Val Leu Leu Tyr Tyr
450                 455                 460

His Asp Leu Ile Asn Leu Lys Glu Lys Ala Lys Gly Glu Leu Arg Gly
465                 470                 475                 480

His Pro Phe Glu Gly Lys Pro Ile Pro Asn Pro Leu Leu Gly Leu Asp
                485                 490                 495

Ser Thr Arg Thr Gly His His His His His His
            500                 505

<210> SEQ ID NO 71
<211> LENGTH: 572
<212> TYPE: PRT
<213> ORGANISM: Artificial Sequence
<220> FEATURE:
<223> OTHER INFORMATION: O. sativa-L

<400> SEQUENCE: 71

Met Val Gly Ser Asp Gly Asp Gly Asp Gly Gly Gly Gly Glu Ala His
1               5                   10                  15

Ala Pro Ala Ala Pro Ala His His Arg Arg Pro Arg Pro Arg
                20                  25                  30

Gly Gly Ser Gly Ala Ile Val Glu Gly Phe Ala Ala Leu Arg Arg
                35                  40                  45

Arg Ile Arg Ser Gly Ala Ala Ala Ala Arg Ala Ser Phe Gly Gly
            50                  55                  60

Asp Ser Gly Asp Glu Ala Ala Ser Gly Glu Pro Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Gly Arg Gly Gly Gly Gly Asp Phe
```

-continued

```
                100                 105                 110
Ser Ala Phe Thr Phe Arg Ala Ala Pro Val His Arg Lys Ala Lys
            115                 120                 125

Glu Ser Pro Leu Ser Ser Asp Ala Ile Phe Lys Gln Ser His Ala Gly
130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Leu Leu Ile Arg Ala Gly Phe
                165                 170                 175

Trp Phe Asn Asp Lys Ser Leu Arg Asp Trp Pro Leu Leu Met Cys Cys
                180                 185                 190

Leu Ser Leu Pro Ala Phe Pro Leu Gly Ala Phe Ala Val Glu Lys Leu
            195                 200                 205

Ala Phe Asn Asn Val Ile Thr Asp Ala Val Ala Thr Cys Leu His Ile
            210                 215                 220

Phe Leu Ser Thr Thr Glu Ile Val Tyr Pro Val Leu Val Ile Leu Lys
225                 230                 235                 240

Cys Asp Ser Ala Val Leu Ser Gly Phe Leu Leu Ile Phe Ile Ala Cys
                245                 250                 255

Ile Val Trp Leu Lys Leu Val Ser Phe Ala His Thr Asn His Asp Ile
                260                 265                 270

Arg Gln Leu Thr Met Gly Gly Lys Lys Val Asp Asn Glu Leu Ser Thr
            275                 280                 285

Val Asp Met Asp Asn Leu Gln Pro Pro Thr Leu Gly Asn Leu Ile Tyr
            290                 295                 300

Phe Met Met Ala Pro Thr Leu Cys Tyr Gln Pro Ser Tyr Pro Arg Thr
305                 310                 315                 320

Ser Cys Val Arg Lys Gly Trp Leu Ile Arg Gln Ile Ile Leu Tyr Leu
                325                 330                 335

Ile Phe Thr Gly Leu Gln Gly Phe Ile Ile Glu Gln Tyr Ile Asn Pro
                340                 345                 350

Ile Val Val Asn Ser Gln His Pro Leu Lys Gly Gly Leu Leu Asn Ala
            355                 360                 365

Val Glu Thr Val Leu Lys Leu Ser Leu Pro Asn Val Tyr Leu Trp Leu
            370                 375                 380

Cys Met Phe Tyr Ala Phe Phe His Leu Trp Leu Ser Ile Leu Ala Glu
385                 390                 395                 400

Ile Leu Arg Phe Gly Asp Arg Glu Phe Tyr Lys Asp Trp Trp Asn Ala
                405                 410                 415

Lys Thr Ile Asp Glu Tyr Trp Arg Lys Trp Asn Met Pro Val His Lys
                420                 425                 430

Trp Val Val Arg His Ile Tyr Phe Pro Cys Met Arg Asn Gly Ile Ser
            435                 440                 445

Lys Glu Val Ala Val Leu Ile Ser Phe Leu Val Ser Ala Val Leu His
            450                 455                 460

Glu Ile Cys Val Ala Val Pro Cys Arg Ile Leu Lys Phe Trp Ala Phe
465                 470                 475                 480

Leu Gly Ile Met Leu Gln Ile Pro Leu Ile Val Leu Thr Ala Tyr Leu
                485                 490                 495

Lys Ser Lys Phe Arg Asp Thr Met Val Gly Asn Met Ile Phe Trp Phe
                500                 505                 510

Phe Phe Cys Ile Tyr Gly Gln Pro Met Cys Leu Leu Leu Tyr Tyr His
            515                 520                 525
```

```
Asp Val Met Asn Arg Ile Glu Lys Ala Arg Ala Lys Gly Glu Leu Arg
        530                 535                 540

Gly His Pro Phe Glu Gly Lys Pro Ile Pro Asn Pro Leu Leu Gly Leu
545                 550                 555                 560

Asp Ser Thr Arg Thr Gly His His His His His
                565                 570
```

<210> SEQ ID NO 72
<211> LENGTH: 564
<212> TYPE: PRT
<213> ORGANISM: Artificial Sequence
<220> FEATURE:
<223> OTHER INFORMATION: O. sativa-L

<400> SEQUENCE: 72

```
Met Val Gly Ser Asp Gly Asp Gly Asp Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Leu Arg Arg
            35                  40                  45

Arg Ile Arg Ser Gly Ala Ala Ala Ala Arg Ala Ser Phe Gly Gly
    50                  55                  60

Asp Ser Gly Asp Glu Ala Ala Ser Gly Glu Pro Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Arg Gly Gly Gly Asp Phe
            100                 105                 110

Ser Ala Phe Thr Phe Arg Ala Ala Ala Pro Val His Arg Lys Ala Lys
            115                 120                 125

Glu Ser Pro Leu Ser Ser Asp Ala Ile Phe Lys Gln Ser His Ala Gly
    130                 135                 140

Leu Phe Asn Leu Cys Val Val Leu Ile Ala Val Asn Ser Arg Leu
145                 150                 155                 160

Ile Ile Glu Asn Leu Met Lys Tyr Gly Trp Leu Ile Arg Thr Asp Phe
                165                 170                 175

Trp Phe Ser Ser Arg Ser Leu Arg Asp Trp Pro Leu Phe Met Cys Cys
            180                 185                 190

Ile Ser Leu Ser Ile Phe Pro Leu Ala Ala Phe Thr Val Glu Lys Leu
            195                 200                 205

Val Leu Gln Lys Tyr Ile Ser Glu Pro Val Val Ile Phe Leu His Ile
    210                 215                 220

Ile Ile Thr Met Thr Glu Val Leu Tyr Pro Val Tyr Val Thr Leu Arg
225                 230                 235                 240

Cys Asp Ser Ala Phe Leu Ser Gly Val Thr Leu Met Leu Leu Thr Cys
                245                 250                 255

Ile Val Trp Leu Lys Leu Val Ser Tyr Ala His Thr Ser Tyr Asp Ile
            260                 265                 270

Arg Ser Leu Ala Asn Ala Ala Asp Lys Ala Asn Pro Glu Val Ser Tyr
    275                 280                 285

Tyr Val Ser Leu Lys Ser Leu Ala Tyr Phe Met Val Ala Pro Thr Leu
    290                 295                 300

Cys Tyr Gln Pro Ser Tyr Pro Arg Ser Ala Cys Ile Arg Lys Gly Trp
305                 310                 315                 320
```

Val Ala Arg Gln Phe Ala Lys Leu Val Ile Phe Thr Gly Phe Met Gly
            325                 330                 335

Phe Ile Ile Glu Gln Tyr Ile Asn Pro Ile Val Arg Asn Ser Lys His
            340                 345                 350

Pro Leu Lys Gly Asp Leu Leu Tyr Ala Ile Glu Arg Val Leu Lys Leu
            355                 360                 365

Ser Val Pro Asn Leu Tyr Val Trp Leu Cys Met Phe Tyr Cys Phe Phe
370                 375                 380

His Leu Trp Leu Asn Ile Leu Ala Glu Leu Leu Cys Phe Gly Asp Arg
385                 390                 395                 400

Glu Phe Tyr Lys Asp Trp Trp Asn Ala Lys Ser Val Gly Asp Tyr Trp
            405                 410                 415

Arg Met Trp Asn Met Pro Val His Lys Trp Met Val Arg His Ile Tyr
            420                 425                 430

Phe Pro Cys Leu Arg Ser Lys Ile Pro Lys Thr Leu Ala Ile Ile Ile
            435                 440                 445

Ala Phe Leu Val Ser Ala Val Phe His Glu Leu Cys Ile Ala Val Pro
            450                 455                 460

Cys Arg Leu Phe Lys Leu Trp Ala Phe Leu Gly Ile Met Phe Gln Val
465                 470                 475                 480

Pro Leu Val Phe Ile Thr Asn Tyr Leu Gln Glu Arg Phe Gly Ser Thr
            485                 490                 495

Val Gly Asn Met Ile Phe Trp Phe Ile Phe Cys Ile Phe Gly Gln Pro
            500                 505                 510

Met Cys Val Leu Leu Tyr Tyr His Asp Leu Met Asn Arg Lys Gly Ser
            515                 520                 525

Met Ser Ala Lys Gly Glu Leu Arg Gly His Pro Phe Glu Gly Lys Pro
            530                 535                 540

Ile Pro Asn Pro Leu Leu Gly Leu Asp Ser Thr Arg Thr Gly His His
545                 550                 555                 560

His His His His

<210> SEQ ID NO 73
<211> LENGTH: 574
<212> TYPE: PRT
<213> ORGANISM: Artificial Sequence
<220> FEATURE:
<223> OTHER INFORMATION: O. sativa-L

<400> SEQUENCE: 73

Met Val Gly Ser Asp Gly Asp Gly Asp Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Ile Val Glu Gly Phe Ala Ala Ala Leu Arg Arg
            35                  40                  45

Arg Ile Arg Ser Gly Ala Ala Ala Ala Arg Ala Ser Phe Gly Gly
            50                  55                  60

Asp Ser Gly Asp Glu Ala Ala Ser Gly Glu Pro Ser Ser Ser Ser
65                  70                  75                  80

Ser Ser Pro Ser Arg Arg Arg Gly Gly Asp Ser Asn Gly Ala Glu Ala
            85                  90                  95

Ser Ser Ala Ala Gly Gly Gly Gly Arg Gly Gly Gly Asp Phe
            100                 105                 110

-continued

```
Ser Ala Phe Thr Phe Arg Ala Ala Pro Val His Arg Lys Ala Lys
            115                 120                 125
Glu Ser Pro Leu Ser Ser Asp Ala Ile Phe Arg Gln Ser His Ala Gly
130                 135                 140
Leu Leu Asn Leu Cys Ile Val Val Leu Val Ala Val Asn Ser Arg Leu
145                 150                 155                 160
Ile Ile Glu Asn Leu Met Lys Tyr Gly Leu Leu Ile Arg Ala Gly Phe
                165                 170                 175
Trp Phe Ser Gly Thr Ser Leu Ala Asp Trp Pro Leu Leu Met Cys Cys
            180                 185                 190
Leu Thr Leu Pro Thr Phe Pro Leu Ala Ala Leu Met Val Glu Lys Leu
            195                 200                 205
Ala Gln Arg Lys Leu Ile Ser Lys His Val Val Ile Leu Leu His Ile
210                 215                 220
Val Ile Thr Thr Ser Val Leu Val Tyr Pro Val Val Ile Leu Lys
225                 230                 235                 240
Cys Asp Ser Ala Val Leu Ser Gly Phe Val Leu Met Phe Leu Ala Ser
                245                 250                 255
Ile Ile Trp Leu Lys Leu Val Ser Phe Ala His Thr Asn Tyr Asp Ile
            260                 265                 270
Arg Met Leu Ser Lys Ser Ile Glu Lys Gly Val Thr His Asp Ile Ser
        275                 280                 285
Ile Asp Pro Glu Asn Ile Lys Trp Pro Thr Phe Lys Arg Leu Ser Tyr
290                 295                 300
Phe Met Leu Ala Pro Thr Leu Cys Tyr Gln Pro Ser Tyr Pro Arg Thr
305                 310                 315                 320
Thr Tyr Ile Arg Lys Gly Trp Val Val Arg Gln Leu Ile Lys Cys Leu
                325                 330                 335
Val Phe Thr Gly Leu Met Gly Phe Ile Ile Glu Gln Tyr Ile Asn Pro
            340                 345                 350
Ile Val Lys Asn Ser Lys His Pro Leu Lys Gly Asn Phe Leu Asn Ala
        355                 360                 365
Ile Glu Arg Val Leu Lys Leu Ser Val Pro Thr Leu Tyr Val Trp Leu
370                 375                 380
Cys Met Phe Tyr Cys Phe His Leu Trp Leu Asn Ile Leu Ala Glu
385                 390                 395                 400
Leu Leu Cys Phe Gly Asp Arg Glu Phe Tyr Lys Asp Trp Trp Asn Ala
                405                 410                 415
Lys Thr Val Glu Glu Tyr Trp Arg Met Trp Asn Met Pro Val His Lys
            420                 425                 430
Trp Val Ile Arg His Ile Tyr Phe Pro Cys Ile Arg Asn Gly Phe Ser
        435                 440                 445
Lys Gly Val Ala Ile Leu Ile Ser Phe Leu Val Ser Ala Ala Phe His
450                 455                 460
Glu Leu Cys Val Ala Val Pro Cys His Ile Phe Lys Phe Trp Ala Phe
465                 470                 475                 480
Ile Gly Ile Met Phe Gln Ile Pro Leu Val Phe Leu Thr Lys Tyr Leu
                485                 490                 495
Gln Asp Lys Phe Asn Asn Thr Met Val Gly Asn Met Ile Phe Trp Phe
            500                 505                 510
Phe Phe Ser Ile Leu Gly Gln Pro Met Cys Val Leu Leu Tyr Tyr His
        515                 520                 525
Asp Val Met Asn Arg Gln Gln Ala Gln Thr Asn Arg Ala Lys Gly Glu
```

```
                530                 535                 540
Leu Arg Gly His Pro Phe Glu Gly Lys Pro Ile Pro Asn Pro Leu Leu
545                 550                 555                 560

Gly Leu Asp Ser Thr Arg Thr Gly His His His His His
                565                 570
```

<210> SEQ ID NO 74
<211> LENGTH: 573
<212> TYPE: PRT
<213> ORGANISM: Artificial Sequence
<220> FEATURE:
<223> OTHER INFORMATION: O. sativa-L

<400> SEQUENCE: 74

```
Met Val Gly Ser Asp Gly Asp Gly Gly Gly Glu Ala His
1               5                   10                  15

Ala Pro Ala Ala Pro Ala His His Arg Arg Pro Arg Pro Arg
                20                  25                  30

Gly Gly Ser Gly Ala Ile Val Glu Gly Phe Ala Ala Leu Arg Arg
                35                  40                  45

Arg Ile Arg Ser Gly Ala Ala Ala Ala Arg Ala Ser Phe Gly Gly
50                  55                  60

Asp Ser Gly Asp Glu Ala Ala Ser Gly Glu Pro Ser Ser Ser Ser
65                  70                  75                  80

Ser Ser Pro Ser Arg Arg Gly Gly Asp Ser Asn Gly Ala Glu Ala
                85                  90                  95

Ser Ser Ala Gly Gly Gly Gly Arg Gly Gly Gly Asp Phe
                100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Arg Gln Ser His Ala Gly
        130                 135                 140

Leu Leu Asn Leu Cys Ile Val Val Leu Ile Ala Val Asn Ser Arg Leu
145                 150                 155                 160

Ile Ile Glu Asn Leu Met Lys Tyr Gly Leu Leu Ile Arg Ala Gly Phe
                165                 170                 175

Trp Phe Ser Ala Arg Ser Leu Gly Asp Trp Pro Leu Leu Met Cys Cys
                180                 185                 190

Leu Thr Leu Pro Val Phe Pro Leu Val Ala Leu Met Ala Glu Lys Leu
        195                 200                 205

Ile Thr Arg Lys Leu Ile Gly Glu His Val Val Ile Leu Leu His Ile
        210                 215                 220

Ile Ile Thr Thr Ser Ala Ile Val Tyr Pro Val Val Thr Leu Lys
225                 230                 235                 240

Cys Asp Ser Ala Val Leu Ser Gly Phe Val Leu Met Phe Leu Ala Ser
                245                 250                 255

Ile Met Trp Met Lys Leu Val Ser Tyr Ala His Thr Asn Tyr Asp Ile
                260                 265                 270

Arg Val Leu Ser Lys Ser Thr Glu Lys Gly Ala Ala Tyr Gly Asn Tyr
        275                 280                 285

Val Asp Pro Glu Asn Met Lys Asp Pro Thr Phe Lys Ser Leu Val Tyr
        290                 295                 300

Phe Met Leu Ala Pro Thr Leu Cys Tyr Gln Pro Thr Tyr Pro Gln Thr
305                 310                 315                 320

Thr Cys Ile Arg Lys Gly Trp Val Thr Gln Gln Leu Ile Lys Cys Val
```

```
                    325                 330                 335
Val Phe Thr Gly Leu Met Gly Phe Ile Ile Glu Gln Tyr Ile Asn Pro
            340                 345                 350
Ile Val Lys Asn Ser Lys His Pro Leu Lys Gly Asn Phe Leu Asn Ala
            355                 360                 365
Ile Glu Arg Val Leu Lys Leu Ser Val Pro Thr Leu Tyr Val Trp Leu
        370                 375                 380
Cys Met Phe Tyr Cys Phe Phe His Leu Trp Leu Asn Ile Val Ala Glu
385                 390                 395                 400
Leu Leu Cys Phe Gly Asp Arg Glu Phe Tyr Lys Asp Trp Trp Asn Ala
                405                 410                 415
Lys Thr Val Glu Glu Tyr Trp Arg Met Trp Asn Met Pro Val His Lys
            420                 425                 430
Trp Ile Ile Arg His Ile Tyr Phe Pro Cys Ile Arg Lys Gly Phe Ser
            435                 440                 445
Arg Gly Val Ala Ile Leu Ile Ser Phe Leu Val Ser Ala Val Phe His
        450                 455                 460
Glu Ile Cys Ile Ala Val Pro Cys His Ile Phe Lys Phe Trp Ala Phe
465                 470                 475                 480
Ser Gly Ile Met Phe Gln Ile Pro Leu Val Phe Leu Thr Arg Tyr Leu
                485                 490                 495
His Ala Thr Phe Lys His Val Met Val Gly Asn Met Ile Phe Trp Phe
            500                 505                 510
Phe Phe Ser Ile Val Gly Gln Pro Met Cys Val Leu Leu Tyr Tyr His
            515                 520                 525
Asp Val Met Asn Arg Gln Ala Gln Ala Ser Arg Ala Lys Gly Glu Leu
        530                 535                 540
Arg Gly His Pro Phe Glu Gly Lys Pro Ile Pro Asn Pro Leu Leu Gly
545                 550                 555                 560
Leu Asp Ser Thr Arg Thr Gly His His His His His
                565                 570

<210> SEQ ID NO 75
<211> LENGTH: 572
<212> TYPE: PRT
<213> ORGANISM: Artificial Sequence
<220> FEATURE:
<223> OTHER INFORMATION: O. sativa-L

<400> SEQUENCE: 75

Met Val Gly Ser Asp Gly Asp Gly Asp Gly Gly Gly Glu Ala His
1               5                   10                  15
Ala Pro Ala Ala Pro Ala His His His Arg Arg Pro Arg Pro Arg
            20                  25                  30
Gly Gly Ser Gly Ala Ile Val Glu Gly Phe Ala Ala Ala Leu Arg Arg
        35                  40                  45
Arg Ile Arg Ser Gly Ala Ala Ala Ala Arg Ala Ser Phe Gly Gly
            50                  55                  60
Asp Ser Gly Asp Glu Ala Ala Ser Gly Glu Pro Ser Ser Ser Ser
65                  70                  75                  80
Ser Ser Pro Ser Arg Arg Arg Gly Gly Asp Ser Asn Gly Ala Glu Ala
                85                  90                  95
Ser Ser Ala Ala Gly Gly Gly Gly Arg Gly Gly Gly Gly Asp Phe
            100                 105                 110
Ser Ala Phe Thr Phe Arg Ala Ala Ala Pro Val His Arg Lys Ala Lys
```

```
            115                 120                 125
Glu Ser Pro Leu Ser Ser Asp Ala Ile Phe Lys Gln Ser His Ala Gly
130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Leu Leu Ile Arg Ser Gly Phe
                165                 170                 175

Trp Phe Asn Ala Thr Ser Leu Arg Asp Trp Pro Leu Leu Met Cys Cys
                180                 185                 190

Leu Ser Leu Pro Ile Phe Pro Leu Gly Ala Phe Ala Val Glu Lys Leu
                195                 200                 205

Ala Phe Asn Asn Leu Ile Ser Asp Pro Ala Thr Thr Cys Phe His Ile
210                 215                 220

Leu Phe Thr Thr Phe Glu Ile Val Tyr Pro Val Leu Val Ile Leu Lys
225                 230                 235                 240

Cys Asp Ser Ala Val Leu Ser Gly Phe Val Leu Met Phe Ile Ala Cys
                245                 250                 255

Ile Val Trp Leu Lys Leu Val Ser Phe Ala His Thr Asn His Asp Ile
                260                 265                 270

Arg Lys Leu Ile Thr Ser Gly Lys Val Asp Asn Glu Leu Thr Ala
                275                 280                 285

Ala Gly Ile Asp Asn Leu Gln Ala Pro Thr Leu Gly Ser Leu Thr Tyr
290                 295                 300

Phe Met Met Ala Pro Thr Leu Cys Tyr Gln Pro Ser Tyr Pro Arg Thr
305                 310                 315                 320

Pro Tyr Val Arg Lys Gly Trp Leu Val Arg Gln Val Ile Leu Tyr Leu
                325                 330                 335

Ile Phe Thr Gly Leu Gln Gly Phe Ile Glu Gln Tyr Ile Asn Pro
                340                 345                 350

Ile Val Val Asn Ser Gln His Pro Leu Met Gly Gly Leu Leu Asn Ala
                355                 360                 365

Val Glu Thr Val Leu Lys Leu Ser Leu Pro Asn Val Tyr Leu Trp Leu
370                 375                 380

Cys Met Phe Tyr Cys Leu Phe His Leu Trp Leu Asn Ile Leu Ala Glu
385                 390                 395                 400

Ile Leu Arg Phe Gly Asp Arg Glu Phe Tyr Lys Asp Trp Trp Asn Ala
                405                 410                 415

Lys Thr Ile Asp Glu Tyr Trp Arg Lys Trp Asn Met Pro Val His Lys
                420                 425                 430

Trp Ile Val Arg His Ile Tyr Phe Pro Cys Met Arg Asn Gly Ile Ser
                435                 440                 445

Lys Glu Val Ala Val Phe Ile Ser Phe Phe Val Ser Ala Val Leu His
                450                 455                 460

Glu Leu Cys Val Ala Val Pro Cys His Ile Leu Lys Phe Trp Ala Phe
465                 470                 475                 480

Leu Gly Ile Met Leu Gln Ile Pro Leu Ile Ile Leu Thr Ser Tyr Leu
                485                 490                 495

Lys Asn Lys Phe Ser Asp Thr Met Val Gly Asn Met Ile Phe Trp Phe
                500                 505                 510

Phe Phe Cys Ile Tyr Gly Gln Pro Met Cys Val Leu Leu Tyr Tyr His
                515                 520                 525

Asp Val Met Asn Arg Thr Glu Lys Ala Lys Ala Lys Gly Glu Leu Arg
530                 535                 540
```

Gly His Pro Phe Glu Gly Lys Pro Ile Pro Asn Pro Leu Leu Gly Leu
545                 550                 555                 560

Asp Ser Thr Arg Thr Gly His His His His His
                565                 570

<210> SEQ ID NO 76
<211> LENGTH: 570
<212> TYPE: PRT
<213> ORGANISM: Artificial Sequence
<220> FEATURE:
<223> OTHER INFORMATION: O. sativa-L

<400> SEQUENCE: 76

Met Val Gly Ser Asp Gly Asp Gly Gly Gly Glu Ala His
1               5                   10                  15

Ala Pro Ala Ala Pro Ala His His Arg Arg Pro Pro Arg Pro Arg
                20                  25                  30

Gly Gly Ser Gly Ala Ile Val Glu Gly Phe Ala Ala Leu Arg Arg
            35                  40                  45

Arg Ile Arg Ser Gly Ala Ala Ala Ala Arg Ala Ser Phe Gly Gly
        50                  55                  60

Asp Ser Gly Asp Glu Ala Ala Ser Gly Glu Pro Ser Ser Ser Ser Ser
65                  70                  75                  80

Ser Ser Pro Ser Arg Arg Gly Gly Asp Ser Asn Gly Ala Glu Ala
                85                  90                  95

Ser Ser Ala Ala Gly Gly Gly Gly Arg Gly Gly Gly Asp Phe
                100                 105                 110

Ser Ala Phe Thr Phe Arg Ala Ala Ala Pro Val His Arg Lys Ala Lys
            115                 120                 125

Glu Ser Pro Leu Ser Ser Asp Ala Ile Phe Lys Gln Ser His Ala Gly
                130                 135                 140

Leu Phe Asn Leu Cys Ile Val Val Leu Ile Ala Val Asn Ser Arg Leu
145                 150                 155                 160

Ile Ile Glu Asn Leu Met Lys Tyr Gly Trp Leu Ile Asp Thr Gly Phe
                165                 170                 175

Trp Phe Ser Ser Arg Ser Leu Gly Asp Trp Ser Ile Phe Met Cys Cys
                180                 185                 190

Leu Thr Leu Pro Ile Phe Pro Leu Ala Ala Phe Ile Val Glu Lys Leu
                195                 200                 205

Val Gln Arg Asn His Ile Ser Glu Leu Val Ala Val Leu Leu His Val
210                 215                 220

Ile Val Ser Thr Ala Ala Val Leu Tyr Pro Val Ile Val Ile Leu Thr
225                 230                 235                 240

Cys Asp Ser Val Tyr Met Ser Gly Val Val Leu Met Leu Phe Gly Cys
                245                 250                 255

Ile Met Trp Leu Lys Leu Val Ser Tyr Ala His Thr Ser Ser Asp Ile
                260                 265                 270

Arg Thr Leu Ala Lys Ser Gly Tyr Lys Gly Asp Ala His Pro Asn Ser
            275                 280                 285

Thr Ile Val Ser Cys Ser Tyr Asp Val Ser Leu Lys Ser Leu Ala Tyr
            290                 295                 300

Phe Met Val Ala Pro Thr Leu Cys Tyr Gln Pro Ser Tyr Pro Arg Ser
305                 310                 315                 320

Ser Cys Ile Arg Lys Gly Trp Val Val Arg Gln Phe Val Lys Leu Ile
                325                 330                 335

```
Val Phe Ile Gly Leu Met Gly Phe Ile Ile Glu Gln Tyr Ile Asn Pro
                340                 345                 350

Ile Val Arg Asn Ser Lys His Pro Leu Lys Gly Asp Phe Leu Tyr Ala
            355                 360                 365

Ile Glu Arg Val Leu Lys Leu Ser Val Pro Asn Leu Tyr Val Trp Leu
    370                 375                 380

Cys Met Phe Tyr Ser Phe Phe His Leu Trp Leu Asn Ile Leu Ala Glu
385                 390                 395                 400

Leu Leu Arg Phe Gly Asp Arg Glu Phe Tyr Lys Asp Trp Trp Asn Ala
                405                 410                 415

Lys Thr Val Ala Glu Tyr Trp Lys Met Trp Asn Met Pro Val His Arg
            420                 425                 430

Trp Met Val Arg His Leu Tyr Phe Pro Cys Leu Arg Asn Gly Ile Pro
        435                 440                 445

Lys Glu Gly Ala Ile Ile Ile Ala Phe Leu Val Ser Gly Ala Phe His
    450                 455                 460

Glu Leu Cys Ile Ala Val Pro Cys His Val Phe Lys Leu Trp Ala Phe
465                 470                 475                 480

Ile Gly Ile Met Phe Gln Val Pro Leu Val Leu Ile Thr Asn Tyr Leu
                485                 490                 495

Gln Glu Lys Phe Ser Asn Ser Met Val Gly Asn Met Ile Phe Trp Phe
            500                 505                 510

Ile Phe Cys Ile Leu Gly Gln Pro Met Cys Val Leu Leu Tyr Tyr His
        515                 520                 525

Asp Leu Ile Asn Leu Lys Glu Lys Ala Lys Gly Glu Leu Arg Gly His
    530                 535                 540

Pro Phe Glu Gly Lys Pro Ile Pro Asn Pro Leu Leu Gly Leu Asp Ser
545                 550                 555                 560

Thr Arg Thr Gly His His His His His His
                565                 570

<210> SEQ ID NO 77
<211> LENGTH: 528
<212> TYPE: PRT
<213> ORGANISM: Artificial Sequence
<220> FEATURE:
<223> OTHER INFORMATION: Z. mays-S

<400> SEQUENCE: 77

Met Ala Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
                20                  25                  30

Ser Ala Asp Ala Gly Asp Leu Ala Gly Asp Ser Ser Gly Gly Leu Arg
            35                  40                  45

Glu Asn Gly Glu Pro Gln Ser Pro Thr Asn Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
        115                 120                 125
```

```
Ala Gly Phe Trp Phe Ser Ala Arg Ser Leu Gly Asp Trp Pro Leu Leu
130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
                180                 185                 190

Thr Leu Lys Cys Asp Ser Ala Val Leu Ser Gly Phe Val Leu Met Phe
            195                 200                 205

Leu Ala Ser Ile Met Trp Met Lys Leu Val Ser Tyr Ala His Thr Asn
210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
                260                 265                 270

Pro Gln Thr Thr Cys Ile Arg Lys Gly Trp Val Thr Gln Gln Leu Ile
            275                 280                 285

Lys Cys Val Val Phe Thr Gly Leu Met Gly Phe Ile Ile Glu Gln Tyr
290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
                340                 345                 350

Val Ala Glu Leu Leu Cys Phe Gly Asp Arg Glu Phe Tyr Lys Asp Trp
            355                 360                 365

Trp Asn Ala Lys Thr Val Glu Glu Tyr Trp Arg Met Trp Asn Met Pro
370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
                420                 425                 430

Trp Ala Phe Ser Gly Ile Met Phe Gln Ile Pro Leu Val Phe Leu Thr
            435                 440                 445

Arg Tyr Leu His Ala Thr Phe Lys His Val Met Val Gly Asn Met Ile
450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg Ala Lys
                485                 490                 495

Gly Glu Leu Arg Gly His Pro Phe Glu Gly Lys Pro Ile Pro Asn Pro
                500                 505                 510

Leu Leu Gly Leu Asp Ser Thr Arg Thr Gly His His His His His
            515                 520                 525

<210> SEQ ID NO 78
<211> LENGTH: 519
```

```
<212> TYPE: PRT
<213> ORGANISM: Artificial Sequence
<220> FEATURE:
<223> OTHER INFORMATION: Z. mays-S

<400> SEQUENCE: 78
```

| | | | | | | | | | | | | | | |
|---|---|---|---|---|---|---|---|---|---|---|---|---|---|---|
| Met | Ala | Pro | Pro | Ser | Met | Pro | Ala | Ala | Ser | Asp | Arg | Ala | Gly | Pro |
| 1 | | | | 5 | | | | | 10 | | | | | 15 |
| Gly | Arg | Asp | Ala | Gly | Asp | Ser | Ser | Leu | Arg | Leu | Arg | Arg | Ala | Pro |
| | | | 20 | | | | | 25 | | | | | 30 | |
| Ser | Ala | Asp | Ala | Gly | Asp | Leu | Ala | Gly | Asp | Ser | Ser | Gly | Gly | Leu | Arg |
| | | 35 | | | | | 40 | | | | | 45 | | |
| Glu | Asn | Gly | Glu | Pro | Gln | Ser | Pro | Thr | Asn | Pro | Pro | Gln | Glu | Gln |
| | 50 | | | | | 55 | | | | | 60 | | | |
| Gln | Gln | His | Glu | Met | Leu | Tyr | Tyr | Arg | Ala | Ser | Ala | Pro | Ala | His | Arg |
| 65 | | | | | 70 | | | | | 75 | | | | | 80 |
| Arg | Val | Lys | Glu | Ser | Pro | Leu | Ser | Ser | Asp | Ala | Ile | Phe | Lys | Gln | Ser |
| | | | | 85 | | | | | 90 | | | | | 95 | |
| His | Ala | Gly | Leu | Phe | Asn | Leu | Cys | Val | Val | Leu | Ile | Ala | Val | Asn |
| | | | 100 | | | | | 105 | | | | | 110 | |
| Ser | Arg | Leu | Ile | Ile | Glu | Asn | Leu | Met | Lys | Tyr | Gly | Trp | Leu | Ile | Arg |
| | | | 115 | | | | | 120 | | | | | 125 | | |
| Thr | Asp | Phe | Trp | Phe | Ser | Ser | Arg | Ser | Leu | Arg | Asp | Trp | Pro | Leu | Phe |
| | | 130 | | | | | 135 | | | | | 140 | | | |
| Met | Cys | Cys | Ile | Ser | Leu | Ser | Ile | Phe | Pro | Leu | Ala | Ala | Phe | Thr | Val |
| 145 | | | | | 150 | | | | | 155 | | | | | 160 |
| Glu | Lys | Leu | Val | Leu | Gln | Lys | Tyr | Ile | Ser | Glu | Pro | Val | Val | Ile | Phe |
| | | | | 165 | | | | | 170 | | | | | 175 | |
| Leu | His | Ile | Ile | Ile | Thr | Met | Thr | Glu | Val | Leu | Tyr | Pro | Val | Tyr | Val |
| | | | 180 | | | | | 185 | | | | | 190 | | |
| Thr | Leu | Arg | Cys | Asp | Ser | Ala | Phe | Leu | Ser | Gly | Val | Thr | Leu | Met | Leu |
| | | 195 | | | | | 200 | | | | | 205 | | | |
| Leu | Thr | Cys | Ile | Val | Trp | Leu | Lys | Leu | Val | Ser | Tyr | Ala | His | Thr | Ser |
| | 210 | | | | | 215 | | | | | 220 | | | | |
| Tyr | Asp | Ile | Arg | Ser | Leu | Ala | Asn | Ala | Ala | Asp | Lys | Ala | Asn | Pro | Glu |
| 225 | | | | | 230 | | | | | 235 | | | | | 240 |
| Val | Ser | Tyr | Tyr | Val | Ser | Leu | Lys | Ser | Leu | Ala | Tyr | Phe | Met | Val | Ala |
| | | | | 245 | | | | | 250 | | | | | 255 | |
| Pro | Thr | Leu | Cys | Tyr | Gln | Pro | Ser | Tyr | Pro | Arg | Ser | Ala | Cys | Ile | Arg |
| | | | 260 | | | | | 265 | | | | | 270 | | |
| Lys | Gly | Trp | Val | Ala | Arg | Gln | Phe | Ala | Lys | Leu | Val | Ile | Phe | Thr | Gly |
| | | 275 | | | | | 280 | | | | | 285 | | | |
| Phe | Met | Gly | Phe | Ile | Ile | Glu | Gln | Tyr | Ile | Asn | Pro | Ile | Val | Arg | Asn |
| | 290 | | | | | 295 | | | | | 300 | | | | |
| Ser | Lys | His | Pro | Leu | Lys | Gly | Asp | Leu | Leu | Tyr | Ala | Ile | Glu | Arg | Val |
| 305 | | | | | 310 | | | | | 315 | | | | | 320 |
| Leu | Lys | Leu | Ser | Val | Pro | Asn | Leu | Tyr | Val | Trp | Leu | Cys | Met | Phe | Tyr |
| | | | | 325 | | | | | 330 | | | | | 335 | |
| Cys | Phe | Phe | His | Leu | Trp | Leu | Asn | Ile | Leu | Ala | Glu | Leu | Leu | Cys | Phe |
| | | | 340 | | | | | 345 | | | | | 350 | | |
| Gly | Asp | Arg | Glu | Phe | Tyr | Lys | Asp | Trp | Trp | Asn | Ala | Lys | Ser | Val | Gly |
| | | 355 | | | | | 360 | | | | | 365 | | | |
| Asp | Tyr | Trp | Arg | Met | Trp | Asn | Met | Pro | Val | His | Lys | Trp | Met | Val | Arg |
| | 370 | | | | | 375 | | | | | 380 | | | | |

```
His Ile Tyr Phe Pro Cys Leu Arg Ser Lys Ile Pro Lys Thr Leu Ala
385                 390                 395                 400

Ile Ile Ile Ala Phe Leu Val Ser Ala Val Phe His Glu Leu Cys Ile
            405                 410                 415

Ala Val Pro Cys Arg Leu Phe Lys Leu Trp Ala Phe Leu Gly Ile Met
        420                 425                 430

Phe Gln Val Pro Leu Val Phe Ile Thr Asn Tyr Leu Gln Glu Arg Phe
    435                 440                 445

Gly Ser Thr Val Gly Asn Met Ile Phe Trp Phe Ile Phe Cys Ile Phe
        450                 455                 460

Gly Gln Pro Met Cys Val Leu Leu Tyr Tyr His Asp Leu Met Asn Arg
465                 470                 475                 480

Lys Gly Ser Met Ser Ala Lys Gly Glu Leu Arg Gly His Pro Phe Glu
            485                 490                 495

Gly Lys Pro Ile Pro Asn Pro Leu Leu Gly Leu Asp Ser Thr Arg Thr
        500                 505                 510

Gly His His His His His His
        515
```

<210> SEQ ID NO 79
<211> LENGTH: 529
<212> TYPE: PRT
<213> ORGANISM: Artificial Sequence
<220> FEATURE:
<223> OTHER INFORMATION: Z. mays-S

<400> SEQUENCE: 79

```
Met Ala Pro Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Pro Gln Glu Gln
50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
            85                  90                  95

His Ala Gly Leu Leu Asn Leu Cys Ile Val Val Leu Ala Val Asn
        100                 105                 110

Ser Arg Leu Ile Ile Glu Asn Leu Met Lys Tyr Gly Leu Leu Ile Arg
    115                 120                 125

Ala Gly Phe Trp Phe Ser Gly Thr Ser Leu Ala Asp Trp Pro Leu Leu
    130                 135                 140

Met Cys Cys Leu Thr Leu Pro Thr Phe Pro Leu Ala Ala Leu Met Val
145                 150                 155                 160

Glu Lys Leu Ala Gln Arg Lys Leu Ile Ser Lys His Val Val Ile Leu
                165                 170                 175

Leu His Ile Val Ile Thr Thr Ser Val Leu Val Tyr Pro Val Val Val
            180                 185                 190

Ile Leu Lys Cys Asp Ser Ala Val Leu Ser Gly Phe Val Leu Met Phe
        195                 200                 205

Leu Ala Ser Ile Ile Trp Leu Lys Leu Val Ser Phe Ala His Thr Asn
    210                 215                 220
```

```
Tyr Asp Ile Arg Met Leu Ser Lys Ser Ile Glu Lys Gly Val Thr His
225                 230                 235                 240

Asp Ile Ser Ile Asp Pro Glu Asn Ile Lys Trp Pro Thr Phe Lys Arg
            245                 250                 255

Leu Ser Tyr Phe Met Leu Ala Pro Thr Leu Cys Tyr Gln Pro Ser Tyr
        260                 265                 270

Pro Arg Thr Thr Tyr Ile Arg Lys Gly Trp Val Val Arg Gln Leu Ile
    275                 280                 285

Lys Cys Leu Val Phe Thr Gly Leu Met Gly Phe Ile Ile Glu Gln Tyr
290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
            325                 330                 335

Val Trp Leu Cys Met Phe Tyr Cys Phe Phe His Leu Trp Leu Asn Ile
        340                 345                 350

Leu Ala Glu Leu Leu Cys Phe Gly Asp Arg Glu Phe Tyr Lys Asp Trp
    355                 360                 365

Trp Asn Ala Lys Thr Val Glu Glu Tyr Trp Arg Met Trp Asn Met Pro
370                 375                 380

Val His Lys Trp Val Ile Arg His Ile Tyr Phe Pro Cys Ile Arg Asn
385                 390                 395                 400

Gly Phe Ser Lys Gly Val Ala Ile Leu Ile Ser Phe Leu Val Ser Ala
            405                 410                 415

Ala Phe His Glu Leu Cys Val Ala Val Pro Cys His Ile Phe Lys Phe
        420                 425                 430

Trp Ala Phe Ile Gly Ile Met Phe Gln Ile Pro Leu Val Phe Leu Thr
    435                 440                 445

Lys Tyr Leu Gln Asp Lys Phe Asn Asn Thr Met Val Gly Asn Met Ile
450                 455                 460

Phe Trp Phe Phe Phe Ser Ile Leu Gly Gln Pro Met Cys Val Leu Leu
465                 470                 475                 480

Tyr Tyr His Asp Val Met Asn Arg Gln Gln Ala Gln Thr Asn Arg Ala
            485                 490                 495

Lys Gly Glu Leu Arg Gly His Pro Phe Glu Gly Lys Pro Ile Pro Asn
        500                 505                 510

Pro Leu Leu Gly Leu Asp Ser Thr Arg Thr Gly His His His His His
    515                 520                 525

His

<210> SEQ ID NO 80
<211> LENGTH: 527
<212> TYPE: PRT
<213> ORGANISM: Artificial Sequence
<220> FEATURE:
<223> OTHER INFORMATION: Z. mays-S

<400> SEQUENCE: 80

Met Ala Pro Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
            20                  25                  30

Ser Ala Asp Ala Gly Asp Leu Ala Gly Asp Ser Gly Gly Leu Arg
        35                  40                  45

Glu Asn Gly Glu Pro Gln Ser Pro Thr Asn Pro Pro Gln Glu Gln
```

```
                50                  55                  60
Gln Gln His Glu Met Leu Tyr Tyr Arg Ala Ser Ala Pro Ala His Arg
 65                  70                  75                  80

Arg Val Lys Glu Ser Pro Leu Ser Ser Asp Ala Ile Phe Lys Gln Ser
                 85                  90                  95

His Ala Gly Leu Phe Asn Leu Cys Ile Val Val Leu Val Ala Val Asn
                100                 105                 110

Ser Arg Leu Ile Ile Glu Asn Leu Met Lys Tyr Gly Leu Leu Ile Arg
                115                 120                 125

Ala Gly Phe Trp Phe Asn Asp Lys Ser Leu Arg Asp Trp Pro Leu Leu
    130                 135                 140

Met Cys Cys Leu Ser Leu Pro Ala Phe Pro Leu Gly Ala Phe Ala Val
145                 150                 155                 160

Glu Lys Leu Ala Phe Asn Asn Val Ile Thr Asp Ala Val Ala Thr Cys
                165                 170                 175

Leu His Ile Phe Leu Ser Thr Thr Glu Ile Val Tyr Pro Val Leu Val
                180                 185                 190

Ile Leu Lys Cys Asp Ser Ala Val Leu Ser Gly Phe Leu Leu Ile Phe
                195                 200                 205

Ile Ala Cys Ile Val Trp Leu Lys Leu Val Ser Phe Ala His Thr Asn
    210                 215                 220

His Asp Ile Arg Gln Leu Thr Met Gly Gly Lys Lys Val Asp Asn Glu
225                 230                 235                 240

Leu Ser Thr Val Asp Met Asp Asn Leu Gln Pro Pro Thr Leu Gly Asn
                245                 250                 255

Leu Ile Tyr Phe Met Met Ala Pro Thr Leu Cys Tyr Gln Pro Ser Tyr
                260                 265                 270

Pro Arg Thr Ser Cys Val Arg Lys Gly Trp Leu Ile Arg Gln Ile Ile
                275                 280                 285

Leu Tyr Leu Ile Phe Thr Gly Leu Gln Gly Phe Ile Ile Glu Gln Tyr
                290                 295                 300

Ile Asn Pro Ile Val Val Asn Ser Gln His Pro Leu Lys Gly Gly Leu
305                 310                 315                 320

Leu Asn Ala Val Glu Thr Val Leu Lys Leu Ser Leu Pro Asn Val Tyr
                325                 330                 335

Leu Trp Leu Cys Met Phe Tyr Ala Phe Phe His Leu Trp Leu Ser Ile
                340                 345                 350

Leu Ala Glu Ile Leu Arg Phe Gly Asp Arg Glu Phe Tyr Lys Asp Trp
                355                 360                 365

Trp Asn Ala Lys Thr Ile Asp Glu Tyr Trp Arg Lys Trp Asn Met Pro
370                 375                 380

Val His Lys Trp Val Arg His Ile Tyr Phe Pro Cys Met Arg Asn
385                 390                 395                 400

Gly Ile Ser Lys Glu Val Ala Val Leu Ile Ser Phe Leu Val Ser Ala
                405                 410                 415

Val Leu His Glu Ile Cys Val Ala Val Pro Cys Arg Ile Leu Lys Phe
                420                 425                 430

Trp Ala Phe Leu Gly Ile Met Leu Gln Ile Pro Leu Ile Val Leu Thr
                435                 440                 445

Ala Tyr Leu Lys Ser Lys Phe Arg Asp Thr Met Val Gly Asn Met Ile
                450                 455                 460

Phe Trp Phe Phe Phe Cys Ile Tyr Gly Gln Pro Met Cys Leu Leu Leu
465                 470                 475                 480
```

Tyr Tyr His Asp Val Met Asn Arg Ile Glu Lys Ala Arg Ala Lys Gly
                485                 490                 495

Glu Leu Arg Gly His Pro Phe Glu Gly Lys Pro Ile Pro Asn Pro Leu
            500                 505                 510

Leu Gly Leu Asp Ser Thr Arg Thr Gly His His His His His His
        515                 520                 525

<210> SEQ ID NO 81
<211> LENGTH: 527
<212> TYPE: PRT
<213> ORGANISM: Artificial Sequence
<220> FEATURE:
<223> OTHER INFORMATION: Z. mays-S

<400> SEQUENCE: 81

Met Ala Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
            20                  25                  30

Ser Ala Asp Ala Gly Asp Leu Ala Gly Asp Ser Ser Gly Gly Leu Arg
            35                  40                  45

Glu Asn Gly Glu Pro Gln Ser Pro Thr Asn Pro Pro Pro Gln Glu Gln
50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Lys Gln Ser
                85                  90                  95

His Ala Gly Leu Phe Asn Leu Cys Ile Val Val Leu Ala Val Asn
            100                 105                 110

Ser Arg Leu Ile Ile Glu Asn Leu Met Lys Tyr Gly Leu Leu Ile Arg
            115                 120                 125

Ser Gly Phe Trp Phe Asn Ala Thr Ser Leu Arg Asp Trp Pro Leu Leu
            130                 135                 140

Met Cys Cys Leu Ser Leu Pro Ile Phe Pro Leu Gly Ala Phe Ala Val
145                 150                 155                 160

Glu Lys Leu Ala Phe Asn Asn Leu Ile Ser Asp Pro Ala Thr Thr Cys
                165                 170                 175

Phe His Ile Leu Phe Thr Thr Phe Glu Ile Val Tyr Pro Val Leu Val
            180                 185                 190

Ile Leu Lys Cys Asp Ser Ala Val Leu Ser Gly Phe Val Leu Met Phe
            195                 200                 205

Ile Ala Cys Ile Val Trp Leu Lys Leu Val Ser Phe Ala His Thr Asn
210                 215                 220

His Asp Ile Arg Lys Leu Ile Thr Ser Gly Lys Lys Val Asp Asn Glu
225                 230                 235                 240

Leu Thr Ala Ala Gly Ile Asp Asn Leu Gln Ala Pro Thr Leu Gly Ser
                245                 250                 255

Leu Thr Tyr Phe Met Met Ala Pro Thr Leu Cys Tyr Gln Pro Ser Tyr
            260                 265                 270

Pro Arg Thr Pro Tyr Val Arg Lys Gly Trp Leu Val Arg Gln Val Ile
            275                 280                 285

Leu Tyr Leu Ile Phe Thr Gly Leu Gln Gly Phe Ile Ile Glu Gln Tyr
            290                 295                 300

Ile Asn Pro Ile Val Val Asn Ser Gln His Pro Leu Met Gly Gly Leu
305                 310                 315                 320

```
Leu Asn Ala Val Glu Thr Val Leu Lys Leu Ser Leu Pro Asn Val Tyr
                325                 330                 335

Leu Trp Leu Cys Met Phe Tyr Cys Leu Phe His Leu Trp Leu Asn Ile
            340                 345                 350

Leu Ala Glu Ile Leu Arg Phe Gly Asp Arg Glu Phe Tyr Lys Asp Trp
        355                 360                 365

Trp Asn Ala Lys Thr Ile Asp Glu Tyr Trp Arg Lys Trp Asn Met Pro
    370                 375                 380

Val His Lys Trp Ile Val Arg His Ile Tyr Phe Pro Cys Met Arg Asn
385                 390                 395                 400

Gly Ile Ser Lys Glu Val Ala Val Phe Ile Ser Phe Phe Val Ser Ala
                405                 410                 415

Val Leu His Glu Leu Cys Val Ala Val Pro Cys His Ile Leu Lys Phe
            420                 425                 430

Trp Ala Phe Leu Gly Ile Met Leu Gln Ile Pro Leu Ile Ile Leu Thr
        435                 440                 445

Ser Tyr Leu Lys Asn Lys Phe Ser Asp Thr Met Val Gly Asn Met Ile
    450                 455                 460

Phe Trp Phe Phe Phe Cys Ile Tyr Gly Gln Pro Met Cys Val Leu Leu
465                 470                 475                 480

Tyr Tyr His Asp Val Met Asn Arg Thr Glu Lys Ala Lys Ala Lys Gly
                485                 490                 495

Glu Leu Arg Gly His Pro Phe Glu Gly Lys Pro Ile Pro Asn Pro Leu
            500                 505                 510

Leu Gly Leu Asp Ser Thr Arg Thr Gly His His His His His His
        515                 520                 525

<210> SEQ ID NO 82
<211> LENGTH: 524
<212> TYPE: PRT
<213> ORGANISM: Artificial Sequence
<220> FEATURE:
<223> OTHER INFORMATION: Z. mays-S

<400> SEQUENCE: 82

Met Ala Pro Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Lys Gln Ser
                85                  90                  95

His Ala Gly Leu Phe Asn Leu Cys Ile Val Val Leu Ile Ala Val Asn
            100                 105                 110

Ser Arg Leu Ile Ile Glu Asn Leu Met Lys Tyr Gly Trp Leu Ile Asp
        115                 120                 125

Thr Gly Phe Trp Phe Ser Ser Arg Ser Leu Gly Asp Trp Ser Ile Phe
    130                 135                 140

Met Cys Cys Leu Thr Leu Pro Ile Phe Pro Leu Ala Ala Phe Ile Val
145                 150                 155                 160
```

Glu Lys Leu Val Gln Arg Asn His Ile Ser Glu Leu Val Ala Val Leu
                165                 170                 175

Leu His Val Ile Val Ser Thr Ala Ala Val Leu Tyr Pro Val Ile Val
                180                 185                 190

Ile Leu Thr Cys Asp Ser Val Tyr Met Ser Gly Val Val Leu Met Leu
                195                 200                 205

Phe Gly Cys Ile Met Trp Leu Lys Leu Val Ser Tyr Ala His Thr Ser
    210                 215                 220

Ser Asp Ile Arg Thr Leu Ala Lys Ser Gly Tyr Lys Gly Asp Ala His
225                 230                 235                 240

Pro Asn Ser Thr Ile Val Ser Cys Ser Tyr Asp Val Ser Leu Lys Ser
                245                 250                 255

Leu Ala Tyr Phe Met Val Ala Pro Thr Leu Cys Tyr Gln Pro Ser Tyr
                260                 265                 270

Pro Arg Ser Ser Cys Ile Arg Lys Gly Trp Val Val Arg Gln Phe Val
                275                 280                 285

Lys Leu Ile Val Phe Ile Gly Leu Met Gly Phe Ile Ile Glu Gln Tyr
                290                 295                 300

Ile Asn Pro Ile Val Arg Asn Ser Lys His Pro Leu Lys Gly Asp Phe
305                 310                 315                 320

Leu Tyr Ala Ile Glu Arg Val Leu Lys Leu Ser Val Pro Asn Leu Tyr
                325                 330                 335

Val Trp Leu Cys Met Phe Tyr Ser Phe Phe His Leu Trp Leu Asn Ile
                340                 345                 350

Leu Ala Glu Leu Leu Arg Phe Gly Asp Arg Glu Phe Tyr Lys Asp Trp
                355                 360                 365

Trp Asn Ala Lys Thr Val Ala Glu Tyr Trp Lys Met Trp Asn Met Pro
                370                 375                 380

Val His Arg Trp Met Val Arg His Leu Tyr Phe Pro Cys Leu Arg Asn
385                 390                 395                 400

Gly Ile Pro Lys Glu Gly Ala Ile Ile Ile Ala Phe Leu Val Ser Gly
                405                 410                 415

Ala Phe His Glu Leu Cys Ile Ala Val Pro Cys His Val Phe Lys Leu
                420                 425                 430

Trp Ala Phe Ile Gly Ile Met Phe Gln Val Pro Leu Val Leu Ile Thr
                435                 440                 445

Asn Tyr Leu Gln Glu Lys Phe Ser Asn Ser Met Val Gly Asn Met Ile
                450                 455                 460

Phe Trp Phe Ile Phe Cys Ile Leu Gly Gln Pro Met Cys Val Leu Leu
465                 470                 475                 480

Tyr Tyr His Asp Leu Ile Asn Leu Lys Glu Lys Ala Lys Gly Glu Leu
                485                 490                 495

Arg Gly His Pro Phe Glu Gly Lys Pro Ile Pro Asn Pro Leu Leu Gly
                500                 505                 510

Leu Asp Ser Thr Arg Thr Gly His His His His
                515                 520

<210> SEQ ID NO 83
<211> LENGTH: 546
<212> TYPE: PRT
<213> ORGANISM: Artificial Sequence
<220> FEATURE:
<223> OTHER INFORMATION: Z. mays-L

<400> SEQUENCE: 83

-continued

```
Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Leu
            20                  25                  30

Arg Arg Arg Leu Arg Ser Gly Ala Ala Val Ala Ala Arg Ala Ser Phe
            35                  40                  45

Ala Ala Asp Ser Gly Asp Glu Ser Gly Pro Gly Glu Pro Ser Ser Ser
        50                  55                  60

Arg Arg Arg Asp Asn Ser Gly Ala Ser Ala Ala Gly Gly Arg
65                  70                  75                  80

Ala Gly Ala Gly Asp Phe Ser Ala Phe Thr Phe Arg Ala Ala Pro
                85                  90                  95

Val His Arg Lys Ala Lys Glu Ser Pro Leu Ser Ser Asp Ala Ile Phe
                100                 105                 110

Lys Gln Ser His Ala Gly Leu Phe Asn Leu Cys Ile Val Val Leu Val
            115                 120                 125

Ala Val Asn Ser Arg Leu Ile Ile Glu Asn Leu Met Lys Tyr Gly Leu
        130                 135                 140

Leu Ile Arg Ser Gly Phe Trp Phe Asn Ala Thr Ser Leu Arg Asp Trp
145                 150                 155                 160

Pro Leu Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
                180                 185                 190

Thr Thr Cys Phe His Ile Leu Phe Thr Thr Phe Glu Ile Val Tyr Pro
            195                 200                 205

Val Leu Val Ile Leu Lys Cys Asp Ser Ala Val Leu Ser Gly Phe Val
    210                 215                 220

Leu Met Phe Ile Ala Cys Ile Val Trp Leu Lys Leu Val Ser Phe Ala
225                 230                 235                 240

His Thr Asn His Asp Ile Arg Lys Leu Ile Thr Ser Gly Lys Lys Val
                245                 250                 255

Asp Asn Glu Leu Thr Ala Ala Gly Ile Asp Asn Leu Gln Ala Pro Thr
                260                 265                 270

Leu Gly Ser Leu Thr Tyr Phe Met Met Ala Pro Thr Leu Cys Tyr Gln
            275                 280                 285

Pro Ser Tyr Pro Arg Thr Pro Tyr Val Arg Lys Gly Trp Leu Val Arg
        290                 295                 300

Gln Val Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Met
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Cys Leu Phe His Leu Trp
            355                 360                 365

Leu Asn Ile Leu Ala Glu Ile Leu Arg Phe Gly Asp Arg Glu Phe Tyr
        370                 375                 380

Lys Asp Trp Trp Asn Ala Lys Thr Ile Asp Glu Tyr Trp Arg Lys Trp
385                 390                 395                 400

Asn Met Pro Val His Lys Trp Ile Val Arg His Ile Tyr Phe Pro Cys
                405                 410                 415
```

Met Arg Asn Gly Ile Ser Lys Glu Val Ala Val Phe Ile Ser Phe Phe
                420                 425                 430

Val Ser Ala Val Leu His Glu Leu Cys Val Ala Val Pro Cys His Ile
            435                 440                 445

Leu Lys Phe Trp Ala Phe Leu Gly Ile Met Leu Gln Ile Pro Leu Ile
450                 455                 460

Ile Leu Thr Ser Tyr Leu Lys Asn Lys Phe Ser Asp Thr Met Val Gly
465                 470                 475                 480

Asn Met Ile Phe Trp Phe Phe Phe Cys Ile Tyr Gly Gln Pro Met Cys
                485                 490                 495

Val Leu Leu Tyr Tyr His Asp Val Met Asn Arg Thr Glu Lys Ala Lys
            500                 505                 510

Ala Lys Gly Glu Leu Arg Gly His Pro Phe Glu Gly Lys Pro Ile Pro
            515                 520                 525

Asn Pro Leu Leu Gly Leu Asp Ser Thr Arg Thr Gly His His His
530                 535                 540

His His
545

<210> SEQ ID NO 84
<211> LENGTH: 538
<212> TYPE: PRT
<213> ORGANISM: Artificial Sequence
<220> FEATURE:
<223> OTHER INFORMATION: Z. mays-L

<400> SEQUENCE: 84

Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Val Val Leu Ile
        115                 120                 125

Ala Val Asn Ser Arg Leu Ile Ile Glu Asn Leu Met Lys Tyr Gly Trp
130                 135                 140

Leu Ile Arg Thr Asp Phe Trp Phe Ser Arg Ser Leu Arg Asp Trp
145                 150                 155                 160

Pro Leu Phe Met Cys Cys Ile Ser Leu Ser Ile Phe Pro Leu Ala Ala
                165                 170                 175

Phe Thr Val Glu Lys Leu Val Leu Gln Lys Tyr Ile Ser Glu Pro Val
            180                 185                 190

Val Ile Phe Leu His Ile Ile Ile Thr Met Thr Glu Val Leu Tyr Pro
        195                 200                 205

Val Tyr Val Thr Leu Arg Cys Asp Ser Ala Phe Leu Ser Gly Val Thr
    210                 215                 220

Leu Met Leu Leu Thr Cys Ile Val Trp Leu Lys Leu Val Ser Tyr Ala
225                 230                 235                 240

His Thr Ser Tyr Asp Ile Arg Ser Leu Ala Asn Ala Ala Asp Lys Ala
            245                 250                 255

Asn Pro Glu Val Ser Tyr Tyr Val Ser Leu Lys Ser Leu Ala Tyr Phe
        260                 265                 270

Met Val Ala Pro Thr Leu Cys Tyr Gln Pro Ser Tyr Pro Arg Ser Ala
    275                 280                 285

Cys Ile Arg Lys Gly Trp Val Ala Arg Gln Phe Ala Lys Leu Val Ile
290                 295                 300

Phe Thr Gly Phe Met Gly Phe Ile Ile Glu Gln Tyr Ile Asn Pro Ile
305                 310                 315                 320

Val Arg Asn Ser Lys His Pro Leu Lys Gly Asp Leu Leu Tyr Ala Ile
                325                 330                 335

Glu Arg Val Leu Lys Leu Ser Val Pro Asn Leu Tyr Val Trp Leu Cys
            340                 345                 350

Met Phe Tyr Cys Phe Phe His Leu Trp Leu Asn Ile Leu Ala Glu Leu
        355                 360                 365

Leu Cys Phe Gly Asp Arg Glu Phe Tyr Lys Asp Trp Trp Asn Ala Lys
370                 375                 380

Ser Val Gly Asp Tyr Trp Arg Met Trp Asn Met Pro Val His Lys Trp
385                 390                 395                 400

Met Val Arg His Ile Tyr Phe Pro Cys Leu Arg Ser Lys Ile Pro Lys
                405                 410                 415

Thr Leu Ala Ile Ile Ile Ala Phe Leu Val Ser Ala Val Phe His Glu
            420                 425                 430

Leu Cys Ile Ala Val Pro Cys Arg Leu Phe Lys Leu Trp Ala Phe Leu
        435                 440                 445

Gly Ile Met Phe Gln Val Pro Leu Val Phe Ile Thr Asn Tyr Leu Gln
450                 455                 460

Glu Arg Phe Gly Ser Thr Val Gly Asn Met Ile Phe Trp Phe Ile Phe
465                 470                 475                 480

Cys Ile Phe Gly Gln Pro Met Cys Val Leu Leu Tyr Tyr His Asp Leu
                485                 490                 495

Met Asn Arg Lys Gly Ser Met Ser Ala Lys Gly Glu Leu Arg Gly His
            500                 505                 510

Pro Phe Glu Gly Lys Pro Ile Pro Asn Pro Leu Leu Gly Leu Asp Ser
        515                 520                 525

Thr Arg Thr Gly His His His His His
530                 535

<210> SEQ ID NO 85
<211> LENGTH: 548
<212> TYPE: PRT
<213> ORGANISM: Artificial Sequence
<220> FEATURE:
<223> OTHER INFORMATION: Z. mays-L

<400> SEQUENCE: 85

Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

-continued

```
Ala Ala Asp Ser Gly Asp Glu Ser Gly Pro Gly Glu Pro Ser Ser Ser
    50                  55                  60

Arg Arg Arg Asp Asn Ser Gly Ala Ser Ala Ala Gly Gly Arg
65              70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Arg Gln Ser His Ala Gly Leu Leu Asn Leu Cys Ile Val Val Leu Val
            115                 120                 125

Ala Val Asn Ser Arg Leu Ile Ile Glu Asn Leu Met Lys Tyr Gly Leu
        130                 135                 140

Leu Ile Arg Ala Gly Phe Trp Phe Ser Gly Thr Ser Leu Ala Asp Trp
145                 150                 155                 160

Pro Leu Leu Met Cys Cys Leu Thr Leu Pro Thr Phe Pro Leu Ala Ala
                165                 170                 175

Leu Met Val Glu Lys Leu Ala Gln Arg Lys Leu Ile Ser Lys His Val
            180                 185                 190

Val Ile Leu Leu His Ile Val Ile Thr Thr Ser Val Leu Val Tyr Pro
        195                 200                 205

Val Val Val Ile Leu Lys Cys Asp Ser Ala Val Leu Ser Gly Phe Val
    210                 215                 220

Leu Met Phe Leu Ala Ser Ile Ile Trp Leu Lys Leu Val Ser Phe Ala
225                 230                 235                 240

His Thr Asn Tyr Asp Ile Arg Met Leu Ser Lys Ser Ile Glu Lys Gly
                245                 250                 255

Val Thr His Asp Ile Ser Ile Asp Pro Glu Asn Ile Lys Trp Pro Thr
            260                 265                 270

Phe Lys Arg Leu Ser Tyr Phe Met Leu Ala Pro Thr Leu Cys Tyr Gln
        275                 280                 285

Pro Ser Tyr Pro Arg Thr Thr Tyr Ile Arg Lys Gly Trp Val Val Arg
    290                 295                 300

Gln Leu Ile Lys Cys Leu Val Phe Thr Gly Leu Met Gly Phe Ile Ile
305                 310                 315                 320

Glu Gln Tyr Ile Asn Pro Ile Val Lys Asn Ser Lys His Pro Leu Lys
                325                 330                 335

Gly Asn Phe Leu Asn Ala Ile Glu Arg Val Leu Lys Leu Ser Val Pro
            340                 345                 350

Thr Leu Tyr Val Trp Leu Cys Met Phe Tyr Cys Phe Phe His Leu Trp
        355                 360                 365

Leu Asn Ile Leu Ala Glu Leu Leu Cys Phe Gly Asp Arg Glu Phe Tyr
    370                 375                 380

Lys Asp Trp Trp Asn Ala Lys Thr Val Glu Glu Tyr Trp Arg Met Trp
385                 390                 395                 400

Asn Met Pro Val His Lys Trp Val Ile Arg His Ile Tyr Phe Pro Cys
                405                 410                 415

Ile Arg Asn Gly Phe Ser Lys Gly Val Ala Ile Leu Ile Ser Phe Leu
            420                 425                 430

Val Ser Ala Ala Phe His Glu Leu Cys Val Ala Val Pro Cys His Ile
        435                 440                 445

Phe Lys Phe Trp Ala Phe Ile Gly Ile Met Phe Gln Ile Pro Leu Val
    450                 455                 460

Phe Leu Thr Lys Tyr Leu Gln Asp Lys Phe Asn Asn Thr Met Val Gly
```

```
                465                 470                 475                 480
Asn Met Ile Phe Trp Phe Phe Phe Ser Ile Leu Gly Gln Pro Met Cys
            485                 490                 495

Val Leu Leu Tyr Tyr His Asp Val Met Asn Arg Gln Gln Ala Gln Thr
            500                 505                 510

Asn Arg Ala Lys Gly Glu Leu Arg Gly His Pro Phe Glu Gly Lys Pro
            515                 520                 525

Ile Pro Asn Pro Leu Leu Gly Leu Asp Ser Thr Arg Thr Gly His His
            530                 535                 540

His His His His
545

<210> SEQ ID NO 86
<211> LENGTH: 546
<212> TYPE: PRT
<213> ORGANISM: Artificial Sequence
<220> FEATURE:
<223> OTHER INFORMATION: Z. mays-L

<400> SEQUENCE: 86

Met Ala Asp Ser Glu Asp Ala Pro Pro Ala Val His Arg Arg Pro Pro
1               5                  10                  15

Arg Pro Ala Arg Gly Ala Ala Ala Gln Gly Phe Ala Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Val
        115                 120                 125

Ala Val Asn Ser Arg Leu Ile Ile Glu Asn Leu Met Lys Tyr Gly Leu
    130                 135                 140

Leu Ile Arg Ala Gly Phe Trp Phe Asn Asp Lys Ser Leu Arg Asp Trp
145                 150                 155                 160

Pro Leu Leu Met Cys Cys Leu Ser Leu Pro Ala Phe Pro Leu Gly Ala
                165                 170                 175

Phe Ala Val Glu Lys Leu Ala Phe Asn Asn Val Ile Thr Asp Ala Val
            180                 185                 190

Ala Thr Cys Leu His Ile Phe Leu Ser Thr Thr Glu Ile Val Tyr Pro
        195                 200                 205

Val Leu Val Ile Leu Lys Cys Asp Ser Ala Val Leu Ser Gly Phe Leu
    210                 215                 220

Leu Ile Phe Ile Ala Cys Ile Val Trp Leu Lys Leu Val Ser Phe Ala
225                 230                 235                 240

His Thr Asn His Asp Ile Arg Gln Leu Thr Met Gly Gly Lys Lys Val
                245                 250                 255

Asp Asn Glu Leu Ser Thr Val Asp Met Asp Asn Leu Gln Pro Pro Thr
            260                 265                 270

Leu Gly Asn Leu Ile Tyr Phe Met Met Ala Pro Thr Leu Cys Tyr Gln
```

```
                    275                 280                 285
Pro Ser Tyr Pro Arg Thr Ser Cys Val Arg Lys Gly Trp Leu Ile Arg
    290                 295                 300

Gln Ile Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Lys
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Ala Phe Phe His Leu Trp
        355                 360                 365

Leu Ser Ile Leu Ala Glu Ile Leu Arg Phe Gly Asp Arg Glu Phe Tyr
    370                 375                 380

Lys Asp Trp Trp Asn Ala Lys Thr Ile Asp Glu Tyr Trp Arg Lys Trp
385                 390                 395                 400

Asn Met Pro Val His Lys Trp Val Val Arg His Ile Tyr Phe Pro Cys
                405                 410                 415

Met Arg Asn Gly Ile Ser Lys Glu Val Ala Val Leu Ile Ser Phe Leu
            420                 425                 430

Val Ser Ala Val Leu His Glu Ile Cys Val Ala Val Pro Cys Arg Ile
        435                 440                 445

Leu Lys Phe Trp Ala Phe Leu Gly Ile Met Leu Gln Ile Pro Leu Ile
    450                 455                 460

Val Leu Thr Ala Tyr Leu Lys Ser Lys Phe Arg Asp Thr Met Val Gly
465                 470                 475                 480

Asn Met Ile Phe Trp Phe Phe Phe Cys Ile Tyr Gly Gln Pro Met Cys
                485                 490                 495

Leu Leu Leu Tyr Tyr His Asp Val Met Asn Arg Ile Glu Lys Ala Arg
            500                 505                 510

Ala Lys Gly Glu Leu Arg Gly His Pro Phe Glu Gly Lys Pro Ile Pro
        515                 520                 525

Asn Pro Leu Leu Gly Leu Asp Ser Thr Arg Thr Gly His His His His
    530                 535                 540

His His
545

<210> SEQ ID NO 87
<211> LENGTH: 547
<212> TYPE: PRT
<213> ORGANISM: Artificial Sequence
<220> FEATURE:
<223> OTHER INFORMATION: Z. mays-L

<400> SEQUENCE: 87

Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
```

```
                    85                  90                  95
Val His Arg Lys Ala Lys Glu Ser Pro Leu Ser Ser Asp Ala Ile Phe
                100                 105                 110

Arg Gln Ser His Ala Gly Leu Leu Asn Leu Cys Ile Val Val Leu Ile
                115                 120                 125

Ala Val Asn Ser Arg Leu Ile Ile Glu Asn Leu Met Lys Tyr Gly Leu
    130                 135                 140

Leu Ile Arg Ala Gly Phe Trp Phe Ser Ala Arg Ser Leu Gly Asp Trp
145                 150                 155                 160

Pro Leu Leu Met Cys Cys Leu Thr Leu Pro Val Phe Pro Leu Val Ala
                165                 170                 175

Leu Met Ala Glu Lys Leu Ile Thr Arg Lys Leu Ile Gly Glu His Val
                180                 185                 190

Val Ile Leu Leu His Ile Ile Thr Thr Ser Ala Ile Val Tyr Pro
                195                 200                 205

Val Val Val Thr Leu Lys Cys Asp Ser Ala Val Leu Ser Gly Phe Val
    210                 215                 220

Leu Met Phe Leu Ala Ser Ile Met Trp Met Lys Leu Val Ser Tyr Ala
225                 230                 235                 240

His Thr Asn Tyr Asp Ile Arg Val Leu Ser Lys Ser Thr Glu Lys Gly
                245                 250                 255

Ala Ala Tyr Gly Asn Tyr Val Asp Pro Glu Asn Met Lys Asp Pro Thr
                260                 265                 270

Phe Lys Ser Leu Val Tyr Phe Met Leu Ala Pro Thr Leu Cys Tyr Gln
                275                 280                 285

Pro Thr Tyr Pro Gln Thr Thr Cys Ile Arg Lys Gly Trp Val Thr Gln
                290                 295                 300

Gln Leu Ile Lys Cys Val Val Phe Thr Gly Leu Met Gly Phe Ile Ile
305                 310                 315                 320

Glu Gln Tyr Ile Asn Pro Ile Val Lys Asn Ser Lys His Pro Leu Lys
                325                 330                 335

Gly Asn Phe Leu Asn Ala Ile Glu Arg Val Leu Lys Leu Ser Val Pro
                340                 345                 350

Thr Leu Tyr Val Trp Leu Cys Met Phe Tyr Cys Phe Phe His Leu Trp
                355                 360                 365

Leu Asn Ile Val Ala Glu Leu Leu Cys Phe Gly Asp Arg Glu Phe Tyr
                370                 375                 380

Lys Asp Trp Trp Asn Ala Lys Thr Val Glu Glu Tyr Trp Arg Met Trp
385                 390                 395                 400

Asn Met Pro Val His Lys Trp Ile Ile Arg His Ile Tyr Phe Pro Cys
                405                 410                 415

Ile Arg Lys Gly Phe Ser Arg Gly Val Ala Ile Leu Ile Ser Phe Leu
                420                 425                 430

Val Ser Ala Val Phe His Glu Ile Cys Ile Ala Val Pro Cys His Ile
                435                 440                 445

Phe Lys Phe Trp Ala Phe Ser Gly Ile Met Phe Gln Ile Pro Leu Val
                450                 455                 460

Phe Leu Thr Arg Tyr Leu His Ala Thr Phe Lys His Val Met Val Gly
465                 470                 475                 480

Asn Met Ile Phe Trp Phe Phe Ser Ile Val Gly Gln Pro Met Cys
                485                 490                 495

Val Leu Leu Tyr Tyr His Asp Val Met Asn Arg Gln Ala Gln Ala Ser
                500                 505                 510
```

```
Arg Ala Lys Gly Glu Leu Arg Gly His Pro Phe Glu Gly Lys Pro Ile
        515                 520                 525

Pro Asn Pro Leu Leu Gly Leu Asp Ser Thr Arg Thr Gly His His His
        530                 535                 540

His His His
545

<210> SEQ ID NO 88
<211> LENGTH: 544
<212> TYPE: PRT
<213> ORGANISM: Artificial Sequence
<220> FEATURE:
<223> OTHER INFORMATION: Z. mays-L

<400> SEQUENCE: 88

Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Ile
        115                 120                 125

Ala Val Asn Ser Arg Leu Ile Ile Glu Asn Leu Met Lys Tyr Gly Trp
    130                 135                 140

Leu Ile Asp Thr Gly Phe Trp Phe Ser Ser Arg Ser Leu Gly Asp Trp
145                 150                 155                 160

Ser Ile Phe Met Cys Cys Leu Thr Leu Pro Ile Phe Pro Leu Ala Ala
                165                 170                 175

Phe Ile Val Glu Lys Leu Val Gln Arg Asn His Ile Ser Glu Leu Val
            180                 185                 190

Ala Val Leu Leu His Val Ile Val Ser Thr Ala Ala Val Leu Tyr Pro
        195                 200                 205

Val Ile Val Ile Leu Thr Cys Asp Ser Val Tyr Met Ser Gly Val Val
    210                 215                 220

Leu Met Leu Phe Gly Cys Ile Met Trp Leu Lys Leu Val Ser Tyr Ala
225                 230                 235                 240

His Thr Ser Ser Asp Ile Arg Thr Leu Ala Lys Ser Gly Tyr Lys Gly
                245                 250                 255

Asp Ala His Pro Asn Ser Thr Ile Val Ser Cys Ser Tyr Asp Val Ser
            260                 265                 270

Leu Lys Ser Leu Ala Tyr Phe Met Val Ala Pro Thr Leu Cys Tyr Gln
        275                 280                 285

Pro Ser Tyr Pro Arg Ser Ser Cys Ile Arg Lys Gly Trp Val Val Arg
    290                 295                 300

Gln Phe Val Lys Leu Ile Val Phe Ile Gly Leu Met Gly Phe Ile Ile
305                 310                 315                 320
```

Glu Gln Tyr Ile Asn Pro Ile Val Arg Asn Ser Lys His Pro Leu Lys
                325                 330                 335

Gly Asp Phe Leu Tyr Ala Ile Glu Arg Val Leu Lys Leu Ser Val Pro
            340                 345                 350

Asn Leu Tyr Val Trp Leu Cys Met Phe Tyr Ser Phe Phe His Leu Trp
        355                 360                 365

Leu Asn Ile Leu Ala Glu Leu Leu Arg Phe Gly Asp Arg Glu Phe Tyr
370                 375                 380

Lys Asp Trp Trp Asn Ala Lys Thr Val Ala Glu Tyr Trp Lys Met Trp
385                 390                 395                 400

Asn Met Pro Val His Arg Trp Met Val Arg His Leu Tyr Phe Pro Cys
                405                 410                 415

Leu Arg Asn Gly Ile Pro Lys Glu Gly Ala Ile Ile Ala Phe Leu
            420                 425                 430

Val Ser Gly Ala Phe His Glu Leu Cys Ile Ala Val Pro Cys His Val
        435                 440                 445

Phe Lys Leu Trp Ala Phe Ile Gly Ile Met Phe Gln Val Pro Leu Val
    450                 455                 460

Leu Ile Thr Asn Tyr Leu Gln Glu Lys Phe Ser Asn Ser Met Val Gly
465                 470                 475                 480

Asn Met Ile Phe Trp Phe Ile Phe Cys Ile Leu Gly Gln Pro Met Cys
                485                 490                 495

Val Leu Leu Tyr Tyr His Asp Leu Ile Asn Leu Lys Glu Lys Ala Lys
            500                 505                 510

Gly Glu Leu Arg Gly His Pro Phe Glu Gly Lys Pro Ile Pro Asn Pro
        515                 520                 525

Leu Leu Gly Leu Asp Ser Thr Arg Thr Gly His His His His His His
530                 535                 540

<210> SEQ ID NO 89
<211> LENGTH: 552
<212> TYPE: PRT
<213> ORGANISM: Artificial Sequence
<220> FEATURE:
<223> OTHER INFORMATION: T. majus

<400> SEQUENCE: 89

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

```
Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
            165                 170                 175

Leu Pro Ile Phe Pro Leu Ala Ala Phe Ile Val Glu Lys Leu Val Gln
        180                 185                 190

Arg Asn His Ile Ser Glu Leu Val Ala Val Leu Leu His Val Ile Val
            195                 200                 205

Ser Thr Ala Ala Val Leu Tyr Pro Val Ile Val Ile Leu Thr Cys Asp
210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
            245                 250                 255

Leu Ala Lys Ser Gly Tyr Lys Gly Asp Ala His Pro Asn Ser Thr Ile
        260                 265                 270

Val Ser Cys Ser Tyr Asp Val Ser Leu Lys Ser Leu Ala Tyr Phe Met
            275                 280                 285

Val Ala Pro Thr Leu Cys Tyr Gln Pro Ser Tyr Pro Arg Ser Ser Cys
290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
            355                 360                 365

Phe Tyr Ser Phe Phe His Leu Trp Leu Asn Ile Leu Ala Glu Leu Leu
        370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys Ala Lys Gly Glu Leu Arg Gly His Pro Phe
            515                 520                 525

Glu Gly Lys Pro Ile Pro Asn Pro Leu Leu Gly Leu Asp Ser Thr Arg
        530                 535                 540

Thr Gly His His His His His His
545                 550
```

<210> SEQ ID NO 90
<211> LENGTH: 546
<212> TYPE: PRT
<213> ORGANISM: Artificial Sequence
<220> FEATURE:
<223> OTHER INFORMATION: T. majus

<400> SEQUENCE: 90

```
Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
                100                 105                 110

Pro Leu Ser Ser Asp Ala Ile Phe Lys Gln Ser His Ala Gly Leu Phe
            115                 120                 125

Asn Leu Cys Val Val Val Leu Ile Ala Val Asn Ser Arg Leu Ile Ile
        130                 135                 140

Glu Asn Leu Met Lys Tyr Gly Trp Leu Ile Arg Thr Asp Phe Trp Phe
145                 150                 155                 160

Ser Ser Arg Ser Leu Arg Asp Trp Pro Leu Phe Met Cys Cys Ile Ser
                165                 170                 175

Leu Ser Ile Phe Pro Leu Ala Ala Phe Thr Val Glu Lys Leu Val Leu
            180                 185                 190

Gln Lys Tyr Ile Ser Glu Pro Val Val Ile Phe Leu His Ile Ile Ile
        195                 200                 205

Thr Met Thr Glu Val Leu Tyr Pro Val Tyr Val Thr Leu Arg Cys Asp
    210                 215                 220

Ser Ala Phe Leu Ser Gly Val Thr Leu Met Leu Leu Thr Cys Ile Val
225                 230                 235                 240

Trp Leu Lys Leu Val Ser Tyr Ala His Thr Ser Tyr Asp Ile Arg Ser
                245                 250                 255

Leu Ala Asn Ala Ala Asp Lys Ala Asn Pro Glu Val Ser Tyr Tyr Val
            260                 265                 270

Ser Leu Lys Ser Leu Ala Tyr Phe Met Val Ala Pro Thr Leu Cys Tyr
        275                 280                 285

Gln Pro Ser Tyr Pro Arg Ser Ala Cys Ile Arg Lys Gly Trp Val Ala
    290                 295                 300

Arg Gln Phe Ala Lys Leu Val Ile Phe Thr Gly Phe Met Gly Phe Ile
305                 310                 315                 320

Ile Glu Gln Tyr Ile Asn Pro Ile Val Arg Asn Ser Lys His Pro Leu
                325                 330                 335

Lys Gly Asp Leu Leu Tyr Ala Ile Glu Arg Val Leu Lys Leu Ser Val
            340                 345                 350

Pro Asn Leu Tyr Val Trp Leu Cys Met Phe Tyr Cys Phe Phe His Leu
        355                 360                 365
```

Trp Leu Asn Ile Leu Ala Glu Leu Leu Cys Phe Gly Asp Arg Glu Phe
    370                 375                 380

Tyr Lys Asp Trp Trp Asn Ala Lys Ser Val Gly Asp Tyr Trp Arg Met
385                 390                 395                 400

Trp Asn Met Pro Val His Lys Trp Met Val Arg His Ile Tyr Phe Pro
                405                 410                 415

Cys Leu Arg Ser Lys Ile Pro Lys Thr Leu Ala Ile Ile Ala Phe
                420                 425                 430

Leu Val Ser Ala Val Phe His Glu Leu Cys Ile Ala Val Pro Cys Arg
            435                 440                 445

Leu Phe Lys Leu Trp Ala Phe Leu Gly Ile Met Phe Gln Val Pro Leu
450                 455                 460

Val Phe Ile Thr Asn Tyr Leu Gln Glu Arg Phe Gly Ser Thr Val Gly
465                 470                 475                 480

Asn Met Ile Phe Trp Phe Ile Phe Cys Ile Phe Gly Gln Pro Met Cys
                485                 490                 495

Val Leu Leu Tyr Tyr His Asp Leu Met Asn Arg Lys Gly Ser Met Ser
                500                 505                 510

Ala Lys Gly Glu Leu Arg Gly His Pro Phe Glu Gly Lys Pro Ile Pro
            515                 520                 525

Asn Pro Leu Leu Gly Leu Asp Ser Thr Arg Thr Gly His His His
            530                 535                 540

His His
545

<210> SEQ ID NO 91
<211> LENGTH: 556
<212> TYPE: PRT
<213> ORGANISM: Artificial Sequence
<220> FEATURE:
<223> OTHER INFORMATION: T. majus

<400> SEQUENCE: 91

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
                20                  25                  30

Val Ile Glu Pro Ser Ser Ser Gly Phe Thr Ser Thr Asn Gly Val Pro
            35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Val Arg Glu Ser
            100                 105                 110

Pro Leu Ser Ser Asp Ala Ile Phe Arg Gln Ser His Ala Gly Leu Leu
        115                 120                 125

Asn Leu Cys Ile Val Val Leu Val Ala Val Asn Ser Arg Leu Ile Ile
    130                 135                 140

Glu Asn Leu Met Lys Tyr Gly Leu Leu Ile Arg Ala Gly Phe Trp Phe
145                 150                 155                 160

Ser Gly Thr Ser Leu Ala Asp Trp Pro Leu Leu Met Cys Cys Leu Thr
                165                 170                 175

Leu Pro Thr Phe Pro Leu Ala Ala Leu Met Val Glu Lys Leu Ala Gln
            180                 185                 190

Arg Lys Leu Ile Ser Lys His Val Val Ile Leu Leu His Ile Val Ile
        195                 200                 205

Thr Thr Ser Val Leu Val Tyr Pro Val Val Ile Leu Lys Cys Asp
    210                 215                 220

Ser Ala Val Leu Ser Gly Phe Val Leu Met Phe Leu Ala Ser Ile Ile
225                 230                 235                 240

Trp Leu Lys Leu Val Ser Phe Ala His Thr Asn Tyr Asp Ile Arg Met
                245                 250                 255

Leu Ser Lys Ser Ile Glu Lys Gly Val Thr His Asp Ile Ser Ile Asp
            260                 265                 270

Pro Glu Asn Ile Lys Trp Pro Thr Phe Lys Arg Leu Ser Tyr Phe Met
        275                 280                 285

Leu Ala Pro Thr Leu Cys Tyr Gln Pro Ser Tyr Pro Arg Thr Thr Tyr
    290                 295                 300

Ile Arg Lys Gly Trp Val Val Arg Gln Leu Ile Lys Cys Leu Val Phe
305                 310                 315                 320

Thr Gly Leu Met Gly Phe Ile Ile Glu Gln Tyr Ile Asn Pro Ile Val
                325                 330                 335

Lys Asn Ser Lys His Pro Leu Lys Gly Asn Phe Leu Asn Ala Ile Glu
            340                 345                 350

Arg Val Leu Lys Leu Ser Val Pro Thr Leu Tyr Val Trp Leu Cys Met
        355                 360                 365

Phe Tyr Cys Phe Phe His Leu Trp Leu Asn Ile Leu Ala Glu Leu Leu
    370                 375                 380

Cys Phe Gly Asp Arg Glu Phe Tyr Lys Asp Trp Trp Asn Ala Lys Thr
385                 390                 395                 400

Val Glu Glu Tyr Trp Arg Met Trp Asn Met Pro Val His Lys Trp Val
                405                 410                 415

Ile Arg His Ile Tyr Phe Pro Cys Ile Arg Asn Gly Phe Ser Lys Gly
            420                 425                 430

Val Ala Ile Leu Ile Ser Phe Leu Val Ser Ala Ala Phe His Glu Leu
        435                 440                 445

Cys Val Ala Val Pro Cys His Ile Phe Lys Phe Trp Ala Phe Ile Gly
    450                 455                 460

Ile Met Phe Gln Ile Pro Leu Val Phe Leu Thr Lys Tyr Leu Gln Asp
465                 470                 475                 480

Lys Phe Asn Asn Thr Met Val Gly Asn Met Ile Phe Trp Phe Phe
                485                 490                 495

Ser Ile Leu Gly Gln Pro Met Cys Val Leu Leu Tyr Tyr His Asp Val
            500                 505                 510

Met Asn Arg Gln Gln Ala Gln Thr Asn Arg Ala Lys Gly Glu Leu Arg
        515                 520                 525

Gly His Pro Phe Glu Gly Lys Pro Ile Pro Asn Pro Leu Leu Gly Leu
    530                 535                 540

Asp Ser Thr Arg Thr Gly His His His His His
545                 550                 555

<210> SEQ ID NO 92
<211> LENGTH: 554
<212> TYPE: PRT
<213> ORGANISM: Artificial Sequence
<220> FEATURE:
<223> OTHER INFORMATION: T. majus

<400> SEQUENCE: 92

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Val Ala Val Asn Ser Arg Leu Ile Ile
130                 135                 140

Glu Asn Leu Met Lys Tyr Gly Leu Leu Ile Arg Ala Gly Phe Trp Phe
145                 150                 155                 160

Asn Asp Lys Ser Leu Arg Asp Trp Pro Leu Leu Met Cys Cys Leu Ser
            165                 170                 175

Leu Pro Ala Phe Pro Leu Gly Ala Phe Ala Val Glu Lys Leu Ala Phe
        180                 185                 190

Asn Asn Val Ile Thr Asp Ala Val Ala Thr Cys Leu His Ile Phe Leu
            195                 200                 205

Ser Thr Thr Glu Ile Val Tyr Pro Val Leu Val Ile Leu Lys Cys Asp
210                 215                 220

Ser Ala Val Leu Ser Gly Phe Leu Leu Ile Phe Ile Ala Cys Ile Val
225                 230                 235                 240

Trp Leu Lys Leu Val Ser Phe Ala His Thr Asn His Asp Ile Arg Gln
            245                 250                 255

Leu Thr Met Gly Gly Lys Lys Val Asp Asn Glu Leu Ser Thr Val Asp
        260                 265                 270

Met Asp Asn Leu Gln Pro Pro Thr Leu Gly Asn Leu Ile Tyr Phe Met
            275                 280                 285

Met Ala Pro Thr Leu Cys Tyr Gln Pro Ser Tyr Pro Arg Thr Ser Cys
        290                 295                 300

Val Arg Lys Gly Trp Leu Ile Arg Gln Ile Ile Leu Tyr Leu Ile Phe
305                 310                 315                 320

Thr Gly Leu Gln Gly Phe Ile Ile Glu Gln Tyr Ile Asn Pro Ile Val
            325                 330                 335

Val Asn Ser Gln His Pro Leu Lys Gly Gly Leu Leu Asn Ala Val Glu
        340                 345                 350

Thr Val Leu Lys Leu Ser Leu Pro Asn Val Tyr Leu Trp Leu Cys Met
        355                 360                 365

Phe Tyr Ala Phe Phe His Leu Trp Leu Ser Ile Leu Ala Glu Ile Leu
        370                 375                 380

Arg Phe Gly Asp Arg Glu Phe Tyr Lys Asp Trp Trp Asn Ala Lys Thr
385                 390                 395                 400

Ile Asp Glu Tyr Trp Arg Lys Trp Asn Met Pro Val His Lys Trp Val

```
                    405                 410                 415
Val Arg His Ile Tyr Phe Pro Cys Met Arg Asn Gly Ile Ser Lys Glu
                420                 425                 430

Val Ala Val Leu Ile Ser Phe Leu Val Ser Ala Val Leu His Glu Ile
            435                 440                 445

Cys Val Ala Val Pro Cys Arg Ile Leu Lys Phe Trp Ala Phe Leu Gly
        450                 455                 460

Ile Met Leu Gln Ile Pro Leu Ile Val Leu Thr Ala Tyr Leu Lys Ser
465                 470                 475                 480

Lys Phe Arg Asp Thr Met Val Gly Asn Met Ile Phe Trp Phe Phe
                485                 490                 495

Cys Ile Tyr Gly Gln Pro Met Cys Leu Leu Leu Tyr Tyr His Asp Val
            500                 505                 510

Met Asn Arg Ile Glu Lys Ala Arg Ala Lys Gly Glu Leu Arg Gly His
                515                 520                 525

Pro Phe Glu Gly Lys Pro Ile Pro Asn Pro Leu Leu Gly Leu Asp Ser
            530                 535                 540

Thr Arg Thr Gly His His His His His
545                 550

<210> SEQ ID NO 93
<211> LENGTH: 555
<212> TYPE: PRT
<213> ORGANISM: Artificial Sequence
<220> FEATURE:
<223> OTHER INFORMATION: T. majus

<400> SEQUENCE: 93

Met Ala Val Ala Glu Ser Ser Gln Asn Thr Thr Thr Met Ser Gly His
1               5                   10                  15

Gly Asp Ser Asp Leu Asn Asn Phe Arg Arg Lys Pro Ser Ser Ser
                20                  25                  30

Val Ile Glu Pro Ser Ser Ser Gly Phe Thr Ser Thr Asn Gly Val Pro
            35                  40                  45

Ala Thr Gly His Val Ala Glu Asn Arg Asp Gln Asp Arg Val Gly Ala
        50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Val Arg Glu Ser
            100                 105                 110

Pro Leu Ser Ser Asp Ala Ile Phe Arg Gln Ser His Ala Gly Leu Leu
        115                 120                 125

Asn Leu Cys Ile Val Val Leu Ile Ala Val Asn Ser Arg Leu Ile Ile
    130                 135                 140

Glu Asn Leu Met Lys Tyr Gly Leu Leu Ile Arg Ala Gly Phe Trp Phe
145                 150                 155                 160

Ser Ala Arg Ser Leu Gly Asp Trp Pro Leu Leu Met Cys Cys Leu Thr
                165                 170                 175

Leu Pro Val Phe Pro Leu Val Ala Leu Met Ala Glu Lys Leu Ile Thr
            180                 185                 190

Arg Lys Leu Ile Gly Glu His Val Val Leu Leu His Ile Ile Ile
        195                 200                 205

Thr Thr Ser Ala Ile Val Tyr Pro Val Val Val Thr Leu Lys Cys Asp
```

```
                      210                 215                 220
Ser Ala Val Leu Ser Gly Phe Val Leu Met Phe Leu Ala Ser Ile Met
225                 230                 235                 240

Trp Met Lys Leu Val Ser Tyr Ala His Thr Asn Tyr Asp Ile Arg Val
                245                 250                 255

Leu Ser Lys Ser Thr Glu Lys Gly Ala Ala Tyr Gly Asn Tyr Val Asp
            260                 265                 270

Pro Glu Asn Met Lys Asp Pro Thr Phe Lys Ser Leu Val Tyr Phe Met
        275                 280                 285

Leu Ala Pro Thr Leu Cys Tyr Gln Pro Thr Tyr Pro Gln Thr Thr Cys
    290                 295                 300

Ile Arg Lys Gly Trp Val Thr Gln Gln Leu Ile Lys Cys Val Val Phe
305                 310                 315                 320

Thr Gly Leu Met Gly Phe Ile Ile Glu Gln Tyr Ile Asn Pro Ile Val
                325                 330                 335

Lys Asn Ser Lys His Pro Leu Lys Gly Asn Phe Leu Asn Ala Ile Glu
            340                 345                 350

Arg Val Leu Lys Leu Ser Val Pro Thr Leu Tyr Val Trp Leu Cys Met
        355                 360                 365

Phe Tyr Cys Phe Phe His Leu Trp Leu Asn Ile Val Ala Glu Leu Leu
    370                 375                 380

Cys Phe Gly Asp Arg Glu Phe Tyr Lys Asp Trp Trp Asn Ala Lys Thr
385                 390                 395                 400

Val Glu Glu Tyr Trp Arg Met Trp Asn Met Pro Val His Lys Trp Ile
                405                 410                 415

Ile Arg His Ile Tyr Phe Pro Cys Ile Arg Lys Gly Phe Ser Arg Gly
            420                 425                 430

Val Ala Ile Leu Ile Ser Phe Leu Val Ser Ala Val Phe His Glu Ile
        435                 440                 445

Cys Ile Ala Val Pro Cys His Ile Phe Lys Phe Trp Ala Phe Ser Gly
    450                 455                 460

Ile Met Phe Gln Ile Pro Leu Val Phe Leu Thr Arg Tyr Leu His Ala
465                 470                 475                 480

Thr Phe Lys His Val Met Val Gly Asn Met Ile Phe Trp Phe Phe Phe
                485                 490                 495

Ser Ile Val Gly Gln Pro Met Cys Val Leu Leu Tyr Tyr His Asp Val
            500                 505                 510

Met Asn Arg Gln Ala Gln Ala Ser Arg Ala Lys Gly Glu Leu Arg Gly
        515                 520                 525

His Pro Phe Glu Gly Lys Pro Ile Pro Asn Pro Leu Leu Gly Leu Asp
    530                 535                 540

Ser Thr Arg Thr Gly His His His His His
545                 550                 555

<210> SEQ ID NO 94
<211> LENGTH: 554
<212> TYPE: PRT
<213> ORGANISM: Artificial Sequence
<220> FEATURE:
<223> OTHER INFORMATION: T. majus

<400> SEQUENCE: 94

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
```

```
                 20                  25                  30
Val Ile Glu Pro Ser Ser Ser Gly Phe Thr Ser Thr Asn Gly Val Pro
             35                  40                  45

Ala Thr Gly His Val Ala Glu Asn Arg Asp Gln Asp Arg Val Gly Ala
 50                  55                  60

Met Glu Asn Ala Thr Gly Ser Val Asn Leu Ile Gly Asn Gly Gly Gly
 65                  70                  75                  80

Val Val Ile Gly Asn Glu Glu Lys Gln Val Gly Glu Thr Asp Ile Arg
                 85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
            115                 120                 125

Asn Leu Cys Ile Val Val Leu Val Ala Val Asn Ser Arg Leu Ile Ile
            130                 135                 140

Glu Asn Leu Met Lys Tyr Gly Leu Leu Ile Arg Ser Gly Phe Trp Phe
145                 150                 155                 160

Asn Ala Thr Ser Leu Arg Asp Trp Pro Leu Leu Met Cys Cys Leu Ser
                165                 170                 175

Leu Pro Ile Phe Pro Leu Gly Ala Phe Ala Val Glu Lys Leu Ala Phe
            180                 185                 190

Asn Asn Leu Ile Ser Asp Pro Ala Thr Thr Cys Phe His Ile Leu Phe
            195                 200                 205

Thr Thr Phe Glu Ile Val Tyr Pro Val Leu Val Ile Leu Lys Cys Asp
        210                 215                 220

Ser Ala Val Leu Ser Gly Phe Val Leu Met Phe Ile Ala Cys Ile Val
225                 230                 235                 240

Trp Leu Lys Leu Val Ser Phe Ala His Thr Asn His Asp Ile Arg Lys
                245                 250                 255

Leu Ile Thr Ser Gly Lys Lys Val Asp Asn Glu Leu Thr Ala Ala Gly
            260                 265                 270

Ile Asp Asn Leu Gln Ala Pro Thr Leu Gly Ser Leu Thr Tyr Phe Met
            275                 280                 285

Met Ala Pro Thr Leu Cys Tyr Gln Pro Ser Tyr Pro Arg Thr Pro Tyr
        290                 295                 300

Val Arg Lys Gly Trp Leu Val Arg Gln Val Ile Leu Tyr Leu Ile Phe
305                 310                 315                 320

Thr Gly Leu Gln Gly Phe Ile Ile Glu Gln Tyr Ile Asn Pro Ile Val
                325                 330                 335

Val Asn Ser Gln His Pro Leu Met Gly Gly Leu Leu Asn Ala Val Glu
            340                 345                 350

Thr Val Leu Lys Leu Ser Leu Pro Asn Val Tyr Leu Trp Leu Cys Met
            355                 360                 365

Phe Tyr Cys Leu Phe His Leu Trp Leu Asn Ile Leu Ala Glu Ile Leu
        370                 375                 380

Arg Phe Gly Asp Arg Glu Phe Tyr Lys Asp Trp Trp Asn Ala Lys Thr
385                 390                 395                 400

Ile Asp Glu Tyr Trp Arg Lys Trp Asn Met Pro Val His Lys Trp Ile
                405                 410                 415

Val Arg His Ile Tyr Phe Pro Cys Met Arg Asn Gly Ile Ser Lys Glu
            420                 425                 430

Val Ala Val Phe Ile Ser Phe Val Ser Ala Val Leu His Glu Leu
            435                 440                 445
```

```
Cys Val Ala Val Pro Cys His Ile Leu Lys Phe Trp Ala Phe Leu Gly
        450                 455                 460

Ile Met Leu Gln Ile Pro Leu Ile Ile Leu Thr Ser Tyr Leu Lys Asn
465                 470                 475                 480

Lys Phe Ser Asp Thr Met Val Gly Asn Met Ile Phe Trp Phe Phe
                    485                 490                 495

Cys Ile Tyr Gly Gln Pro Met Cys Val Leu Leu Tyr Tyr His Asp Val
            500                 505                 510

Met Asn Arg Thr Glu Lys Ala Lys Ala Lys Gly Glu Leu Arg Gly His
        515                 520                 525

Pro Phe Glu Gly Lys Pro Ile Pro Asn Pro Leu Leu Gly Leu Asp Ser
    530                 535                 540

Thr Arg Thr Gly His His His His His His
545                 550
```

<210> SEQ ID NO 95
<211> LENGTH: 1812
<212> TYPE: DNA
<213> ORGANISM: Artificial Sequence
<220> FEATURE:
<223> OTHER INFORMATION: T. majus

<400> SEQUENCE: 95

```
ggatccacaa gtttgtacaa aaaagcaggc ttctagattt ctagtttttct ccatataaaa      60
aaaatattct ctgagcttct cgattctcta aaaagacaag gccaaaaaaa acaccatggc     120
tgttgctgaa tcttctcaga acaccactac tatgtctgga cacggtgatt ctgacctcaa     180
cgtaaaagaa gatgtttttt atttccagca atgttacatt gttatacgta atgatgag      240
tttagtgatc aagttcctct tgattcttc tttcttgttg cagaacttca gacgtagaaa     300
gccttctagc tctgttatcg agccttcttc ttctggattc acctctacta acggtgttcc     360
tgctactgga catgttgctg agaacagaga tcaggataga gttggagcta tggaaaacgc     420
taccggatct gttaacctta tcggaaacgg tggaggtgtt gttatcggta acgaggaaaa     480
gcaagttgga gagactgata tcagattcac ctacagacca tcttttcccag ctcacagaag     540
agttagggag tctccactct cgagtgatgc tatcttcaag cagtctcacg ctggactttt     600
caacctctgc atcgttgttc ttatcgctgt taatagcaga cttatcatcg agaacctcat     660
gaagtacgga tggcttatcg atactggatt ctggttctct tctcgttctc ttggtgactg     720
gtctatcttc atgtgctgtc ttactctccc tatcttccct cttgctgctt catcgttga      780
gaagcttgtt cagaggaacc atatcgctga gcttgttgct gttcttctcc acgttatcgt     840
ttctactgct gctgttctct accctgttat cgttatcctt acctgcgatt ctgtttacat     900
gtctggtgtt gtgcttatgc ttttcggatg catcatgtgg cttaagctcg tttcttacgc     960
tcacacctct tcagatatca gaaccctcgc taagtctgga tacaaaggtg atgctcaccc    1020
taactctact atcgtgtctt gctcttacga tgtgtctctt aagtctctcg cttacttcat    1080
ggttgctcct acccttttgtt accaaccttc ttaccctaga tctagctgca tcagaaaggg    1140
atgggttgtg agacaattcg ttaagctcat cgtgttcatc ggactatgg gattcatcat    1200
cgagcagtac atcaacccta tcgtgagaaa ctctaagcac cctctcaagg gagatttcct    1260
ttacgctatc gagagagtgc ttaagctttc tgtgcctaac cttacgtttt ggctctgcat    1320
gttctactca ttcttccacc tttgcttaa catccttgct gagttgctta gattcggaga    1380
cagagagttc tacaaggatt ggtggaacgc taagactgtt gctgagtact ggaagatgtg    1440
```

-continued

```
gaacatgcct gttcatagat ggatggttag gcacctttac ttcccttgtc tcagaaacgg    1500
aatccctaaa gagggtgcta tcatcattgc tttcttggtg tctggtgctt ccatgagtt    1560
gtgtatcgct gttccttgtc acgttttcaa gctctgggct ttcatcggaa tcatgttcca    1620
agttcctctc gttcttatca ctaactacct ccaagagaag ttctctaaca gcatggtggg    1680
aaacatgatt ttctggttca ttttctgcat ccttggacag cctatgtgtg ttcttctcta    1740
ctaccacgat ctcatcaacc tcaaagagaa gtgaaggtac cacccagctt tcttgtacaa    1800
agtggtgagc tc                                                        1812
```

<210> SEQ ID NO 96
<211> LENGTH: 1740
<212> TYPE: DNA
<213> ORGANISM: Artificial Sequence
<220> FEATURE:
<223> OTHER INFORMATION: Z. mays-S

<400> SEQUENCE: 96

```
gaattcacaa gtttgtacaa aaaagcaggc ttctagattt ctagttttct ccatataaaa      60
aaaatattct ctgagcttct cgattctcta aaaagacaag gccaaaaaaa acaccatggc     120
tcctccacct tctatgcctg ctgcttctga tagagctgga cctggaagag atgctggcga     180
ttctgtaaaa gaagatgttt tttatttcca gcaatgttac attgttatac gtataatgat     240
gagtttagtg atcaagttcc tctttgattc ttctttcttg ttgcagtcat ctctcagact     300
tagaagggct ccatcgctg acgctggtga ccttgctggt gatagctctg gtggacttag     360
agaaaacggt gagcctcaat ctcctactaa ccctccacct caagagcaac aacagcacga     420
gatgctttac tacagagctt ctgctcctgc tcatagaaga gtgaaagaat ctccactctc     480
gagtgatgct atcttcagac agtctcatgc tggacttctc aacctctgca tcgttgttct     540
tatcgctgtg aacagcagac ttatcatcga gaacctcatg aagtacggac ttctcatcag     600
agctggattc tggttctctg ctagatctct tggagattgg cctcttctta tgtgctgtct     660
taccccttcct gttttccctc ttgttgctct tatggccgag aagcttatca ctagaaagct     720
catcggagag catgttgtta tccttctcca catcatcatc actacctctg ctatcgttta     780
ccctgttgtt gttacccta agtgcgattc tgctgttctt tctggattcg tgcttatgtt     840
cctcgcttct atcatgtgga tgaagctcgt ttcttacgct cacaccaact acgatatcag     900
agtgctctct aagtctactg agaagggtgc tgcttacgga aactatgtgg accctgagaa     960
catgaaggat cctaccttca gtctctcgt gtacttcatg cttgctccta ccctttgtta    1020
ccaacctact taccctcaga ctacctgtat cagaaaggga tgggttaccc aacaactcat    1080
caagtgcgtt gtgttcactg gacttatggg attcatcatc gagcagtaca tcaacctat    1140
cgtgaagaac tctaagcacc ctcttaaggg aaacttcctc aacgctatcg agagagttct    1200
caagcttctct gttcctactc tttacgtttg gctctgcatg ttctactgtt tcttccacct    1260
ttggctcaac atcgttgctg agcttctctg tttcggagat cgtgagttct acaaggattg    1320
gtggaacgct aagactgttg aggaatactg gcgtatgtgg aacatgcctg ttcataagtg    1380
gatcatcagg cacatctact ccccttgcat caggaaggga ttctctaggg gagttgctat    1440
ccttatctct ttcctcgttt ctgctgtttt ccatgagatc tgtatcgctg ttccttgtca    1500
catcttcaag ttctggggctt tctctggtat catgttccag atccctcttg ttttccttac    1560
cagatacctt cacgctactt tcaagcacgt tatggtggga aacatgattt tctggttctt    1620
```

```
tttcagcatc gttggacagc ctatgtgtgt tcttctctac taccacgatg ttatgaacag    1680
acaagctcag gcttctaggt gaaggtacca cccagctttc ttgtacaaag tggtgagctc    1740
```

<210> SEQ ID NO 97
<211> LENGTH: 1794
<212> TYPE: DNA
<213> ORGANISM: Artificial Sequence
<220> FEATURE:
<223> OTHER INFORMATION: Z. mays-L

<400> SEQUENCE: 97

```
ggatccacaa gtttgtacaa aaaagcaggc ttctagattt ctagttttct ccatataaaa      60
aaaatattct ctgagcttct cgattctcta aaaagacaag gccaaaaaaa acaccatggc     120
tgattctgag gatgctcctc ctgctgttca tagaaggcct ccaagacctg ctagaggtgc     180
tgctgctgct gtaaaagaag atgttttta tttccagcaa tgttacattg ttatacgtat      240
aatgatgagt ttagtgatca agttcctctt tgattcttct ttcttgttgc agcaaggatt     300
cgctgctgct cttagaagaa ggcttagaag cggagctgct gttgctgcta gagcttcttt     360
cgctgctgat tctggtgatg agtctggacc tggtgagcct tcttcatcta ggcgtagaga     420
taactctggt ggagcttctt ctgctgctgg tggtagagct ggtgctggtg atttctctgc     480
tttcaccttc agagctgctg ctcctgttca cagaaaggct aaagaatctc cactctcgag     540
tgatgctatc ttcaagcagt ctcacgctgg acttttcaac ctctgcatcg ttgttcttgt     600
tgctgtgaac agcagactca tcatcgagaa cctcatgaag tacggacttc tcatcagatc     660
tggattctgg ttcaacgcta cctctcttag agattggcct cttcttatgt gctgtctctc     720
tcttccaatc ttccctcttg gtgctttcgc tgttgagaag cttgctttca caacctcat     780 ctctgatcct gctactactt gcttccacat cctttcact accttcgaga tcgtttaccc     840
tgttctcgtt atccttaaat gcgattctgc tgttctttct ggattcgtgc tcatgttcat     900
tgcttgcatc gtttggctta agctcgtttc tttcgctcac actaaccacg atatcagaaa     960
gctcatcacc tctggaaaga aggttgacaa cgagcttact gctgctggaa tcgataacct    1020
tcaggctcct actcttggat ctctcaccta cttcatgatg ctcctaccc tttgttacca    1080 accttcttac cctagaaccc cttacgttag aaagggatgg cttgttagac aggttatcct    1140
ctaccttatc ttcactggac ttcagggatt catcatcgag cagtacatca ccctatcgt    1200 tgttaactct cagcatcctc ttatgggagg acttcttaac gctgttgaga ctgtgcttaa    1260
gctttctctc cctaacgttt acctttggct ctgtatgttc tactgccttt tccaccttg    1320 gcttaacatc cttgctgaga tccttagatt cggagacaga gagttctaca aggattggtg    1380
gaacgctaag actatcgatg agtactggcg taagtggaac atgcctgttc ataagtggat    1440
cgtgaggcat atctacttcc cttgcatgag aaacggaatc tctaaagagg ttgccgtttt    1500
catctctttc ttcgtgtctg ctgttctcca tgagctttgt gttgctgttc cttgccacat    1560
ccttaagttc tgggctttcc ttggaatcat gcttcagatc cctcttatca tccttaccag    1620
ctacctcaag aacaagttct ctgataccat ggtgggaaac atgatttct ggttctttt      1680 ctgcatctac ggacaaccta tgtgtgttct tctctactac cacgatgtta tgaacagaac    1740
cgagaaggcc aagtgaaggt accacccagc tttcttgtac aaagtggtga gctc         1794
```

<210> SEQ ID NO 98
<211> LENGTH: 518
<212> TYPE: PRT
<213> ORGANISM: Artificial Sequence
<220> FEATURE:
<223> OTHER INFORMATION: T. majus

<400> SEQUENCE: 98

Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Ser Gly Phe Thr Ser Thr Asn Gly Val Pro
        35                  40                      45

Ala Thr Gly His Val Ala Glu Asn Arg Asp Gln Asp Arg Val Gly Ala
    50                  55                      60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ala Glu Leu Val Ala Val Leu Leu His Val Ile Val
        195                 200                 205

Ser Thr Ala Ala Val Leu Tyr Pro Val Ile Val Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
        275                 280                 285

Val Ala Pro Thr Leu Cys Tyr Gln Pro Ser Tyr Pro Arg Ser Ser Cys
    290                 295                 300

Ile Arg Lys Gly Trp Val Val Arg Gln Phe Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
        355                 360                 365

Phe Tyr Ser Phe Phe His Leu Trp Leu Asn Ile Leu Ala Glu Leu Leu
    370                 375                 380

Arg Phe Gly Asp Arg Glu Phe Tyr Lys Asp Trp Trp Asn Ala Lys Thr
385                 390                 395                 400

```
Val Ala Glu Tyr Trp Lys Met Trp Asn Met Pro Val His Arg Trp Met
            405                 410                 415

Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
            435                 440                 445

Cys Ile Ala Val Pro Cys His Val Phe Lys Leu Trp Ala Phe Ile Gly
450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
            485                 490                 495

Cys Ile Leu Gly Gln Pro Met Cys Val Leu Leu Tyr Tyr His Asp Leu
            500                 505                 510

Ile Asn Leu Lys Glu Lys
            515

<210> SEQ ID NO 99
<211> LENGTH: 494
<212> TYPE: PRT
<213> ORGANISM: Artificial Sequence
<220> FEATURE:
<223> OTHER INFORMATION: Z. mays-S

<400> SEQUENCE: 99

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
            35                  40                  45

Glu Asn Gly Glu Pro Gln Ser Pro Thr Asn Pro Pro Pro Gln Glu Gln
    50                  55                  60

Gln Gln His Glu Met Leu Tyr Tyr Arg Ala Ser Ala Pro Ala His Arg
65              70                  75                  80

Arg Val Lys Glu Ser Pro Leu Ser Ser Asp Ala Ile Phe Arg Gln Ser
            85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
            115                 120                 125

Ala Gly Phe Trp Phe Ser Ala Arg Ser Leu Gly Asp Trp Pro Leu Leu
            130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
            165                 170                 175

Leu His Ile Ile Ile Thr Thr Ser Ala Ile Val Tyr Pro Val Val Val
            180                 185                 190

Thr Leu Lys Cys Asp Ser Ala Val Leu Ser Gly Phe Val Leu Met Phe
            195                 200                 205

Leu Ala Ser Ile Met Trp Met Lys Leu Val Ser Tyr Ala His Thr Asn
            210                 215                 220

Tyr Asp Ile Arg Val Leu Ser Lys Ser Thr Glu Lys Gly Ala Ala Tyr
225                 230                 235                 240
```

```
Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
            260                 265                 270

Pro Gln Thr Thr Cys Ile Arg Lys Gly Trp Val Thr Gln Gln Leu Ile
            275                 280                 285

Lys Cys Val Val Phe Thr Gly Leu Met Gly Phe Ile Ile Glu Gln Tyr
        290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
            340                 345                 350

Val Ala Glu Leu Leu Cys Phe Gly Asp Arg Glu Phe Tyr Lys Asp Trp
            355                 360                 365

Trp Asn Ala Lys Thr Val Glu Glu Tyr Trp Arg Met Trp Asn Met Pro
        370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
            420                 425                 430

Trp Ala Phe Ser Gly Ile Met Phe Gln Ile Pro Leu Val Phe Leu Thr
            435                 440                 445

Arg Tyr Leu His Ala Thr Phe Lys His Val Met Val Gly Asn Met Ile
        450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg
                485                 490

<210> SEQ ID NO 100
<211> LENGTH: 512
<212> TYPE: PRT
<213> ORGANISM: Artificial Sequence
<220> FEATURE:
<223> OTHER INFORMATION: Z. mays-L

<400> SEQUENCE: 100

Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110
```

```
Lys Gln Ser His Ala Gly Leu Phe Asn Leu Cys Ile Val Val Leu Val
            115                 120                 125

Ala Val Asn Ser Arg Leu Ile Ile Glu Asn Leu Met Lys Tyr Gly Leu
        130                 135                 140

Leu Ile Arg Ser Gly Phe Trp Phe Asn Ala Thr Ser Leu Arg Asp Trp
145                 150                 155                 160

Pro Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
                180                 185                 190

Thr Thr Cys Phe His Ile Leu Phe Thr Thr Phe Glu Ile Val Tyr Pro
                195                 200                 205

Val Leu Val Ile Leu Lys Cys Asp Ser Ala Val Leu Ser Gly Phe Val
            210                 215                 220

Leu Met Phe Ile Ala Cys Ile Val Trp Leu Lys Leu Val Ser Phe Ala
225                 230                 235                 240

His Thr Asn His Asp Ile Arg Lys Leu Ile Thr Ser Gly Lys Lys Val
                245                 250                 255

Asp Asn Glu Leu Thr Ala Ala Gly Ile Asp Asn Leu Gln Ala Pro Thr
                260                 265                 270

Leu Gly Ser Leu Thr Tyr Phe Met Met Ala Pro Thr Leu Cys Tyr Gln
            275                 280                 285

Pro Ser Tyr Pro Arg Thr Pro Tyr Val Arg Lys Gly Trp Leu Val Arg
            290                 295                 300

Gln Val Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Met
                325                 330                 335

Gly Gly Leu Leu Asn Ala Val Glu Thr Val Leu Lys Leu Ser Leu Pro
                340                 345                 350

Asn Val Tyr Leu Trp Leu Cys Met Phe Tyr Cys Leu Phe His Leu Trp
            355                 360                 365

Leu Asn Ile Leu Ala Glu Ile Leu Arg Phe Gly Asp Arg Glu Phe Tyr
            370                 375                 380

Lys Asp Trp Trp Asn Ala Lys Thr Ile Asp Glu Tyr Trp Arg Lys Trp
385                 390                 395                 400

Asn Met Pro Val His Lys Trp Ile Val Arg His Ile Tyr Phe Pro Cys
                405                 410                 415

Met Arg Asn Gly Ile Ser Lys Glu Val Ala Val Phe Ile Ser Phe Phe
                420                 425                 430

Val Ser Ala Val Leu His Glu Leu Cys Val Ala Val Pro Cys His Ile
            435                 440                 445

Leu Lys Phe Trp Ala Phe Leu Gly Ile Met Leu Gln Ile Pro Leu Ile
            450                 455                 460

Ile Leu Thr Ser Tyr Leu Lys Asn Lys Phe Ser Asp Thr Met Val Gly
465                 470                 475                 480

Asn Met Ile Phe Trp Phe Phe Phe Cys Ile Tyr Gly Gln Pro Met Cys
                485                 490                 495

Val Leu Leu Tyr Tyr His Asp Val Met Asn Arg Thr Glu Lys Ala Lys
            500                 505                 510

<210> SEQ ID NO 101
<211> LENGTH: 521
```

```
<212> TYPE: PRT
<213> ORGANISM: Artificial Sequence
<220> FEATURE:
<223> OTHER INFORMATION: T. majus

<400> SEQUENCE: 101
```

| | | | | | | | | | | | | | | |
|---|---|---|---|---|---|---|---|---|---|---|---|---|---|---|
| Met | Ala | Val | Ala | Glu | Ser | Ser | Gln | Asn | Thr | Thr | Thr | Met | Ser | Gly | His |
| 1 | | | | 5 | | | | | 10 | | | | | 15 | |

Gly Asp Ser Asp Leu Asn Asn Phe Arg Arg Arg Lys Pro Ser Ser Ser
                20                  25                  30

Val Ile Glu Pro Ser Ser Ser Gly Phe Thr Ser Thr Asn Gly Val Pro
            35                  40                  45

Ala Thr Gly His Val Ala Glu Asn Arg Asp Gln Asp Arg Val Gly Ala
        50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Arg Gln Ser His Ala Gly Leu Leu
        115                 120                 125

Asn Leu Cys Ile Val Val Leu Ile Ala Val Asn Ser Arg Leu Ile Ile
130                 135                 140

Glu Asn Leu Met Lys Tyr Gly Leu Leu Ile Arg Ala Gly Phe Trp Phe
145                 150                 155                 160

Ser Ala Arg Ser Leu Gly Asp Trp Pro Leu Leu Met Cys Cys Leu Thr
                165                 170                 175

Leu Pro Val Phe Pro Leu Val Ala Leu Met Ala Glu Lys Leu Ile Thr
            180                 185                 190

Arg Lys Leu Ile Gly Glu His Val Val Leu Leu His Ile Ile Ile
        195                 200                 205

Thr Thr Ser Ala Ile Val Tyr Pro Val Val Val Thr Leu Lys Cys Asp
210                 215                 220

Ser Ala Val Leu Ser Gly Phe Val Leu Met Phe Leu Ala Ser Ile Met
225                 230                 235                 240

Trp Met Lys Leu Val Ser Tyr Ala His Thr Asn Tyr Asp Ile Arg Val
                245                 250                 255

Leu Ser Lys Ser Thr Glu Lys Gly Ala Ala Tyr Gly Asn Tyr Val Asp
            260                 265                 270

Pro Glu Asn Met Lys Asp Pro Thr Phe Lys Ser Leu Val Tyr Phe Met
        275                 280                 285

Leu Ala Pro Thr Leu Cys Tyr Gln Pro Thr Tyr Pro Gln Thr Thr Cys
290                 295                 300

Ile Arg Lys Gly Trp Val Thr Gln Gln Leu Ile Lys Cys Val Val Phe
305                 310                 315                 320

Thr Gly Leu Met Gly Phe Ile Ile Glu Gln Tyr Ile Asn Pro Ile Val
                325                 330                 335

Lys Asn Ser Lys His Pro Leu Lys Gly Asn Phe Leu Asn Ala Ile Glu
            340                 345                 350

Arg Val Leu Lys Leu Ser Val Pro Thr Leu Tyr Val Trp Leu Cys Met
        355                 360                 365

Phe Tyr Cys Phe Phe His Leu Trp Leu Asn Ile Val Ala Glu Leu Leu
370                 375                 380

```
Cys Phe Gly Asp Arg Glu Phe Tyr Lys Asp Trp Trp Asn Ala Lys Thr
385                 390                 395                 400

Val Glu Glu Tyr Trp Arg Met Trp Asn Met Pro Val His Lys Trp Ile
                405                 410                 415

Ile Arg His Ile Tyr Phe Pro Cys Ile Arg Lys Gly Phe Ser Arg Gly
            420                 425                 430

Val Ala Ile Leu Ile Ser Phe Leu Val Ser Ala Val Phe His Glu Ile
            435                 440                 445

Cys Ile Ala Val Pro Cys His Ile Phe Lys Phe Trp Ala Phe Ser Gly
        450                 455                 460

Ile Met Phe Gln Ile Pro Leu Val Phe Leu Thr Arg Tyr Leu His Ala
465                 470                 475                 480

Thr Phe Lys His Val Met Val Gly Asn Met Ile Phe Trp Phe Phe
                485                 490                 495

Ser Ile Val Gly Gln Pro Met Cys Val Leu Leu Tyr Tyr His Asp Val
            500                 505                 510

Met Asn Arg Gln Ala Gln Ala Ser Arg
            515                 520

<210> SEQ ID NO 102
<211> LENGTH: 520
<212> TYPE: PRT
<213> ORGANISM: Artificial Sequence
<220> FEATURE:
<223> OTHER INFORMATION: T. majus

<400> SEQUENCE: 102

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Val Ala Val Asn Ser Arg Leu Ile Ile
130                 135                 140

Glu Asn Leu Met Lys Tyr Gly Leu Leu Ile Arg Ser Gly Phe Trp Phe
145                 150                 155                 160

Asn Ala Thr Ser Leu Arg Asp Trp Pro Leu Leu Met Cys Cys Leu Ser
                165                 170                 175

Leu Pro Ile Phe Pro Leu Gly Ala Phe Ala Val Glu Lys Leu Ala Phe
            180                 185                 190

Asn Asn Leu Ile Ser Asp Pro Ala Thr Thr Cys Phe His Ile Leu Phe
        195                 200                 205

Thr Thr Phe Glu Ile Val Tyr Pro Val Leu Val Ile Leu Lys Cys Asp
    210                 215                 220
```

```
Ser Ala Val Leu Ser Gly Phe Val Leu Met Phe Ile Ala Cys Ile Val
225                 230                 235                 240

Trp Leu Lys Leu Val Ser Phe Ala His Thr Asn His Asp Ile Arg Lys
            245                 250                 255

Leu Ile Thr Ser Gly Lys Lys Val Asp Asn Glu Leu Thr Ala Ala Gly
        260                 265                 270

Ile Asp Asn Leu Gln Ala Pro Thr Leu Gly Ser Leu Thr Tyr Phe Met
    275                 280                 285

Met Ala Pro Thr Leu Cys Tyr Gln Pro Ser Tyr Pro Arg Thr Pro Tyr
290                 295                 300

Val Arg Lys Gly Trp Leu Val Arg Gln Val Ile Leu Tyr Leu Ile Phe
305                 310                 315                 320

Thr Gly Leu Gln Gly Phe Ile Ile Glu Gln Tyr Ile Asn Pro Ile Val
            325                 330                 335

Val Asn Ser Gln His Pro Leu Met Gly Gly Leu Leu Asn Ala Val Glu
        340                 345                 350

Thr Val Leu Lys Leu Ser Leu Pro Asn Val Tyr Leu Trp Leu Cys Met
    355                 360                 365

Phe Tyr Cys Leu Phe His Leu Trp Leu Asn Ile Leu Ala Glu Ile Leu
370                 375                 380

Arg Phe Gly Asp Arg Glu Phe Tyr Lys Asp Trp Trp Asn Ala Lys Thr
385                 390                 395                 400

Ile Asp Glu Tyr Trp Arg Lys Trp Asn Met Pro Val His Lys Trp Ile
            405                 410                 415

Val Arg His Ile Tyr Phe Pro Cys Met Arg Asn Gly Ile Ser Lys Glu
        420                 425                 430

Val Ala Val Phe Ile Ser Phe Phe Val Ser Ala Val Leu His Glu Leu
    435                 440                 445

Cys Val Ala Val Pro Cys His Ile Leu Lys Phe Trp Ala Phe Leu Gly
450                 455                 460

Ile Met Leu Gln Ile Pro Leu Ile Ile Leu Thr Ser Tyr Leu Lys Asn
465                 470                 475                 480

Lys Phe Ser Asp Thr Met Val Gly Asn Met Ile Phe Trp Phe Phe Phe
            485                 490                 495

Cys Ile Tyr Gly Gln Pro Met Cys Val Leu Leu Tyr Tyr His Asp Val
        500                 505                 510

Met Asn Arg Thr Glu Lys Ala Lys
            515                 520

<210> SEQ ID NO 103
<211> LENGTH: 491
<212> TYPE: PRT
<213> ORGANISM: Artificial Sequence
<220> FEATURE:
<223> OTHER INFORMATION: Z. mays-S

<400> SEQUENCE: 103

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Gln Glu Gln
    50                  55                  60
```

```
Gln Gln His Glu Met Leu Tyr Tyr Arg Ala Ser Ala Pro Ala His Arg
 65                  70                  75                  80

Arg Val Lys Glu Ser Pro Leu Ser Ser Asp Ala Ile Phe Lys Gln Ser
             85                  90                  95

His Ala Gly Leu Phe Asn Leu Cys Ile Val Val Leu Ile Ala Val Asn
        100                 105                 110

Ser Arg Leu Ile Ile Glu Asn Leu Met Lys Tyr Gly Trp Leu Ile Asp
        115                 120                 125

Thr Gly Phe Trp Phe Ser Ser Arg Ser Leu Gly Asp Trp Ser Ile Phe
    130                 135                 140

Met Cys Cys Leu Thr Leu Pro Ile Phe Pro Leu Ala Ala Phe Ile Val
145                 150                 155                 160

Glu Lys Leu Val Gln Arg Asn His Ile Ala Glu Leu Val Ala Val Leu
                165                 170                 175

Leu His Val Ile Val Ser Thr Ala Ala Val Leu Tyr Pro Val Ile Val
            180                 185                 190

Ile Leu Thr Cys Asp Ser Val Tyr Met Ser Gly Val Val Leu Met Leu
        195                 200                 205

Phe Gly Cys Ile Met Trp Leu Lys Leu Val Ser Tyr Ala His Thr Ser
    210                 215                 220

Ser Asp Ile Arg Thr Leu Ala Lys Ser Gly Tyr Lys Gly Asp Ala His
225                 230                 235                 240

Pro Asn Ser Thr Ile Val Ser Cys Ser Tyr Asp Val Ser Leu Lys Ser
                245                 250                 255

Leu Ala Tyr Phe Met Val Ala Pro Thr Leu Cys Tyr Gln Pro Ser Tyr
            260                 265                 270

Pro Arg Ser Ser Cys Ile Arg Lys Gly Trp Val Val Arg Gln Phe Val
        275                 280                 285

Lys Leu Ile Val Phe Ile Gly Leu Met Gly Phe Ile Ile Glu Gln Tyr
    290                 295                 300

Ile Asn Pro Ile Val Arg Asn Ser Lys His Pro Leu Lys Gly Asp Phe
305                 310                 315                 320

Leu Tyr Ala Ile Glu Arg Val Leu Lys Leu Ser Val Pro Asn Leu Tyr
                325                 330                 335

Val Trp Leu Cys Met Phe Tyr Ser Phe Phe His Leu Trp Leu Asn Ile
            340                 345                 350

Leu Ala Glu Leu Leu Arg Phe Gly Asp Arg Glu Phe Tyr Lys Asp Trp
        355                 360                 365

Trp Asn Ala Lys Thr Val Ala Glu Tyr Trp Lys Met Trp Asn Met Pro
    370                 375                 380

Val His Arg Trp Met Val Arg His Leu Tyr Phe Pro Cys Leu Arg Asn
385                 390                 395                 400

Gly Ile Pro Lys Glu Gly Ala Ile Ile Ala Phe Leu Val Ser Gly
                405                 410                 415

Ala Phe His Glu Leu Cys Ile Ala Val Pro Cys His Val Phe Lys Leu
            420                 425                 430

Trp Ala Phe Ile Gly Ile Met Phe Gln Val Pro Leu Val Leu Ile Thr
        435                 440                 445

Asn Tyr Leu Gln Glu Lys Phe Ser Asn Ser Met Val Gly Asn Met Ile
    450                 455                 460

Phe Trp Phe Ile Phe Cys Ile Leu Gly Gln Pro Met Cys Val Leu Leu
465                 470                 475                 480

Tyr Tyr His Asp Leu Ile Asn Leu Lys Glu Lys
```

<210> SEQ ID NO 104
<211> LENGTH: 510
<212> TYPE: PRT
<213> ORGANISM: Artificial Sequence
<220> FEATURE:
<223> OTHER INFORMATION: Z. mays-L

<400> SEQUENCE: 104

```
Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Ile
        115                 120                 125

Ala Val Asn Ser Arg Leu Ile Ile Glu Asn Leu Met Lys Tyr Gly Trp
    130                 135                 140

Leu Ile Asp Thr Gly Phe Trp Phe Ser Ser Arg Ser Leu Gly Asp Trp
145                 150                 155                 160

Ser Ile Phe Met Cys Cys Leu Thr Leu Pro Ile Phe Pro Leu Ala Ala
                165                 170                 175

Phe Ile Val Glu Lys Leu Val Gln Arg Asn His Ile Ala Glu Leu Val
            180                 185                 190

Ala Val Leu Leu His Val Ile Val Ser Thr Ala Ala Val Leu Tyr Pro
        195                 200                 205

Val Ile Val Ile Leu Thr Cys Asp Ser Val Tyr Met Ser Gly Val Val
    210                 215                 220

Leu Met Leu Phe Gly Cys Ile Met Trp Leu Lys Leu Val Ser Tyr Ala
225                 230                 235                 240

His Thr Ser Ser Asp Ile Arg Thr Leu Ala Lys Ser Gly Tyr Lys Gly
                245                 250                 255

Asp Ala His Pro Asn Ser Thr Ile Val Ser Cys Ser Tyr Asp Val Ser
            260                 265                 270

Leu Lys Ser Leu Ala Tyr Phe Met Val Ala Pro Thr Leu Cys Tyr Gln
        275                 280                 285

Pro Ser Tyr Pro Arg Ser Ser Cys Ile Arg Lys Gly Trp Val Val Arg
    290                 295                 300

Gln Phe Val Lys Leu Ile Val Phe Ile Gly Leu Met Gly Phe Ile Ile
305                 310                 315                 320

Glu Gln Tyr Ile Asn Pro Ile Val Arg Asn Ser Lys His Pro Leu Lys
                325                 330                 335

Gly Asp Phe Leu Tyr Ala Ile Glu Arg Val Leu Lys Leu Ser Val Pro
            340                 345                 350

Asn Leu Tyr Val Trp Leu Cys Met Phe Tyr Ser Phe Phe His Leu Trp
```

```
                355                 360                 365
Leu Asn Ile Leu Ala Glu Leu Leu Arg Phe Gly Asp Arg Glu Phe Tyr
    370                 375                 380
Lys Asp Trp Trp Asn Ala Lys Thr Val Ala Glu Tyr Trp Lys Met Trp
385                 390                 395                 400
Asn Met Pro Val His Arg Trp Met Val Arg His Leu Tyr Phe Pro Cys
                405                 410                 415
Leu Arg Asn Gly Ile Pro Lys Glu Gly Ala Ile Ile Ala Phe Leu
            420                 425                 430
Val Ser Gly Ala Phe His Glu Leu Cys Ile Ala Val Pro Cys His Val
            435                 440                 445
Phe Lys Leu Trp Ala Phe Ile Gly Ile Met Phe Gln Val Pro Leu Val
        450                 455                 460
Leu Ile Thr Asn Tyr Leu Gln Glu Lys Phe Ser Asn Ser Met Val Gly
465                 470                 475                 480
Asn Met Ile Phe Trp Phe Ile Phe Cys Ile Leu Gly Gln Pro Met Cys
                485                 490                 495
Val Leu Leu Tyr Tyr His Asp Leu Ile Asn Leu Lys Glu Lys
            500                 505                 510

<210> SEQ ID NO 105
<211> LENGTH: 102
<212> TYPE: DNA
<213> ORGANISM: Arabidopsis thaliana

<400> SEQUENCE: 105
gtaaaagaag atgttttta tttccagcaa tgttacattg ttatacgtat aatgatgagt    60
ttagtgatca agttcctctt tgattcttct ttcttgttgc ag                     102

<210> SEQ ID NO 106
<211> LENGTH: 1761
<212> TYPE: DNA
<213> ORGANISM: Artificial Sequence
<220> FEATURE:
<223> OTHER INFORMATION: Brassica optimised

<400> SEQUENCE: 106
atggctgttg ctgaatcttc tcagaacacc actactatgt ctggacacgg tgattctgac    60
ctcaacgtaa aagaagatgt tttttatttc agcaatgtt acattgttat acgtataatg   120
atgagtttag tgatcaagtt cctctttgat tcttctttct tgttgcagaa cttcagacgt   180
agaaagccct tagctctgt atcgagcct tcttcttctg gattcacctc tactaacggt   240
gttcctgcta ctggacatgt tgctgagaac agagatcagg atagagttgg agctatggaa   300
aacgctaccg gatctgttaa ccttatcgga aacggtggag tgttgttat cggtaacgag   360 gaaaagcaag ttggagagac tgatatcaga ttcacctaca gaccatcttt cccagctcac   420
agaagagtta gggagtctcc actctcgagt gatgctatct tcaagcagtc tcacgctgga   480
cttttcaacc tctgcatcgt tgttcttatc gctgttaata gcagacttat catcgagaac   540
ctcatgaagt acggatggct tatcgatact ggattctggt tctcttctcg ttctcttggt   600
gactggtcta tcttcatgtg ctgtcttact ctccctatct tccctcttgc tgctttcatc   660
gttgagaagc ttgttcagag gaaccatatc gctgagcttg ttgctgttct tctccacgtt   720
atcgtttcta ctgctgctgt tctctaccct gttatcgtta tccttacctg cgattctgtt   780
tacatgtctg gtgttgtgct tatgcttttc ggatgcatca tgtggcttaa gctcgtttct   840
```

| | | | |
|---|---|---|---|
| tacgctcaca | cctcttcaga tatcagaacc ctcgctaagt ctggatacaa aggtgatgct | 900 | |
| caccctaact | ctactatcgt gtcttgctct tacgatgtgt ctcttaagtc tctcgcttac | 960 | |
| ttcatggttg | ctcctaccct ttgttaccaa ccttcttacc ctagatctag ctgcatcaga | 1020 | |
| aagggatggg | ttgtgagaca attcgttaag ctcatcgtgt tcatcggact tatgggattc | 1080 | |
| atcatcgagc | agtacatcaa ccctatcgtg agaaactcta agcaccctct caagggagat | 1140 | |
| ttcctttacg | ctatcgagag agtgcttaag cttttctgtgc ctaacctta cgtttggctc | 1200 | |
| tgcatgttct | actcattctt ccacctttgg cttaacatcc ttgctgagtt gcttagattc | 1260 | |
| ggagacagag | agttctacaa ggattggtgg aacgctaaga ctgttgctga gtactggaag | 1320 | |
| atgtggaaca | tgcctgttca tagatggatg gttaggcacc tttacttccc ttgtctcaga | 1380 | |
| aacggaatcc | ctaaagaggg tgctatcatc attgctttct tggtgtctgg tgctttccat | 1440 | |
| gagttgtgta | tcgctgttcc ttgtcacgtt ttcaagctct gggctttcat cggaatcatg | 1500 | |
| ttccaagttc | ctctcgttct tatcactaac tacctccaag agaagttctc taacagcatg | 1560 | |
| gtgggaaaca | tgatttttctg gttcatttttc tgcatccttg acagcctat gtgtgttctt | 1620 | |
| ctctactacc | acgatctcat caacctcaaa gagaaggcta agggtgagct tagaggtcat | 1680 | |
| cctttcgagg | gtaagcctat ccctaaccct cttctcggtc tcgattctac tagaactggt | 1740 | |
| catcatcatc | accatcactg a | 1761 | |

<210> SEQ ID NO 107
<211> LENGTH: 1659
<212> TYPE: DNA
<213> ORGANISM: Artificial Sequence
<220> FEATURE:
<223> OTHER INFORMATION: Brassica optimised

<400> SEQUENCE: 107

| | | | |
|---|---|---|---|
| atggctgttg | ctgaatcttc tcagaacacc actactatgt ctggacacgg tgattctgac | 60 | |
| ctcaacaact | tcagacgtag aaagccttct agctctgtta tcgagccttc ttcttctgga | 120 | |
| ttcacctcta | ctaacggtgt tcctgctact ggacatgttg ctgagaacag agatcaggat | 180 | |
| agagttggag | ctatggaaaa cgctaccgga tctgttaacc ttatcggaaa cggtggaggt | 240 | |
| gttgttatcg | gtaacgagga aaagcaagtt ggagagactg atatcagatt cacctacaga | 300 | |
| ccatctttcc | cagctcacag aagagttagg gagtctccac tctcgagtga tgctatcttc | 360 | |
| aagcagtctc | acgctggact tttcaacctc tgcatcgttg ttcttatcgc tgttaatagc | 420 | |
| agacttatca | tcgagaacct catgaagtac ggatggctta tcgatactgg attctggttc | 480 | |
| tcttctcgtt | ctcttggtga ctggtctatc ttcatgtgct gtcttactct ccctatcttc | 540 | |
| cctcttgctg | ctttcatcgt tgagaagctt gttcagagga accatatcgc tgagcttgtt | 600 | |
| gctgttcttc | tccacgttat cgtttctact gctgctgttc tctaccctgt tatcgttatc | 660 | |
| cttacctgcg | attctgttta catgtctggt gttgtgctta tgcttttcgg atgcatcatg | 720 | |
| tggcttaagc | tcgtttctta cgctcacacc tcttcagata tcagaaccct cgctaagtct | 780 | |
| ggatacaaag | gtgatgctca ccctaactct actatcgtgt cttgctctta cgatgtgtct | 840 | |
| cttaagtctc | tcgcttactt catggttgct cctacccttt gttaccaacc ttcttaccct | 900 | |
| agatctagct | gcatcagaaa gggatgggtt gtgagacaat cgttaagct catcgtgttc | 960 | |
| atcggactta | tgggattcat catcgagcag tacatcaacc ctatcgtgag aaactctaag | 1020 | |
| cacccctctca | agggagattt cctttacgct atcgagagag tgcttaagct ttctgtgcct | 1080 | |
| aaccctttacg | tttggctctg catgttctac tcattcttcc acctttggct taacatcctt | 1140 | |

```
gctgagttgc ttagattcgg agacagagag ttctacaagg attggtggaa cgctaagact    1200
gttgctgagt actggaagat gtggaacatg cctgttcata gatggatggt taggcacctt    1260
tacttccctt gtctcagaaa cggaatccct aaagagggtg ctatcatcat tgctttcttg    1320
gtgtctggtg ctttccatga gttgtgtatc gctgttcctt gtcacgtttt caagctctgg    1380
gctttcatcg gaatcatgtt ccaagttcct ctcgttctta tcactaacta cctccaagag    1440
aagttctcta cagcatggt gggaaacatg atttctggt tcattttctg catccttgga    1500
cagcctatgt gtgttcttct ctactaccac gatctcatca acctcaaaga gaaggctaag    1560
ggtgagctta gaggtcatcc tttcgagggt aagcctatcc ctaaccctct tctcggtctc    1620
gattctacta gaactggtca tcatcatcac catcactga                          1659
```

<210> SEQ ID NO 108
<211> LENGTH: 552
<212> TYPE: PRT
<213> ORGANISM: Artificial Sequence
<220> FEATURE:
<223> OTHER INFORMATION: Brassica optimised

<400> SEQUENCE: 108

```
Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ala Glu Leu Val Ala Val Leu Leu His Val Ile Val
        195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
            260                 265                 270
```

Val Ser Cys Ser Tyr Asp Val Ser Leu Lys Ser Leu Ala Tyr Phe Met
            275                 280                 285

Val Ala Pro Thr Leu Cys Tyr Gln Pro Ser Tyr Pro Arg Ser Ser Cys
    290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
            355                 360                 365

Phe Tyr Ser Phe Phe His Leu Trp Leu Asn Ile Leu Ala Glu Leu Leu
        370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
    450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys Ala Lys Gly Glu Leu Arg Gly His Pro Phe
        515                 520                 525

Glu Gly Lys Pro Ile Pro Asn Pro Leu Leu Gly Leu Asp Ser Thr Arg
    530                 535                 540

Thr Gly His His His His His His
545                 550

<210> SEQ ID NO 109
<211> LENGTH: 1743
<212> TYPE: DNA
<213> ORGANISM: Artificial Sequence
<220> FEATURE:
<223> OTHER INFORMATION: Brassica optimised

<400> SEQUENCE: 109
atggctgatt ctgaggatgc tcctcctgct gttcatagaa ggcctccaag acctgctaga      60
ggtgctgctg ctgctgtaaa agaagatgtt ttttatttcc agcaatgtta cattgttata     120
cgtataatga tgagtttagt gatcaagttc ctctttgatt cttctttctt gttgcagcaa     180
ggattcgctg ctgctcttag aagaaggctt agaagcggag ctgctgttgc tgctagagct     240
tctttcgctg ctgattctgg tgatgagtct ggacctggtg agccttcttc atctaggcgt     300
agagataact ctggtggagc ttcttctgct gctggtggta gagctggtgc tggtgatttc     360
tctgctttca ccttcagagc tgctgctcct gttcacagaa aggctaaaga atctccactc     420

| | |
|---|---|
| tcgagtgatg ctatcttcaa gcagtctcac gctggacttt tcaacctctg catcgttgtt | 480 |
| cttgttgctg tgaacagcag actcatcatc gagaacctca tgaagtacgg acttctcatc | 540 |
| agatctggat tctggttcaa cgctacctct cttagagatt ggcctcttct tatgtgctgt | 600 |
| ctctctcttc caatcttccc tcttggtgct ttcgctgttg agaagcttgc tttcaacaac | 660 |
| ctcatctctg atcctgctac tacttgcttc cacatccttt tcactacctt cgagatcgtt | 720 |
| taccctgttc tcgttatcct taaatgcgat tctgctgttc tttctggatt cgtgctcatg | 780 |
| ttcattgctt gcatcgtttg gcttaagctc gtttctttcg ctcacactaa ccacgatatc | 840 |
| agaaagctca tcacctctgg aaagaaggtt gacaacgagc ttactgctgc tggaatcgat | 900 |
| aaccttcagg ctcctactct tggatctctc acctacttca tgatggctcc taccctttgt | 960 |
| taccaacctt cttaccctag aaccccttac gttagaaagg gatggcttgt tagacaggtt | 1020 |
| atcctctacc ttatcttcac tggacttcag ggattcatca tcgagcagta catcaaccct | 1080 |
| atcgttgtta actctcagca tcctcttatg ggaggacttc ttaacgctgt tgagactgtg | 1140 |
| cttaagcttt ctctccctaa cgtttacctt tggctctgta tgttctactg ccttttccac | 1200 |
| ctttggctta acatccttgc tgagatcctt agattcggag acagagagtt ctacaaggat | 1260 |
| tggtggaacg ctaagactat cgatgagtac tggcgtaagt ggaacatgcc tgttcataag | 1320 |
| tggatcgtga ggcatatcta cttcccttgc atgagaaacg gaatctctaa agaggttgcc | 1380 |
| gttttcatct ctttcttcgt gtctgctgtt ctccatgagc tttgtgttgc tgttccttgc | 1440 |
| cacatcctta gttctgggc tttccttgga atcatgcttc agatccctct tatcatcctt | 1500 |
| accagctacc tcaagaacaa gttctctgat accatggtgg gaaacatgat tttctggttc | 1560 |
| tttttctgca tctacggaca acctatgtgt gttcttctct actaccacga tgttatgaac | 1620 |
| agaaccgaga aggccaaggc taagggtgag cttagaggtc atcctttcga gggtaagcct | 1680 |
| atccctaacc ctcttctcgg tctcgattct actagaactg gtcatcatca tcaccatcac | 1740 |
| tga | 1743 |

<210> SEQ ID NO 110
<211> LENGTH: 1641
<212> TYPE: DNA
<213> ORGANISM: Artificial Sequence
<220> FEATURE:
<223> OTHER INFORMATION: Brassica optimised

<400> SEQUENCE: 110

| | |
|---|---|
| atggctgatt ctgaggatgc tcctcctgct gttcatagaa ggcctccaag acctgctaga | 60 |
| ggtgctgctg ctgctcaagg attcgctgct gctcttagaa gaaggcttag aagcggagct | 120 |
| gctgttgctg ctagagcttc tttcgctgct gattctggtg atgagtctgg acctggtgag | 180 |
| ccttcttcat ctaggcgtag agataactct ggtggagctt cttctgctgc tggtggtaga | 240 |
| gctggtgctg tgatttctc tgctttcacc ttcagctg ctgctcctgt tcacagaaag | 300 |
| gctaaagaat ctccactctc gagtgatgct atcttcaagc agtctcacgc tggacttttc | 360 |
| aacctctgca tcgttgttct tgttgctgtg aacagcagac tcatcatcga gaacctcatg | 420 |
| aagtacggac ttctcatcag atctggattc tggttcaacg ctacctctct tagagattgg | 480 |
| cctcttctta tgtgctgtct ctctcttcca atcttccctc ttggtgcttt cgctgttgag | 540 |
| aagcttgctt tcaacaacct catctctgat cctgctacta cttgcttcca catcttttc | 600 |
| actaccttcg agatcgttta ccctgttctc gttatcctta aatgcgattc tgctgttctt | 660 |
| tctggattcg tgctcatgtt cattgcttgc atcgtttggc ttaagctcgt ttctttcgct | 720 |

```
cacactaacc acgatatcag aaagctcatc acctctggaa agaaggttga caacgagctt    780
actgctgctg gaatcgataa ccttcaggct cctactcttg gatctctcac ctacttcatg    840
atggctccta ccctttgtta ccaaccttct taccctagaa ccccttacgt tagaaaggga    900
tggcttgtta gacaggttat cctctacctt atcttcactg gacttcaggg attcatcatc    960
gagcagtaca tcaaccctat cgttgttaac tctcagcatc ctcttatggg aggacttctt   1020
aacgctgttg agactgtgct taagctttct ctccctaacg tttacctttg gctctgtatg   1080
ttctactgcc ttttccacct ttggcttaac atccttgctg agatccttag attcggagac   1140
agagagttct acaaggattg gtggaacgct aagactatcg atgagtactg gcgtaagtgg   1200
aacatgcctg ttcataagtg gatcgtgagg catatctact tcccttgcat gagaaacgga   1260
atctctaaag aggttgccgt tttcatctct ttcttcgtgt ctgctgttct ccatgagctt   1320
tgtgttgctg ttccttgcca catccttaag ttctgggctt ccttggaat catgcttcag    1380 atccctctta tcatccttac cagctacctc aagaacaagt tctctgatac catggtggga   1440
aacatgattt tctggttctt tttctgcatc tacggacaac ctatgtgtgt tcttctctac   1500
taccacgatg ttatgaacag aaccgagaag gccaaggcta agggtgagct tagaggtcat   1560
cctttcgagg gtaagcctat ccctaaccct cttctcggtc tcgattctac tagaactggt   1620
catcatcatc accatcactg a                                             1641
```

<210> SEQ ID NO 111
<211> LENGTH: 546
<212> TYPE: PRT
<213> ORGANISM: Artificial Sequence
<220> FEATURE:
<223> OTHER INFORMATION: Brassica optimised

<400> SEQUENCE: 111

```
Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Ala Ser Ala Ala Gly Gly Arg
65                  70                  75                  80

Ala Gly Ala Gly Asp Phe Ser Ala Phe Thr Phe Arg Ala Ala Ala Pro
            85                  90                  95

Val His Arg Lys Ala Lys Glu Ser Pro Leu Ser Ser Asp Ala Ile Phe
        100                 105                 110

Lys Gln Ser His Ala Gly Leu Phe Asn Leu Cys Ile Val Val Leu Val
    115                 120                 125

Ala Val Asn Ser Arg Leu Ile Ile Glu Asn Leu Met Lys Tyr Gly Leu
    130                 135                 140

Leu Ile Arg Ser Gly Phe Trp Phe Asn Ala Thr Ser Leu Arg Asp Trp
145                 150                 155                 160

Pro Leu Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
            180                 185                 190
```

```
Thr Thr Cys Phe His Ile Leu Phe Thr Thr Phe Glu Ile Val Tyr Pro
            195                 200                 205

Val Leu Val Ile Leu Lys Cys Asp Ser Ala Val Leu Ser Gly Phe Val
    210                 215                 220

Leu Met Phe Ile Ala Cys Ile Val Trp Leu Lys Leu Val Ser Phe Ala
225                 230                 235                 240

His Thr Asn His Asp Ile Arg Lys Leu Ile Thr Ser Gly Lys Lys Val
                245                 250                 255

Asp Asn Glu Leu Thr Ala Ala Gly Ile Asp Asn Leu Gln Ala Pro Thr
                260                 265                 270

Leu Gly Ser Leu Thr Tyr Phe Met Met Ala Pro Thr Leu Cys Tyr Gln
            275                 280                 285

Pro Ser Tyr Pro Arg Thr Pro Tyr Val Arg Lys Gly Trp Leu Val Arg
    290                 295                 300

Gln Val Ile Leu Tyr Leu Ile Phe Thr Gly Leu Gln Gly Phe Ile Ile
305                 310                 315                 320

Glu Gln Tyr Ile Asn Pro Ile Val Val Asn Ser Gln His Pro Leu Met
                325                 330                 335

Gly Gly Leu Leu Asn Ala Val Glu Thr Val Leu Lys Leu Ser Leu Pro
            340                 345                 350

Asn Val Tyr Leu Trp Leu Cys Met Phe Tyr Cys Leu Phe His Leu Trp
    355                 360                 365

Leu Asn Ile Leu Ala Glu Ile Leu Arg Phe Gly Asp Arg Glu Phe Tyr
370                 375                 380

Lys Asp Trp Trp Asn Ala Lys Thr Ile Asp Glu Tyr Trp Arg Lys Trp
385                 390                 395                 400

Asn Met Pro Val His Lys Trp Ile Val Arg His Ile Tyr Phe Pro Cys
                405                 410                 415

Met Arg Asn Gly Ile Ser Lys Glu Val Ala Val Phe Ile Ser Phe Phe
            420                 425                 430

Val Ser Ala Val Leu His Glu Leu Cys Val Ala Val Pro Cys His Ile
    435                 440                 445

Leu Lys Phe Trp Ala Phe Leu Gly Ile Met Leu Gln Ile Pro Leu Ile
450                 455                 460

Ile Leu Thr Ser Tyr Leu Lys Asn Lys Phe Ser Asp Thr Met Val Gly
465                 470                 475                 480

Asn Met Ile Phe Trp Phe Phe Cys Ile Tyr Gly Gln Pro Met Cys
                485                 490                 495

Val Leu Leu Tyr Tyr His Asp Val Met Asn Arg Thr Glu Lys Ala Lys
                500                 505                 510

Ala Lys Gly Glu Leu Arg Gly His Pro Phe Glu Gly Lys Pro Ile Pro
            515                 520                 525

Asn Pro Leu Leu Gly Leu Asp Ser Thr Arg Thr Gly His His His His
530                 535                 540

His His
545

<210> SEQ ID NO 112
<211> LENGTH: 1767
<212> TYPE: DNA
<213> ORGANISM: Artificial Sequence
<220> FEATURE:
<223> OTHER INFORMATION: Brassica optimised

<400> SEQUENCE: 112
```

| | |
|---|---|
| atggctgttg ctgaatcttc tcagaacacc actactatgt ctggacacgg tgattctgac | 60 |
| ctcaacgtaa agaagatgt tttttatttc cagcaatgtt acattgttat acgtataatg | 120 |
| atgagtttag tgatcaagtt cctctttgat tcttctttct tgttgcagaa cttcagacgt | 180 |
| agaaagcctt ctagctctgt tatcgagcct tcttcttctg gattcacctc tactaacggt | 240 |
| gttcctgcta ctggacatgt tgctgagaac agagatcagg atagagttgg agctatggaa | 300 |
| aacgctaccg gatctgttaa ccttatcgga aacggtggag tgttgttat cggtaacgag | 360 |
| gaaaagcaag ttggagagac tgatatcaga ttcacctaca gaccatcttt cccagctcac | 420 |
| agaagagtta gggagtctcc actctcgagt gatgctatct tcaagcagtc tcacgctgga | 480 |
| cttttcaacc tctgcatcgt tgttcttgtt gctgtgaaca gcagactcat catcgagaac | 540 |
| ctcatgaagt acggacttct catcagatct ggattctggt tcaacgctac ctctcttaga | 600 |
| gattggcctc ttcttatgtg ctgtctctct cttccaatct ccctcttggg tgctttcgct | 660 |
| gttgagaagc ttgctttcaa caacctcatc tctgatcctg ctactacttg cttccacatc | 720 |
| cttttcacta ccttcgagat cgtttaccct gttctcgtta tccttaaatg cgattctgct | 780 |
| gttctttctg gattcgtgct catgttcatt gcttgcatcg tttggcttaa gctcgtttct | 840 |
| ttcgctcaca ctaaccacga tatcagaaag ctcatcacct ctggaaagaa ggttgacaac | 900 |
| gagcttactg ctgctggaat cgataacctt caggctccta ctcttggatc tctcacctac | 960 |
| ttcatgatgg ctcctaccct tgttaccaa ccttcttacc ctagaacccc ttacgttaga | 1020 |
| aagggatggc ttgttagaca ggttatcctc taccttatct tcactggact tcagggattc | 1080 |
| atcatcgagc agtacatcaa ccctatcgtt gttaactctc agcatcctct tatgggagga | 1140 |
| cttcttaacg ctgttgagac tgtgcttaag cttctctctcc ctaacgttta cctttggctc | 1200 |
| tgtatgttct actgcctttt ccacctttgg cttaacatcc ttgctgagat ccttagattc | 1260 |
| ggagacagag agttctacaa ggattggtgg aacgctaaga ctatcgatga gtactggcgt | 1320 |
| aagtggaaca tgcctgttca taagtggatc gtgaggcata tctacttccc ttgcatgaga | 1380 |
| aacggaatct ctaaagaggt tgccgttttc atctctttct tcgtgtctgc tgttctccat | 1440 |
| gagctttgtg ttgctgttcc ttgccacatc cttaagttct gggctttcct tggaatcatg | 1500 |
| cttcagatcc ctcttatcat ccttaccagc tacctcaaga acaagttctc tgataccatg | 1560 |
| gtgggaaaca tgattttctg gttcttttc tgcatctacg acaacctat gtgtgttctt | 1620 |
| ctctactacc acgatgttat gaacagaacc gagaaggcca aggctaaggg tgagcttaga | 1680 |
| ggtcatcctt tcgagggtaa gcctatccct aaccctcttc tcggtctcga ttctactaga | 1740 |
| actggtcatc atcatcacca tcactga | 1767 |

<210> SEQ ID NO 113
<211> LENGTH: 1665
<212> TYPE: DNA
<213> ORGANISM: Artificial Sequence
<220> FEATURE:
<223> OTHER INFORMATION: Brassica optimised

<400> SEQUENCE: 113

| | |
|---|---|
| atggctgttg ctgaatcttc tcagaacacc actactatgt ctggacacgg tgattctgac | 60 |
| ctcaacaact tcagacgtag aaagccttct agctctgtta tcgagccttc ttcttctgga | 120 |
| ttcacctcta ctaacggtgt tcctgctact ggacatgttg ctgagaacag agatcaggat | 180 |
| agagttggag ctatggaaaa cgctaccgga tctgttaacc ttatcggaaa cggtggaggt | 240 |
| gttgttatcg gtaacgagga aaagcaagtt ggagagactg atatcagatt cacctacaga | 300 |

```
ccatctttcc cagctcacag aagagttagg gagtctccac tctcgagtga tgctatcttc      360
aagcagtctc acgctggact tttcaacctc tgcatcgttg ttcttgttgc tgtgaacagc      420
agactcatca tcgagaacct catgaagtac ggacttctca tcagatctgg attctggttc      480
aacgctacct ctcttagaga ttggcctctt cttatgtgct gtctctctct tccaatcttc      540
cctcttggtg ctttcgctgt tgagaagctt gctttcaaca acctcatctc tgatcctgct      600
actacttgct tccacatcct tttcactacc ttcgagatcg tttaccctgt tctcgttatc      660
cttaaatgcg attctgctgt tctttctgga ttcgtgctca tgttcattgc ttgcatcgtt      720
tggcttaagc tcgtttcttt cgctcacact aaccacgata tcagaaagct catcacctct      780
ggaaagaagg ttgacaacga gcttactgct gctggaatcg ataaccttca ggctcctact      840
cttggatctc tcacctactt catgatggct cctacccttt gttaccaacc ttcttaccct      900 agaaccccctt acgttagaaa gggatggctt gttagacagg ttatcctcta ccttatcttc      960
actggacttc agggattcat catcgagcag tacatcaacc ctatcgttgt taactctcag     1020
catcctctta tgggaggact tcttaacgct gttgagactg tgcttaagct ttctctccct     1080
aacgtttacc tttggctctg tatgttctac tgccttttcc acctttggct taacatcctt     1140
gctgagatcc ttagattcgg agacagagag ttctacaagg attggtggaa cgctaagact     1200
atcgatgagt actggcgtaa gtggaacatg cctgttcata gtggatcgt gaggcatatc     1260 tacttcccctt gcatgagaaa cggaatctct aaagaggttg ccgttttcat ctctttcttc     1320
gtgtctgctg ttctccatga gctttgtgtt gctgttcctt gccacatcct taagttctgg     1380
gctttccttg gaatcatgct tcagatccct cttatcatcc ttaccagcta cctcaagaac     1440
aagttctctg ataccatggt gggaaacatg attttctggt tcttttctg catctacgga     1500 caacctatgt gtgttcttct ctactaccac gatgttatga acagaaccga gaaggccaag     1560
gctaagggtg agcttagagg tcatcctttc gagggtaagc ctatccctaa ccctcttctc     1620
ggtctcgatt ctactagaac tggtcatcat catcaccatc actga                     1665
```

<210> SEQ ID NO 114
<211> LENGTH: 554
<212> TYPE: PRT
<213> ORGANISM: Artificial Sequence
<220> FEATURE:
<223> OTHER INFORMATION: Brassica optimised

<400> SEQUENCE: 114

```
Met Ala Val Ala Glu Ser Ser Gln Asn Thr Thr Met Ser Gly His
1               5                   10                  15

Gly Asp Ser Asp Leu Asn Asn Phe Arg Arg Arg Lys Pro Ser Ser
                20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
```

```
            115                 120                 125
Asn Leu Cys Ile Val Val Leu Val Ala Val Asn Ser Arg Leu Ile Ile
130                 135                 140

Glu Asn Leu Met Lys Tyr Gly Leu Leu Ile Arg Ser Gly Phe Trp Phe
145                 150                 155                 160

Asn Ala Thr Ser Leu Arg Asp Trp Pro Leu Leu Met Cys Cys Leu Ser
                165                 170                 175

Leu Pro Ile Phe Pro Leu Gly Ala Phe Ala Val Glu Lys Leu Ala Phe
                180                 185                 190

Asn Asn Leu Ile Ser Asp Pro Ala Thr Thr Cys Phe His Ile Leu Phe
                195                 200                 205

Thr Thr Phe Glu Ile Val Tyr Pro Val Leu Val Ile Leu Lys Cys Asp
210                 215                 220

Ser Ala Val Leu Ser Gly Phe Val Leu Met Phe Ile Ala Cys Ile Val
225                 230                 235                 240

Trp Leu Lys Leu Val Ser Phe Ala His Thr Asn His Asp Ile Arg Lys
                245                 250                 255

Leu Ile Thr Ser Gly Lys Lys Val Asp Asn Glu Leu Thr Ala Ala Gly
                260                 265                 270

Ile Asp Asn Leu Gln Ala Pro Thr Leu Gly Ser Leu Thr Tyr Phe Met
                275                 280                 285

Met Ala Pro Thr Leu Cys Tyr Gln Pro Ser Tyr Pro Arg Thr Pro Tyr
290                 295                 300

Val Arg Lys Gly Trp Leu Val Arg Gln Val Ile Leu Tyr Leu Ile Phe
305                 310                 315                 320

Thr Gly Leu Gln Gly Phe Ile Ile Glu Gln Tyr Ile Asn Pro Ile Val
                325                 330                 335

Val Asn Ser Gln His Pro Leu Met Gly Gly Leu Leu Asn Ala Val Glu
                340                 345                 350

Thr Val Leu Lys Leu Ser Leu Pro Asn Val Tyr Leu Trp Leu Cys Met
                355                 360                 365

Phe Tyr Cys Leu Phe His Leu Trp Leu Asn Ile Leu Ala Glu Ile Leu
370                 375                 380

Arg Phe Gly Asp Arg Glu Phe Tyr Lys Asp Trp Trp Asn Ala Lys Thr
385                 390                 395                 400

Ile Asp Glu Tyr Trp Arg Lys Trp Asn Met Pro Val His Lys Trp Ile
                405                 410                 415

Val Arg His Ile Tyr Phe Pro Cys Met Arg Asn Gly Ile Ser Lys Glu
                420                 425                 430

Val Ala Val Phe Ile Ser Phe Val Ser Ala Val Leu His Glu Leu
                435                 440                 445

Cys Val Ala Val Pro Cys His Ile Leu Lys Phe Trp Ala Phe Leu Gly
450                 455                 460

Ile Met Leu Gln Ile Pro Leu Ile Ile Leu Thr Ser Tyr Leu Lys Asn
465                 470                 475                 480

Lys Phe Ser Asp Thr Met Val Gly Asn Met Ile Phe Trp Phe Phe Phe
                485                 490                 495

Cys Ile Tyr Gly Gln Pro Met Cys Val Leu Leu Tyr Tyr His Asp Val
                500                 505                 510

Met Asn Arg Thr Glu Lys Ala Lys Ala Lys Gly Glu Leu Arg Gly His
                515                 520                 525

Pro Phe Glu Gly Lys Pro Ile Pro Asn Pro Leu Leu Gly Leu Asp Ser
530                 535                 540
```

Thr Arg Thr Gly His His His His His His
545             550

<210> SEQ ID NO 115
<211> LENGTH: 1737
<212> TYPE: DNA
<213> ORGANISM: Artificial Sequence
<220> FEATURE:
<223> OTHER INFORMATION: Brassica optimised

<400> SEQUENCE: 115

| | | | | | |
|---|---|---|---|---|---|
| atggctgatt | ctgaggatgc | tcctcctgct | gttcatagaa | ggcctccaag | acctgctaga | 60 |
| ggtgctgctg | ctgctgtaaa | agaagatgtt | ttttatttcc | agcaatgtta | cattgttata | 120 |
| cgtataatga | tgagtttagt | gatcaagttc | ctctttgatt | cttctttctt | gttgcagcaa | 180 |
| ggattcgctg | ctgctcttag | aagaaggctt | agaagcggag | ctgctgttgc | tgctagagct | 240 |
| tctttcgctg | ctgattctgg | tgatgagtct | ggacctggtg | agccttcttc | atctaggcgt | 300 |
| agagataact | ctggtggagc | ttcttctgct | gctggtggta | gagctggtgc | tggtgatttc | 360 |
| tctgctttca | ccttcagagc | tgctgctcct | gttcacagaa | aggctaaaga | atctccactc | 420 |
| tcgagtgatg | ctatcttcaa | gcagtctcac | gctggacttt | tcaacctctg | catcgttgtt | 480 |
| cttatcgctg | ttaatagcag | acttatcatc | gagaacctca | tgaagtacgg | atggcttatc | 540 |
| gatactggat | tctggttctc | ttctcgttct | cttggtgact | ggtctatctt | catgtgctgt | 600 |
| cttactctcc | ctatcttccc | tcttgctgct | ttcatcgttg | agaagcttgt | tcagaggaac | 660 |
| catatcgctg | agcttgttgc | tgttcttctc | cacgttatcg | tttctactgc | tgctgttctc | 720 |
| taccctgtta | tcgttatcct | tacctgcgat | tctgtttaca | tgtctggtgt | tgtgcttatg | 780 |
| cttttcggat | gcatcatgtg | gcttaagctc | gtttcttacg | ctcacacctc | ttcagatatc | 840 |
| agaaccctcg | ctaagtctgg | atacaaaggt | gatgctcacc | ctaactctac | tatcgtgtct | 900 |
| tgctcttacg | atgtgtctct | taagtctctc | gcttacttca | tggttgctcc | tacccctttgt | 960 |
| taccaacctt | cttaccctag | atctagctgc | atcagaaagg | gatgggttgt | gagacaattc | 1020 |
| gttaagctca | tcgtgttcat | cggacttatg | ggattcatca | tcgagcagta | catcaaccct | 1080 |
| atcgtgagaa | actctaagca | ccctctcaag | ggagatttcc | tttacgctat | cgagagagtg | 1140 |
| cttaagcttt | ctgtgcctaa | cctttacgtt | tggctctgca | tgttctactc | attcttccac | 1200 |
| ctttggctta | acatccttgc | tgagttgctt | agattcggag | acagagagtt | ctacaaggat | 1260 |
| tggtggaacg | ctaagactgt | tgctgagtac | tggaagatgt | ggaacatgcc | tgttcataga | 1320 |
| tggatggtta | ggcacctta | cttcccttgt | ctcagaaacg | gaatccctaa | agagggtgct | 1380 |
| atcatcattg | cttttcttggt | gtctggtgct | ttccatgagt | tgtgtatcgc | tgttccttgt | 1440 |
| cacgttttca | agctctgggc | tttcatcgga | atcatgttcc | aagttcctct | cgttcttatc | 1500 |
| actaactacc | tccaagagaa | gttctctaac | agcatggtgg | aaacatgat | tttctggttc | 1560 |
| attttctgca | tccttggaca | gcctatgtgt | gttcttctct | actaccacga | tctcatcaac | 1620 |
| ctcaaagaga | aggctaaggg | tgagcttaga | ggtcatcctt | tcgagggtaa | gcctatccct | 1680 |
| aaccctcttc | tcggtctcga | ttctactaga | actggtcatc | atcatcacca | tcactga | 1737 |

<210> SEQ ID NO 116
<211> LENGTH: 1635
<212> TYPE: DNA
<213> ORGANISM: Artificial Sequence
<220> FEATURE:
<223> OTHER INFORMATION: Brassica optimised

<400> SEQUENCE: 116

```
atggctgatt ctgaggatgc tcctcctgct gttcatagaa ggcctccaag acctgctaga      60
ggtgctgctg ctgctcaagg attcgctgct gctcttagaa gaaggcttag aagcggagct     120
gctgttgctg ctagagcttc tttcgctgct gattctggtg atgagtctgg acctggtgag     180
ccttcttcat ctaggcgtag agataactct ggtggagctt cttctgctgc tggtggtaga     240
gctggtgctg tgatttctc tgctttcacc ttcagctg ctgctcctgt tcacagaaag        300
gctaaagaat ctccactctc gagtgatgct atcttcaagc agtctcacgc tggactttc     360
aacctctgca tcgttgttct tatcgctgtt aatagcagac ttatcatcga acctcatg       420
aagtacggat ggcttatcga tactggattc tggttctctt ctcgttctct tggtgactgg    480
tctatcttca tgtgctgtct tactctccct atcttccctc ttgctgcttt catcgttgag   540
aagcttgttc agaggaacca tatcgctgag cttgttgctg ttcttctcca cgttatcgtt   600
tctactgctg ctgttctcta ccctgttatc gttatcctta cctgcgattc tgtttacatg   660
tctggtgttg tgcttatgct tttcggatgc atcatgtggc ttaagctcgt ttcttacgct   720
cacacctctt cagatatcag aaccctcgct aagtctggat acaaaggtga tgctcaccct   780
aactctacta tcgtgtcttg ctcttacgat gtgtctctta agtctctcgc ttacttcatg   840
gttgctccta ccctttgtta ccaaccttct taccctagat ctagctgcat cagaaaggga   900
tgggttgtga acaattcgt taagctcatc gtgttcatcg acttatggg attcatcatc     960
gagcagtaca tcaaccctat cgtgagaaac tctaagcacc ctctcaaggg agatttcctt  1020
tacgctatcg agagagtgct taagctttct gtgcctaacc tttacgtttg gctctgcatg  1080
ttctactcat tcttccacct ttggcttaac atccttgctg agttgcttag attcggagac  1140
agagagttct acaaggattg gtgaacgct aagactgttg ctgagtactg gaagatgtgg   1200
aacatgcctg ttcatagatg gatggttagg cacctttact tcccttgtct cagaaacgga  1260
atccctaaag agggtgctat catcattgct ttcttggtgt ctggtgcttt ccatgagttg  1320
tgtatcgctg ttccttgtca cgttttcaag ctctgggctt tcatcggaat catgttccaa  1380
gttcctctcg ttcttatcac taactacctc caagagaagt tctctaacag catggtggga  1440
aacatgattt tctggttcat ttctgcatc cttggacagc ctatgtgtgt tcttctctac  1500
taccacgatc tcatcaacct caaagagaag gctaagggtg agcttagagg tcatcctttc  1560
gagggtaagc ctatccctaa ccctcttctc ggtctcgatt ctactagaac tggtcatcat  1620
catcaccatc actga                                                     1635
```

<210> SEQ ID NO 117
<211> LENGTH: 544
<212> TYPE: PRT
<213> ORGANISM: Artificial Sequence
<220> FEATURE:
<223> OTHER INFORMATION: Brassica optimised

<400> SEQUENCE: 117

```
Met Ala Asp Ser Glu Asp Ala Pro Pro Ala Val His Arg Arg Pro Pro
1               5                   10                  15

Arg Pro Ala Arg Gly Ala Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
```

```
                50                  55                  60
Arg Arg Arg Asp Asn Ser Gly Gly Ala Ser Ser Ala Ala Gly Gly Arg
 65                  70                  75                  80

Ala Gly Ala Gly Asp Phe Ser Ala Phe Thr Phe Arg Ala Ala Ala Pro
                     85                  90                  95

Val His Arg Lys Ala Lys Glu Ser Pro Leu Ser Ser Asp Ala Ile Phe
                100                 105                 110

Lys Gln Ser His Ala Gly Leu Phe Asn Leu Cys Ile Val Val Leu Ile
                115                 120                 125

Ala Val Asn Ser Arg Leu Ile Ile Glu Asn Leu Met Lys Tyr Gly Trp
            130                 135                 140

Leu Ile Asp Thr Gly Phe Trp Phe Ser Ser Arg Ser Leu Gly Asp Trp
145                 150                 155                 160

Ser Ile Phe Met Cys Cys Leu Thr Leu Pro Ile Phe Pro Leu Ala Ala
                165                 170                 175

Phe Ile Val Glu Lys Leu Val Gln Arg Asn His Ile Ala Glu Leu Val
                180                 185                 190

Ala Val Leu Leu His Val Ile Val Ser Thr Ala Ala Val Leu Tyr Pro
            195                 200                 205

Val Ile Val Ile Leu Thr Cys Asp Ser Val Tyr Met Ser Gly Val Val
            210                 215                 220

Leu Met Leu Phe Gly Cys Ile Met Trp Leu Lys Leu Val Ser Tyr Ala
225                 230                 235                 240

His Thr Ser Ser Asp Ile Arg Thr Leu Ala Lys Ser Gly Tyr Lys Gly
                245                 250                 255

Asp Ala His Pro Asn Ser Thr Ile Val Ser Cys Ser Tyr Asp Val Ser
                260                 265                 270

Leu Lys Ser Leu Ala Tyr Phe Met Val Ala Pro Thr Leu Cys Tyr Gln
            275                 280                 285

Pro Ser Tyr Pro Arg Ser Ser Cys Ile Arg Lys Gly Trp Val Val Arg
            290                 295                 300

Gln Phe Val Lys Leu Ile Val Phe Ile Gly Leu Met Gly Phe Ile Ile
305                 310                 315                 320

Glu Gln Tyr Ile Asn Pro Ile Val Arg Asn Ser Lys His Pro Leu Lys
                325                 330                 335

Gly Asp Phe Leu Tyr Ala Ile Glu Arg Val Leu Lys Leu Ser Val Pro
            340                 345                 350

Asn Leu Tyr Val Trp Leu Cys Met Phe Tyr Ser Phe Phe His Leu Trp
            355                 360                 365

Leu Asn Ile Leu Ala Glu Leu Leu Arg Phe Gly Asp Arg Glu Phe Tyr
        370                 375                 380

Lys Asp Trp Trp Asn Ala Lys Thr Val Ala Glu Tyr Trp Lys Met Trp
385                 390                 395                 400

Asn Met Pro Val His Arg Trp Met Val Arg His Leu Tyr Phe Pro Cys
                405                 410                 415

Leu Arg Asn Gly Ile Pro Lys Glu Gly Ala Ile Ile Ala Phe Leu
            420                 425                 430

Val Ser Gly Ala Phe His Glu Leu Cys Ile Ala Val Pro Cys His Val
            435                 440                 445

Phe Lys Leu Trp Ala Phe Ile Gly Ile Met Phe Gln Val Pro Leu Val
            450                 455                 460

Leu Ile Thr Asn Tyr Leu Gln Glu Lys Phe Ser Asn Ser Met Val Gly
465                 470                 475                 480
```

```
Asn Met Ile Phe Trp Phe Ile Phe Cys Ile Leu Gly Gln Pro Met Cys
                485                 490                 495

Val Leu Leu Tyr Tyr His Asp Leu Ile Asn Leu Lys Glu Lys Ala Lys
            500                 505                 510

Gly Glu Leu Arg Gly His Pro Phe Glu Gly Lys Pro Ile Pro Asn Pro
        515                 520                 525

Leu Leu Gly Leu Asp Ser Thr Arg Thr Gly His His His His His His
    530                 535                 540
```

<210> SEQ ID NO 118
<211> LENGTH: 1689
<212> TYPE: DNA
<213> ORGANISM: Artificial Sequence
<220> FEATURE:
<223> OTHER INFORMATION: Brassica optimised

<400> SEQUENCE: 118

| | | | | |
|---|---|---|---|---|
| atggctcctc | caccttctat | gcctgctgct | tctgatagag | ctggacctgg aagagatgct | 60 |
| ggcgattctg | taaaagaaga | tgttttttat | ttccagcaat | gttacattgt tatacgtata | 120 |
| atgatgagtt | tagtgatcaa | gttcctcttt | gattcttctt | tcttgttgca gtcatctctc | 180 |
| agacttagaa | gggctccatc | tgctgacgct | ggtgaccttg | ctggtgatag ctctggtgga | 240 |
| cttagagaaa | acggtgagcc | tcaatctcct | actaaccctc | cacctcaaga gcaacaacag | 300 |
| cacgagatgc | tttactacag | agcttctgct | cctgctcata | agagagtgaa agaatctcca | 360 |
| ctctcgagtg | atgctatctt | cagacagtct | catgctggac | ttctcaacct ctgcatcgtt | 420 |
| gttcttatcg | ctgtgaacag | cagacttatc | atcgagaacc | tcatgaagta cggacttctc | 480 |
| atcagagctg | gattctggtt | ctctgctaga | tctcttggag | attggcctct tcttatgtgc | 540 |
| tgtcttaccc | ttcctgtttt | ccctcttgtt | gctcttatgg | ccgagaagct tatcactaga | 600 |
| aagctcatcg | gagagcatgt | tgttatcctt | ctccacatca | tcatcactac ctctgctatc | 660 |
| gtttaccctg | ttgttgttac | ccttaagtgc | gattctgctg | ttctttctgg attcgtgctt | 720 |
| atgttcctcg | cttctatcat | gtggatgaag | ctcgtttctt | acgctcacac caactacgat | 780 |
| atcagagtgc | tctctaagtc | tactgagaag | ggtgctgctt | acggaaacta tgtggaccct | 840 |
| gagaacatga | aggatcctac | cttcaagtct | ctcgtgtact | tcatgcttgc tcctaccctt | 900 |
| tgttaccaac | ctacttaccc | tcagactacc | tgtatcagaa | agggatgggt tacccaacaa | 960 |
| ctcatcaagt | gcgttgtgtt | cactggactt | atgggattca | tcatcgagca gtacatcaac | 1020 |
| cctatcgtga | agaactctaa | gcaccctctt | aagggaaact | tcctcaacgc tatcgagaga | 1080 |
| gttctcaagc | tttctgttcc | tactctttac | gtttggctct | gcatgttcta ctgtttcttc | 1140 |
| cacctttggc | tcaacatcgt | tgctgagctt | ctctgtttcg | gagatcgtga gttctacaag | 1200 |
| gattggtgga | acgctaagac | tgttgaggaa | tactggcgta | tgtggaacat gcctgttcat | 1260 |
| aagtggatca | tcaggcacat | ctacttccct | tgcatcagga | agggattctc tagggggagtt | 1320 |
| gctatcctta | tctctttcct | cgtttctgct | gttttccatg | agatctgtat cgctgttcct | 1380 |
| tgtcacatct | tcaagttctg | ggctttctct | ggtatcatgt | tccagatccc tcttgttttc | 1440 |
| cttaccagat | accttcacgc | tactttcaag | cacgttatgg | tgggaaacat gattttctgg | 1500 |
| ttctttttca | gcatcgttgg | acagcctatg | tgtgttcttc | tctactacca cgatgttatg | 1560 |
| aacagacaag | ctcaggcttc | tagggctaag | ggtgagctta | gaggtcatcc tttcgagggt | 1620 |
| aagcctatcc | ctaaccctct | ttctcggtctc | gattctacta | gaactggtca tcatcatcac | 1680 | catcactga 1689

<210> SEQ ID NO 119
<211> LENGTH: 1587
<212> TYPE: DNA
<213> ORGANISM: Artificial Sequence
<220> FEATURE:
<223> OTHER INFORMATION: Brassica optimised

<400> SEQUENCE: 119

| | | | | | |
|---|---|---|---|---|---|
| atggctcctc | caccttctat | gcctgctgct | tctgatagag | ctggacctgg | aagagatgct | 60 |
| ggcgattctt | catctctcag | acttagaagg | gctccatctg | ctgacgctgg | tgaccttgct | 120 |
| ggtgatagct | ctggtggact | tagagaaaac | ggtgagcctc | aatctcctac | taaccctcca | 180 |
| cctcaagagc | aacaacagca | cgagatgctt | tactacagag | cttctgctcc | tgctcataga | 240 |
| agagtgaaag | aatctccact | ctcgagtgat | gctatcttca | gacagtctca | tgctggactt | 300 |
| ctcaacctct | gcatcgttgt | tcttatcgct | gtgaacagca | gacttatcat | cgagaacctc | 360 |
| atgaagtacg | gacttctcat | cagagctgga | ttctggttct | ctgctagatc | tcttggagat | 420 |
| tggcctcttc | ttatgtgctg | tcttacccct | cctgttttcc | ctcttgttgc | tcttatggcc | 480 |
| gagaagctta | tcactagaaa | gctcatcgga | gagcatgttg | ttatccttct | ccacatcatc | 540 |
| atcactacct | ctgctatcgt | ttaccctgtt | gttgttaccc | ttaagtgcga | ttctgctgtt | 600 |
| ctttctggat | tcgtgcttat | gttcctcgct | tctatcatgt | ggatgaagct | cgtttcttac | 660 |
| gctcacacca | actacgatat | cagagtgctc | tctaagtcta | ctgagaaggg | tgctgcttac | 720 |
| ggaaactatg | tggaccctga | aacatgaag | gatcctacct | tcaagtctct | cgtgtacttc | 780 |
| atgcttgctc | ctacccttg | ttaccaacct | acttaccctc | agactacctg | tatcagaaag | 840 |
| ggatgggtta | cccaacaact | catcaagtgc | gttgtgttca | ctggacttat | gggattcatc | 900 |
| atcgagcagt | acatcaaccc | tatcgtgaag | aactctaagc | accctcttaa | gggaaacttc | 960 |
| ctcaacgcta | tcgagagagt | tctcaagctt | tctgttccta | ctctttacgt | ttggctctgc | 1020 |
| atgttctact | gtttcttcca | cctttggctc | aacatcgttg | ctgagcttct | ctgtttcgga | 1080 |
| gatcgtgagt | tctacaagga | ttggtggaac | gctaagactg | ttgaggaata | ctggcgtatg | 1140 |
| tggaacatgc | tgttcataa | gtggatcatc | aggcacatct | acttcccttg | catcaggaag | 1200 |
| ggattctcta | ggggagttgc | tatccttatc | tcttcctcg | tttctgctgt | tttccatgag | 1260 |
| atctgtatcg | ctgttccttg | tcacatcttc | aagttctggg | ctttctctgg | tatcatgttc | 1320 |
| cagatccctc | ttgttttcct | taccagatac | cttcacgcta | cttcaagca | cgttatggtg | 1380 |
| ggaaacatga | ttttctggtt | cttttcagc | atcgttggac | agcctatgtg | tgttcttctc | 1440 |
| tactaccacg | atgttatgaa | cagacaagct | caggcttcta | gggctaaggg | tgagcttaga | 1500 |
| ggtcatcctt | tcgagggtaa | gcctatccct | aaccctcttc | tcggtctcga | ttctactaga | 1560 |
| actggtcatc | atcatcacca | tcactga | | | | 1587 |

<210> SEQ ID NO 120
<211> LENGTH: 528
<212> TYPE: PRT
<213> ORGANISM: Artificial Sequence
<220> FEATURE:
<223> OTHER INFORMATION: Brassica optimised

<400> SEQUENCE: 120

Met Ala Pro Pro Pro Ser Met Pro Ala Ala Ser Asp Arg Ala Gly Pro
1               5                   10                  15

-continued

```
Gly Arg Asp Ala Gly Asp Ser Ser Leu Arg Leu Arg Ala Pro
             20                  25                  30

Ser Ala Asp Ala Gly Asp Leu Ala Gly Asp Ser Ser Gly Gly Leu Arg
             35                  40                  45

Glu Asn Gly Glu Pro Gln Ser Pro Thr Asn Pro Pro Gln Glu Gln
 50                  55                  60

Gln Gln His Glu Met Leu Tyr Tyr Arg Ala Ser Ala Pro Ala His Arg
 65                  70                  75                  80

Arg Val Lys Glu Ser Pro Leu Ser Ser Asp Ala Ile Phe Arg Gln Ser
                 85                  90                  95

His Ala Gly Leu Leu Asn Leu Cys Ile Val Val Leu Ile Ala Val Asn
                100                 105                 110

Ser Arg Leu Ile Ile Glu Asn Leu Met Lys Tyr Gly Leu Leu Ile Arg
                115                 120                 125

Ala Gly Phe Trp Phe Ser Ala Arg Ser Leu Gly Asp Trp Pro Leu Leu
                130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
                180                 185                 190

Thr Leu Lys Cys Asp Ser Ala Val Leu Ser Gly Phe Val Leu Met Phe
                195                 200                 205

Leu Ala Ser Ile Met Trp Met Lys Leu Val Ser Tyr Ala His Thr Asn
210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
                260                 265                 270

Pro Gln Thr Thr Cys Ile Arg Lys Gly Trp Val Thr Gln Gln Leu Ile
                275                 280                 285

Lys Cys Val Val Phe Thr Gly Leu Met Gly Phe Ile Ile Glu Gln Tyr
290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
                340                 345                 350

Val Ala Glu Leu Leu Cys Phe Gly Asp Arg Glu Phe Tyr Lys Asp Trp
                355                 360                 365

Trp Asn Ala Lys Thr Val Glu Glu Tyr Trp Arg Met Trp Asn Met Pro
                370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
                420                 425                 430

Trp Ala Phe Ser Gly Ile Met Phe Gln Ile Pro Leu Val Phe Leu Thr
```

|  |  |  |  |  |  |  |  |  |  |  |
|---|---|---|---|---|---|---|---|---|---|---|
|  | 435 |  |  |  | 440 |  |  |  | 445 |  |
| Arg | Tyr | Leu | His | Ala | Thr | Phe | Lys | His | Val | Met | Val | Gly | Asn | Met | Ile |
|  | 450 |  |  |  |  | 455 |  |  |  | 460 |  |

Phe Trp Phe Phe Phe Ser Ile Val Gly Gln Pro Met Cys Val Leu Leu
465              470                475                480

Tyr Tyr His Asp Val Met Asn Arg Gln Ala Gln Ala Ser Arg Ala Lys
                 485                490                495

Gly Glu Leu Arg Gly His Pro Phe Glu Gly Lys Pro Ile Pro Asn Pro
            500                505                510

Leu Leu Gly Leu Asp Ser Thr Arg Thr Gly His His His His His His
            515                520                525

<210> SEQ ID NO 121
<211> LENGTH: 1778
<212> TYPE: DNA
<213> ORGANISM: Artificial Sequence
<220> FEATURE:
<223> OTHER INFORMATION: Brassica optimised

<400> SEQUENCE: 121

```
tctagatttc tagttttctc catataaaaa aaatattctc tgagcttctc gattctctaa      60
aaagacaagg ccaaaaaaaa caccatggct cctccacctt ctatgcctgc tgcttctgat     120
agagctggac ctggaagaga tgctggcgat tctgtaaaag aagatgtttt ttatttccag     180
caatgttaca ttgttatacg tataatgatg agtttagtga tcaagttcct ctttgattct     240
tctttcttgt tgcagtcatc tctcagactt agaagggctc catctgctga cgctggtgac     300
cttgctggtg atagctctgg tggacttaga gaaaacggtg agcctcaatc tcctactaac     360
cctccacctc aagagcaaca acagcacgag atgctttact acagagcttc tgctcctgct     420
catagaagag tgaaagaatc tccactctcg agtgatgcta tcttcaagca gtctcacgct     480
ggacttttca acctctgcat cgttgttctt atcgctgtta atagcagact tatcatcgag     540
aacctcatga agtacggatg gcttatcgat actggattct ggttctcttc tcgttctctt     600
ggtgactggt ctatcttcat gtgctgtctt actctcccta tcttccctct tgctgctttc     660
atcgttgaga agcttgttca gaggaaccat atcgctgagc ttgttgctgt tcttctccac     720
gttatcgttt ctactgctgc tgttctctac cctgttatcg ttatccttac ctgcgattct     780
gtttacatgt ctggtgttgt gcttatgctt tcggatgca tcatgtggct taagctcgtt     840
tcttacgctc acacctcttc agatatcaga acctcgcta gtctggata caaaggtgat     900
gctcaccta actctactat cgtgtcttgc tcttacgatg tgtctcttaa gtctctcgct     960
tacttcatgg ttgctcctac cctttgttac caaccttctt accctagatc tagctgcatc    1020
agaaagggat gggttgtgag acaattcgtt aagctcatcg tgttcatcgg acttatggga    1080
ttcatcatcg agcagtacat caaccctatc gtgagaaact ctaagcaccc tctcaaggga    1140
gatttccttt acgctatcga gagtgctt aagcttctg tgcctaacct ttacgtttgg       1200
ctctgcatgt tctactcatt cttccacctt tggcttaaca tccttgctga gttgcttaga    1260
ttcggagaca gagagttcta caaggattgg tggaacgcta agactgttgc tgagtactgg    1320
aagatgtgga acatgcctgt tcatagatgg atggttaggc acctttactt cccttgtctc    1380
agaaacggaa tccctaaaga gggtgctatc atcattgctt tcttggtgtc tggtgctttc    1440
catgagttgt gtatcgctgt tccttgtcac gttttcaagc tctgggcttt catcggaatc    1500
atgttccaag ttcctctcgt tcttatcact aactacctcc aagagaagtt ctctaacagc    1560
```

```
atggtgggaa acatgatttt ctggttcatt ttctgcatcc ttggacagcc tatgtgtgtt    1620
cttctctact accacgatct catcaacctc aaagagaagg ctaagggtga gcttagaggt    1680
catcctttcg agggtaagcc tatccctaac cctcttctcg gtctcgattc tactagaact    1740
ggtcatcatc atcaccatca ctgaaggtac cacccagc                            1778

<210> SEQ ID NO 122
<211> LENGTH: 1578
<212> TYPE: DNA
<213> ORGANISM: Artificial Sequence
<220> FEATURE:
<223> OTHER INFORMATION: Brassica optimised

<400> SEQUENCE: 122
atggctcctc caccttctat gcctgctgct tctgatagag ctggacctgg aagagatgct      60
ggcgattctt catctctcag acttagaagg ctccatctg ctgacgctgg tgaccttgct     120
ggtgatagct ctggtggact tagagaaaac ggtgagcctc aatctcctac taaccctcca     180
cctcaagagc aacaacagca cgagatgctt tactacagag cttctgctcc tgctcataga     240
agagtgaaag aatctccact ctcgagtgat gctatcttca agcagtctca cgctggactt     300
ttcaacctct gcatcgttgt tcttatcgct gttaatagca gacttatcat cgagaacctc     360
atgaagtacg gatggcttat cgatactgga ttctggttct cttctcgttc tcttggtgac     420
tggtctatct tcatgtgctg tcttactctc cctatcttcc ctcttgctgc tttcatcgtt     480
gagaagcttg ttcagaggaa ccatatcgct gagcttgttg ctgttcttct ccacgttatc     540
gtttctactg ctgctgttct ctaccctgtt atcgttatcc ttacctgcga ttctgtttac     600
atgtctggtg ttgtgcttat gcttttcgga tgcatcatgt ggcttaagct cgtttcttac     660
gctcacacct cttcagatat cagaacccc gctaagtctg gatacaaagg tgatgctcac     720
cctaactcta ctatcgtgtc ttgctcttac gatgtgtctc ttaagtctct cgcttacttc     780
atggttgctc ctaccctttg ttaccaacct tcttaccca gatctagctg catcagaaag     840
ggatgggttg tgagacaatt cgttaagctc atcgtgttca tcggacttat gggattcatc     900
atcgagcagt acatcaaccc tatcgtgaga aactctaagc accctctcaa gggagatttc     960
ctttacgcta tcgagagagt gcttaagctt tctgtgccta acctttacgt ttggctctgc    1020
atgttctact cattcttcca cctttggctt aacatccttg ctgagttgct tagattcgga    1080
gacagagagt tctacaagga ttggtggaac gctaagactg ttgctgagta ctggaagatg    1140
tggaacatgc tgttcatag atggatggtt aggcaccttt acttcccttg tctcagaaac    1200
ggaatcccta agagggtgc tatcatcatt gctttcttgg tgtctggtgc tttccatgag    1260
ttgtgtatcg ctgttccttg tcacgttttc aagctctggg ctttcatcgg aatcatgttc    1320
caagttcctc tcgttcttat cactaactac ctccaagaga gttctctaa cagcatggtg    1380 ggaaacatga tttctggtt cattttctgc atccttggac agcctatgtg tgttcttctc    1440
tactaccacg atctcatcaa cctcaaagag aaggctaagg gtgagcttag aggtcatcct    1500
ttcgagggta agcctatccc taaccctctt ctcggtctcg attctactag aactggtcat    1560
catcatcacc atcactga                                                 1578

<210> SEQ ID NO 123
<211> LENGTH: 525
<212> TYPE: PRT
<213> ORGANISM: Artificial Sequence
<220> FEATURE:
<223> OTHER INFORMATION: Brassica optimised
```

<400> SEQUENCE: 123

```
Met Ala Pro Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
            20                  25                  30

Ser Ala Asp Ala Gly Asp Leu Ala Gly Asp Ser Ser Gly Gly Leu Arg
            35                  40                  45

Glu Asn Gly Glu Pro Gln Ser Pro Thr Asn Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Lys Gln Ser
                85                  90                  95

His Ala Gly Leu Phe Asn Leu Cys Ile Val Val Leu Ile Ala Val Asn
            100                 105                 110

Ser Arg Leu Ile Ile Glu Asn Leu Met Lys Tyr Gly Trp Leu Ile Asp
            115                 120                 125

Thr Gly Phe Trp Phe Ser Ser Arg Ser Leu Gly Asp Trp Ser Ile Phe
        130                 135                 140

Met Cys Cys Leu Thr Leu Pro Ile Phe Pro Leu Ala Ala Phe Ile Val
145                 150                 155                 160

Glu Lys Leu Val Gln Arg Asn His Ile Ala Glu Leu Val Ala Val Leu
                165                 170                 175

Leu His Val Ile Val Ser Thr Ala Ala Val Leu Tyr Pro Val Ile Val
            180                 185                 190

Ile Leu Thr Cys Asp Ser Val Tyr Met Ser Gly Val Val Leu Met Leu
        195                 200                 205

Phe Gly Cys Ile Met Trp Leu Lys Leu Val Ser Tyr Ala His Thr Ser
210                 215                 220

Ser Asp Ile Arg Thr Leu Ala Lys Ser Gly Tyr Lys Gly Asp Ala His
225                 230                 235                 240

Pro Asn Ser Thr Ile Val Ser Cys Ser Tyr Asp Val Ser Leu Lys Ser
                245                 250                 255

Leu Ala Tyr Phe Met Val Ala Pro Thr Leu Cys Tyr Gln Pro Ser Tyr
            260                 265                 270

Pro Arg Ser Ser Cys Ile Arg Lys Gly Trp Val Val Arg Gln Phe Val
        275                 280                 285

Lys Leu Ile Val Phe Ile Gly Leu Met Gly Phe Ile Ile Glu Gln Tyr
290                 295                 300

Ile Asn Pro Ile Val Arg Asn Ser Lys His Pro Leu Lys Gly Asp Phe
305                 310                 315                 320

Leu Tyr Ala Ile Glu Arg Val Leu Lys Leu Ser Val Pro Asn Leu Tyr
                325                 330                 335

Val Trp Leu Cys Met Phe Tyr Ser Phe Phe His Leu Trp Leu Asn Ile
            340                 345                 350

Leu Ala Glu Leu Leu Arg Phe Gly Asp Arg Glu Phe Tyr Lys Asp Trp
        355                 360                 365

Trp Asn Ala Lys Thr Val Ala Glu Tyr Trp Lys Met Trp Asn Met Pro
            370                 375                 380

Val His Arg Trp Met Val Arg His Leu Tyr Phe Pro Cys Leu Arg Asn
385                 390                 395                 400

Gly Ile Pro Lys Glu Gly Ala Ile Ile Ile Ala Phe Leu Val Ser Gly
```

```
                405                  410                  415
Ala Phe His Glu Leu Cys Ile Ala Val Pro Cys His Val Phe Lys Leu
            420                  425                  430

Trp Ala Phe Ile Gly Ile Met Phe Gln Val Pro Leu Val Leu Ile Thr
        435                  440                  445

Asn Tyr Leu Gln Glu Lys Phe Ser Asn Ser Met Val Gly Asn Met Ile
    450                  455                  460

Phe Trp Phe Ile Phe Cys Ile Leu Gly Gln Pro Met Cys Val Leu Leu
465                  470                  475                  480

Tyr Tyr His Asp Leu Ile Asn Leu Lys Glu Lys Ala Lys Gly Glu Leu
                485                  490                  495

Arg Gly His Pro Phe Glu Gly Lys Pro Ile Pro Asn Pro Leu Leu Gly
            500                  505                  510

Leu Asp Ser Thr Arg Thr Gly His His His His His
        515                  520                  525

<210> SEQ ID NO 124
<211> LENGTH: 1770
<212> TYPE: DNA
<213> ORGANISM: Artificial Sequence
<220> FEATURE:
<223> OTHER INFORMATION: Brassica optimised

<400> SEQUENCE: 124
atggctgttg ctgaatcttc tcagaacacc actactatgt ctggacacgg tgattctgac      60
ctcaacgtaa agaagatgt tttttatttc cagcaatgtt acattgttat acgtataatg     120
atgagtttag tgatcaagtt cctctttgat tcttctttct tgttgcagaa cttcagacgt     180
agaaagcctt ctagctctgt tatcgagcct tcttcttctg gattcacctc tactaacggt     240
gttcctgcta ctggacatgt tgctgagaac agagatcagg atagagttgg agctatggaa     300
aacgctaccg gatctgttaa ccttatcgga acggtggag tgttgttat cggtaacgag       360 gaaaagcaag ttggagagac tgatatcaga ttcacctaca gaccatcttt cccagctcac     420
agaagagtta gggagtctcc actctcgagt gatgctatct tcagacagtc tcatgctgga     480
cttctcaacc tctgcatcgt tgttcttatc gctgtgaaca gcagacttat catcgagaac     540
ctcatgaagt acggacttct catcagagct ggattctggt tctctgctag atctcttgga     600
gattggcctc ttcttatgtg ctgtcttacc cttcctgttt tccctcttgt tgctcttatg     660
gccgagaagc ttatcactag aaagctcatc ggagagcatg ttgttatcct tctccacatc     720
atcatcacta cctctgctat cgtttaccct gttgttgtta cccttaagtg cgattctgct     780
gttctttctg gattcgtgct tatgttcctc gcttctatca tgtggatgaa gctcgtttct     840
tacgctcaca ccaactacga tatcagagtg ctctctaagt ctactgagaa gggtgctgct     900
tacggaaact atgtggaccc tgagaacatg aaggatccta ccttcaagtc tctcgtgtac     960
ttcatgcttg ctcctaccct tgttaccaa cctacttacc ctcagactac ctgtatcaga    1020
aagggatggg ttacccaaca actcatcaag tgcgttgtgt tcactggact tatgggattc    1080
atcatcgagc agtacatcaa ccctatcgtg aagaactcta agcaccctct aagggaaac     1140 ttcctcaacg ctatcgagag agttctcaag cttttctgttc ctactcttta cgtttggctc    1200
tgcatgttct actgtttctt ccacctttgg ctcaacatcg ttgctgagct tctctgtttc    1260
ggagatcgtg agttctacaa ggattggtgg aacgctaaga ctgttgagga atactggcgt    1320
atgtggaaca tgcctgttca taagtggatc atcaggcaca tctacttccc ttgcatcagg    1380
```

| | |
|---|---:|
| aagggattct ctaggggagt tgctatcctt atctctttcc tcgtttctgc tgttttccat | 1440 |
| gagatctgta tcgctgttcc ttgtcacatc ttcaagttct gggctttctc tggtatcatg | 1500 |
| ttccagatcc ctcttgtttt ccttaccaga taccttcacg ctactttcaa gcacgttatg | 1560 |
| gtgggaaaca tgattttctg gttcttttc agcatcgttg gacagcctat gtgtgttctt | 1620 |
| ctctactacc acgatgttat gaacagacaa gctcaggctt ctagggctaa gggtgagctt | 1680 |
| agaggtcatc ctttcgaggg taagcctatc cctaaccctc ttctcggtct cgattctact | 1740 |
| agaactggtc atcatcatca ccatcactga | 1770 |

<210> SEQ ID NO 125
<211> LENGTH: 1668
<212> TYPE: DNA
<213> ORGANISM: Artificial Sequence
<220> FEATURE:
<223> OTHER INFORMATION: Brassica optimised

<400> SEQUENCE: 125

| | |
|---|---:|
| atggctgttg ctgaatcttc tcagaacacc actactatgt ctggacacgg tgattctgac | 60 |
| ctcaacaact tcagacgtag aaagccttct agctctgtta tcgagccttc ttcttctgga | 120 |
| ttcacctcta ctaacggtgt tcctgctact ggacatgttg ctgagaacag agatcaggat | 180 |
| agagttggag ctatggaaaa cgctaccgga tctgttaacc ttatcggaaa cggtggaggt | 240 |
| gttgttatcg gtaacgagga aaagcaagtt ggagagactg atatcagatt cacctacaga | 300 |
| ccatctttcc cagctcacag aagagttagg gagtctccac tctcgagtga tgctatcttc | 360 |
| agacagtctc atgctggact tctcaacctc tgcatcgttg ttcttatcgc tgtgaacagc | 420 |
| agacttatca tcgagaacct catgaagtac ggacttctca tcagagctgg attctggttc | 480 |
| tctgctagat ctcttggaga ttggcctctt cttatgtgct gtcttaccct tcctgttttc | 540 |
| cctcttgttg ctcttatggc cgagaagctt atcactagaa agctcatcgg agagcatgtt | 600 |
| gttatccttc tccacatcat catcactacc tctgctatcg tttaccctgt tgttgttacc | 660 |
| cttaagtgcg attctgctgt tctttctgga ttcgtgctta tgttcctcgc ttctatcatg | 720 |
| tggatgaagc tcgtttctta cgctcacacc aactacgata tcagtgctc tctaagtct | 780 |
| actgagaagg gtgctgctta cggaaactat gtggaccctg agaacatgaa ggatcctacc | 840 |
| ttcaagtctc tcgtgtactt catgcttgct cctacccttt gttaccaacc tacttaccct | 900 |
| cagactacct gtatcagaaa gggatgggtt acccaacaac tcatcaagtg cgttgtgttc | 960 |
| actggactta tgggattcat catcgagcag tacatcaacc ctatcgtgaa gaactctaag | 1020 |
| caccctctta agggaaactt cctcaacgct atcgagagag ttctcaagct ttctgttcct | 1080 |
| actctttacg tttggctctg catgttctac tgtttcttcc acctttggct caacatcgtt | 1140 |
| gctgagcttc tctgtttcgg agatcgtgag ttctacaagg attggtggaa cgctaagact | 1200 |
| gttgaggaat actggcgtat gtggaacatg cctgttcata gtggatcat caggcacatc | 1260 |
| tacttcccctt gcatcaggaa gggattctct aggggagttg ctatccttat ctctttcctc | 1320 |
| gtttctgctg ttttccatga gatctgtatc gctgttcctt gtcacatctt caagttctgg | 1380 |
| gctttctctg gtatcatgtt ccagatccct cttgttttcc ttaccagata ccttcacgct | 1440 |
| actttcaagc acgttatggt gggaaacatg attttctggt tcttttcag catcgttgga | 1500 |
| cagcctatgt gtgttcttct ctactaccac gatgttatga acagacaagc tcaggcttct | 1560 |
| agggctaagg gtgagcttag aggtcatcct ttcgaggta agcctatccc taaccctctt | 1620 |
| ctcggtctcg attctactag aactggtcat catcatcacc atcactga | 1668 |

```
<210> SEQ ID NO 126
<211> LENGTH: 555
<212> TYPE: PRT
<213> ORGANISM: Artificial Sequence
<220> FEATURE:
<223> OTHER INFORMATION: Brassica optimised

<400> SEQUENCE: 126
```

| | | | | | | | | | | | | | | |
|---|---|---|---|---|---|---|---|---|---|---|---|---|---|---|
| Met | Ala | Val | Ala | Glu | Ser | Ser | Gln | Asn | Thr | Thr | Met | Ser | Gly | His |
| 1 | | | | 5 | | | | | 10 | | | | | 15 |
| Gly | Asp | Ser | Asp | Leu | Asn | Asn | Phe | Arg | Arg | Arg | Lys | Pro | Ser | Ser |
| | | | 20 | | | | | 25 | | | | | 30 | |
| Val | Ile | Glu | Pro | Ser | Ser | Ser | Gly | Phe | Thr | Ser | Thr | Asn | Gly | Val | Pro |
| | | | 35 | | | | | 40 | | | | | 45 | |
| Ala | Thr | Gly | His | Val | Ala | Glu | Asn | Arg | Asp | Gln | Asp | Arg | Val | Gly | Ala |
| | | 50 | | | | | 55 | | | | | 60 | | |
| Met | Glu | Asn | Ala | Thr | Gly | Ser | Val | Asn | Leu | Ile | Gly | Asn | Gly | Gly |
| 65 | | | | | 70 | | | | | 75 | | | | | 80 |
| Val | Val | Ile | Gly | Asn | Glu | Glu | Lys | Gln | Val | Gly | Glu | Thr | Asp | Ile | Arg |
| | | | | 85 | | | | | 90 | | | | | 95 | |
| Phe | Thr | Tyr | Arg | Pro | Ser | Phe | Pro | Ala | His | Arg | Arg | Val | Arg | Glu | Ser |
| | | | 100 | | | | | 105 | | | | | 110 | | |
| Pro | Leu | Ser | Ser | Asp | Ala | Ile | Phe | Arg | Gln | Ser | His | Ala | Gly | Leu | Leu |
| | | | 115 | | | | | 120 | | | | | 125 | | |
| Asn | Leu | Cys | Ile | Val | Val | Leu | Ile | Ala | Val | Asn | Ser | Arg | Leu | Ile | Ile |
| | 130 | | | | | 135 | | | | | 140 | | | | |
| Glu | Asn | Leu | Met | Lys | Tyr | Gly | Leu | Leu | Ile | Arg | Ala | Gly | Phe | Trp | Phe |
| 145 | | | | | 150 | | | | | 155 | | | | | 160 |
| Ser | Ala | Arg | Ser | Leu | Gly | Asp | Trp | Pro | Leu | Leu | Met | Cys | Cys | Leu | Thr |
| | | | | 165 | | | | | 170 | | | | | 175 | |
| Leu | Pro | Val | Phe | Pro | Leu | Val | Ala | Leu | Met | Ala | Glu | Lys | Leu | Ile | Thr |
| | | | 180 | | | | | 185 | | | | | 190 | | |
| Arg | Lys | Leu | Ile | Gly | Glu | His | Val | Val | Ile | Leu | Leu | His | Ile | Ile | Ile |
| | | 195 | | | | | 200 | | | | | 205 | | | |
| Thr | Thr | Ser | Ala | Ile | Val | Tyr | Pro | Val | Val | Val | Thr | Leu | Lys | Cys | Asp |
| 210 | | | | | 215 | | | | | 220 | | | | | |
| Ser | Ala | Val | Leu | Ser | Gly | Phe | Val | Leu | Met | Phe | Leu | Ala | Ser | Ile | Met |
| 225 | | | | | 230 | | | | | 235 | | | | | 240 |
| Trp | Met | Lys | Leu | Val | Ser | Tyr | Ala | His | Thr | Asn | Tyr | Asp | Ile | Arg | Val |
| | | | 245 | | | | | 250 | | | | | 255 | | |
| Leu | Ser | Lys | Ser | Thr | Glu | Lys | Gly | Ala | Ala | Tyr | Gly | Asn | Tyr | Val | Asp |
| | | | 260 | | | | | 265 | | | | | 270 | | |
| Pro | Glu | Asn | Met | Lys | Asp | Pro | Thr | Phe | Lys | Ser | Leu | Val | Tyr | Phe | Met |
| | | 275 | | | | | 280 | | | | | 285 | | | |
| Leu | Ala | Pro | Thr | Leu | Cys | Tyr | Gln | Pro | Thr | Tyr | Pro | Gln | Thr | Thr | Cys |
| | 290 | | | | | 295 | | | | | 300 | | | | |
| Ile | Arg | Lys | Gly | Trp | Val | Thr | Gln | Gln | Leu | Ile | Lys | Cys | Val | Val | Phe |
| 305 | | | | | 310 | | | | | 315 | | | | | 320 |
| Thr | Gly | Leu | Met | Gly | Phe | Ile | Ile | Glu | Gln | Tyr | Ile | Asn | Pro | Ile | Val |
| | | | | 325 | | | | | 330 | | | | | 335 | |
| Lys | Asn | Ser | Lys | His | Pro | Leu | Lys | Gly | Asn | Phe | Leu | Asn | Ala | Ile | Glu |
| | | | 340 | | | | | 345 | | | | | 350 | | |
| Arg | Val | Leu | Lys | Leu | Ser | Val | Pro | Thr | Leu | Tyr | Val | Trp | Leu | Cys | Met |
| | | 355 | | | | | 360 | | | | | 365 | | | |

```
Phe Tyr Cys Phe Phe His Leu Trp Leu Asn Ile Val Ala Glu Leu Leu
            370                 375                 380
Cys Phe Gly Asp Arg Glu Phe Tyr Lys Asp Trp Asn Ala Lys Thr
385                 390                 395                 400
Val Glu Glu Tyr Trp Arg Met Trp Asn Met Pro Val His Lys Trp Ile
                405                 410                 415
Ile Arg His Ile Tyr Phe Pro Cys Ile Arg Lys Gly Phe Ser Arg Gly
            420                 425                 430
Val Ala Ile Leu Ile Ser Phe Leu Val Ser Ala Val Phe His Glu Ile
            435                 440                 445
Cys Ile Ala Val Pro Cys His Ile Phe Lys Phe Trp Ala Phe Ser Gly
450                 455                 460
Ile Met Phe Gln Ile Pro Leu Val Phe Leu Thr Arg Tyr Leu His Ala
465                 470                 475                 480
Thr Phe Lys His Val Met Val Gly Asn Met Ile Phe Trp Phe Phe Phe
                485                 490                 495
Ser Ile Val Gly Gln Pro Met Cys Val Leu Leu Tyr Tyr His Asp Val
            500                 505                 510
Met Asn Arg Gln Ala Gln Ala Ser Arg Ala Lys Gly Glu Leu Arg Gly
            515                 520                 525
His Pro Phe Glu Gly Lys Pro Ile Pro Asn Pro Leu Leu Gly Leu Asp
            530                 535                 540
Ser Thr Arg Thr Gly His His His His His His
545                 550                 555

<210> SEQ ID NO 127
<211> LENGTH: 1148
<212> TYPE: DNA
<213> ORGANISM: Artificial Sequence
<220> FEATURE:
<223> OTHER INFORMATION: Brassica napus

<400> SEQUENCE: 127
tttcttcatc ggtgattgat tcctttaaag acttatgttt cttatcttgc ttctgaggca     60
agtattcagt taccagttac cacttatatt ctggactttc tgactgcatc ctcatttttc    120
caacatttta aatttcacta ttggctgaat gcttcttctt tgaggaagaa acaattcaga    180
tggcagaaat gtatcaacca atgcatatat acaaatgtac ctcttgttct caaaacatct    240
atcggatggt tccatttgct ttgtcatcca attagtgact actttatatt attcactcct    300
ctttattact attttcatgc gaggttgcca tgtacattat atttgtaagg attgacgcta    360
ttgagcgttt tcttcaatt ttctttattt tagacatggg tatgaaatgt gtgttagagt     420
tgggttgaat gagatatacg ttcaagtgaa gtggcatacc gttctcgagt aaggatgacc    480
tacccattct tgagacaaat gttacatttt agtatcagag taaatgtgt acctataact     540
caaattcgat tgcatgtat ccattcaaca taaaattaaa ccagcctgca cctgcatcca    600
catttcaagt atttcaaac cgttcggctc ctatccaccg ggtgtaacaa gacggattcc     660
gaatttggaa gattttgact caaattccca atttatattg accgtgacta aatcaacttt    720
aacttctata attctgatta agctcccaat ttatattccc aacggcacta cctccaaaat    780
ttatagactc tcatcccctt taaaccaac ttagtaaacg tttttttttt taattttatg     840
aagttaagtt tttaccttgt ttttaaaaag aatcgttcat aagatgccat gccagaaacat   900
tagctacacg ttcacatag catgcagccg cggagaattg ttttcttcg ccacttgtca     960
```

```
ctcccttcaa acacctaaga gcttctctct cacagcacac acatacaatc acatgcgtgc    1020
atgcattatt acacgtgatc gccatgcaaa tctcctttat agcctataaa ttaactcatc    1080
cgcttcactc tttactcaaa ccaaaactca tcaatacaaa caagattaaa aacatacacg    1140
gactctag                                                             1148

<210> SEQ ID NO 128
<211> LENGTH: 3531
<212> TYPE: DNA
<213> ORGANISM: Arabidopsis thaliana

<400> SEQUENCE: 128
tgaatccttt ttcctttctt cttcttcttc tcttcagaga aaactttgct tctctttcta      60
taaggaacca gacacgaatc ccattcccac cgatttctta gcttcttcct tcaatccgct     120 cttccctct ccattagatt ctgtttcctc tttcaatttc ttctgcatgc ttctcgattc      180
tctctgacgc ctcttttctc ccgacgctgt ttcgtcaaac gcttttcgaa atggcgattt     240
tggattctgc tggcgttact acggtgacgg agaacggtgg cggagagttc gtcgatcttg     300
ataggcttcg tcgacggaaa tcgagatcgg attcttctaa cggacttctt ctctctggtt     360
ccgataataa ttctccttcg gatgatgttg gagctcccgc cgacgttagg gatcggattg     420
attccgttgt taacgatgac gctcagggaa cagccaattt ggccggagat aataacggtg     480
gtggcgataa taacggtggt ggaagaggcg gcggagaagg aagaggaaac gccgatgcta     540
cgtttacgta tcgaccgtcg gttccagctc atcgagggc gagagagagt ccacttagct      600
ccgacgcaat cttcaaacag gtttaaaatc tcagaaatct tcgaatttgg tgtttgcttg     660
ttgttttata tggaattgag tttggtgatt gttttgcatt gcagagccat gccggattat     720
tcaacctctg tgtagtagtt cttattgctg taaacagtag actcatcatc gaaaatctta     780
tgaaggtttg ctgttacttg tttctccttt taggaattga attgcttgaa aatttatcag     840
agacgaataa ctttgttgtt gctatcattc atgtagtatg gttggttgat cagaacggat     900
ttctggttta gttcaagatc gctgcgagat tggccgcttt tcatgtgttg gtaaaagaag     960
atgtttttta tttccagcaa tgttacattg ttatacgtat aatgatgagt ttagtgatca    1020
agttcctctt tgattcttct ttcttgttgc agtatatccc tttcgatctt tcctttggct    1080
gcctttacgg ttgagaaatt ggtacttcag aaatacatat cagaacctgt gagtaattac    1140
tattctccag ccattactgt aatttttatt gaagacaagt ttgtatcatg aagaacttac    1200
aagttctgtt tgaaaatgc tcaaggttgt catctttctt catattatta tcaccatgac     1260
agaggttttg tatccagttt acgtcaccct aaggtgatac tgttttctg gtctcagttt     1320 gtgatactgt ttttaagttt agttgtctga cccggtgatc ttgaaaatgg acaggtgtga    1380
ttctgctttt ttatcaggtg tcactttgat gctcctcact tgcattgtgt ggctaaagtt    1440
ggtttcttat gctcatacta gctatgacat aagatcccta gccaatgcag ctgataaggt    1500
aaaatacgaa aagaagcgt atgtattagt cacttgcact gtgttactgt tttaaccaaa     1560
cactgttatg aactttaggc caatcctgaa gtctcctact acgttagctt gaagagcttg    1620
gcatatttca tggtcgctcc cacattgtgt tatcaggtaa ctgcaaagtg catcaaccat    1680
tcttatactt gcaagagttt cttgtctaaa cctcggatct ttgcttttcc ccagccaagt    1740
tatccacgtt ctgcatgtat acggaagggt tgggtggctc gtcaatttgc aaaactggtc    1800
atattcaccg gattcatggg atttataata gaacaagtac gttttcacat cttgctttat    1860
tagttttcct tggtgaaaat catcatccct gcgttgtcac cacttgactt catgttcttt    1920
```

```
tgttacattt tggcagtata taaatcctat tgtcaggaac tcaaagcatc ctttgaaagg    1980
cgatcttcta tatgctattg aaagagtgtt gaagctttca gttccaaatt tatatgtgtg    2040
gctctgcatg ttctactgct tcttccacct ttggtatgct gtgatcccat ctctttcaaa    2100
ataatttgca aattcgaaaa accgaaaaag gctaaatctc atacgaattt gatattttta    2160
gtttcttaga gtcggtgatg taatttcagt tactgaacgc aaatctcttg tccaaaggtt    2220
aaacatattg gcagagcttc tctgcttcgg ggatcgtgaa ttctacaaag attggtggaa    2280
tgcaaaaagt gtgggagatg tgagctattt tactcaaaag aaaacttatg attttaatg     2340 ttgtcgttgt ttttgggtca tctaactaac caaattcatg tattcactgt cttcctttat    2400
cagtactgga gaatgtggaa tatggtatgg ttctcttcct aaacatcacc ttcttttgta    2460
cacaaaatag aagaagagag ctaattaaga tcttgttttc cttgacagcc tgttcataaa    2520
tggatggttc gacatatata cttcccgtgc ttgcgcagca agataccaaa ggtgagtgag    2580
atatataccg atatgcaatt gtcgagattt gtttctgtga tataaattta accctccaca    2640
cacttgtttt tcagacactc gccattatca ttgctttcct agtctctgca gtctttcatg    2700
aggtatacat actttctaca ttgccctgtc tctagacgca tgaacacacg ctagtgaaag    2760
aaatgctaat attcaaagca ttgttttttac ttaacgatct tgtgttacaa atttcctttt   2820
gacagctatg catcgcagtt ccttgtcgtc tcttcaagct atgggctttt cttgggatta    2880
tgtttcaggt taaaaaatta ctaaactgct gcagtcgatt tttactaaac tctaatctca    2940
tattctgacc aaccaatttg tttgagtagg tgcctttggt cttcatcaca aactatctac    3000
aggaaaggtt tggctcaacg gtatgctctc aaaacccgag aaaatagaac gaataactct    3060
ttctttcata gcctagccat ttaaatcgca atgctgaaac ttaataataa aggtgatctg    3120
ttttggaatg ggatcatatt attaggtggg gaacatgatc ttctggttca tcttctgcat    3180
tttcggacaa ccgatgtgtg tgcttctttta ttaccgac ctgatgaacc gaaaaggatc     3240
gatgtcatga acaactgtt caaaaaatga ctttcttcaa acatctatgg cctcgttgga    3300
tctccgttga tgttgtggtg gttctgatgc taaaacgaca aatagtgtta taaccattga    3360
agaagaaaag aaaattagag ttgttgtatc tgcaaaaatt ttggtagaga cacgcgaacc    3420
cgtttggatt tgttatggt gtaaagaaat ttcaatcaaa aaactgttgt aataattgtt     3480
accaaaaaga aatgctttc tggaaacgag gggaaaaata gtagttttgt t              3531
```

<210> SEQ ID NO 129
<211> LENGTH: 6346
<212> TYPE: DNA
<213> ORGANISM: Zea mays

<400> SEQUENCE: 129

```
atggccccgc cccctccat gcctgccgcc tccgatcgcg ccggccctgg ccgcgacgcg      60
ggcgactcgt cctcccttcg cctccgccgc gccccctcag ccgacgccgg cgaccttgcc    120
ggcgattcct cggtaggctt gcgggagaac ggcgagccgc aaccgccgac gaatccgccg    180
ccgcaggagc agcagcagca gcacgagatg ctatactacc gcgcgtcggc gcccgcccac    240
cgccgcgtca aggagagccc cctcagctct gacgccatct tccggcaggt gaggagacgc    300
gaattttagg ctcgctgttt gtaagcgatt gtttgatccc cgcgcttgtg cttcgatcca    360
cgccagttgc aaaatcctgc aaattgtttg ttgcttccag tcaactctgc ctctgttttt    420
ttttggttgg tgtgtgtgtg tgtgtgtgtg ttcaaatcac actttgtgct atcggtagct    480
```

```
taacactgcc ggttgccatc tcgcgcgcac ggatgtttta ttgtgggcct tgggcttcgg    540
aattgtggat agattgtgcg cgtgtactcg aatgggcaca attcgtttcg tgggggggcat    600 atgctgctgc gattgaggtc ggtgtttact tgttttggga tcaggggggac cagtgccggt    660 gcgcgggtgc cagatgcatg ccacgcagaa tttggcatcg gccggctgaa gcagcaaaca    720
acgagcgtaa ccgttaccac tggaggagct ttggcttgtc gaaacggatg actggatgag    780
cgaatgaatc attgaattca ttgttggcgg tactcactat agtgatgtgg acagttgttg    840
ggacagcacc tgcagtgccc ccagtattat taatgctgac ttttctaact acaatgcgtg    900
ttacattgtt tgtacacctt ggctttcctg cttggggcat tgcttcttgt tgaggaccat    960
ataactgtgc acctacatag aactgtattg gaccacttgt aagttttaac tggttagccc   1020
tccatttttt aataggtata ttattagaca attttttattg tcattgacat tattttttgtt   1080 tgctactctc ggagcccttt tcccagtgta atcttaatag ggctcaaatc acagcagaaa   1140
cacgtgagac gtaattttct agtgatactt ttattagact ttgttgtttc tgcacatact   1200
ctaaatctgt tttgaaggta ggagtgctta tttggatgat aaataatcct gggattacac   1260
agtggacaac gctttgataa ttgagtccat gctaacttga ttataatata tcagtattcc   1320
atatatcatt ttatcttgta cttcaactga gatcatcctt attttttgca aaccgtattt   1380
attggttgct ctggagaatt gaagtcttga aactaagcac ttctcctgat gcagagcca   1440 tgctggtctt ctgaatctat gcattgttgt tctgatcgca gtgaacagca gactcattat   1500
tgagaattta atgaaggttt attacttttct ttcttttttc attttcctca ccttcattta   1560
cagatccctc aatccatctc cttctgaaat acatctggtc ttcttcctgc gcatttgtct   1620
agtgtaaatc tgacacattc tgtgttttat ttaaattggc tggtgcagta tggcctgttg   1680
ataagagctg gattttggtt tagtgcaaga tcgctgggtg actggcccct tctaatgtgc   1740
tggtagaaat tgttgtcatt tttaattcag atgggtttca aataagaact gtggagtaat   1800
caatctgtca atttcagcct cactctacca gttttcccac tagttgcact catggctgag   1860
aagctgatca caagaaagct cattggtgaa catgtaagtt tgactcacaa gattgcgtag   1920
tattttgtag agaagttctc ttttgttatt tcttaggtat aagtgttgag gattgaatta   1980
gatgtaaaac tagacagtcc tctattctgc atcttccagg tgccatttat cgtttatgac   2040
ttctatacac ctcttgcagg tggttattct actccatatc attattacaa catctgccat   2100
tgtctatcca gttgttgtga ctcttaagta agcatttctt tctgctttgc agtttgtttg   2160
gatgcatctt attttgacat tcgttgagct ctagtatttc atggtatgga atacattcaa   2220
ttaatcttgt tcgtaatttg ctgtacttca tggtatggtg gccaactaca ttattgtgcc   2280
ccaaacattt agtctttccc ttcaagatac gtactatact atgcaaattg ggtggataaa   2340
aaggtagcta cataacactt ttatttaatt gtatctggtg actccacact ataatacaaa   2400
gaaacgcaac tctccagcat attcaagaaa aaaatgtatc tggtgataaa aatctattgc   2460
aaatgttcat ttatctctag tagaagaaat ccttactatc ttactctgtc ttgatctgtt   2520
cactgactgc atctaatagg gaagatttgt tagtccatca atattgatac acattttatt   2580
atgcagatat tttgtttctt tcatgtagct tctagcttgt aacccctttc ctaacatgaa   2640
gctgatcttt ccattgtaca agaaaaattg gatatatttg ttcacatgct tggaaattga   2700
ataaacaaac tgtagtattt ctgatgttga tgtgcaagta gtagactttg gttgagtcaa   2760
ttgttatctc tcaaaaagag ccattaggag caagttacct tttcattgat tatatttttct   2820 gtgagactgc aagagttaag aatgttgtat ggttgatgcc ttatgctgtt tagtttaagt   2880
```

```
ttgttataat tgccaagaaa tgttacttga aaagatattg tcccatgcat caattatgga    2940
ttatcagttc agtcatattc cgaaaaattt caggtgtgac tcagcagtac tatctggatt    3000
tgtgctaatg tttcttgcga gcatcatgtg gatgaagctt gtctcttatg cacatacaaa    3060
ttatgatata agggtattgt ccaaaagtac tgagaaggta atgcattgac atgttaatct    3120
gaatcagttc aaatattttg ttaacatgtt gcccatttct caaaattgat ttgttgacgt    3180
tcaaactttt cttaaaactc cttttggtgg ccaaattttt ctgaagctag aatatctccc    3240
acttgtttaa acttcttttc cagtttcatt tcatgaatgt cttatatcta gtttcaattt    3300
ttgcatagga tgaaatgtgg tgccaatcaa tatacgttac catcaagaga gtaaaaaaat    3360
tgttcttaac ttctcataca gtgttttgt tacatgggct gatcatatat actctcatgt     3420
gttagcttaa ctgttagtgt atacctctat tgtaatgggc cttggtccac ctaaccctgt    3480
tatatcaatg cattcccaac cctaattagg gttagggttt ccctcattct aacttcaggc    3540
aacggtagca tatgattata tcccttcatt ttcattttc atgcaaataa ccactattgc     3600
tatattctta tttttagggt gctgcatatg gaaattatgt cgatcctgag aatatgaaag    3660
atccaacctt taaagtcta gtgtacttca tgttggcccc aacactttgt taccaggtac     3720
tattattgga ccaatgcccc gttttgtttt taatgtcta cactctgctt ttcttcatcg     3780
cgtctatcta gttatgccag tgacaacatg aatttcctga tgtcactttg gcatgttatg    3840
cagccaactt atcctcaaac tacatgtatt agaaagggtt gggtgaccca gcaactcata    3900
aagtgcgtgg ttttacagg cttgatgggc ttcataattg agcaagtgag cctcctatat     3960
tccttaagta acttgtattt atacataact ttggattaaa ttaccaatt tcttctatt      4020 ttgcagtata taaacccaat tgtgaagaat tccaaacatc cactgaaagg gaattttttg    4080
aatgctatag aaagagtctt aaaactctca gtgccaacat tatatgtatg gctttgcatg    4140
ttctattgct ttttcatttt atggttagta tcttgcttca gttcaacagt accttaaatt    4200
tgtgcggcag tgattggttt ataacagg ttaattgggt tttgacctgc atgggacttt      4260
gatttccatt ttccatggca ttcttgtttt ctcttttggt tggtttcagg ctgaacattg    4320
tagctgaact cctctgtttc ggtgaccgtg aattctataa ggactggtgg aatgccaaaa    4380
ctgttgaaga ggtgagatgc ctgttaaaat tgagttcgtt tcttttgaag tgagaacttt    4440
aaataggact gacatcaatt atattctcat gtacttaaat gtgatggtat tttggggctt    4500
tacctcagta ctggaggatg tggaacatgg taatcttttt gttacttcta tattcagatt    4560 ctatacccctt ttatttagtt gagactttgt tacttaacta aggacagttg tgatggtagt   4620
ggtactcttc tatttagtta agacttcctt aacttctgtc actgagcttg agatatttgt    4680
ctaataatat ctttcaaata actgacaatt agtctatttt ttgtcagcct gttcataagt    4740
ggatcatcag acacatatat tttccatgta taaggaaagg cttttccagg gtaattgctt    4800
ctatatgtgt acaaaactct acatttgttc tttgcttttg aattctccaa atgcagttta    4860
gtttggaaca tcgatgcaat atagaattca caatatacaa atgatgttct ttagaaaatg    4920
gggaagcaga gctggacaga gtgttagcac tcaattgtca atttgtcata ataataatga   4980
atacaactga acaagtggct gaaactgttg tgagaaaatc agaacactag tggtcaatat    5040
tatttgcata gtaaatcaat ttggtaatgt aaattaagat atgaagttct tacttcttat    5100
ataaagattt actatgcttg aattttatag tggctgaaac tttactgttc ttggataaag    5160 atttttaaata aaaacaaagg atatctagac ttggcaacaa aatgctgcct tctgctgact   5220
```

```
ggcaaaagta aattagacaa tgtgaataca tggacataca taaaattttg ttggtccttt   5280 cattttttgca gaactgacat gattttcact gcctacttct caaattcgta ttgtatctac   5340
actgcagggt gtagctattc taatctcgtt tctggtttca gctgtattcc atgaggtact   5400
ttaagttctt cagaagcctt tttcatgatc ggttcaattt ctgttttccc taagacatgc   5460
tattgttcga attccactca gcacattact aacaatacgt ttgaccttac gtaccaatat   5520
atcatcacca catctctttt tacattgtga attcacagat atgtattgcg gtgccgtgcc   5580 acatttttcaa attctgggca ttttctggga tcatgtttca ggtatagaaa taacactaat   5640
atataactac tacctccatt ccgaattata agtctttctg gcttggcttt tctagttaca   5700
ttatactagg tatatatcta gattataata gttatatatc tagacattgt gtatatctag   5760
atgcatacca aatgttacct atctagaaaa taggatcatg gtttcaggta tagaagtagt   5820
aataatataa taactactac ctccatttcg aactgtaagt cattatgact tggcttttat   5880
agataatgct aagagttata tatctggaca ttatctagat gcgtagctac gaatctagga   5940
aaactagaac gacttgtaat tatccctgcc ttttcttttg agtccatcag tgtctattct   6000
cttacgtttt gattccatca ttacatccat aagaacaata ctacatcttg gatacaatgt   6060
accttccact gttttcacat aggctgacac tggttgatgt ctgactcaca gataccgttg   6120
gtattcttga caagatatct ccatgctacg ttcaagcatg taatggtacg ctgtgtcaat   6180
tatgtccttt ttttcccatt acctcttgcc actacctaac catcatcttc ttatttggca   6240
ggtgggcaac atgatatttt ggttcttcag tatagtcgga cagccgatgt gtgtccttct   6300
atactaccat gacgtcatga acaggcaggc ccaggcaagt agatag              6346

<210> SEQ ID NO 130
<211> LENGTH: 157
<212> TYPE: PRT
<213> ORGANISM: Arabidopsis thaliana

<400> SEQUENCE: 130

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Leu Ile
    130                 135                 140

Ala Val Asn Ser Arg Leu Ile Ile Glu Asn Leu Asn Lys
145                 150                 155

<210> SEQ ID NO 131
<211> LENGTH: 140
```

<212> TYPE: PRT
<213> ORGANISM: Brassica juncea

<400> SEQUENCE: 131

```
Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Arg Ser Asp
                20                  25                  30

Ser Ser Asn Gly Leu Leu Ser Asp Thr Ser Pro Ser Asp Asp Val Gly
            35                  40                  45

Ala Ala Ala Ala Glu Arg Asp Arg Val Asp Ser Ala Ala Glu Glu Glu
        50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
                100                 105                 110

Gln Ser His Ala Gly Leu Phe Asn Leu Cys Val Val Leu Val Ala
            115                 120                 125

Val Asn Ser Arg Pro Ile Ile Glu Asn Leu Met Lys
    130                 135                 140
```

<210> SEQ ID NO 132
<211> LENGTH: 140
<212> TYPE: PRT
<213> ORGANISM: Brassica napus

<400> SEQUENCE: 132

```
Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Ser Asp
                20                  25                  30

Ser Ser Asn Gly Leu Leu Ser Asp Thr Ser Pro Ser Asp Asp Val Gly
            35                  40                  45

Ala Ala Ala Ala Glu Arg Asp Arg Val Asp Ser Ala Ala Glu Glu Glu
        50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
                100                 105                 110

Gln Ser His Ala Gly Leu Phe Asn Leu Cys Val Val Leu Val Ala
            115                 120                 125

Val Asn Ser Arg Leu Ile Ile Glu Asn Leu Met Lys
    130                 135                 140
```

<210> SEQ ID NO 133
<211> LENGTH: 140
<212> TYPE: PRT
<213> ORGANISM: Brassica juncea

<400> SEQUENCE: 133

```
Met Ala Ile Leu Asp Ser Gly Thr Val Thr Met Ala Thr Glu Asn Gly
1               5                   10                  15

Val Ala Asp Leu Asp Met Leu Arg Arg Arg Lys Ser Arg Ser Asp Ser
```

```
                    20                  25                  30
Ser Asn Gly Leu Leu Ser Glu Thr Ser Pro Ser Asp Asp Ala Gly Ala
            35                  40                  45

Pro Ala Asp Val Glu Asp Arg Val Asp Ser Ala Ala Gln Gly Thr Ala
 50                  55                  60

Asn Leu Ala Gly Asp Thr Glu Thr Arg Glu Ser Gly Gly Gly Gly Gly
 65                  70                  75                  80

Gly Gly Asn Gly Glu Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
            115                 120                 125

Val Asn Ser Arg Leu Ile Ile Glu Asn Leu Met Lys
        130                 135                 140

<210> SEQ ID NO 134
<211> LENGTH: 149
<212> TYPE: PRT
<213> ORGANISM: Tropaeolum majus

<400> SEQUENCE: 134

Met Ala Val Ala Glu Ser Ser Gln Asn Thr Thr Met Ser Gly His
 1               5                  10                  15

Gly Asp Ser Asp Leu Asn Asn Phe Arg Arg Arg Lys Pro Ser Ser Ser
                20                  25                  30

Val Ile Glu Pro Ser Ser Ser Gly Phe Thr Ser Thr Asn Gly Val Pro
            35                  40                  45

Ala Thr Gly His Val Ala Glu Asn Arg Asp Gln Asp Arg Val Gly Ala
 50                  55                  60

Met Glu Asn Ala Thr Gly Ser Val Asn Leu Ile Gly Asn Gly Gly Gly
 65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Val Arg Glu Ser
            100                 105                 110

Pro Leu Ser Ser Asp Ala Ile Phe Lys Gln Ser His Ala Gly Leu Phe
            115                 120                 125

Asn Leu Cys Ile Val Leu Ile Ala Val Asn Ser Arg Leu Ile Ile
        130                 135                 140

Glu Asn Leu Asn Lys
145

<210> SEQ ID NO 135
<211> LENGTH: 103
<212> TYPE: PRT
<213> ORGANISM: Echium pitardii

<400> SEQUENCE: 135

Met Thr Ile Trp Glu Ser Pro Glu Ile Ile Ser Ser Asp Glu Ala Ala
 1               5                  10                  15

Ala Ala Leu Arg Arg Arg Gly Gly Ala Lys Glu Val Ala Glu Gln Arg
                20                  25                  30

Leu Asp Ser Glu Glu Glu Lys Lys Lys Glu Glu Asn Gly Lys Leu
            35                  40                  45

Lys Tyr Thr Tyr Arg Ala Ser Ala Pro Ala His Arg Arg Ile Lys Glu
```

```
                    50                  55                  60
Ser Pro Leu Ser Ser Asp Ala Ile Phe Lys Gln Ser His Ala Gly Leu
 65                  70                  75                  80

Phe Asn Leu Cys Ile Val Val Leu Val Ala Val Asn Ser Arg Leu Ile
                 85                  90                  95

Ile Glu Asn Leu Pro Met Lys
            100

<210> SEQ ID NO 136
<211> LENGTH: 152
<212> TYPE: PRT
<213> ORGANISM: Vernonia galamensis

<400> SEQUENCE: 136

Met Ala Leu Leu Asp Thr Pro Gln Ile Gly Glu Ile Thr Thr Thr Ala
 1               5                  10                  15

Thr Thr Thr Ile Arg Arg Arg Thr Thr Val Lys Pro Asp Ala Gly Ile
             20                  25                  30

Gly Asp Gly Leu Phe Asp Ser Ser Ser Ser Lys Thr Asn Ser Ser
         35                  40                  45

Phe Glu Asp Gly Asp Ser Leu Asn Gly Asp Phe Asn Asp Lys Phe Lys
     50                  55                  60

Glu Gln Ile Gly Ala Gly Asp Glu Ser Lys Asp Ser Lys Gly Asn
 65                  70                  75                  80

Gly Gln Lys Ile Asp His Gly Gly Val Lys Lys Gly Arg Glu Thr Thr
                 85                  90                  95

Val Val His Tyr Ala Tyr Arg Pro Ser Ser Pro Ala His Arg Arg Ile
            100                 105                 110

Lys Glu Ser Pro Leu Ser Ser Asp Ala Ile Phe Lys Gln Ser His Ala
        115                 120                 125

Gly Leu Phe Asn Leu Cys Ile Val Val Leu Val Ala Val Asn Gly Arg
    130                 135                 140

Leu Ile Ile Glu Asn Leu Asn Lys
145                 150

<210> SEQ ID NO 137
<211> LENGTH: 165
<212> TYPE: PRT
<213> ORGANISM: Nicotiana tabacum

<400> SEQUENCE: 137

Met Val Ile Met Glu Leu Pro Glu Ser Val Glu Met Thr Thr Thr Thr
 1               5                  10                  15

Thr Thr Ser Gly Ile Glu Asn Leu Asn Ser Asp Leu Asn His Ser Val
             20                  25                  30

Arg Arg Arg Arg Cys Ser Asn Gly Phe Glu Ala Ala Ser Ala Ile Asn
         35                  40                  45

Ser Ser Asp Ala Asn Met Ser Gly Asp Arg Arg Asp Val Cys Gly Ser
     50                  55                  60

Gly Ala Gly Leu Glu Thr Val Asn Glu Arg Ser Lys Ser Val Gly Glu
 65                  70                  75                  80

Ser Ser Asp Val Ile Arg Lys Glu Asp Arg Asn Asp Asn Val Ala
                 85                  90                  95

Asn Gly Glu Glu Ser Lys Ser Thr Glu Thr Thr Thr Pro Phe Lys
            100                 105                 110

Phe Ala Tyr Arg Ala Ser Ala Pro Ala His Arg Arg Ile Lys Glu Ser
```

```
                   115                 120                 125

Pro Leu Ser Ser Asp Ala Ile Phe Lys Gln Ser His Ala Gly Leu Phe
    130                 135                 140

Asn Leu Cys Val Val Val Leu Ile Ala Val Asn Ser Arg Leu Ile Ile
145                 150                 155                 160

Glu Asn Leu Asn Lys
                165

<210> SEQ ID NO 138
<211> LENGTH: 163
<212> TYPE: PRT
<213> ORGANISM: Perilla frutescens

<400> SEQUENCE: 138

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Arg Arg Ser
            20                  25                  30

Ala Arg Ser Val Pro Pro Leu Leu Asp Ser Asp Ser Asn Ser Leu Glu
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110

Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
    130                 135                 140

Cys Ile Val Val Leu Val Ala Val Asn Ser Arg Leu Ile Ile Glu Asn
145                 150                 155                 160

Leu Asn Lys

<210> SEQ ID NO 139
<211> LENGTH: 141
<212> TYPE: PRT
<213> ORGANISM: Zea mays

<400> SEQUENCE: 139

Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110
```

```
Lys Gln Ser His Ala Gly Leu Phe Asn Leu Cys Ile Val Val Leu Val
            115                 120                 125

Ala Val Asn Ser Arg Leu Ile Ile Glu Asn Leu Met Lys
130                 135                 140
```

<210> SEQ ID NO 140
<211> LENGTH: 141
<212> TYPE: PRT
<213> ORGANISM: Sorghum bicolor

<400> SEQUENCE: 140

```
Met Ala Asp Thr Asp Ala Pro Pro Ala Pro Ala Val His Arg Arg
1               5                   10                  15

Pro Pro Arg Pro Ala Arg Gly Ala Ala Ala Gln Ala Ala Glu Leu
            20                  25                  30

Arg Arg Arg Leu Ser Ser Gly Ala Ala Ala Ala Arg Ala Ser Phe
            35                  40                  45

Ala Ala Asp Ser Gly Asp Glu Ser Gly Pro Glu Pro Ser Ser Ser
    50                  55                  60

Arg Arg Arg Asp Asn Gly Gly Asp Ala Ser Ala Ala Asp Gly Gly
65                  70                  75                  80

Arg Gly Gly Ala Gly Asp Phe Ser Ala Phe Ile Phe Arg Ala Ala
                85                  90                  95

Pro Val His Phe Glu Ala Lys Glu Ser Pro Leu Ser Ser Asp Ala Ile
            100                 105                 110

Phe Glu Gln Ser His Ala Leu Glu Asn Leu Cys Ile Val Val Leu Val
            115                 120                 125

Ala Val Asn Ser Pro Leu Ile Ile Glu Asn Leu Asn Lys
130                 135                 140
```

<210> SEQ ID NO 141
<211> LENGTH: 167
<212> TYPE: PRT
<213> ORGANISM: Oryza sativa

<400> SEQUENCE: 141

```
Met Val Gly Ser Asp Gly Asp Gly Asp Gly Gly Gly Glu Ala His
1               5                   10                  15

Ala Pro Ala Ala Pro Ala His His His Arg Arg Pro Pro Arg Pro Arg
            20                  25                  30

Gly Gly Ser Gly Ala Thr Val Glu Gly Phe Ala Ala Ala Leu Arg Arg
            35                  40                  45

Pro Ile Arg Ser Gly Ala Ala Ala Ala Arg Ala Ser Phe Gly Gly
    50                  55                  60

Asp Ser Gly Asp Glu Ala Ala Ser Gly Glu Pro Ser Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Arg Gly Gly Gly Asp Phe
            100                 105                 110

Ser Ala Phe Thr Phe Arg Ala Ala Ala Pro Val His Arg Lys Ala Lys
            115                 120                 125

Glu Ser Pro Leu Ser Ser Asp Ala Ile Phe Lys Gln Ser His Ala Gly
            130                 135                 140

Leu Phe Asn Leu Cys Ile Val Val Leu Val Ala Val Asn Ser Arg Leu
145                 150                 155                 160
```

```
Ile Ile Glu Asn Leu Asn Lys
                165

<210> SEQ ID NO 142
<211> LENGTH: 104
<212> TYPE: PRT
<213> ORGANISM: Oryza sativa

<400> SEQUENCE: 142

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys
                100

<210> SEQ ID NO 143
<211> LENGTH: 118
<212> TYPE: PRT
<213> ORGANISM: Sorghum bicolor

<400> SEQUENCE: 143

Met Ala Pro Pro Pro Ser Met Ala Ala Ser Asp Arg Ala Val Pro
1               5                   10                  15

Gly Ala Asp Ala Thr Glu Ala Ser Ser Leu Arg Leu Arg Arg Ala Pro
            20                  25                  30

Ser Ala Asp Ala Gly Asp Leu Ala Asp Ser Ser Gly Asp Arg Arg
        35                  40                  45

Glu Asn Gly Glu Pro Gln Pro Pro Gln Glu Gln Gln Gln Gln His Glu
    50                  55                  60

Met Leu Tyr Tyr Arg Ala Ser Ala Pro Ala His Arg Arg Val Lys Glu
65                  70                  75                  80

Ser Pro Leu Ser Ser Asp Ala Ile Phe Arg Gln Ser His Ala Gly Leu
                85                  90                  95

Leu Asn Leu Cys Ile Val Val Leu Ile Ala Val Asn Ser Arg Leu Ile
            100                 105                 110

Ile Glu Asn Leu Met Lys
        115

<210> SEQ ID NO 144
<211> LENGTH: 122
<212> TYPE: PRT
<213> ORGANISM: Zea mays

<400> SEQUENCE: 144

Met Ala Pro Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
            20                  25                  30
```

```
Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Gln Glu Gln
 50                  55                  60

Gln Gln His Glu Met Leu Tyr Tyr Arg Ala Ser Ala Pro Ala His Arg
 65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys
        115                 120

<210> SEQ ID NO 145
<211> LENGTH: 76
<212> TYPE: PRT
<213> ORGANISM: Physcomitrella patens

<400> SEQUENCE: 145

Met Pro Val Lys Ser Ser Asn Leu Ala Gly Glu Arg Ala Ala Thr Ser
1                5                  10                  15

His Ile Asn Ala Asn Thr Lys Phe Asp Leu Arg Gly Cys Thr Pro Ala
                20                  25                  30

His Arg Val Arg Arg Glu Ser Pro Leu Ser Ser Asp Ala Ile Phe His
            35                  40                  45

Gln Ser His Ala Gly Leu Phe Asn Leu Cys Ile Val Val Leu Ile Ala
        50                  55                  60

Val Asn Ser Arg Leu Ile Ile Glu Asn Leu Met Lys
 65                  70                  75

<210> SEQ ID NO 146
<211> LENGTH: 51
<212> TYPE: PRT
<213> ORGANISM: Selaginella moellendorffii

<400> SEQUENCE: 146

Met Arg Pro Ser Leu Pro Ala His Arg Arg Ser Lys Glu Ser Pro Leu
1                5                  10                  15

Ser Ser Asp Ala Ile Phe Thr Gln Ser His Ala Gly Leu Phe Asn Leu
                20                  25                  30

Cys Ile Val Val Leu Val Ala Val Asn Ser Arg Leu Ile Ile Glu Asn
            35                  40                  45

Leu Met Lys
        50

<210> SEQ ID NO 147
<211> LENGTH: 136
<212> TYPE: PRT
<213> ORGANISM: Euonymus alatus

<400> SEQUENCE: 147

Met Ala Ala Asn Leu Asn Glu Ala Ser Asp Leu Asn Phe Ser Leu Arg
1                5                  10                  15

Arg Arg Thr Gly Gly Ile Ser Ser Thr Thr Val Pro Asp Ser Ser Ser
                20                  25                  30

Glu Thr Ser Ser Ser Glu Ala Asp Phe Leu Asp Gly Lys Gly Ala
            35                  40                  45

Ala Asp Val Lys Asp Arg Gly Asp Gly Ala Val Glu Phe Gln Asn Ser
```

```
Met Lys Asn Val Glu Arg Ile Glu Lys His Glu Ser Arg Val Gly Leu
 65                  70                  75                  80

Asp Ser Arg Phe Thr Tyr Arg Pro Ser Val Pro Ala His Arg Thr Ile
                 85                  90                  95

Lys Glu Ser Pro Leu Ser Ser Asp Ala Ile Phe Lys Gln Ser His Ala
            100                 105                 110

Gly Leu Phe Asn Leu Cys Ile Val Val Leu Val Ala Val Asn Ser Arg
            115                 120                 125

Leu Ile Ile Glu Asn Leu Asn Lys
            130                 135

<210> SEQ ID NO 148
<211> LENGTH: 146
<212> TYPE: PRT
<213> ORGANISM: Vitis vinifera

<400> SEQUENCE: 148

Met Ala Ile Cys Asn Ser Phe Pro Ser Val Thr Thr Ser Ser Ser Ser
  1               5                  10                  15

Ser His Ala Asp Ser Asp Leu Asp Phe Ser Ile Arg Lys Arg Phe Gly
             20                  25                  30

Gly Lys Gly Lys Ala Val Ala Asp Ser Ser Leu Glu Thr Glu Thr Glu
         35                  40                  45

Ala Ala Ala Ala Ala Val Leu Glu Ala Glu Lys Ser Val Gly Glu Val
     50                  55                  60

Gly Ser Gly Gly Asp Arg Gly Ser Gly Ser Gln Val Val Arg Asn
 65                  70                  75                  80

Gly Glu Asn Gly Val Ala Glu Val Ala Ala Lys Phe Ala Tyr Arg Pro
                 85                  90                  95

Cys Ala Pro Ala His Arg Lys Val Lys Glu Ser Pro Leu Ser Ser Asp
            100                 105                 110

Ala Ile Phe Arg Gln Ser His Ala Cys Gly Leu Phe Asn Leu Cys Ile
            115                 120                 125

Val Val Leu Val Ala Val Asn Ser Arg Leu Ile Ile Glu Asn Leu Asn
        130                 135                 140

Asn Lys
145

<210> SEQ ID NO 149
<211> LENGTH: 128
<212> TYPE: PRT
<213> ORGANISM: Glycine max

<400> SEQUENCE: 149

Met Ala Ile Ser Asp Glu Pro Glu Thr Val Ala Thr Ala Leu Asn His
  1               5                  10                  15

Ser Ser Leu Arg Arg Arg Pro Thr Ala Ala Gly Leu Phe Asn Ser Pro
             20                  25                  30

Glu Thr Thr Thr Asp Ser Ser Gly Asp Asp Leu Ala Lys Asp Ser Gly
         35                  40                  45

Ser Asp Asp Ser Ile Ser Ser Asp Ala Ala Asn Ser Gln Pro Gln Gln
     50                  55                  60

Lys Lys Gln Asp Thr Asp Phe Ser Val Leu Lys Phe Ala Tyr Arg Pro
 65                  70                  75                  80

Ser Val Pro Ala His Arg Glu Val Glu Glu Ser Pro Leu Ser Ser Asp
```

```
                    85                  90                  95
Thr Ile Phe Arg Gln Ser His Ala Gly Leu Phe Asn Leu Cys Ile Val
                100                 105                 110
Val Leu Val Ala Val Asn Ser Arg Leu Ile Ile Glu Asn Leu Met Lys
            115                 120                 125

<210> SEQ ID NO 150
<211> LENGTH: 133
<212> TYPE: PRT
<213> ORGANISM: Glycine max

<400> SEQUENCE: 150

Met Ala Ile Ser Asp Glu Pro Glu Ser Val Ala Thr Ala Leu Asn His
1               5                   10                  15
Ser Ser Leu Arg Arg Arg Pro Ser Ala Thr Ser Thr Ala Gly Leu Phe
            20                  25                  30
Asn Ser Pro Glu Thr Thr Thr Asp Ser Ser Gly Asp Asp Leu Ala Lys
        35                  40                  45
Asp Ser Gly Ser Asp Asp Ser Ile Asn Ser Asp Asp Ala Ala Val Asn
    50                  55                  60
Ser Gln Gln Gln Asn Glu Lys Gln Asp Thr Asp Phe Ser Val Leu Lys
65                  70                  75                  80
Phe Ala Tyr Arg Pro Ser Val Pro Ala His Arg Lys Val Lys Glu Ser
                85                  90                  95
Pro Leu Ser Ser Asp Thr Ile Phe Arg Gln Ser His Ala Gly Leu Phe
                100                 105                 110
Asn Leu Cys Ile Val Val Leu Val Ala Val Asn Ser Arg Leu Ile Ile
            115                 120                 125
Glu Asn Leu Met Lys
        130

<210> SEQ ID NO 151
<211> LENGTH: 139
<212> TYPE: PRT
<213> ORGANISM: Lotus japonicus

<400> SEQUENCE: 151

Met Ala Ile Ser Glu Asp Ser Glu Ser Leu Phe Ala Ala Ala Ala Ala
1               5                   10                  15
Ser Ser Val Ile Gln Ser Gly Ser Ser Val Arg Arg Pro Ser Ala
            20                  25                  30
Ile Ser Ala Val Ala Thr Val Glu Asp Glu Ser Ser Glu Glu Pro
        35                  40                  45
Val Pro Val Arg Asp Ser Gly Ser Asp Val Asp Asp Ser Val Ser Ser
    50                  55                  60
Glu Gln His Val Ser Pro Ala Thr Ala Asn Arg Glu Lys Asn Gln Val
65                  70                  75                  80
His Asp Ile Ser Ala Thr Lys Phe Ala Tyr Arg Pro Ser Ala Pro Ala
                85                  90                  95
His Arg Arg Val Lys Glu Ser Pro Leu Ser Ser Asp Asn Ile Phe Arg
                100                 105                 110
His His Ala Gly Leu Phe Asn Leu Cys Ile Val Val Leu Val Ala Val
            115                 120                 125
Asn Ser Arg Leu Ile Ile Glu Asn Leu Asn Lys
        130                 135
```

-continued

```
<210> SEQ ID NO 152
<211> LENGTH: 167
<212> TYPE: PRT
<213> ORGANISM: Medicago truncatula

<400> SEQUENCE: 152

Met Ala Ile Ser Asp Thr Pro Glu Thr Thr Ala Thr Ala Thr Ala Thr
1               5                   10                  15

Val Thr Thr Ile Glu Thr Asp Thr Asp Leu Lys Arg Ser Ser Leu Arg
            20                  25                  30

Arg Arg Pro Ser Ala Thr Ser Thr Ala Gly Gly Leu Phe Asp Ala Glu
        35                  40                  45

Ser Ala Ala Asp Ala Val Arg Asp Ser Gly Ser Asp Ser Leu
    50                  55                  60

Asn Gly Lys Ile Asn Asn Glu Glu Val Lys Asp Arg Lys Thr Asp
65                  70                  75                  80

His Ala Glu Gly Ile Val Asp Asp Asp Asn Ala Val Lys Lys
                85                  90                  95

Asn Gly Gly Asn Asp Val Ile Asn Asp Arg Glu Asn Val Ala Val Asp
                100                 105                 110

Phe Lys Phe Thr Tyr Arg Pro Ser Val Pro Ala His Arg Arg Ser Lys
            115                 120                 125

Glu Ser Pro Leu Ser Ser Gly Asn Ile Phe Arg Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Asn Lys
                165

<210> SEQ ID NO 153
<211> LENGTH: 148
<212> TYPE: PRT
<213> ORGANISM: Jatropha curcas

<400> SEQUENCE: 153

Met Thr Ile Leu Glu Thr Thr Thr Ser Gly Gly Asp Gly Val Ala Glu
1               5                   10                  15

Ser Ser Ser Asp Leu Asn Val Ser Leu Arg Arg Arg Lys Gly Thr
            20                  25                  30

Ser Ser Asp Gly Ala Leu Pro Glu Leu Thr Ser Asn Ile Val Glu Leu
        35                  40                  45

Glu Ser Glu Ser Gly Gly Gln Val Met Met Asp Pro Gly Met Val Thr
    50                  55                  60

Glu Pro Glu Thr Glu Lys Ile Asn Gly Lys Asp Cys Gly Gly Asp Lys
65                  70                  75                  80

Asp Lys Ile Asp Asn Arg Glu Asn Arg Gly Arg Ser Asp Ile Lys Phe
                85                  90                  95

Thr Tyr Arg Pro Ser Val Pro Ala His Arg Ala Leu Arg Glu Ser Pro
                100                 105                 110

Leu Ser Ser Asp Ala Ile Phe Lys Gln Ser His Ala Gly Leu Phe Asn
            115                 120                 125

Leu Cys Ile Val Val Leu Val Ala Val Asn Ser Arg Leu Ile Ile Glu
        130                 135                 140

Asn Leu Asn Lys
145
```

```
<210> SEQ ID NO 154
<211> LENGTH: 153
<212> TYPE: PRT
<213> ORGANISM: Vernicia fordii

<400> SEQUENCE: 154

Met Thr Ile Pro Glu Thr Pro Asp Asn Ser Thr Asp Ala Thr Thr Ser
1               5                   10                  15

Gly Gly Ala Glu Ser Ser Ser Asp Leu Asn Leu Ser Leu Arg Arg Arg
            20                  25                  30

Arg Thr Ala Ser Asn Ser Asp Gly Ala Val Ala Glu Leu Ala Ser Lys
        35                  40                  45

Ile Asp Glu Leu Glu Ser Asp Ala Gly Gly Gln Val Ile Lys Asp
    50                  55                  60

Pro Gly Ala Glu Met Asp Ser Gly Thr Leu Lys Ser Asn Gly Lys Asp
65                  70                  75                  80

Cys Gly Thr Val Lys Asp Arg Ile Glu Asn Arg Glu Asn Arg Gly Gly
                85                  90                  95

Ser Asp Val Lys Phe Thr Tyr Arg Pro Ser Val Pro Ala His Arg Ala
            100                 105                 110

Leu Lys Glu Ser Pro Leu Ser Ser Asp Asn Ile Phe Lys Gln Ser His
        115                 120                 125

Ala Gly Leu Phe Asn Leu Cys Ile Val Val Leu Val Ala Val Asn Ser
    130                 135                 140

Arg Leu Ile Ile Glu Asn Ile Asn Lys
145                 150

<210> SEQ ID NO 155
<211> LENGTH: 153
<212> TYPE: PRT
<213> ORGANISM: Vernonia galamensis

<400> SEQUENCE: 155

Met Thr Ile Leu Glu Thr Pro Glu Thr Leu Gly Val Ile Ser Ser Ser
1               5                   10                  15

Ala Thr Ser Asp Leu Asn Leu Ser Leu Arg Arg Arg Arg Thr Ser Asn
            20                  25                  30

Asp Ser Asp Gly Ala Leu Ala Asp Leu Ala Ser Lys Phe Asp Asp Asp
        35                  40                  45

Asp Asp Val Arg Ser Glu Asp Ser Ala Glu Asn Ile Ile Glu Asp Pro
    50                  55                  60

Val Ala Ala Val Thr Glu Leu Ala Thr Ala Lys Ser Asn Gly Lys Asp
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
            100                 105                 110

Leu Lys Glu Ser Pro Leu Ser Ser Asp Leu Ile Phe Lys Gln Ser His
        115                 120                 125

Ala Gly Leu Phe Asn Leu Cys Ile Val Val Leu Val Ala Val Asn Ser
    130                 135                 140

Arg Leu Ile Ile Glu Asn Leu Asn Lys
145                 150

<210> SEQ ID NO 156
<211> LENGTH: 79
<212> TYPE: PRT
```

```
<213> ORGANISM: Ricinus communis

<400> SEQUENCE: 156

Met Met Glu Ser Glu Asp Leu Lys Ser Asn Gly Lys Glu Cys Asp Lys
1               5                   10                  15

Val Thr Asn Glu Asn Arg Ser Asp Ile Lys Phe Asn Tyr Arg Pro Ser
            20                  25                  30

Met Pro Ala His Arg Gly Val Arg Glu Ser Pro Leu Ser Ser Asp Ala
        35                  40                  45

Ile Phe Lys Gln Ser His Ala Gly Leu Phe Asn Leu Cys Ile Val Val
    50                  55                  60

Leu Val Ala Ile Asn Ser Arg Leu Ile Ile Glu Asn Ile Ile Lys
65                  70                  75

<210> SEQ ID NO 157
<211> LENGTH: 120
<212> TYPE: PRT
<213> ORGANISM: Populus trichocarpa

<400> SEQUENCE: 157

Met Ala Glu Ser Glu Ser Pro Glu Asn Arg Ile Ala Ala Met Glu Ser
1               5                   10                  15

Thr Ser Ser Thr Ser Asp Leu Asn Phe Ser Ile Arg Arg Arg Ser
            20                  25                  30

Thr Val Met Asp Ser Ala Ser Thr Glu Met Met Gly Ser Glu Gly Leu
        35                  40                  45

Lys Ser Ser Gly Lys Ala Cys Asp Lys Val Lys Ile Glu Lys Gln Ser
    50                  55                  60

Asp Met Lys Phe Asn Tyr Arg Pro Ser Met Pro Ala His Ser Gly Val
65                  70                  75                  80

Arg Glu Ser Pro Leu Ser Ser Asp Ala Ile Phe Lys Gln Ser His Ala
            85                  90                  95

Gly Leu Phe Asn Leu Cys Ile Val Val Leu Val Ala Val Asn Ser Arg
                100                 105                 110

Leu Ile Ile Glu Asn Leu Ile Lys
            115                 120
```